(12) United States Patent
Mahajan et al.

(10) Patent No.: US 9,850,216 B2
(45) Date of Patent: Dec. 26, 2017

(54) INHIBITORS OF ACK1/TNK2 TYROSINE KINASE

(71) Applicant: H. LEE MOFFITT CANCER CENTER AND RESEARCH INSTITUTE, INC., Tampa, FL (US)

(72) Inventors: Nupam P. Mahajan, Tampa, FL (US); Kiran N. Mahajan, Tampa, FL (US); Nicholas J. Lawrence, Tampa, FL (US); Harshani R. Lawrence, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/910,486

(22) PCT Filed: Aug. 6, 2014

(86) PCT No.: PCT/US2014/049935
§ 371 (c)(1),
(2) Date: Feb. 5, 2016

(87) PCT Pub. No.: WO2015/021149
PCT Pub. Date: Feb. 12, 2015

(65) Prior Publication Data
US 2016/0176826 A1    Jun. 23, 2016

Related U.S. Application Data

(60) Provisional application No. 61/862,763, filed on Aug. 6, 2013.

(51) Int. Cl.
| C07D 405/14 | (2006.01) |
| C07D 239/49 | (2006.01) |
| C07D 405/12 | (2006.01) |
| C07D 239/42 | (2006.01) |
| C07D 239/48 | (2006.01) |
| C07C 53/18  | (2006.01) |

(52) U.S. Cl.
CPC ............ *C07D 239/49* (2013.01); *C07C 53/18* (2013.01); *C07D 239/42* (2013.01); *C07D 239/48* (2013.01); *C07D 405/12* (2013.01); *C07D 405/14* (2013.01)

(58) Field of Classification Search
CPC .................................................. C07D 405/14
See application file for complete search history.

(56) References Cited

U.S. PATENT DOCUMENTS

| 4,559,157 A | 12/1985 | Reilly et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook et al. |
| 6,960,648 B2 | 11/2005 | Bonny et al. |
| 8,349,860 B2 | 1/2013 | Jia et al. |
| 2002/0035243 A1 | 3/2002 | Imfeld et al. |
| 2002/0120100 A1 | 8/2002 | Bonny et al. |
| 2003/0032594 A1 | 2/2003 | Bonny et al. |
| 2006/0025406 A1 | 2/2006 | Zembower et al. |
| 2010/0137313 A1* | 6/2010 | Boriack-Sjodin .... C07D 239/48 514/236.5 |
| 2010/0298557 A1* | 11/2010 | Yagi .................... C07D 519/00 540/544 |
| 2011/0301141 A1* | 12/2011 | Baker-Glenn ....... C07D 403/14 514/210.16 |
| 2012/0045454 A1 | 2/2012 | Singh et al. |

OTHER PUBLICATIONS

International Search Report and Written Opinion issued for International Application No. PCT/US2014/49935, dated Nov. 28, 2014.
Aqeilan, et al., "WWOX in biological control and tumorigenesis", J. Cell. Physiol. 2007, 212:307-10.
Arora, et al., "Glucocorticoid receptor confers resistance to antiandrogens by bypassing androgen receptor blockade", Cell. 2013, 155(6):1309-1322.
Balbas, et al., "Overcoming mutation-based resistance to antiandrogens with rational drug design", eLife. 2013, 2:e00499.
Bebbington, et al., "The discovery of the potent aurora inhibitor MK-0457 (VX-680)", Bioorg. Med. Chem. Lett. 2009, 19:3586-92.
Bennett, et al., "Enzalutamide (Xtandi) for patients with metastatic, resistant prostate cancer", Ann. Pharmacotherapy. 2014, 48(4):530-7.
Bollag, et al., "Clinical efficacy of a RAF inhibitor needs broad target blockade in BRAF-mutant melanoma" Nature. 2010, 467(7315):596-9.
Bossi, et al., "Crystal structures of anaplastic lymphoma kinase in complex with ATP competitive inhibitors", Biochem. 2010, 49:6813-25.
Burgering, et al., "Protein kinase B (c-Akt) in phosphatidylinositol-3-OH kinase signal transduction", Nature 1995, 376:599-602.
Burnstein, "Regulation of androgen receptor levels: implications for prostate cancer progression and therapy", J. Cell. Biochem. 2005, 95(4):657-69.
Cai, et al., "Androgen receptor gene expression in prostate cancer is directly suppressed by the androgen receptor through recruitment of lysine-specific demethylase 1", Cancer Cell. 2011, 20(4):457-71.
Carter, et al., "Inhibition of drug-resistant mutants of ABL, KIT, and EGF receptor kinases", Natl. Acad. Sci. USA 2005, 102:11011-6.
Chen, et al., "Molecular determinants of resistance to antiandrogen therapy", Nature Med. 2004, 10(1):33-9.
Davis, et al., "Comprehensive analysis of kinase inhibitor selectivity", Nat. Biotechnol. 2011, 29:1046-51.
Dimauro, et al., "Discovery of 4-amino-5,6-biaryl-furo[2,3-d]pyrimidines as inhibitors of Lck: development of an expedient and divergent synthetic route and preliminary SAR", Bioorg. Med. Chem. Lett. 2007, 17:2305-9.

(Continued)

*Primary Examiner* — Robert Hayun
(74) *Attorney, Agent, or Firm* — Meunier Carlin & Curfman LLC

(57) ABSTRACT

Described are cancer therapies and anti-cancer compounds. In particular, disclosed are inhibitors of Ack1 tyrosine kinase and their use in the treatment of cancer. Methods of screening for new Ack1 tyrosine kinase inhibitors are also disclosed. In specific example, compound having Formula I through IV are disclosed.

6 Claims, 10 Drawing Sheets

(56) References Cited

OTHER PUBLICATIONS

Edwards, et al., "The androgen receptor and signal-transduction pathways in hormone-refractory prostate cancer. Part 1: Modifications to the androgen receptor", BJU Intl. 2005, 95(9):1320-6.

Edwards, et al., "The androgen receptor and signal-transduction pathways in hormone-refractory prostate cancer. Part 2: Androgen-receptor cofactors and bypass pathways", BJU Int. 2005, 95(9):1327-35.

Feldman, et al., "The development of androgen-independent prostate cancer", Nature Rev. 2001, 1(1):34-45.

Franke, et al., "The protein kinase encoded by the Akt proto-oncogene is a target of the PDGF-activated phosphatidylinositol 3-kinase", Cell 1995, 81:727-36.

Galkin, et al., "Identification of NVP-TAE684, a potent, selective, and efficacious inhibitor of NPM-ALK", Proc. Natl. Acad. Sci. USA 2007, 104:270-5.

Golas, et al., "SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice", Cancer Res. 2003, 63:375-81.

Grasso, et al., "The mutational landscape of lethal castration-resistant prostate cancer", Nature. 2012, 487(7406):239-43.

Greenlee, et al., Cancer Statistics, 2000. CA: a cancer journal for clinicians. 2000, 50(1):7-33.

Jiao, et al., "Synthesis and optimization of substituted furo[2,3-d]-pyrimidin-4-amines and 7H-pyrrolo[2,3-d]pyrimidin-4-amines as ACK1 inhibitors", Bioorg. Med. Chem. Lett. 2012, 22:6212-7.

Joseph, et al., "A clinically relevant androgen receptor mutation confers resistance to second-generation antiandrogens enzalutamide and ARN-509", Cancer Discovery. 2013, 3(9):1020-9.

Jin, et al., "Discovery of potent, selective and orally bioavailable imidazo[1,5-a]pyrazine derived ACK1 inhibitors", Bioorg. Med. Chem. Lett. 2013, 23:979-84.

Knuuttila, et al. Castration Induces Up-Regulation of Intratumoral Androgen Biosynthesis and Androgen Receptor Expression in an Orthotopic VCaP Human Prostate Cancer Xenograft Model. Am. J. Pathol. 2014.

Kopecky, et al., "Identification and optimization of N3,N6-diaryl-1H-pyrazolo[3,4-d]pyrimidine-3,6-diamines as a novel class of ACK1 inhibitors", Bioorg. Med. Chem. Lett. 2008, 18:6352-6.

Korpal, et al., "An F876L mutation in androgen receptor confers genetic and phenotypic resistance to MDV3100 (enzalutamide)", Cancer Discovery. 2013, 3(9):1030-43.

Lawrence, et al., "Development of o-chlorophenyl substituted pyrimidines as exceptionally potent aurora kinase inhibitors." J. Med. Chem. 2012, 55:7392-416.

Li, et al., "A chemical and phosphoproteomic characterization of dasatinib action in lung cancer", Nat. Chem. Biol. 2010, 6:291-9.

Liu, et al., "Dasatinib inhibits site-specific tyrosine phosphorylation of androgen receptor by Ack1 and Src kinases", Oncogene 2010, 29:3208-16.

Mahajan, et al., "Ack1 mediated AKT/PKB tyrosine 176 phosphorylation regulates its activation", PLoS one 2010, 5:e9646.

Mahajan, et al., "Ack1 tyrosine kinase activation correlates with pancreatic cancer progression", Am. J. Pathol. 2012, 180:1386-93.

Mahajan, et al., "ACK1 tyrosine kinase: targeted inhibition to block cancer cell proliferation", Cancer Lett. 2013, 338:185-92.

Mahajan, et al., "Ack1-mediated androgen receptor phosphorylation modulates radiation resistance in castration-resistant prostate cancer", J. Biol. Chem. 2012, 287:22112-22.

Mahajan, et al., "Activated Cdc42-associated kinase Ack1 promotes prostate cancer progression via androgen receptor tyrosine phosphorylation", Proc. Natl. Acad. Sci. USA 2007, 104:8438-43.

Mahajan, et al., "Activated Tyrosine Kinase Ack1 Promotes Prostate Tumorigenesis: Role of Ack1 in Polyubiquitination of Tumor Suppressor Wwox", Cancer Res. 2005, 65:10514-23.

Mahajan, et al., "Effect of Ack1 tyrosine kinase inhibitor on ligand-independent androgen receptor activity", Prostate 2010, 70:1274-85.

Mahajan, et al., "Shepherding AKT and androgen receptor by Ack1 tyrosine kinase", J. Cell. Physiol. 2010, 224:327-33.

Manning, "AKT/PKB signaling: navigating downstream", Cell 2007, 129:1261-74.

Martin, et al., "A novel mechanism by which small molecule inhibitors induce the DFG flip in Aurora A", ACS Chem. Biol. 2012, 7:698-706.

Martin, "Discovery of novel 2,3-diarylfuro[2,3-b]pyridin-4-amines as potent and selective inhibitors of Lck: synthesis, SAR, and pharmacokinetic properties", Bioorg. Med. Chem. Lett. 2007, 17:2299-304.

Metz, et al., "Navigating the kinome", Nat. Chem. Biol. 2011, 7:200-2.

Miduturu, et al., "High-throughput kinase profiling: a more efficient approach toward the discovery of new kinase inhibitors", Chem. Biol. 2011, 18:868-879.

Moriarty, et al., "The synthesis and SAR of 2-amino-pyrrolo[2,3-d]pyrimidines: a new class of Aurora-A kinase inhibitors", Bioorg. Med. Chem. Lett. 2006, 16:5778-83.

Rix, et al., "Global target profile of the kinase inhibitor bosutinib in primary chronic myeloid leukemia cells", Leukemia 2009, 23:477-85.

Shahbazian, et al., "Functions of site-specific histone acetylation and deacetylation", Ann. Rev. Biochem. 2007, 76:75-100.

Shilatifard, "Molecular implementation and physiological roles for histone H3 lysine 4 (H3K4) methylation", Curr. Opin. Cell Biol. 2008, 20(3):341-8.

Tan, "Bosutinib inhibits migration and invasion via ACK1 in KRAS mutant non-small cell lung cancer", Mol. Cancer 2014, 13:13, 10 pages.

Tari, et al., "Structural basis for the inhibition of Aurora A kinase by a novel class of high affinity disubstituted pyrimidine inhibitors", Bioorg. Med. Chem. Lett. 2007, 17:688-691.

Toyoizumi, et al., "Combined therapy with chemotherapeutic agents and herpes simplex virus type IICP34.5 mutant (HSV-1716) in human non-small cell lung cancer", Human Gene Therapy 10(18), 1999, 3013-3029.

Tran, et al., "Development of a second-generation antiandrogen for treatment of advanced prostate cancer", Science. 2009, 324(5928):787-90.

Van Der Horst, et al., "Metastatic properties and genomic amplification of the tyrosine kinase gene ACK1", Proc. Nat. Acad. Sci. U.S.A. 2005, 102(44):15901-6.

Xu, et al., "EZH2 oncogenic activity in castration-resistant prostate cancer cells is Polycomb-independent", Science. 2012, 338(6113):1465-9.

Xu, et al., "Regulation of androgen receptor transcriptional activity and specificity by RNF6-induced ubiquitination", Cancer Cell. 2009, 5(4):270-82.

Yang, "Dual Aurora A and JAK2 kinase blockade effectively suppresses malignant transformation", Oncotarget 2014, 5:2947-61.

\* cited by examiner a b

INHIBITORS OF ACK1/TNK2 TYROSINE KINASE

CROSS REFERENCE TO RELATED APPLICATIONS

This application claims the benefit of priority to U.S. Provisional Application No. 61/862,763, filed Aug. 6, 2013, which is incorporated by reference herein in its entirety.

ACKNOWLEDGEMENT OF GOVERNMENT SUPPORT

This invention was made with Government support under Grant No. CA135328 awarded by the National Institutes of Health. The Government has certain rights in the invention.

FIELD

The subject matter disclosed herein relates generally to cancer therapy and to anti-cancer compounds. More specifically, the subject matter disclosed herein relates to inhibitors of Ack1 tyrosine kinase and their use in the treatment of cancer. Methods of screening for selective inhibitors of Ack1 kinases are also disclosed.

BACKGROUND

Ack1, also known as TNK2, is a non-receptor tyrosine kinase that is expressed in diverse cell types. It integrates signals from several important ligand-activated receptor tyrosine kinases (RTKs), for example, EGFR, MerTK, HER2, PDGFR and insulin receptor to initiate intracellular signaling cascades. The ACK1 tyrosine kinase is aberrantly activated, amplified or mutated in many types of human cancers including prostate, breast, pancreatic, ovarian and lung cancers (Mahajan K, et al. ACK1 tyrosine kinase: targeted inhibition to block cancer cell proliferation. *Cancer Lett.* 2013; 338:185-92). Aberrantly activated ACK1 drives cell growth via a number of molecular mechanisms (Mahajan K, et al. Shepherding AKT and androgen receptor by Ack1 tyrosine kinase. *J. Cell. Physiol.* 2010; 224:327-33). Several recent discoveries underscore its tumor promoting functions. For example, ACK1 phosphorylates the androgen receptor, at Tyr267 in its transactivation domain, in an androgen-independent manner to promote castration resistant prostate cancer (CRPC) growth (Mahajan K, et al. Activated Cdc42-associated kinase Ack1 promotes prostate cancer progression via androgen receptor tyrosine phosphorylation. *Proc. Natl. Acad. Sci. USA* 2007; 104:8438-43; Mahajan K, et al. Ack1-mediated androgen receptor phosphorylation modulates radiation resistance in castration-resistant prostate cancer. *J. Biol. Chem.* 2012; 287(26): 22112-22). ACK1 has been shown to promote prostate tumorogenesis by phosphorylating the WW domain-containing oxidoreductase (Wwox) tumor suppressor (Aqeilan R I, et al. WWOX in biological control and tumorigenesis. *J. Cell. Physiol.* 2007; 212:307-10) on Tyr287 leading to its polyubiquitination and subsequent degradation (Mahajan K, et al. Activated tyrosine kinase Ack1 promotes prostate tumorigenesis: role of Ack1 in polyubiquitination of tumor suppressor Wwox. *Cancer Res.* 2005; 65:10514-23). It has also been shown that ACK1 phosphorylates and activates the key signaling kinase AKT, which plays important roles in human physiology and disease (Franke T F, et al. The protein kinase encoded by the Akt proto-oncogene is a target of the PDGF-activated phosphatidylinositol 3-kinase. *Cell* 1995; 81:727-36; Burgering B M, et al. Protein kinase B (c-Akt) in phosphatidylinositol-3-OH kinase signal transduction. *Nature* 1995; 376:599-602; Manning B D, et al. AKT/PKB signaling: navigating downstream. *Cell* 2007; 129:1261-74). When AKT is phosphorylated on Tyr176 by ACK1 it functionally participates in the progression of breast cancer by suppressing pro-apoptotic pathways (Mahajan K, et al. *Ack1* mediated AKT/PKB tyrosine 176 phosphorylation regulates its activation. *PloS one* 2010; 5:e9646). Conversely knockdown of ACK1 expression by siRNA suppressed AKT activation in MCF7 breast cancer cell line and increased expression of pro-apoptotic genes such as Bim and Fas (Id.). ACK1 transgenic mice developed prostatic intraepithelial neoplasia (PINs), indicating that its activation is crucial in tumorigenesis (Id.). Significant evidence in pre-clinical models therefore validates ACK1 as a target for anticancer drugs, and has driven the development of many ACK1 inhibitors. Selected examples of ACK1 inhibitors are as follows:

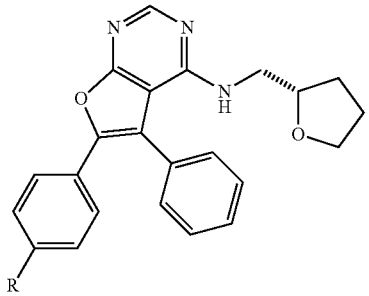

1a R = O(CH$_2$)$_2$NMe$_2$
ACK1 IC$_{50}$ 11 nM; Lck IC$_{50}$ 6 nM
1b (AIM-100), R = H
ACK1 IC$_{50}$ 24 nM; Lck IC$_{50}$ 122 nM

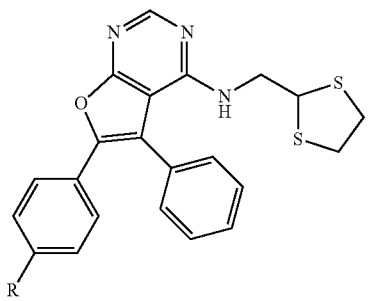

1c, R = O(CH$_2$)$_2$NMe$_2$
ACK1 K$_i$ 0.3 nM; Lck K$_i$ 138 nM

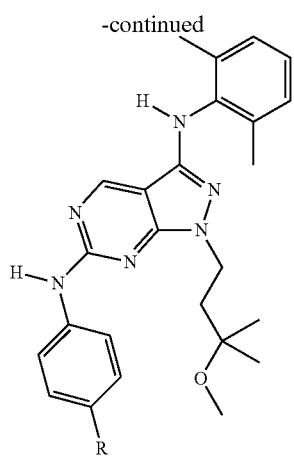

2, R = H  ACK1 IC$_{50}$ 2 nM

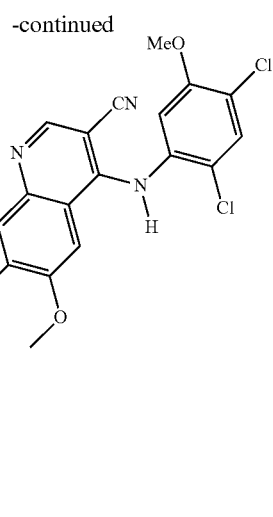

Bosutinib, ACK1 IC$_{50}$ 2.7 nM

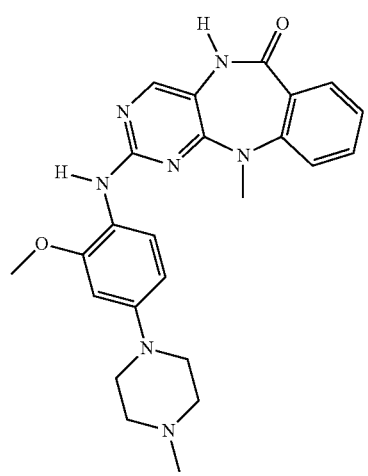

3, ACK1 K$_d$ 2 nM

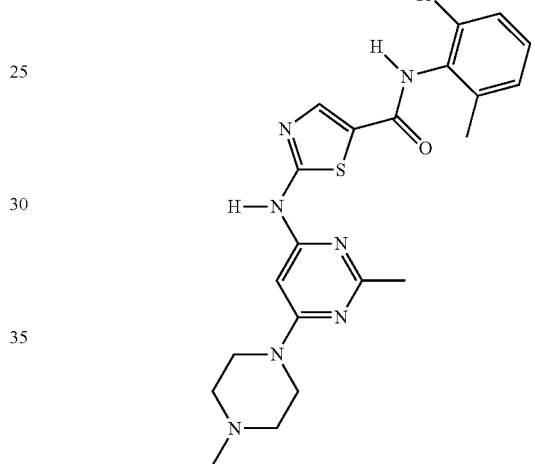

Dasatinib, ACK1 K$_D$ 6 nM

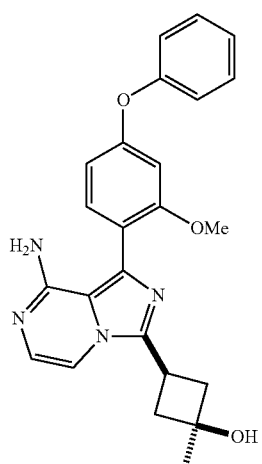

4, ACK1 IC$_{50}$ 110 nM;
ACK1 IC$_{50}$ (cell) 35 nM

A series of 4-amino-5,6-biaryl-furo[2,3-d]pyrimidines (structures 1a-1c) were found to inhibit ACK1 and the related member of the src kinase family Lck (lymphocyte-specific kinase) (DiMauro E F, et al. Discovery of 4-amino-5,6-biaryl-furo[2,3-d]pyrimidines as inhibitors of Lck: development of an expedient and divergent synthetic route and preliminary SAR. *Bioorg. Med. Chem. Lett.* 2007; 17, 2305-9; Martin M W, et al. Discovery of novel 2,3-diaryl-furo[2,3-b]pyridin-4-amines as potent and selective inhibitors of Lck: synthesis, SAR, and pharmacokinetic properties. *Bioorg. Med. Chem. Lett.* 2007; 17:2299-304). For example, compound 1a potently inhibits both ACK1 and Lck and was useful in the development of further compounds for the treatment of T cell-mediated automimmune and inflammatory disease as a consequence of Lck inhibition. Compound 1b (AIM-100) was used as a chemical probe for ACK1 inhibition, since it was reported to inhibit Lck to a lesser extent (ACK1:Lck 5:1) than 1a (Lck:ACK1 1.8:1). AIM-100 inhibits ACK1 dependent AKT Tyr176 (Mahajan K, et al. Ack1 tyrosine kinase activation correlates with pancreatic cancer progression. *Am. J. Pathol.* 2012; 180:1386-93) in pancreatic cancer cells and AR Tyr267

(Mahajan K, et al. Effect of Ack1 tyrosine kinase inhibitor on ligand-independent androgen receptor activity. *Prostate* 2010; 70:1274-85) phosphorylation. AIM-100 also inhibits castration and radioresistant prostate xenograft tumor growth via inhibition of AR Tyr267 phosphorylation (Mahajan K, et al. Ack1-mediated androgen receptor phosphorylation modulates radiation resistance in castration-resistant prostate cancer. *J. Biol. Chem.* 2012; 287:22112-22). A study of further members of the 4-amino-5,6-biaryl-furo[2,3-d]pyrimidine series showed that the dithiolane 1c was an exceptionally potent ACK1 inhibitor ($K_i$ 0.3 nM). This compound inhibits the growth of a cell line which is dependent upon ACK1 with an $IC_{50}$ of 5 nM. However, its poor pharmacokinetic properties (attributed to oxidation of both the dithiolane ring and $NMe_2$) precluded use in an animal model. A series of pyrazolopyrimidines of type 2 have also been developed by Amgen as ACK1 inhibitors (Kopecky D J, et al. Identification and optimization of N3,N6-diaryl-1H-pyrazolo[3,4-d]pyrimidine-3,6-diamines as a novel class of ACK1 inhibitors. *Bioorg. Med. Chem. Lett.* 2008; 18:6352-6). For example, compound 2 potently inhibits ACK1 in vitro ($IC_{50}$ 2 nM) and in intact cells, as measured by inhibition of ACK1 autophosphorylation ($IC_{50}$ 20 nM). Gray and co-workers have identified the ACK1 inhibitor 3, by high throughput kinase profiling of a focused library of pyrimidine-diazepines (Miduturu C V, et al. High-throughput kinase profiling: a more efficient approach toward the discovery of new kinase inhibitors. *Chem. Biol.* 2011; 18:868-79). This compound abolishes EGF induced ACK1 autophosphorylation (Tyr284) in HEK293 cells at concentrations of 2 µM. It also inhibits A549 lung cancer cell growth at 10 µM. A series of imidazopyrazine based ACK1 inhibitors have been developed by Jin and co-workers at OSI/Astellas (Jin M, et al. Discovery of potent, selective and orally bioavailable imidazo[1,5-a]pyrazine derived ACK1 inhibitors. *Bioorg. Med. Chem. Lett.* 2013; 23:979-84). For example, compound 4 is a potent ACK1 inhibitor orally bioavailable in mouse models and good experimental ADMET properties. It inhibits ACK1 mediated phosphorylation of poly-(GT) in an AlphaScreen assay with an $IC_{50}$ of 110 nM. It potently inhibits ACK1 in a cellular context. In NCI-H1703 human non-small cell lung cancer cells its $IC_{50}$ for ACK1 inhibition is 35 nM as measured by an ELISA assay. In this assay ACK1 from the cell lysates is captured on an ELISA plate by ACK1 antibodies. The extent of phosphorylation of ACK1 was determined using an enzyme-linked antibody that recognizes phosphotyrosine residues. Several promiscuous kinase inhibitors have been shown to inhibit ACK1. For example, the Src/Abl kinase inhibitor bosutinib (Golas J M, et al. SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice. *Cancer Res.* 2003; 63:375-81) inhibits ACK1 with an $IC_{50}$ of 2.7 nM (Remsing R, et al. Global target profile of the kinase inhibitor bosutinib in primary chronic myeloid leukemia cells. *Leukemia* 2009; 23:477-85). Bosutinib was found to inhibit cell migration and invasion but not viability in a panel of non-small cell lung cancer (NSCLC) cell lines (Tan D S, et al. Bosutinib inhibits migration and invasion via ACK1 in KRAS mutant non-small cell lung cancer. *Mol. Cancer* 2014; 13:13). These effects were not seen when ACK1 was knocked-down specifically in K-Ras mutant cell lines. Dasatinib, another BCR/Abl and Src family tyrosine kinase inhibitor, inhibits ACK1 with a $K_D$ of 6 nM (Carter T A, et al. Inhibition of drug-resistant mutants of ABL, KIT, and EGF receptor kinases. *Proc. Natl. Acad. Sci. USA* 2005; 102:11011-6). Dasatinib was shown to inhibit both ACK1 autophosphorylation and AR phosphorylation of Tyr-267 in heregulin-stimulated human prostate cancer LNCaP cells with $IC_{50}$s<5 nM (Liu Y, et al. Dasatinib inhibits site-specific tyrosine phosphorylation of androgen receptor by Ack1 and Src kinases. *Oncogene* 2010; 29:3208-16). Additionally, dasatinib significantly reduced the growth of LNCaP cells expressing constitutively activated ACK1 in a mouse xenograft model (Id.). Chemical and phosphoproteomic approaches revealed ACK1 to be a target of dasatinib in human lung cancer cells (Li J, et al. A chemical and phosphoproteomic characterization of dasatinib action in lung cancer. *Nat. Chem. Biol.* 2010; 6:291-9).

ACK1 inhibitors are developed by analysis of known ACK1 inhibitors including 1b (AIM-100), the pyrazolopyrimidine derivative 5 (Kopecky D J, et al. Identification and optimization of N3,N6-diaryl-1H-pyrazolo[3,4-d]pyrimidine-3,6-diamines as a novel class of ACK1 inhibitors. *Bioorg. Med. Chem. Lett.* 2008; 18:6352-6) and the ALK inhibitor 6 (TAE684) (Galkin A V, et al. Identification of NVP-TAE684, a potent, selective, and efficacious inhibitor of NPM-ALK. *Proc. Natl. Acad. Sci. USA* 2007; 104:270-5) (which strongly cross-inhibits ACK1 from published inhibitor profiling data sets; $K_d$ 2 nM (Davis M I, et al. Comprehensive analysis of kinase inhibitor selectivity. *Nat. Biotechnol.* 2011; 29:1046-51) and $K_i$ 1 nM (Metz J T, et al. Navigating the kinome. *Nat. Chem. Biol.* 2011; 7:200-2)). The binding modes of the three inhibitors are shown in FIG. 1, as derived from the X-ray structure of 5 with ACK1 (pdb 3EQR); 1b (AIM-100) modeled from the X-ray structure of an analog with ACK1 (Jiao X, et al. Synthesis and optimization of substituted furo[2,3-d]-pyrimidin-4-amines and 7H-pyrrolo[2,3-d]pyrimidin-4-amines as ACK1 inhibitors. *Bioorg. Med. Chem. Lett.* 2012; 22:6212-7) (pdb 4EWH); 6 modeled from its X-ray structure with ALK (Bossi R T, et al. Crystal structures of anaplastic lymphoma kinase in complex with ATP competitive inhibitors. *Biochem.* 2010; 49:6813-25) (pdb 2XB7). These bind the ACK1 hinge residues Ala-208 via the pyrimidyl group, positioning groups in the hydrophobic pocket beyond the gatekeeper, and in the ribose binding region (Galkin A V, et al. Identification of NVP-TAE684, a potent, selective, and efficacious inhibitor of NPM-ALK. *Proc. Natl. Acad. Sci. USA* 2007; 104:270-5). The bisanilinopyrimidine scaffold has been long recognized as a classical kinase inhibitor motif (Bebbington D, et al. The discovery of the potent aurora inhibitor MK-0457 (VX-680). *Bioorg. Med. Chem. Lett.* 2009; 19:3586-92; Moriarty K J, et al. The synthesis and SAR of 2-amino-pyrrolo[2,3-d]pyrimidines: a new class of Aurora-A kinase inhibitors. *Bioorg. Med. Chem. Lett.* 2006; 16:5778-83; Taxi L W, et al. Structural basis for the inhibition of Aurora A kinase by a novel class of high affinity disubstituted pyrimidine inhibitors. *Bioorg. Med. Chem. Lett.* 2007; 17:688-691). Aurora A inhibitors were reported using a bisanilinopyrimidine scaffold (Lawrence H R, et al. Development of o-chlorophenyl substituted pyrimidines as exceptionally potent aurora kinase inhibitors. *J. Med. Chem.* 2012; 55:7392-416; Martin M P, et al. A novel mechanism by which small molecule inhibitors induce the DFG flip in Aurora A. *ACS Chem. Biol.* 2012; 7:698-706; Yang H, et al. Dual Aurora A and JAK2 kinase blockade effectively suppresses malignant transformation. *Oncotarget* 2014; 5:2947-61). In the development of novel ACK1 inhibitors, the design process incorporated an aminopyrimidine structure as the hinge binding group (FIG. 1(*d*)) and the fragments of 1b, 5 and 6 as $R^1$, $R^2$ and $R^3$ (FIG. 1(d)) groups to create hybrid structures in a mix and match process (FIG. 1).

What are needed are new compounds and methods for inhibiting ACK1 and uses of such compounds. The subject matter disclosed herein addresses these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anticancer compounds. More specifically, the subject matter disclosed herein relates to inhibitors of Ack1 tyrosine kinase and their use in the treatment of cancer. Methods of screening for new Ack1 tyrosine kinase inhibitors are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

In FIG. 1(a) compound 5 is taken from its crystal structure with ACK1 (pdb 3EQP). In FIG. 1(b) compound 1b is modeled with ACK1, based on similar compounds bound to Lck (pdb 2OF2). In FIG. 1(c) compound 6 is modeled with ACK1, based on its crystal structure with ALK (pdb 2XB7). FIG. 1(d) shows a bisanilinopyrimidine scaffold for design of novel ACK1 inhibitors by analysis of known ACK1 inhibitors.

In FIG. 2(a), androgen starved LAPC4 cells were treated with DHT (10 nM, 16 Hrs), AIM-100, DZ1-067, Enzalutamide or PLX4032 (7 μM, 36 Hr) and AR. pACK1 and Actin levels were determined by immunoblotting (IB). The relative level of AR is shown below. In FIG. 2(b), androgen deprived LNCaP and VCaP cell were untreated or treated with 2.5, 5, and 10 μM of AIM-100 and lysates were immunoblotted. The quantitation of AR expression is shown. In FIG. 2(c), androgen deprived LNCaP and VCaP cell were untreated or treated with 2.5, 5, and 10 μM of AIM-100 and lysates were immunoblotted. The quantitation of AR expression is shown.

FIG. 3(a) shows VCaP and FIG. 3(b) shows LNCaP cells grown in absence of androgen and treated overnight with DZ1-067 (7 μM in LAPC4, 2.5 & 5 μM in LnCaP), PLX4032 (7 μM), Casodex, Enzalutamide (10 μM), and DHT (10 nM, 3 Hr). Total RNA was isolated followed by qPCR with AR primers. VCaP, *p=0.022; LNCaP, *p=0.042, **p=0.047. FIG. 3(c) shows VCaP and FIG. 3(d) shows LNCaP cells grown in absence of androgen and treated overnight with DZ1-067 (7 μM in LAPC4, 2.5 & 5 μM in LnCaP), AIM-100 (7 μM), PLX4032 (7 μM), Casodex, Enzalutamide (10 μM), and DHT (10 nM, 3 Hr). Total RNA was isolated followed by qPCR with PSA primers.

FIG. 4(a) shows LNCaP and FIG. 4(b) shows VCaP cells grown in charcoal stripped media and treated with 1, 2.5, 5, and 10 μM of inhibitors (36 hrs). The number of viable cells was counted by trypan blue exclusion assay.

In FIG. 5(a), equimolar amounts of purified ACK1 and H4 proteins were incubated in the presence of DZ1-067 (100 nM) and reaction subjected to immunoblotting with pY88-H4 antibodies. FIG. 5(b) shows H4 Y88-phosphorylation in vivo. LNCaP cells were treated with DZ1-067 (5 μM, 16 hrs), DHT, or Enzalutamide (7 μM, 16 hrs). The nuclear lysates were immunoprecipitated with pY88-H4 antibodies followed by immunoblotting with H4. Lower panel is input lysate.

In FIG. 6(a), the human AR gene and two pY88-H4 binding sites are shown. FIG. 6(b) shows VCaP and FIG. 6(c) shows LNCaP cells treated with ACK1 inhibitor; ChIP was performed followed by qPCR using primers corresponding to promoter, intron 2, 3'UTR or control region. VCaP: *p<0.05, **p<0.05; LNCaP: *p<0.05, **p<0.05

DETAILED DESCRIPTION

Figure 1:
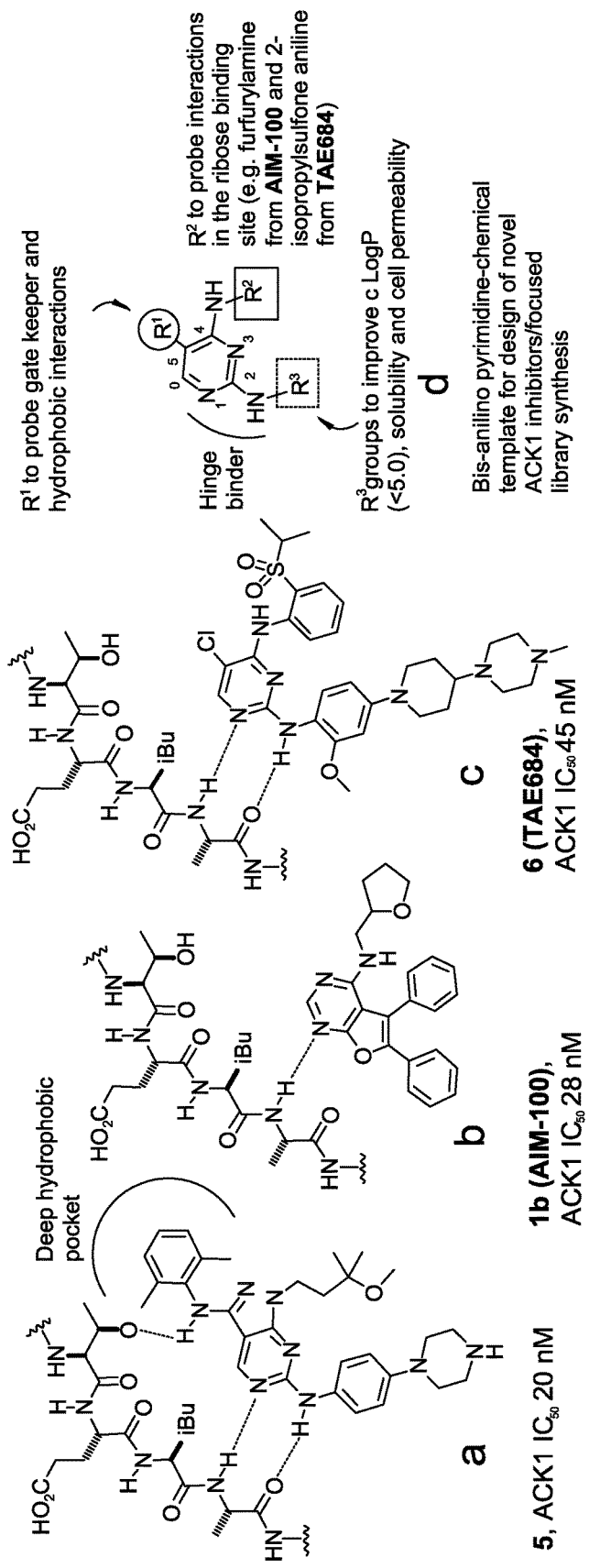
FIG. 1 shows binding modes of known ACK1 inhibitors to ACK1.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

CHEMICAL DEFINITIONS

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "heteroalkyl" as used herein is a branched or unbranched saturated hydrocarbon group of 1-24 carbon atoms where one or more of the carbon atoms and its attached hydrogen atoms, if any, have been replaced by a O, S, N, or NH. The heteroalkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substitutent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "heterocycloalkyl" is a type of cycloalkyl group as defined above where at least one of the carbon atoms and its attached hydrogen atoms, if any, are replaced by O, S, N, or NH. The heterocycloalkyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with O, S, N, or NH. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN The term "azido" as used herein is represented by the formula —$N_3$.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

It has been found that Ack1 directly phosphorylates AKT at Tyr176 resulting in AKT membrane localization and activation. In prostate cancer cells Ack1 phosphorylates AR at Tyr-267 in an androgen-independent manner. In addition, Tyr284-phosphorylated-Ack1, Tyr176-phosphorylated-AKT and Tyr267-phosphorylated-AR levels were positively correlated with the severity of disease progression, and inversely correlated with the survival of prostate cancer patients. Similarly, Ack1 mediated AKT tyrosine phosphorylation was found to correlate positively with breast cancer progression.

Further, it has been found that an inhibitor of Ack1, 4-amino-5,6-biaryl-furo[2,3-d]pyrimidine (AIM-100) not only inhibited Ack1 activation but suppresses pTyr267-AR phosphorylation and AKT Tyr176-phosphorylation, inhibiting AR and AKT activity. These findings indicate that Ack1 is prognostic of progression of prostate cancer and inhibitors of Ack1 activity are therapeutic agents to treat prostate cancer.

Focused chemical libraries of Ack1 inhibitors were developed by scaffold-hopping and fragment structure-based design. From the library, several compounds were identified as being capable of inhibiting Ack1 in vitro at low concentrations, and in many cases nanomolar concentrations. Compounds from the library were shown to inhibit, in intact cancer cells, the phosphorylation of AKT at Tyr176, a surrogate for Ack1 inhibition in vivo.

Thus, disclosed are compounds that are Ack1 tyrosine kinase inhibitors. These disclosed compounds can be used in various compositions as anti-cancer therapeutics.

In certain embodiments, the disclosed compounds have a pyrimidine based structure as shown in Formula IA or IB.

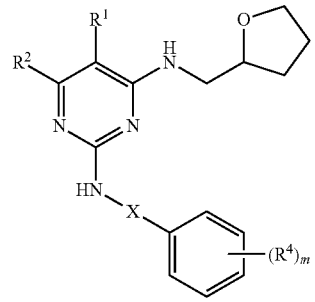

IA

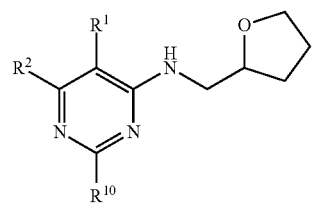

IB wherein

X is a bond or $CH_2$;

$R^1$ is Cl, Br, F, $CH_3$, or $C_2H_5$;

$R^2$ is H, Cl, Br, or F, or $R^1$ and $R^2$ together form a fused aryl or heteroaryl group;

m is 1, 2, 3, 4, or 5, preferably m is 1 or 2; and each $R^4$ is, independently, OH, Cl, Br, F, $C_1$-$C_6$ alkyl, CN, $NO_2$, $CO_2H$, $CO_2R^5$, $(CH_2)_{1-6}CO_2H$, $(CH_2)_{1-6}CO_2R^5$, $OR^5$, $C(O)R^5$, $C(O)NH_2$, $C(O)NHR^5$, $NHSO_2R^5$, $SO_2NH_2$, $SO_2NHR^5$, or $C(O)NHSO_2R^5$, or a cycloalkyl or heterocycloalkyl that is unsubstituted or substituted with $R^6$, where $R^5$ is $C_1$-$C_6$ alkyl, heteroalkyl, cycloalkyl, heterocycloalkyl, or heteroaryl; and $R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group, or PEG-sterol; and $R^{10}$ is Cl, Br, or F.

In certain embodiments, the disclosed compounds have a pyrimidine-based structure as shown in Formula IIA or IIB.

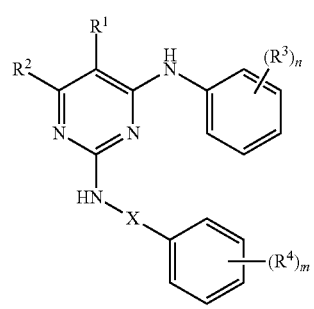

IIA

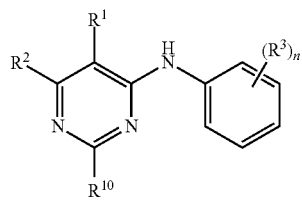

IIB wherein

X is a bond or $CH_2$;

$R^1$ is Cl, Br, F, $CH_3$, or $C_2H_5$;

$R^2$ is H, Cl, Br, or F, or $R^1$ and $R^2$ together form a fused aryl or heteroaryl group;

n is 1, 2, 3, 4, or 5, preferably 1;

each $R^3$ is, independently, $COR^5$, $C(O)NH_2$, $C(O)NR^5$, $C(O)_2NH_2$, $SR^5$, or $SO_2R^5$;

m is 1, 2, 3, 4, or 5, preferably m is 1 or 2; and each $R^4$ is, independently, OH, Cl, Br, F, $C_1$-$C_6$ alkyl, CN, $NO_2$, $CO_2H$, $CO_2R^5$, $(CH_2)_{1-6}CO_2H$, $(CH_2)_{1-6}CO_2R^5$, $OR^5$, $C(O)R^5$, $C(O)NH_2$, $C(O)NHR^5$, $NHSO_2R^5$, $SO_2NH_2$, $SO_2NHR^5$, or $C(O)NHSO_2R^5$, or a cycloalkyl or heterocycloalkyl that is unsubstituted or substituted with $R^6$, where $R^5$ is $C_1$-$C_6$ alkyl, heteroalkyl, cycloalkyl, heterocycloalkyl, or heteroaryl;

$R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group, or PEG-sterol; and $R^{10}$ is Cl, Br, or F.

In certain embodiments, the disclosed compounds have a pyrimidine-based structure as shown in Formula IIIA or IIIB.

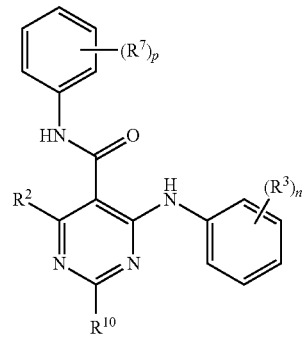

IIIB wherein

X is a bond or $CH_2$;

$R^2$ is H, Cl, Br, or F, n is 1, 2, 3, 4, or 5, preferably 1;

each $R^3$ is, independently, $COR^5$, $C(O)NH_2$, $C(O)NR^5$, $C(O)_2NH_2$, $SR^5$, or $SO_2R^5$;

m is 1, 2, 3, 4, or 5, preferably m is 1 or 2; and each $R^4$ is, independently, OH, Cl, Br, F, $C_1$-$C_6$ alkyl, CN, $NO_2$, $CO_2H$, $CO_2R^5$, $(CH_2)_{1-6}CO_2H$, $(CH_2)_{1-6}CO_2R^5$, $OR^5$, $C(O)R^5$, $C(O)NH_2$, $C(O)NHR^5$, $NHSO_2R^5$, $SO_2NH_2$, $SO_2NHR^5$, or $C(O)NHSO_2R^5$, or a cycloalkyl or heterocycloalkyl that is unsubstituted or substituted with $R^6$, where $R^5$ is $C_1$-$C_6$ alkyl, heteroalkyl, cycloalkyl, heterocycloalkyl, or heteroaryl;

$R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group, or PEG-sterol;

p is 1, 2, 3, 4, or 5, preferably 1 or 2;

$R^7$ is OH, Cl, Br, F, $C_1$-$C_6$ alkyl, $CO_2H$, $CO_2R^5$, $OR^5$, CN, or $NO_2$; and $R^{10}$ is Cl, Br, or F.

In certain embodiments, the disclosed compounds have a pyrimidine-based structure as shown in Formula IVA or IVB.

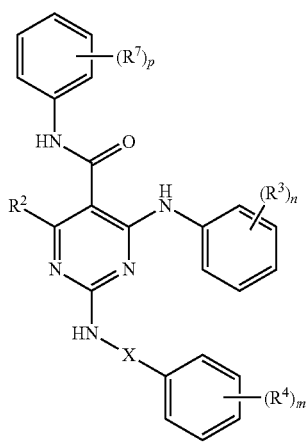

IIIA

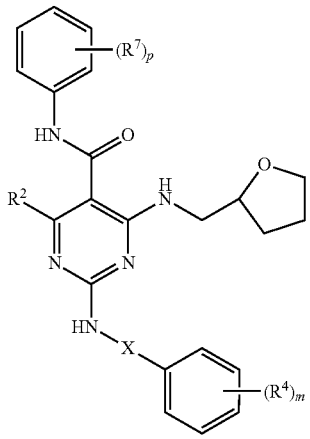

IVA

-continued

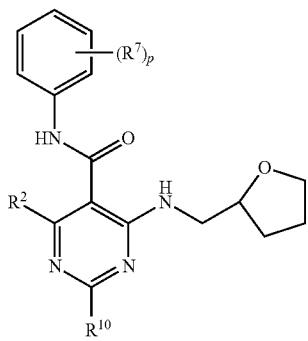

IVB wherein

X is a bond or $CH_2$;

$R^2$ is H, Cl, Br, or F, m is 1, 2, 3, 4, or 5, preferably m is 1 or 2; and each $R^4$ is, independently, OH, Cl, Br, F, $C_1$-$C_6$ alkyl, CN, $NO_2$, $CO_2H$, $CO_2R^5$, $(CH_2)_{1-6}CO_2H$, $(CH_2)_{1-6}CO_2R^5$, $OR^5$, $C(O)R^5$, $C(O)NH_2$, $C(O)NHR^5$, $NHSO_2R^5$, $SO_2NH_2$, $SO_2NHR^5$, or $C(O)NHSO_2R^5$, or a cycloalkyl or heterocycloalkyl that is unsubstituted or substituted with $R^6$, where $R^5$ is $C_1$-$C_6$ alkyl, heteroalkyl, cycloalkyl, heterocycloalkyl, or heteroaryl;

$R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group, or PEG-sterol;

p is 1, 2, 3, 4, or 5, preferably 1 or 2; and $R^7$ is OH, Cl, Br, F, $C_1$-$C_6$ alkyl, $CO_2H$, $CO_2R^5$, $OR^5$, CN, or $NO_2$; and $R^{10}$ is Cl, Br, or F.

The disclosed compounds can also exist as pharmaceutically acceptable salts and examples of such salts are disclosed herein.

In a particular aspect, in all of the formula disclosed herein $R^2$ is preferably H.

In certain examples, $R^1$ is preferably Cl or Br in Formula IA, IB, IIA, or IIB.

In certain examples, $R^{10}$ is preferably Cl or Br in Formula IB, IIB, IIIB, or IVB.

In certain examples of Formula IA, IIA, IIIA, or IVA, X is preferably a bond. Also for these formulae, m can be 1 and $R^4$ can be 4-morpholinyl, 4-piperazinyl, 1-piperidinyl, or 4-piperadinyl group that is unsubstituted or substituted with $R^6$. In other examples with these formula, m can be 1 and $R^4$ is in the para position or m is 2 and each $R^4$ are in the para and meta positions.

In certain examples of Formula IIA, IIB, IIIA, or IIIB, n can be 1 and $R^3$ is in the meta position and is $SR^5$ or $SO_2R^5$.

In certain examples of Formula IIIA, IIIB, IVA, or IVB, p can be 2 and each $R^7$ are in the ortho position and are, independently, Cl or F.

Suitable compounds according to the present disclosure are provided in Table 1.

| Compound Name, Structure, Molecular Weight | $IC_{50}$ | % Inhibition at 10 μM (ELISA) |
|---|---|---|
| YL7-031B2, MW = 423.29 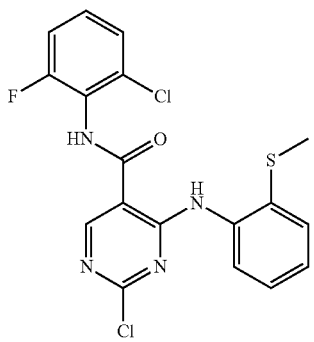 [SMILES: CSc1ccccc1Nc1nc(Cl)ncc1C(=O)Nc1c(F)cccc1Cl] | | 0 |
| YL7-034, MW = 455.29 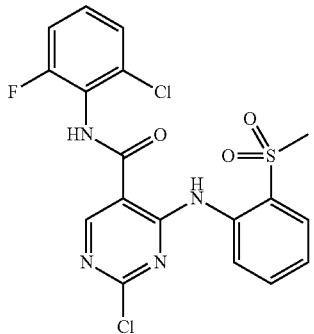 [SMILES: CS(=O)(=O)c1ccccc1Nc1nc(Cl)ncc1C(=O)Nc1c(F)cccc1Cl] | | 16, −3, −6F |

-continued
| Compound Name, Structure, Molecular Weight | IC$_{50}$ | % Inhibition at 10 μM (ELISA) |
|---|---|---|
| YL7-037, MW = 541.98 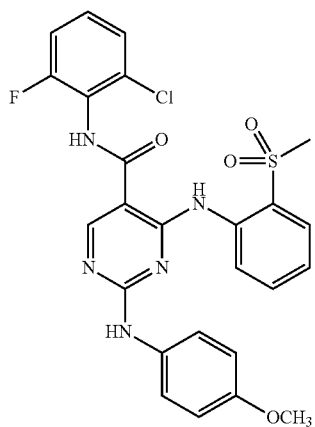 [SMILES: COc1ccc(Nc2ncc(C(=O)Nc3c(F)cccc3Cl)c(Nc3ccccc3S(C)(=O)=O)n2)cc1] | | 4, 0 |
| YL7-038, MW = 527.96 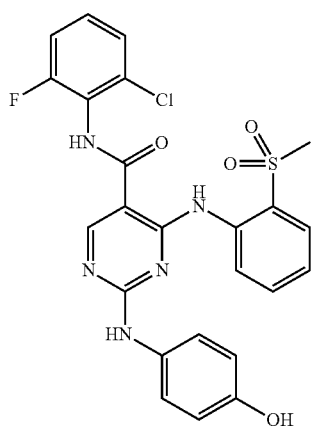 [SMILES: CS(=O)(=O)c1ccccc1Nc1nc(Nc2ccc(O)cc2)ncc1C(=O)Nc1c(F)cccc1Cl] | | 39, 18 |
| YL7-039-1, MW = 509.98 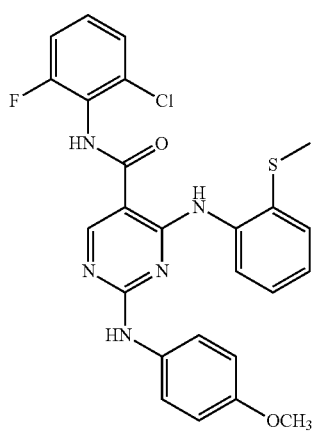 [SMILES: COc1ccc(Nc2ncc(C(=O)Nc3c(F)cccc3Cl)c(Nc3ccccc3SC)n2)cc1] | | 7, 0 |

-continued
| Compound Name, Structure, Molecular Weight | IC$_{50}$ | % Inhibition at 10 μM (ELISA) |
|---|---|---|
| YL7-039-2, MW = 495.96 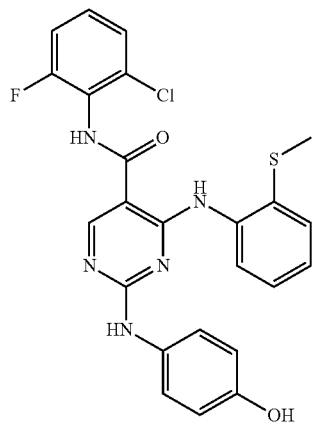 [SMILES: CSc1ccccc1Nc1nc(Nc2ccc(O)cc2)ncc1C(=O)Nc1c(F)cccc1Cl] | | 40, 5 |
| YL7-040, MW = 451.34 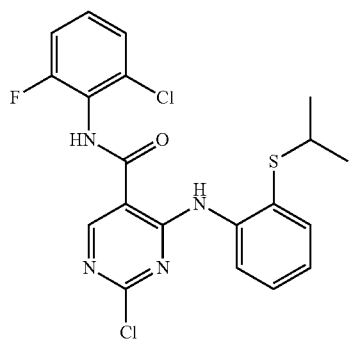 [SMILES: CC(C)Sc1ccccc1Nc1nc(Cl)ncc1C(=O)Nc1c(F)cccc1Cl] | | 0 |
| YL7-041, MW = 483.34 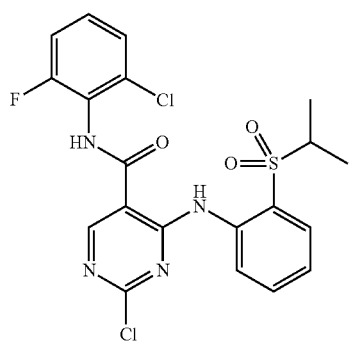 [SMILES: CC(C)S(=O)(=O)c1ccccc1Nc1nc(Cl)ncc1C(=O)Nc1c(F)cccc1Cl] | | 7, −21, −27 |

-continued
| Compound Name, Structure, Molecular Weight | IC$_{50}$ | % Inhibition at 10 μM (ELISA) |
|---|---|---|
| YL7-045-1, MW = 570.03 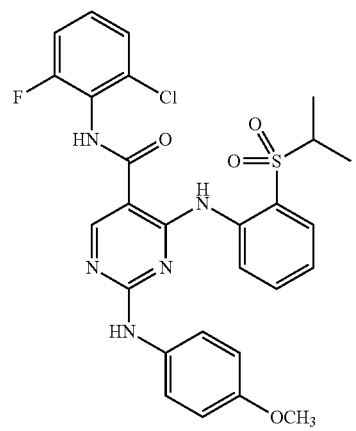 [SMILES: COc1ccc(Nc2ncc(C(=O)Nc3c(F)cccc3Cl)c(Nc3ccccc3S(=O)(=O)C(C)C)n2)cc1] | | 37, 18 |
| YL7-045-2, MW = 556.01 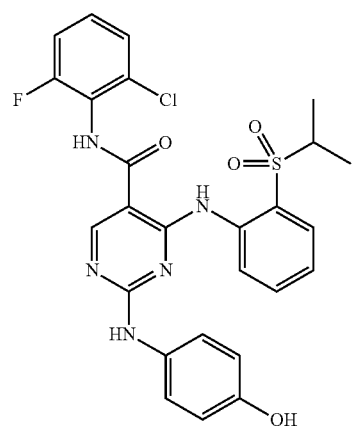 | | 47, 50 |
| YL7-045-3, MW = 538.04 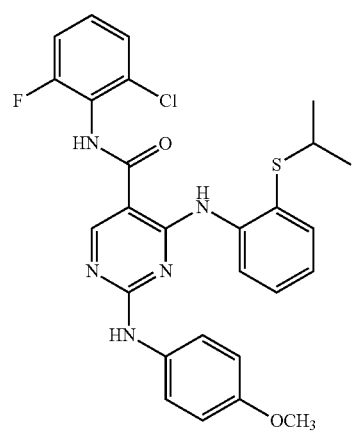 | | −15, 0 |

| Compound Name, Structure, Molecular Weight | IC$_{50}$ | % Inhibition at 10 μM (ELISA) |
|---|---|---|
| YL7-045-4, MW = 524.01 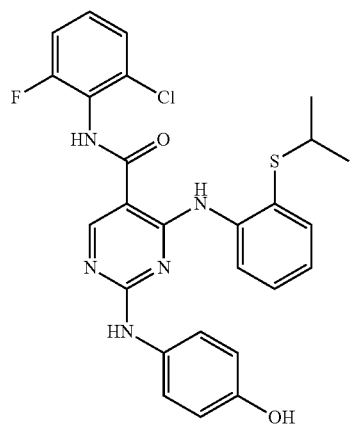 [SMILES: CC(C)Sc1ccccc1Nc1nc(Nc2ccc(O)cc2)ncc1C(=O)Nc1c(F)cccc1Cl] | | 0 |
| YL7-051, MW = 451.34 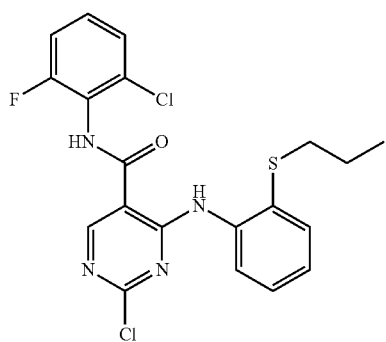 [SMILES: CCCSc1ccccc1Nc1nc(Cl)ncc1C(=O)Nc1c(F)cccc1Cl] | | 0 |
| YL7-052 MW = 483.34 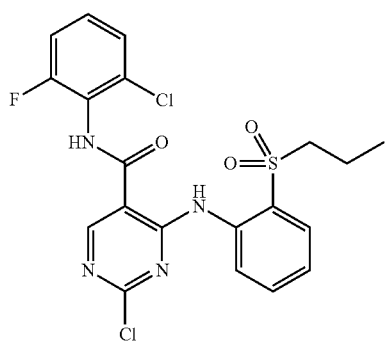 [SMILES: CCCS(=O)(=O)c1ccccc1Nc1nc(Cl)ncc1C(=O)Nc1c(F)cccc1Cl] | | 0, 14, −8 |

| Compound Name, Structure, Molecular Weight | IC$_{50}$ | % Inhibition at 10 μM (ELISA) |
|---|---|---|
| YL7-055-1, MW = 570.03 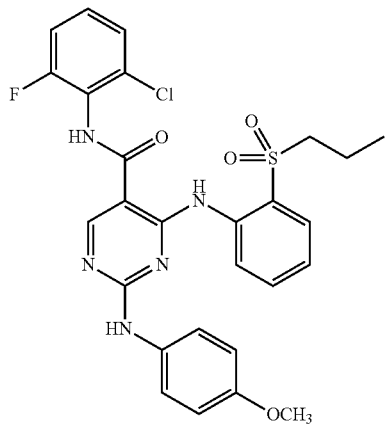 [SMILES: CCCS(=O)(=O)c1ccccc1Nc1nc(Nc2ccc(OC)cc2)ncc1C(=O)Nc1c(F)cccc1Cl] | | 27, 13 |
| YL7-055-2, MW = 556.01 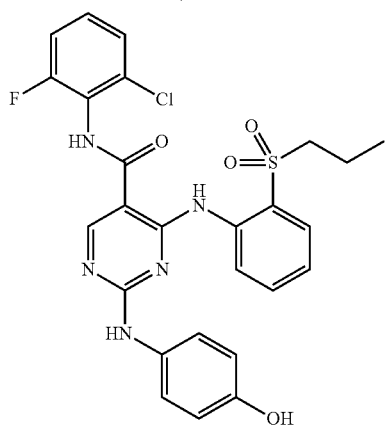 | | 57, 58 |
| YL7-055-3, MW = 538.04 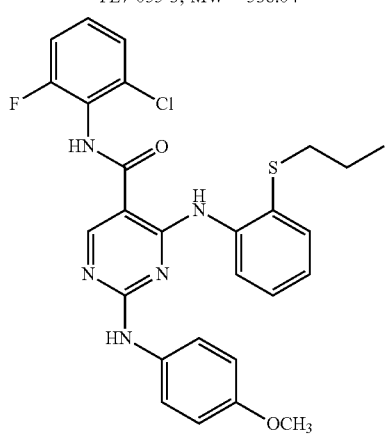 | | 1, 13 |

| Compound Name, Structure, Molecular Weight | IC$_{50}$ | % Inhibition at 10 μM (ELISA) |
|---|---|---|
| YL7-055-4, MW = 524.01 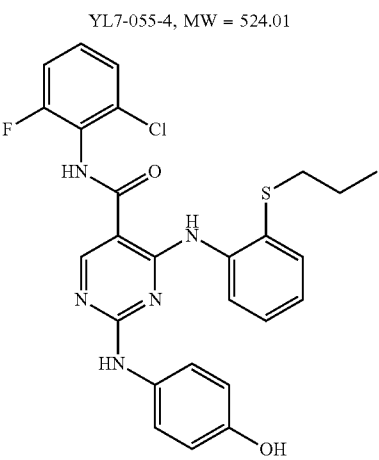 | | 28, 27 |
| YL7-053, MW = 437.32 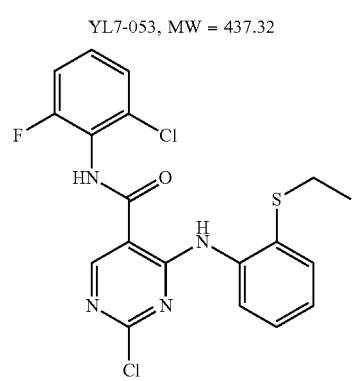 | | 0 |
| YL7-054, MW = 469.32 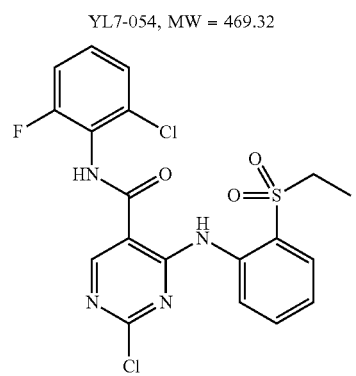 | | 0, −3, −25 |

| Compound Name, Structure, Molecular Weight | IC$_{50}$ | % Inhibition at 10 μM (ELISA) |
|---|---|---|
| YL7-058-1, MW = 556.01 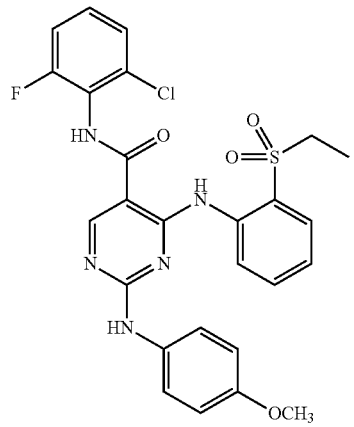 [SMILES: CCS(=O)(=O)c1ccccc1Nc1nc(Nc2ccc(OC)cc2)ncc1C(=O)Nc1c(F)cccc1Cl] | | −6, 0 |
| YL7-058-2, MW = 541.98 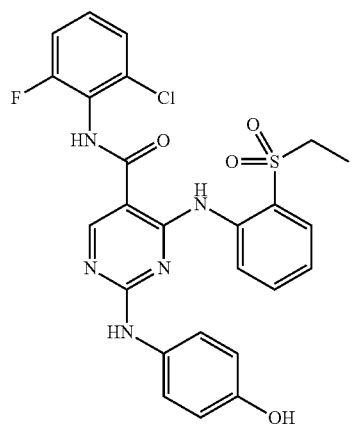 [SMILES: CCS(=O)(=O)c1ccccc1Nc1nc(Nc2ccc(O)cc2)ncc1C(=O)Nc1c(F)cccc1Cl] | | 68, 43 |
| YL7-058-3, MW = 524.01 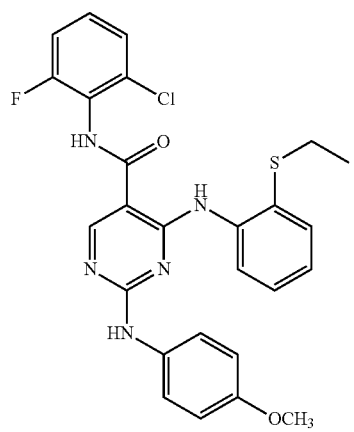 [SMILES: CCSc1ccccc1Nc1nc(Nc2ccc(OC)cc2)ncc1C(=O)Nc1c(F)cccc1Cl] | | 1, 0 |

| Compound Name, Structure, Molecular Weight | IC$_{50}$ | % Inhibition at 10 μM (ELISA) |
|---|---|---|
| YL7-058-4, MW = 509.98 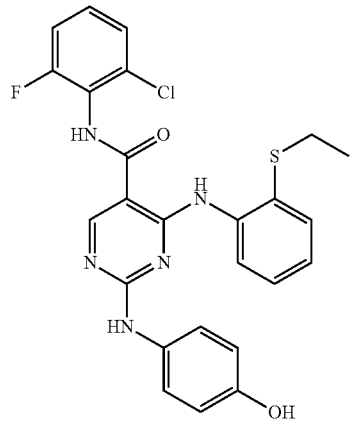 [SMILES: CCSc1ccccc1Nc1nc(Nc2ccc(O)cc2)ncc1C(=O)Nc1c(F)cccc1Cl] | | 24, 47 |
| YL7-097-1, MW = 625.11 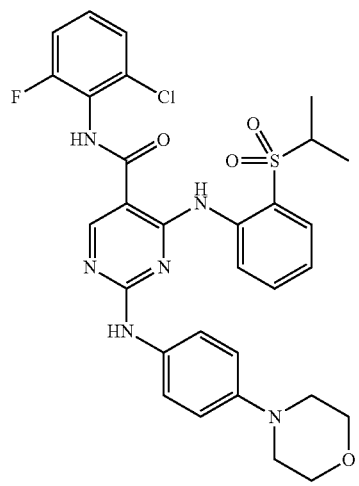 [SMILES: CC(C)S(=O)(=O)c1ccccc1Nc1nc(Nc2ccc(N3CCOCC3)cc2)ncc1C(=O)Nc1c(F)cccc1Cl] | | 85, 65 |
| YL7-100-1, MW = 619.09 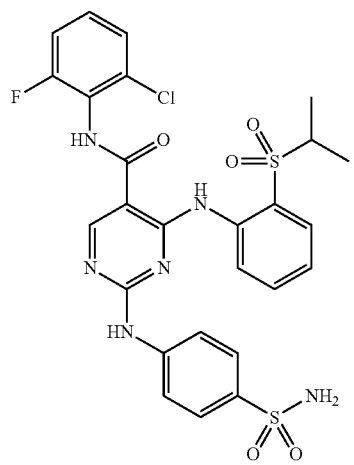 [SMILES: CC(C)S(=O)(=O)c1ccccc1Nc1nc(Nc2ccc(S(N)(=O)=O)cc2)ncc1C(=O)Nc1c(F)cccc1Cl] | | 8, 6 |

-continued
| Compound Name, Structure, Molecular Weight | IC$_{50}$ | % Inhibition at 10 μM (ELISA) |
|---|---|---|
| YL7-102, MW = 385.22 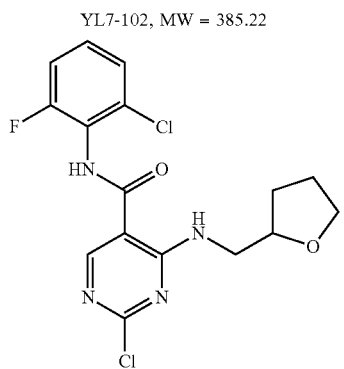 | | 0 |
| YL7-104-1, MW = 471.91 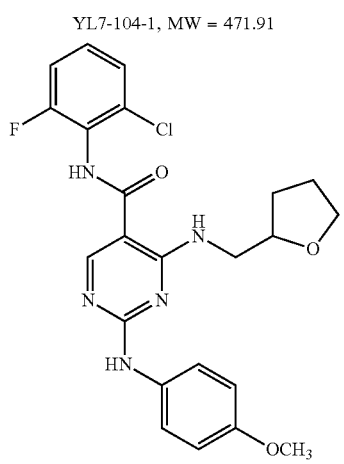 | | 76, 61, 37, 27 |
| YL7-104-2, MW = 457.89 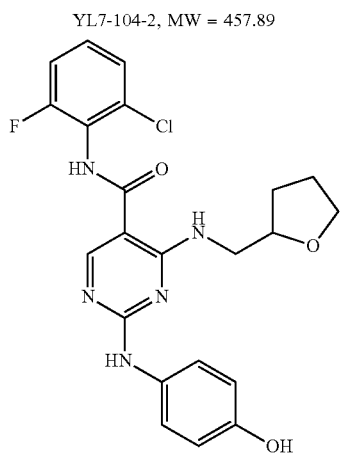 | 54.4 nM (RB) | 85, 76 |

-continued
| Compound Name, Structure, Molecular Weight | IC$_{50}$ | % Inhibition at 10 μM (ELISA) |
|---|---|---|
| YL7-106-1, MW = 584.06 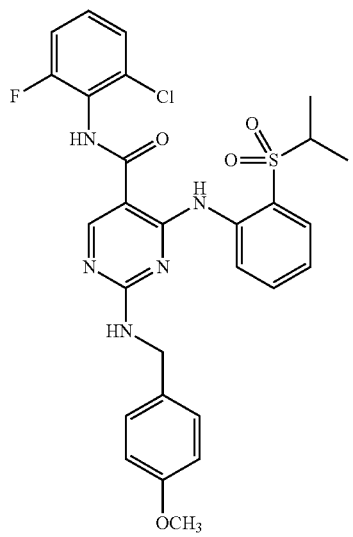 [SMILES: COc1ccc(CNc2ncc(C(=O)Nc3c(F)cccc3Cl)c(Nc3ccccc3S(=O)(=O)C(C)C)n2)cc1] | | 14, 0 |
| YL7-106-3, MW = 583.03 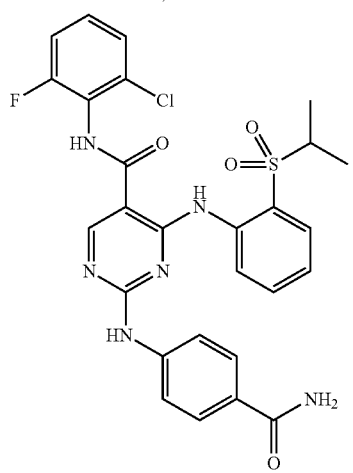 | | 51, 43 |

| Compound Name, Structure, Molecular Weight | IC$_{50}$ | % Inhibition at 10 μM (ELISA) |
|---|---|---|
| YL7-109, MW = 570.03 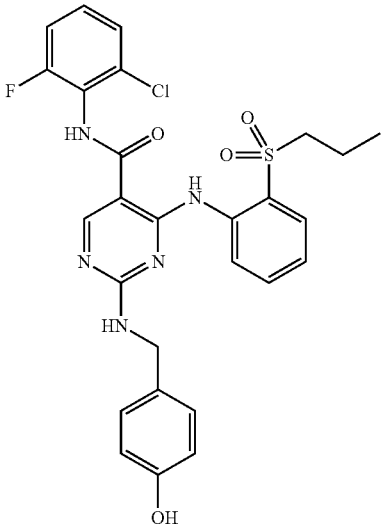 [SMILES: CCCS(=O)(=O)c1ccccc1Nc1nc(NCc2ccc(O)cc2)ncc1C(=O)Nc1c(F)cccc1Cl] | | −15, 15 |
| SK1-022, MW = 415.71 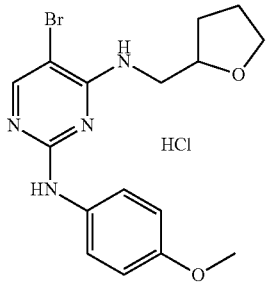 [SMILES: COc1ccc(Nc2ncc(Br)c(NCC3CCCO3)n2)cc1 ; Cl] | | 67, 68 |
| SK1-028, MW = 401.69 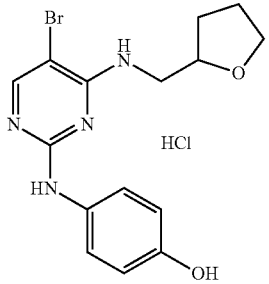 [SMILES: Oc1ccc(Nc2ncc(Br)c(NCC3CCCO3)n2)cc1 ; Cl] | 164 nM (RB) | 59, 81, 85, 65, 67 |
| SK1-040, MW = 415.71 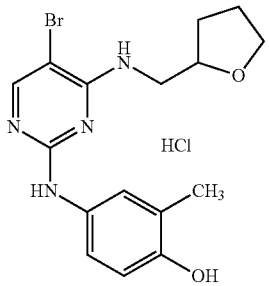 [SMILES: Cc1cc(Nc2ncc(Br)c(NCC3CCCO3)n2)ccc1O ; Cl] | 99.5 nM (RB) | 90, 61, 56, 57 |

-continued
| Compound Name, Structure, Molecular Weight | IC$_{50}$ | % Inhibition at 10 μM (ELISA) |
|---|---|---|
| SK1-044, MW = 419.68 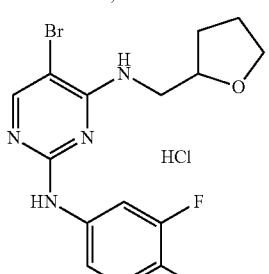 | 299 nM (RB) | 89, 63, 28, 38 |
| MH1-006-3, MW = 426.3 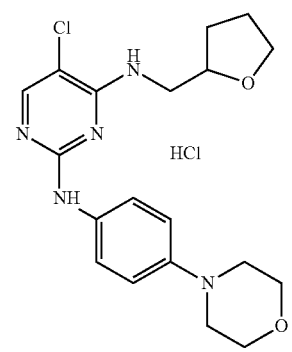 [SMILES: Clc1cnc(Nc2ccc(N3CCOCC3)cc2)nc1NCC1CCCO1 ; Cl] | 67.5 nM (RB) | 90, 88 |
| MH1-007-3, MW = 388.9 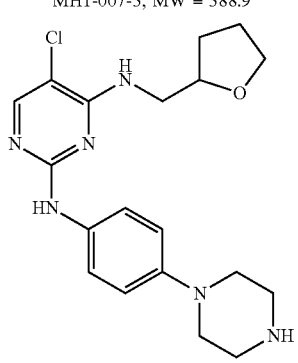 | 81.3 nM (RB) | 91, 73, 78, 78 |
| MH1-022-5, MW = 402.9 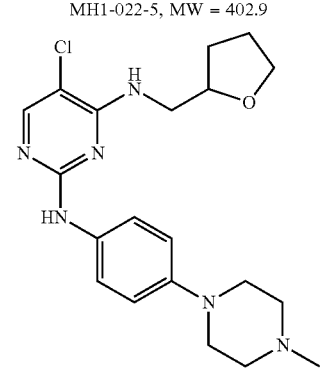 | 54.4 nM (RB) | 90, 91 |

US 9,850,216 B2
45                                                                                                46
-continued
| Compound Name, Structure, Molecular Weight | IC$_{50}$ | % Inhibition at 10 μM (ELISA) |
|---|---|---|
| MH1-030-4, MW = 419.9 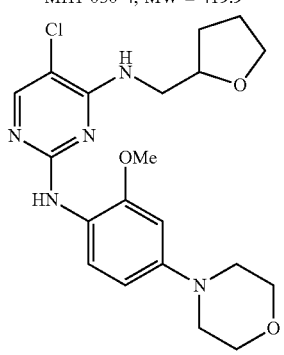 | | 88, 82 |
| MH1-035-3, MW = 401.9 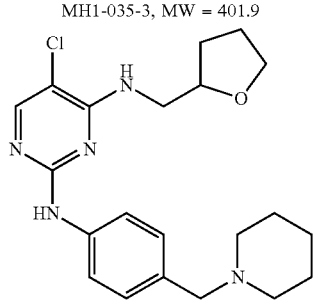 | | 77, 72 |
| TAE684, MW = 614.2 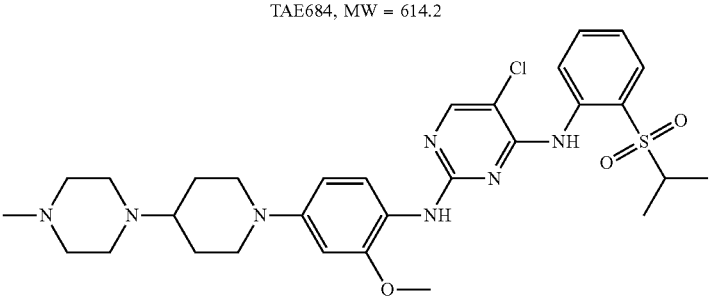 | 27.8, 60.7 nM | 94, 92, 98, 99, 99 |
| LDK, MW = 558.1 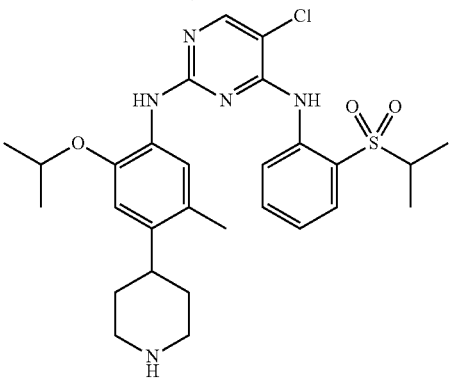 [SMILES: Cc1cc(Nc2ncc(Cl)c(Nc3ccccc3S(=O)(=O)C(C)C)n2)c(OC(C)C)cc1C1CCNCC1] | 88.7 (RB) | |

-continued
| Compound Name, Structure, Molecular Weight | IC$_{50}$ | % Inhibition at 10 μM (ELISA) |
|---|---|---|
| YL8-047, MW = 496.43 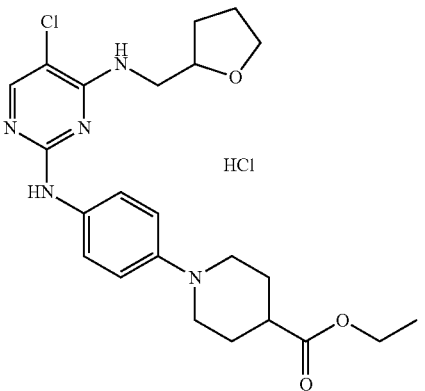 [SMILES: CCOC(=O)C1CCN(c2ccc(Nc3ncc(Cl)c(NCC4CCCO4)n3)cc2)CC1 ; Cl] | 108 nM (RB) | 65, 67, 69 |
| YL8-050, MW = 431.92 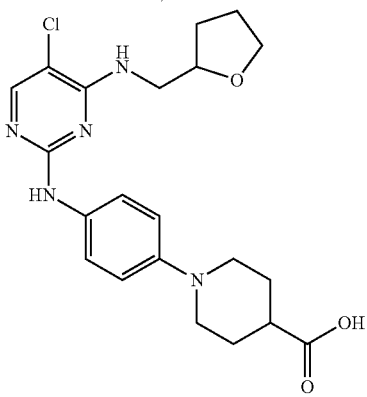 [SMILES: O=C(O)C1CCN(c2ccc(Nc3ncc(Cl)c(NCC4CCCO4)n3)cc2)CC1] | 85 nM (RB) | 87, 96, 96 |
| YL7-164 MW = 358.77 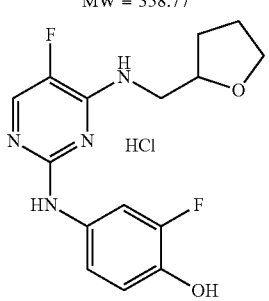 | | 37, 46, 55 |
| YL7-170-1, MW = 354.81 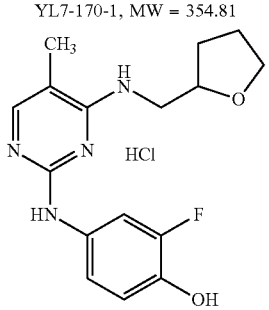 | | 51, 29, 47 |

-continued
| Compound Name, Structure, Molecular Weight | IC$_{50}$ | % Inhibition at 10 μM (ELISA) |
|---|---|---|
| YL7-170-2, MW = 512.34 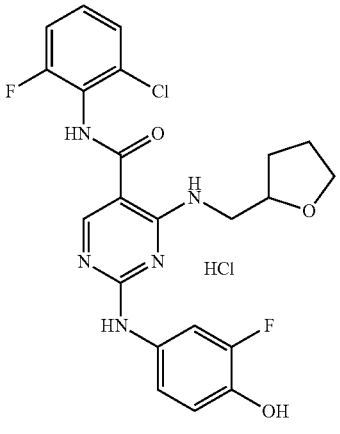 [SMILES: O=C(Nc1c(F)cccc1Cl)c1cnc(Nc2ccc(O)c(F)c2)nc1NCC1CCCO1 ; Cl] | | 65, 68, 67 |
| YL7-172-1, MW = 436.13 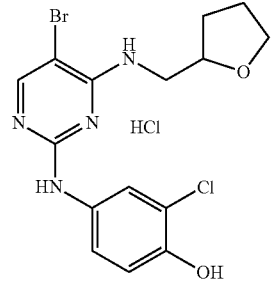 [SMILES: Oc1ccc(Nc2ncc(Br)c(NCC3CCCO3)n2)cc1Cl ; Cl] | | 75, 55, 35 |
| YL7-172-3, MW = 403.68 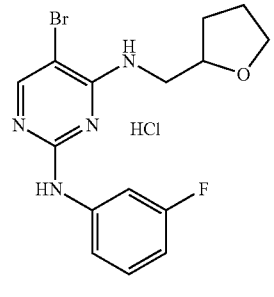 [SMILES: Fc1cccc(Nc2ncc(Br)c(NCC3CCCO3)n2)c1 ; Cl] | | 69, 21, 25 |
| YL7-172-4, MW = 417.70 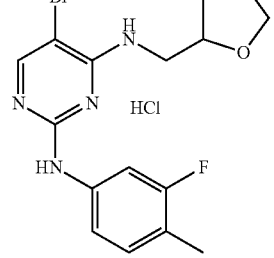 | | 0, −12, 20 |

-continued
| Compound Name, Structure, Molecular Weight | IC$_{50}$ | % Inhibition at 10 μM (ELISA) |
|---|---|---|
| YL7-172-5, MW = 428.71 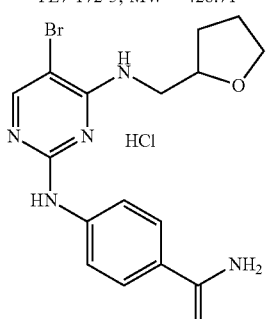 | | 31, 77, 82 |
| YL7-172-7, MW = 438.12 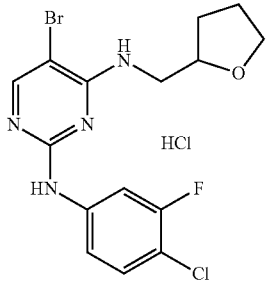 [SMILES: Fc1cc(Nc2ncc(Br)c(NCC3CCCO3)n2)ccc1Cl ; Cl] | | 0, 5, 3 |
| YL7-172-8, MW = 433.70 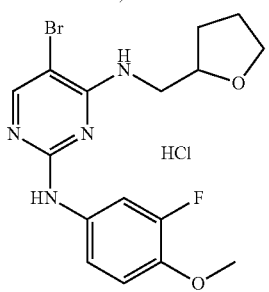 | | 14, 35, 41 |
| YL8-001, MW = 390.84 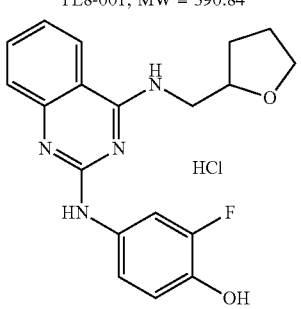 | | 4, 10, −6 |

-continued
| Compound Name, Structure, Molecular Weight | IC$_{50}$ | % Inhibition at 10 μM (ELISA) |
|---|---|---|
| YL8-003-1, MW = 445.70 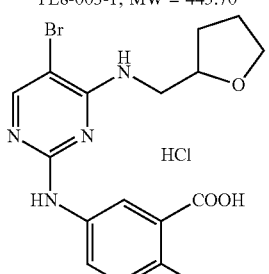 | | 27, 28, 16 |
| YL8-003-3, MW = 464.77 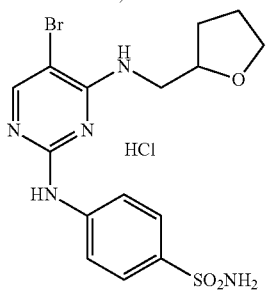 | | 56, 68, 63 |
| YL8-009-1, MW = 528.79 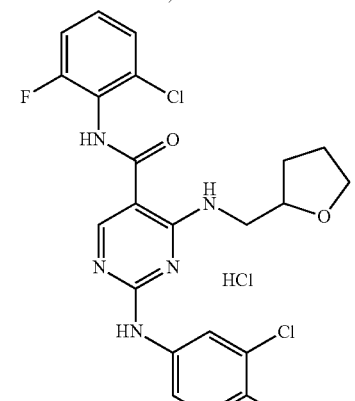 | | 41, 42, 48 |
| YL8-009-2, MW = 538.36 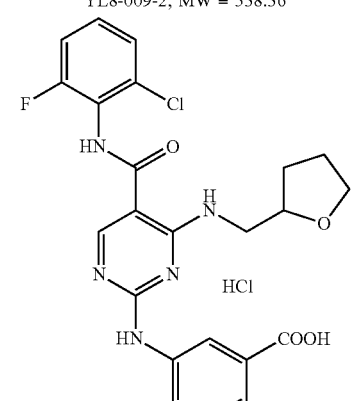 | | 44, 40, 55 |

-continued
| Compound Name, Structure, Molecular Weight | IC$_{50}$ | % Inhibition at 10 μM (ELISA) |
|---|---|---|
| DZ1-064, MW = 426.3 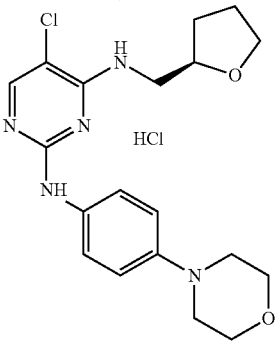 [SMILES: Clc1cnc(Nc2ccc(N3CCOCC3)cc2)nc1NC[C@H]1CCCO1 ; Cl] | 46.5 (RB) | 89, 93 |
| DZ1-067, MW = 402.9 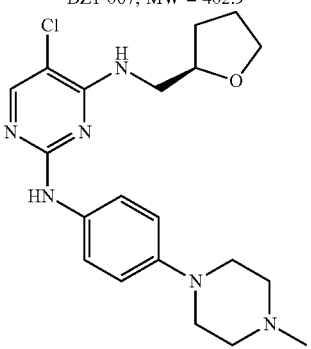 | 56.0, 57.8, 60.5 (RB) | 93, 93, 91 |
| DZ1-070, MW = 496.43 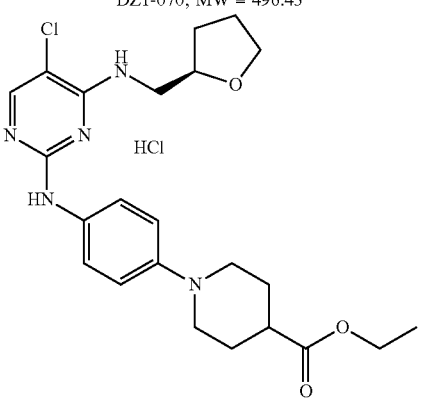 | | 52, 65 |
| DZ1-072, MW = 431.2 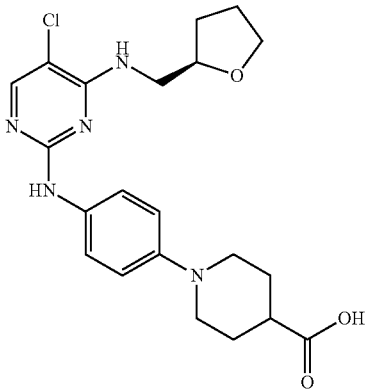 [SMILES: O=C(O)C1CCN(c2ccc(Nc3ncc(Cl)c(NC[C@H]4CCCO4)n3)cc2)CC1] | 91.6 (RB) | 96, 95 |

-continued
| Compound Name, Structure, Molecular Weight | IC$_{50}$ | % Inhibition at 10 μM (ELISA) |
|---|---|---|
| DZ1-074, MW = 426.3 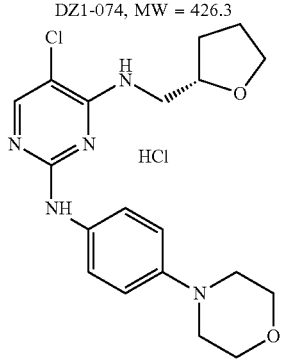 | 74.1 (RB) | 93, 91 |
| DZ1-077, MW = 402.9 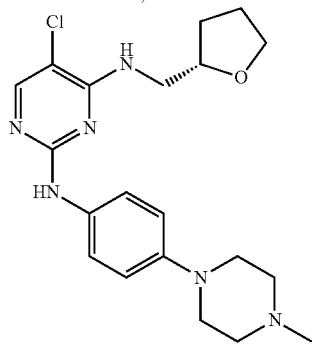 | 80.5, 83.3 (RB) | 93, 94 |
| DZ1-079, MW = 496.43 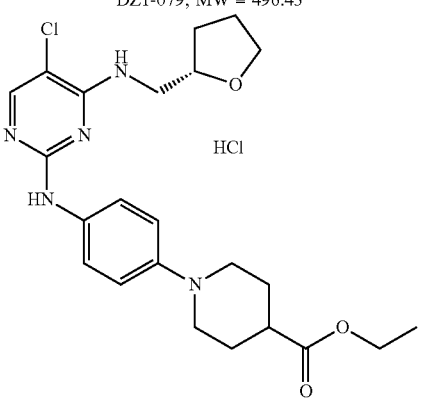 | | 54, 69 |
| DZ1-082, MW = 431.2 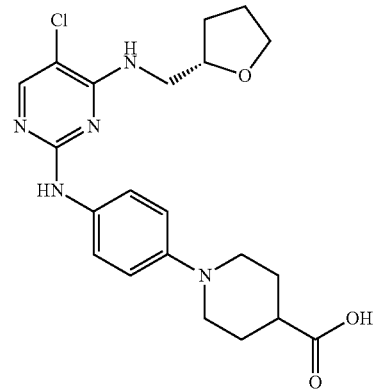 [SMILES: O=C(O)C1CCN(c2ccc(Nc3ncc(Cl)c(NC[C@@H]4CCCO4)n3)cc2)CC1] | 54.7 (RB) | 92, 94 |

-continued
| Compound Name, Structure, Molecular Weight | IC$_{50}$ | % Inhibition at 10 µM (ELISA) |
|---|---|---|
| NT1-005, MW = 424.4 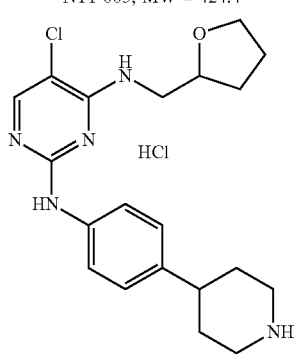 | 231 (RB) | 79, 80 |
| NT1-010, MW = 424.4 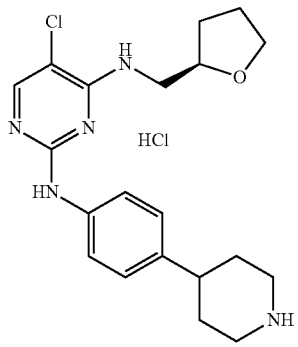 [SMILES: Clc1cnc(Nc2ccc(C3CCNCC3)cc2)nc1NC[C@H]1CCCO1 ; Cl] |  | 67, 76 |
| NT1-011, MW = 424.4 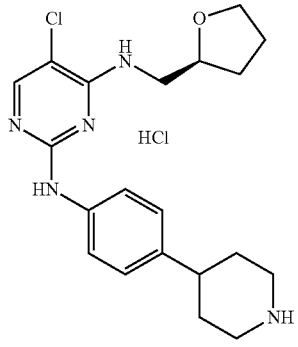 [SMILES: Clc1cnc(Nc2ccc(C3CCNCC3)cc2)nc1NC[C@@H]1CCCO1 ; Cl] |  | 77, 76 |
| NT1-006, MW = 399.3 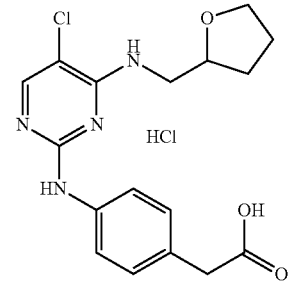 [SMILES: O=C(O)Cc1ccc(Nc2ncc(Cl)c(NCC3CCCO3)n2)cc1 ; Cl] |  | 72, 81 |

-continued
| Compound Name, Structure, Molecular Weight | IC$_{50}$ | % Inhibition at 10 μM (ELISA) |
|---|---|---|
| NT1-012, MW = 399.3 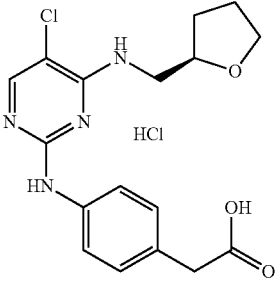 [SMILES: O=C(O)Cc1ccc(Nc2ncc(Cl)c(NC[C@H]3CCCO3)n2)cc1 ; Cl] | | 68, 74 |
| NT1-013, MW = 399.3 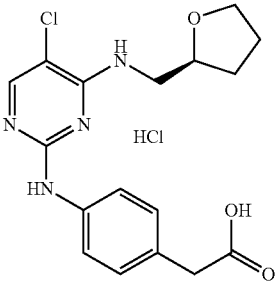 [SMILES: O=C(O)Cc1ccc(Nc2ncc(Cl)c(NC[C@@H]3CCCO3)n2)cc1 ; Cl] | | 73, 46 |
| NT1-007, MW = 413.3 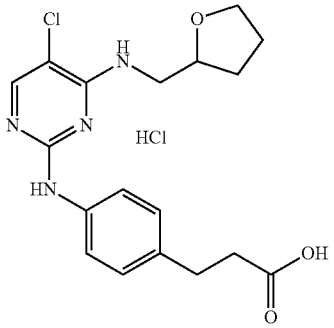 [SMILES: O=C(O)CCc1ccc(Nc2ncc(Cl)c(NCC3CCCO3)n2)cc1 ; Cl] | | 75, 73 |
| NT1-014, MW = 413.3 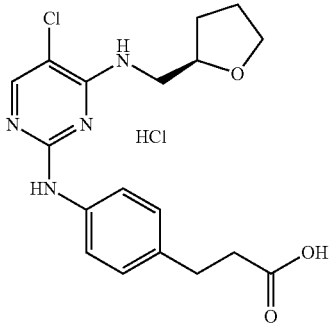 [SMILES: O=C(O)CCc1ccc(Nc2ncc(Cl)c(NC[C@H]3CCCO3)n2)cc1 ; Cl] | | 61, 75 |

| Compound Name, Structure, Molecular Weight | IC$_{50}$ | % Inhibition at 10 μM (ELISA) |
|---|---|---|
| NT1-015, MW = 413.3 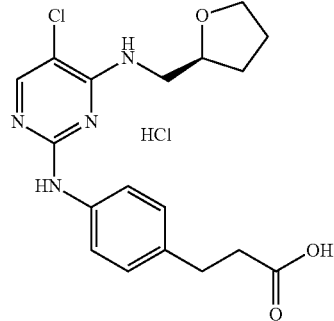 [SMILES: O=C(O)CCc1ccc(Nc2ncc(Cl)c(NC[C@@H]3CCCO3)n2)cc1 ; Cl] | | 70, 72 |
| NT1-025, MW = 390.9 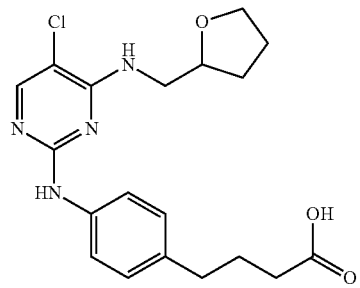 [SMILES: O=C(O)CCCc1ccc(Nc2ncc(Cl)c(NCC3CCCO3)n2)cc1] | | 61, 65 |
| NT1-026, MW = 427.3 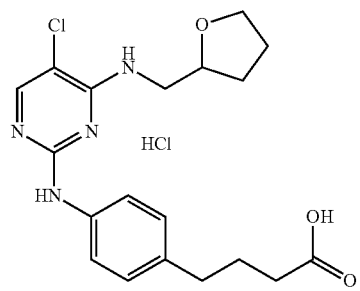 [SMILES: O=C(O)CCCc1ccc(Nc2ncc(Cl)c(NCC3CCCO3)n2)cc1 ; Cl] | | 55, 65 |
| NT1-027, MW = 427.3 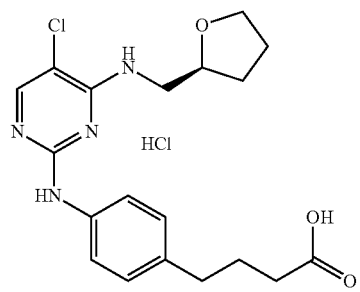 [SMILES: O=C(O)CCCc1ccc(Nc2ncc(Cl)c(NC[C@@H]3CCCO3)n2)cc1 ; Cl] | | 52, 64 |

| Compound Name, Structure, Molecular Weight | IC$_{50}$ | % Inhibition at 10 μM (ELISA) |
|---|---|---|
| NT1-028, MW = 483.4 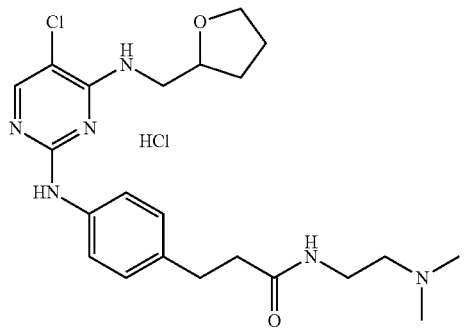 [SMILES: CN(C)CCNC(=O)CCc1ccc(Nc2ncc(Cl)c(NCC3CCCO3)n2)cc1 ; Cl] | | 62, 74 |
| NT1-022, MW = 443.7 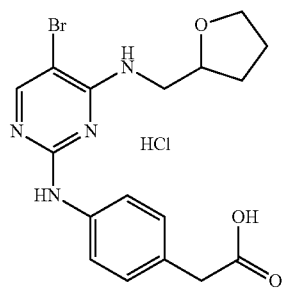 [SMILES: O=C(O)Cc1ccc(Nc2ncc(Br)c(NCC3CCCO3)n2)cc1 ; Cl] | | 59, 63 |
| NT1-023, MW = 457.7 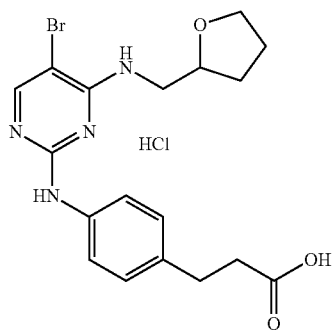 [SMILES: O=C(O)CCc1ccc(Nc2ncc(Br)c(NCC3CCCO3)n2)cc1 ; Cl] | | 74, 75 |
| DZ1-088, MW = 468.8 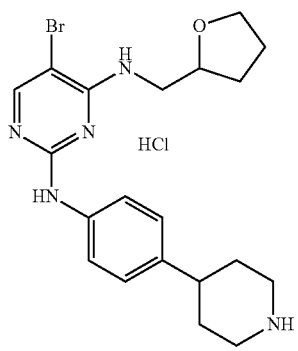 | 169 (RB) | 84, 85 |

-continued
| Compound Name, Structure, Molecular Weight | IC$_{50}$ | % Inhibition at 10 μM (ELISA) |
|---|---|---|
| DZ1-089, MW = 561.5 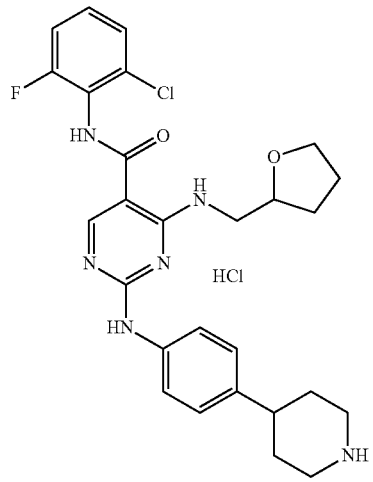 [SMILES: O=C(Nc1c(F)cccc1Cl)c1cnc(Nc2ccc(C3CCNCC3)cc2)nc1NCC1CCCO1 ; Cl] | 53.3 (RB) | 97, 97 |
| DZ1-091, MW = 470.8 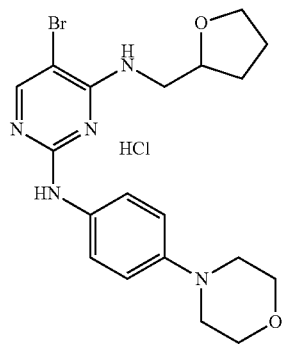 [SMILES: Brc1cnc(Nc2ccc(N3CCOCC3)cc2)nc1NCC1CCCO1 ; Cl] | 106 (RB) | 88, 90 |
| DZ1-092, MW = 563.5 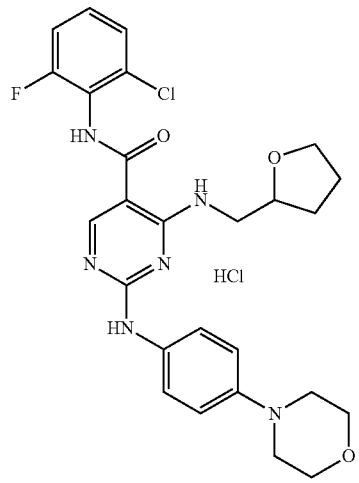 [SMILES: O=C(Nc1c(F)cccc1Cl)c1cnc(Nc2ccc(N3CCOCC3)cc2)nc1NCC1CCCO1 ; Cl] | 47.7 (RB) | 77, 88 |

| Compound Name, Structure, Molecular Weight | IC$_{50}$ | % Inhibition at 10 μM (ELISA) |
|---|---|---|
| DZ1-093, MW = 540.9 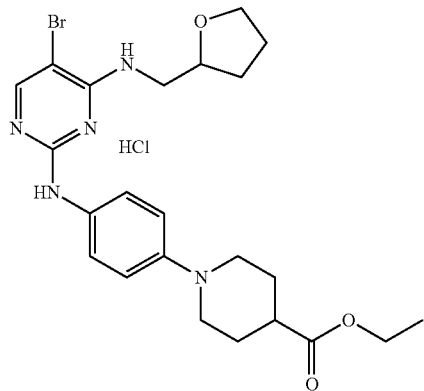 [SMILES: CCOC(=O)C1CCN(c2ccc(Nc3ncc(Br)c(NCC4CCCO4)n3)cc2)CC1 ; Cl] | | 64, 65 |
| DZ1-094, MW = 633.5 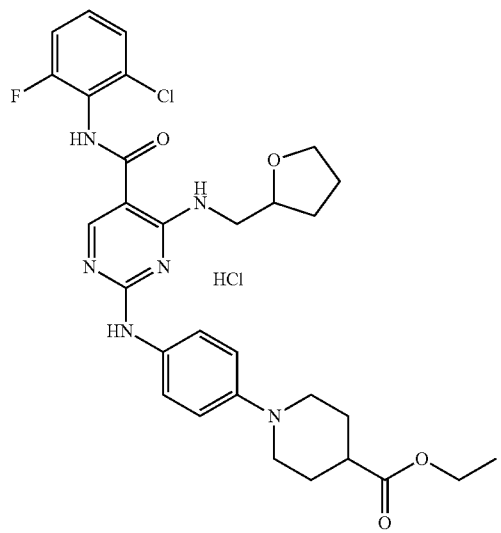 [SMILES: CCOC(=O)C1CCN(c2ccc(Nc3ncc(C(=O)Nc4c(F)cccc4Cl)c(NCC4CCCO4)n3)cc2)CC1 ; Cl] | | 61, 73 |
| DZ1-095, MW = 512.8 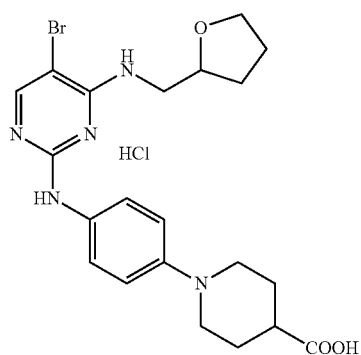 [SMILES: O=C(O)C1CCN(c2ccc(Nc3ncc(Br)c(NCC4CCCO4)n3)cc2)CC1 ; Cl] | | 85, 84, 85, 84 |

-continued
| Compound Name, Structure, Molecular Weight | IC$_{50}$ | % Inhibition at 10 μM (ELISA) |
|---|---|---|
| DZ1-096, MW = 605.5 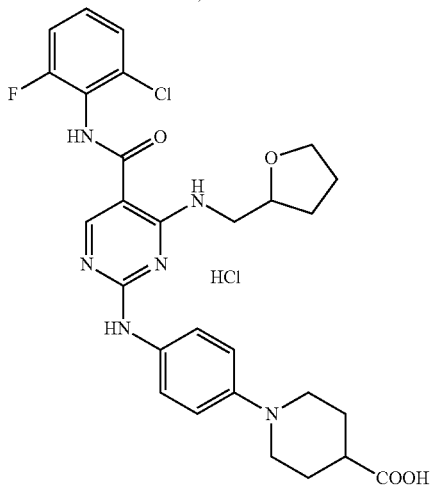 | 36.3, 32.2 (RB) | 98, 98 |
| Crizotinib, MW = 450.3 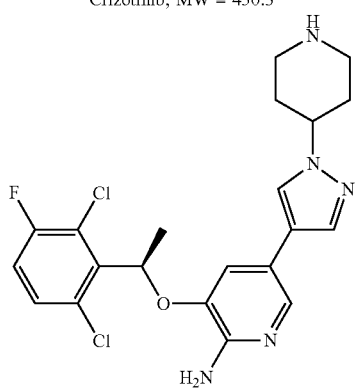 | 171 (RB) | |
| YL9-161, M.W. = 662.58 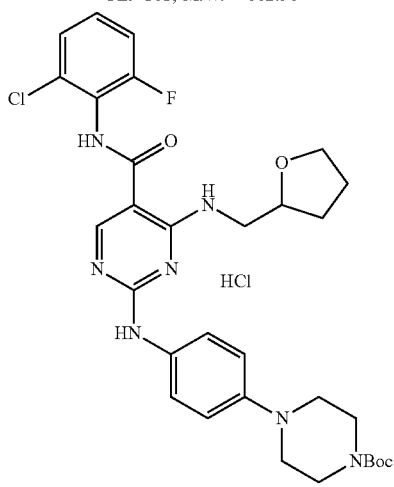 | | 28, 31 |

-continued
| Compound Name, Structure, Molecular Weight | IC$_{50}$ | % Inhibition at 10 μM (ELISA) |
|---|---|---|
| YL9-162, M.W. = 640.03 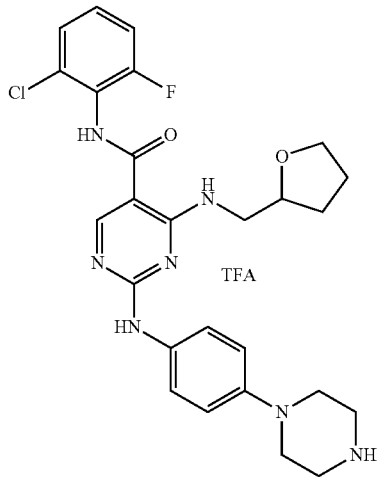 [SMILES: O=C(Nc1c(F)cccc1Cl)c1cnc(Nc2ccc(N3CCNCC3)cc2)nc1NCC1CCCO1 ; "TFA"] | 33.2 (RB) | 91, 88 |
| YL9-163, M.W. = 626.08 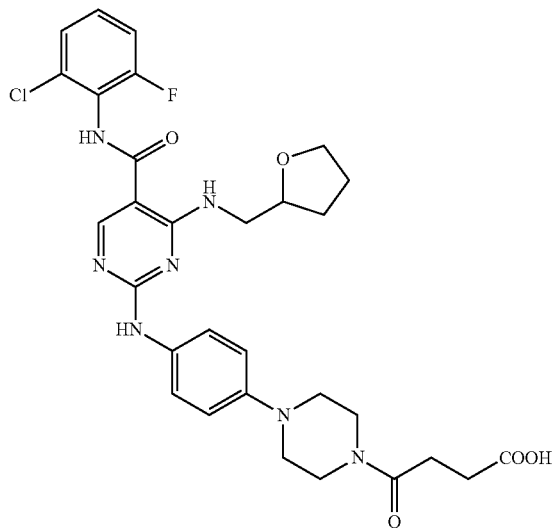 [SMILES: O=C(O)CCC(=O)N1CCN(c2ccc(Nc3ncc(C(=O)Nc4c(F)cccc4Cl)c(NCC4CCCO4)n3)cc2)CC1] | 28.4 (RB) | 85, 93 |
| YL9-157, M.W. = 569.92 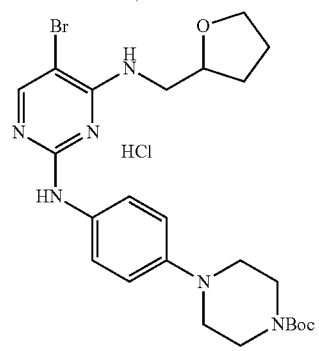 [SMILES: CC(C)(C)OC(=O)N1CCN(c2ccc(Nc3ncc(Br)c(NCC4CCCO4)n3)cc2)CC1 ; Cl] | | 47, 46 |

-continued
| Compound Name, Structure, Molecular Weight | IC$_{50}$ | % Inhibition at 10 μM (ELISA) |
|---|---|---|
| YL9-167, M.W. = 547.37 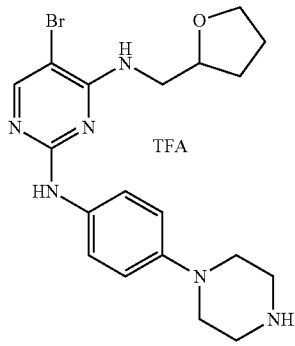 [SMILES: Brc1cnc(Nc2ccc(N3CCNCC3)cc2)nc1NCC1CCCO1 ; "TFA"] | 94.7 (RB) | 86, 85 |
| YL9-168, M.W. = 533.42 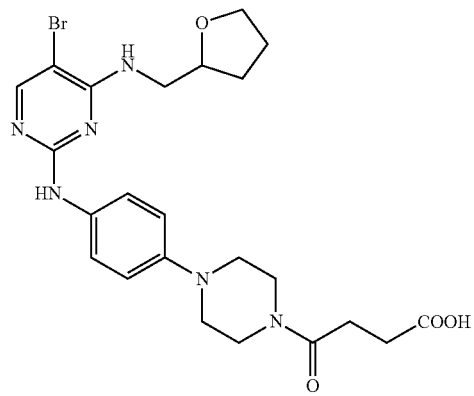 | | 94, 90 |
| SG1-083, M.W. = 458.98 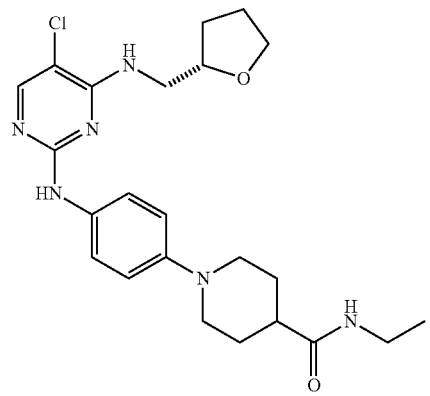 [SMILES: CCNC(=O)C1CCN(c2ccc(Nc3ncc(Cl)c(NC[C@@H]4CCCO4)n3)cc2)CC1] | | 73, 61 |

-continued
| Compound Name, Structure, Molecular Weight | IC$_{50}$ | % Inhibition at 10 μM (ELISA) |
|---|---|---|
| DZ1-098, M.W. = 386.47 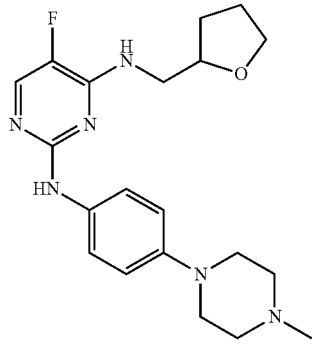 | | 61, 48 |
| DZ1-100, M.W. = 382.50 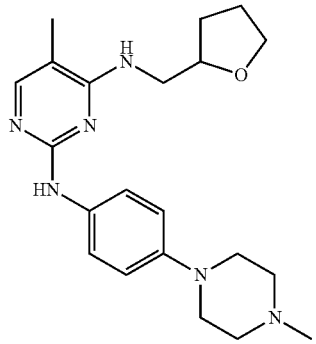 [SMILES: Cc1cnc(Nc2ccc(N3CCN(C)CC3)cc2)nc1NCC1CCCO1] | | 85, 54, 5, 10 |
| DZ1-104, M.W. = 368.48 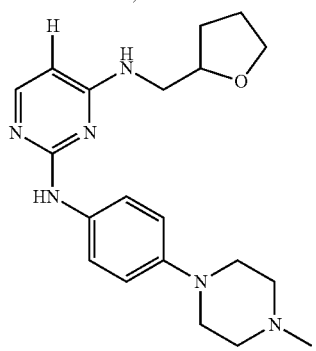 | | 19, 13 |
| DZ1-106, M.W. = 418.53 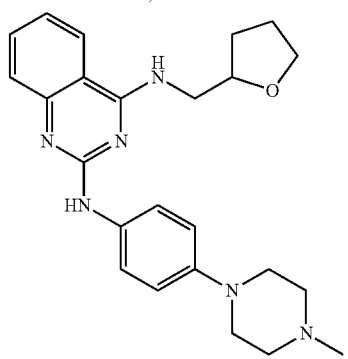 [SMILES: CN1CCN(c2ccc(Nc3nc(NCC4CCCO4)c4ccccc4n3)cc2)CC1] | | 19, 14 |

-continued

| Compound Name, Structure, Molecular Weight | IC$_{50}$ | % Inhibition at 10 μM (ELISA) |
|---|---|---|
| DZ1-108, M.W. = 396.53 | | 72, 48, 34, 46 |
| DZ1-112, M.W. = 304.32 | | 53, 33 |
| DZ1-114, M.W. = 540.03 | 48.3 (RB) | 99, 95 |
| DZ1-116, M.W. = 300.36 | | 15, 5 |

| Compound Name, Structure, Molecular Weight | IC$_{50}$ | % Inhibition at 10 μM (ELISA) |
|---|---|---|
| DZ1-120, M.W. = 320.77 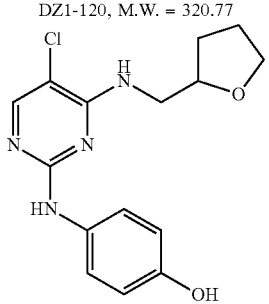 | 163 (RB) | 73, 58 |
| DZ1-122, M.W. = 447.37 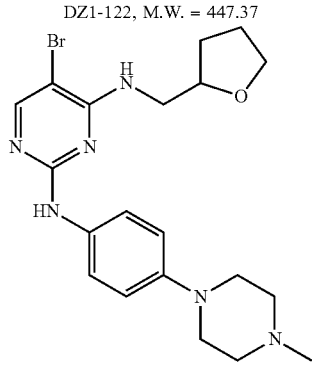 | 48.0 (RB) | 95, 91 |

Method

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, GD[2], GD[3], GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

Examples of immunotherapeutic agents have an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, anti-PDL1. Other immunotherapeutic agents include the TNFα antagonists (e.g. etanercept), the B cell depleting agent rituximab, the anti-IL-6 receptor tocilizumab, and the costimulation blocker abatacept can be administered with the compounds or compositions disclosed herein.

The disclosed compounds can also be administered with toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed compounds can also be administered with an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

Administration

The disclosed compounds can be administered either sequentially or simultaneously in separate or combined pharmaceutical formulations. When one or more of the disclosed compounds is used in combination with a second therapeutic agent, the dose of each compound can be either the same as or differ from that when the compound is used alone. Appropriate doses will be readily appreciated by those skilled in the art.

The term "administration" and variants thereof (e.g., "administering" a compound) in reference to a compound as described herein means introducing the compound or a prodrug of the compound into the system of the animal in need of treatment. When a compound as described herein or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E.W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, N.J.) and HERCEPTIN (Genentech, Inc.; South San Francisco, Calif.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods described herein are further provided. By "kit" is intended any manufacture (e.g., a package or a container) comprising at least one reagent, e.g., anyone of the compounds described in Table 1. The kit can be promoted, distributed, or sold as a unit for performing the methods described herein. Additionally, the kits can contain a package insert describing the kit and methods for its use. Any or all of the kit reagents can be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting an Ack1 tyrosine kinase with a target compound and determining whether the compound binds the kinase in a DFG-out configuration, wherein a compound that binds the DFG-out configuration is identified as a putative anti-cancer compound.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

ACK1, Activated CDC42 associated Kinase 1; DMF, Dimethylformamide; DMSO, Dimethylsulfoxide; DCM, Dichloromethane; ELISA, Enzyme-Linked Immunosorbent Assay; ESI, Electrospray Ionization; HRMS, High Resolution Mass Spectroscopy; HPLC, High Performance Liquid Chromatography; HCL, Hydrochloric Acid; LC-MS, Liquid Chromatography Mass Spectrometry; mCPBA, meta-Chloroperoxybenzoic Acid; SAR, Structure Activity Relationship; TFA, Trifluoroacetic Acid; THF, Tetrahydrofuran.

Compound Synthesis

Compound 7c, which is a building block for further compounds disclosed herein, was synthesized as shown in Scheme 1.

Scheme 1: Synthesis of building block 7c for library synthesis.

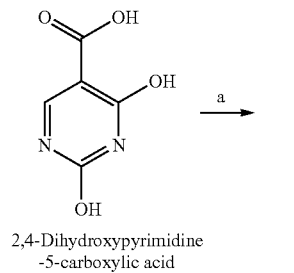

2,4-Dihydroxypyrimidine-5-carboxylic acid

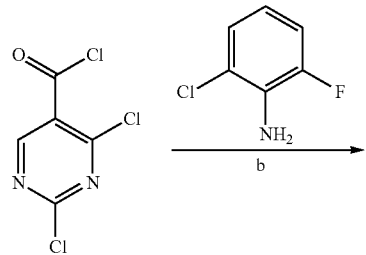

2,4-Dichloroypyrimidine-5-carbonyl chloride
(PE1-028-B2)

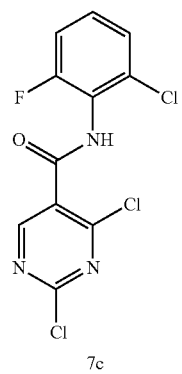

7c a: $POCl_3$, 0° C., $PCl_5$, 16 h, 99%.
b: THF, 15 h, 75%.

With 7c in hand, Scheme 2 illustrates the synthesis of additional compounds.

Scheme 2 Synthesis of bisanilinopyrimidine libraries with sulfon-substituted A-ring. And sulfide-substituted A ring

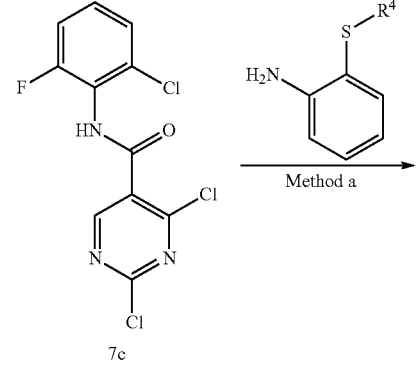

7c

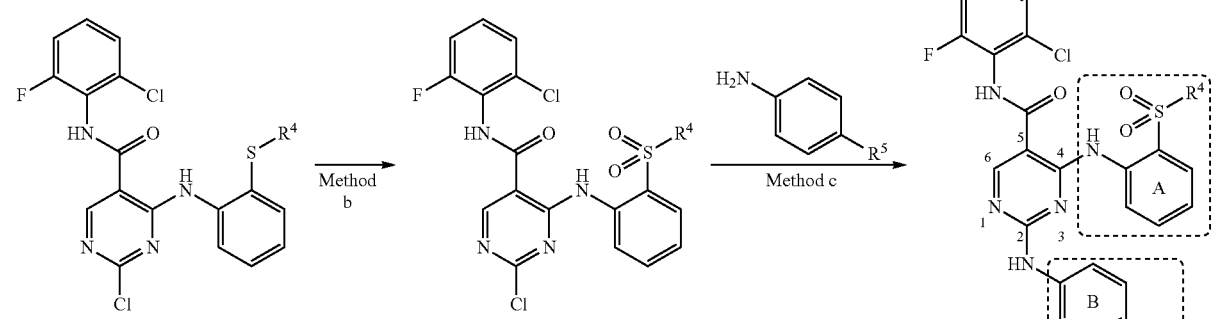

10          10a and 11a: $R^4$ = Methyl          11
            10b and 11b: $R^4$ = Isopropyl
Method c    10c and 11c: $R^4$ = Propyl
            10d and 11d: $R^4$ = Ethyl Sulfone library

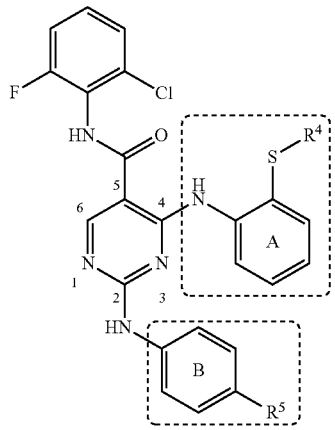

Sulfide library

Method a: DIPEA, THF, 120° C., 1 h, 77-90%. Method b: mCPBA, EtOAc, 0° C.-r.t., 2 h, 70-96%.
Method c: cat. 4M HCl in dioxane, microwave heating 180° C., 30 min., 68-97%.

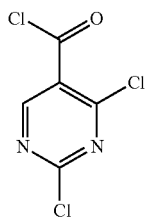 [SMILES: O=C(Cl)c1cnc(Cl)nc1Cl]

2,4-Dichloropyrimidine-5-carbonyl chloride (PE1-028-B2, Scheme 1)

To POCl$_3$ (45 mL, 0.071 mol) in a round bottom flask was added 2,4-dihydroxypyrimidine-5-carboxylic acid (10.00 g, 0.064 mol) portion wise at 0° C., followed by slow addition of PCl$_5$ (46.60 g, 0.229 mol). The reaction mixture was warmed to r.t. and heated to reflux for 16 h. The mixture was concentrated to dryness, slurried with DCM (30 mL), and the solid precipitated was filtered and washed with DCM (2×20 mL). The filtrate was evaporated under reduced pressure to afford the title compound (13.900 g, 99%) as a yellow oil. $^1$H NMR (400 MHz, CDCl$_3$): δ 9.25 (s, 1H).

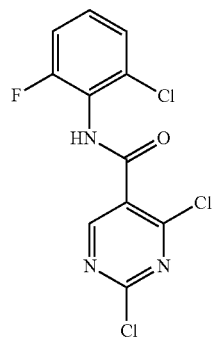 [SMILES: O=C(Nc1c(F)cccc1Cl)c1cnc(Cl)nc1Cl]

2,4-Dichloro-N-(2-chloro-6-fluorophenyl)pyrimidine-5-carboxamide (YL7-011, 7c)

To a solution of PE1-028-B2 acid chloride (6.36 g, 0.030 mol) obtained in the previous step in THF (40 mL) under inert conditions, 2-chloro-6-fluoroaniline (4.38 g, 0.03 mol) was added portion wise and the reaction mixture was stirred at r.t. for 15 h. The resulting precipitate was filtered, washed with DCM (15 mL) and the solid obtained was sonicated in HCl (1M, 100 mL), filtered and washed with water (20 mL), DCM (20 mL) sequentially and dried under high vacuum to obtain the title compound 7c (5.529 g) as a white solid. The first filtrate (i.e., THF and DCM) was concentrated, slurried with DCM (15 mL) and filtered to get a solid. The solid was again sonicated with HCl (1M, 30 mL), filtered and washed with water (20 mL), DCM (15 mL) sequentially and dried under high vacuum to obtain another crop of pure product 7c (1.702 g) also as a white solid. The combined yield of 7c (7.231 g, 75%), mp 207-211° C. $^1$H NMR (400 MHz, DMSO-d$_6$): δ 10.71 (s, 1H), 9.03 (s, 1H), 7.48-7.36 (m, 3H); $^{19}$F NMR (376 MHz, DMSO-d$_6$): −115.25, −115.28 (m); LC-MS (ESI+) m/z 319.96 (M+H)$^+$; HRMS (ESI+) m/z calculated for C$_{11}$H$_6$Cl$_3$FN$_3$O (M+H)$^+$ 319.9555. found 319.9562.

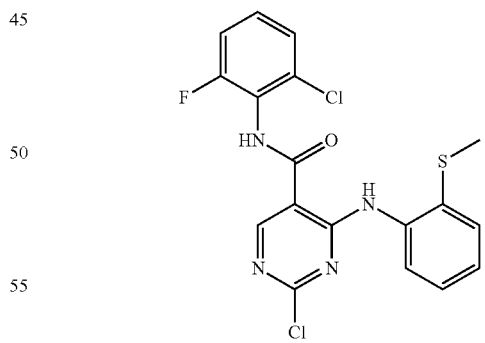

2-Chloro-N-(2-chloro-6-fluorophenyl)-4-(2-(methylthio)phenylamino)pyrimidine-5-carboxamide (YL7-031-B2)

To a solution of YL7-011, (7c) (1.00 g, 3.12 mmol), in THF (5 mL), 2-(methylthio)aniline (0.522 g, 3.750 mmol) and DIPEA (0.652 mL, 3.750 mmol) was added and heated in a microwave reactor at 120° C. for 1 h. The solvent was removed under reduce pressure and the crude mixture was purified using SiO$_2$ chromatography (EtOAc in Hexane, gradient elution) to give the title compound 10a as a pure white solid (1.202 g, 91%), mp 204-206° C. $^1$H NMR (400 MHz, DMSO-d$_6$): δ 10.85 (s, 1H), 10.66 (s, 1H), 8.99 (s, 1H), 7.87 (dd, J=8.0, 1.6 Hz, 1H), 7.78-7.34 (m, 4H), 7.27 (td, J=7.6, 1.6 Hz, 1H), 7.21 (td, J=7.6, 1.6 Hz, 1H), 2.39 (s, 3H); LC-MS (ESI+) m/z 423.03 (M+H)$^+$; HRMS (ESI+) m/z calculated for C$_{18}$H$_{14}$Cl$_2$FN$_4$OS (M+H)$^+$ 423.0244, found 423.0241.

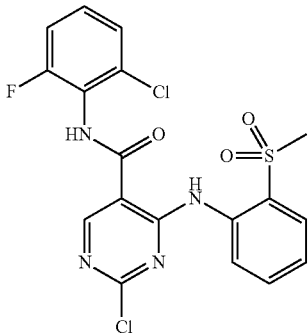 [SMILES: CS(=O)(=O)c1ccccc1Nc1nc(Cl)ncc1C(=O)Nc1c(F)cccc1Cl]

2-Chloro-N-(2-chloro-6-fluorophenyl)-4-(2-(methylsulfonyl)phenylamino)pyrimidine-5-carboxamide (YL7-034)

To a suspension of YL7-031-B2 (0.634 g, 1.50 mmol) in EtOAc (40 mL) was added m-CPBA (77% max, 1.014 g, 4.50 mmol) at 0° C. The mixture was warmed to r.t. and stirred 2 h. The reaction was diluted with EtOAc (20 mL) and washed with sat. Na$_2$S$_2$O$_3$/NaHCO$_3$ (1:1, 20 mL), sat. NaHCO$_3$ (20 mL) and brine (20 mL) sequentially. The organic layer was dried over Na$_2$SO$_4$, filtered and evaporated to dryness. The solid obtained was slurried with DCM/Hexane (1:5 ratio, 5 mL), filtered and dried under high vacuum to afford the title compound as a pure beige color solid (0.657 g, 96%), mp 211-214° C. $^1$H NMR (400 MHz, DMSO-d$_6$): δ 11.10 (s, 1H), 10.63 (s, 1H), 9.03 (s, 1H), 8.02 (d, J=8.0 Hz, 1H), 7.90 (dd, J=8.0, 1.6 Hz, 1H), 7.79-7.71 (m, 1H), 7.55-7.33 (m, 4H), 3.16 (s, 3H); LC-MS (ESI+) m/z 455.02 (M+H)$^+$; HRMS (ESI+) m/z calculated for C$_{18}$H$_{14}$Cl$_2$FN$_4$O$_3$S (M+H)$^+$ 455.0142. found 455.0134.

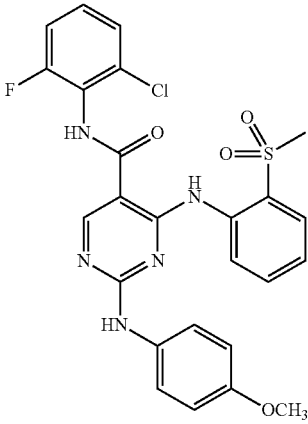 [SMILES: COc1ccc(Nc2ncc(C(=O)Nc3c(F)cccc3Cl)c(Nc3ccccc3S(C)(=O)=O)n2)cc1]

N-(2-chloro-6-fluorophenyl)-2-(4-methoxyphenylamino)-4-(2-(methylsulfonyl)phenylamino)pyrimidine-5-carboxamide (YL7-037)

A mixture of YL7-034 (0.050 g, 0.110 mmol), 4-methoxyaniline (0.016 g, 0.132 mmol), 4M HCl in dioxane (0.033 mL, 0.132 mmol) in dioxane (1 mL) was heated in a microwave reactor at 180° C. for 30 min. The mixture was evaporated to dryness, added EtOAc (5 mL) and sonicated. The resulting solid was filtered, washed with sat. NaHCO$_3$ (5 mL×2), water (5 mL×2) and dried under vacuum to afford the title compound as a pure beige color solid (0.058 g, 97%), mp 267° C. (dec). HPLC 98.8% (t$_R$=10.18 min, 55% CH$_3$OH in 0.1% TFA water, 20 min); $^1$H NMR (400 MHz, DMSO-d$_6$):δ 11.08 (s, 1H disappear on D$_2$O shake), 10.09 (s, 1H disappear on D$_2$O shake), 9.79 (brs, 1H disappear on D$_2$O shake), 8.94 (s, 1H), 8.12 (brs, 1H), 7.87 (dd, J=7.6, 1.2 Hz, 1H), 7.73 (t, J=7.2 Hz, 1H), 7.46-7.33 (m, 6H), 6.75 (brs, 2H), 3.68 (s, 3H), 3.01 (s, 3H); $^{19}$F NMR (376 MHz, DMSO-d$_6$): δ −115.91--−115.95 (m); LC-MS (ESI+) m/z 542.10 (M+H)$^+$; HRMS (ESI+) m/z calculated for C$_{25}$H$_{22}$ClFN$_5$O$_4$S (M+H)$^+$ 542.1060. found 542.1062.

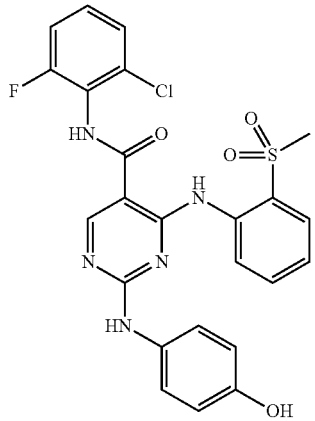 [SMILES: CS(=O)(=O)c1ccccc1Nc1nc(Nc2ccc(O)cc2)ncc1C(=O)Nc1c(F)cccc1Cl]

N-(2-chloro-6-fluorophenyl)-2-(4-hydroxyphenylamino)-4-(2-(methylsulfonyl)phenylamino)pyrimidine-5-carboxamide (YL7-038)

This compound was synthesized using the procedure described for YL7-037 except using 4-aminophenol (0.014 g, 0.132 mmol) and YL7-034 (0.050 g, 0.110 mmol), to obtain the title compound as a pure light brown solid (0.056 g, 97%), mp: 238° C. (dec). HPLC 96.7% (t$_R$=7.34 min, 50% CH$_3$OH in 0.1% TFA water, 20 min); $^1$H NMR (400 MHz, DMSO-d$_6$): δ 11.09 (s, 1H disappear on D$_2$O shake), 10.09 (s, 1H disappear on D$_2$O shake), 9.72 (brs, 1H disappear on D$_2$O shake), 9.15 (brs, 1H disappear on D$_2$O shake), 8.92 (s, 1H), 8.12 (brs, 1H), 7.87 (dd, J=8.0, 1.6 Hz, 1H), 7.70 (t, J=7.8 Hz, 1H), 7.52-7.23 (m, 6H), 6.58 (brs, 2H), 3.11 (s, 3H); $^{19}$F NMR (376 MHz, DMSO-d$_6$): δ −115.99--−116.03 (m); LC-MS (ESI+) m/z 528.09 (M+H)$^+$; HRMS (ESI+) m/z calculated for C$_{24}$H$_{20}$ClFN$_5$O$_4$S (M+H)$^+$ 528.0903. found 528.0899.

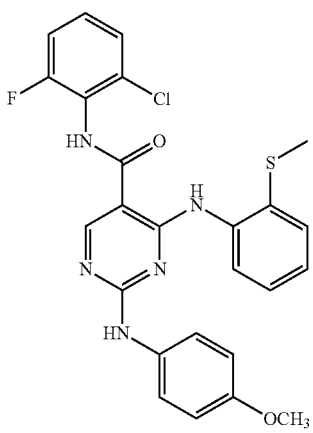 [SMILES: COc1ccc(Nc2ncc(C(=O)Nc3c(F)cccc3Cl)c(Nc3ccccc3SC)n2)cc1]

N-(2-chloro-6-fluorophenyl)-2-(4-methoxyphenylamino)-4-(2-(methylthio)phenylamino)pyrimidine-5-carboxamide (YL7-039-1)

This compound was synthesized using the procedure described for YL7-037 except using 4-methoxyaniline (0.018 g, 0.142 mmol) and YL7-031 B2 (0.050 g, 0.118 mmol), to obtain the title compound as a pure grey solid (0.056 g, 93%), mp: 261° C. (dec). HPLC 95.7% ($t_R$=12.03 min, 65% CH$_3$OH in 0.1% TFA water, 20 min); $^1$H NMR (400 MHz, DMSO-d$_6$): δ 10.85 (s, 1H disappear on D$_2$O shake), 10.10 (s, 1H disappear on D$_2$O shake), 9.72 (brs, 1H disappear on D$_2$O shake), 8.91 (s, 1H), 7.94 (brs, 1H), 7.50-7.35 (m, 6H), 7.23-7.14 (m, 2H), 6.78 (brs, 2H), 3.70 (s, 3H), 2.37 (s, 3H); $^{19}$F NMR (376 MHz, DMSO-d$_6$): δ −116.18−−116.21 (m); LC-MS (ESI+) m/z 510.12 (M+H)$^+$; HRMS (ESI+) m/z calculated for C$_{25}$H$_{22}$ClFN$_5$O$_2$S (M+H)$^+$ 510.1161. found 510.1151.

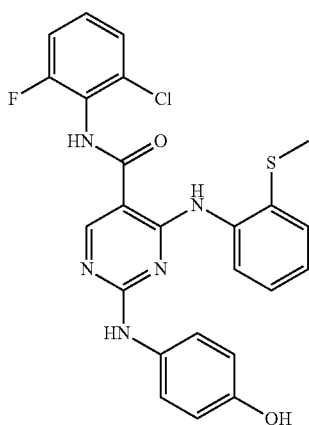 [SMILES: CSc1ccccc1Nc1nc(Nc2ccc(O)cc2)ncc1C(=O)Nc1c(F)cccc1Cl]

N-(2-chloro-6-fluorophenyl)-2-(4-hydroxyphenylamino)-4-(2-(methylthio)phenylamino)pyrimidine-5-carboxamide (YL7-039-2)

This compound was synthesized using the procedure described for YL7-037 except using 4-aminophenol (0.016 g, 0.142 mmol) and YL7-031 B2 (0.050 g, 0.118 mmol) to obtain the title compound as a pure grey solid (0.055 g, 93%), mp: 246° C. (dec). HPLC 99.3% ($t_R$=9.81 min, 60% CH$_3$OH in 0.1% TFA water, 20 min); $^1$H NMR (400 MHz, DMSO-d$_6$): δ 11.04 (s, 1H), 10.34 (s, 1H), 9.99 (s, 1H), 8.91 (s, 1H), 7.86 (brs, 1H), 7.48-7.18 (m, 8H), 6.63 (brs, 2H), 2.38 (s, 3H); $^{19}$F NMR (376 MHz, DMSO-d$_6$): δ −116.06 (s); LC-MS (ESI+) m/z 496.11 (M+H)$^+$; HRMS (ESI+) m/z calculated for C$_{24}$H$_{20}$ClFN$_5$O$_2$S (M+H)$^+$ 496.1005. found 496.0996.

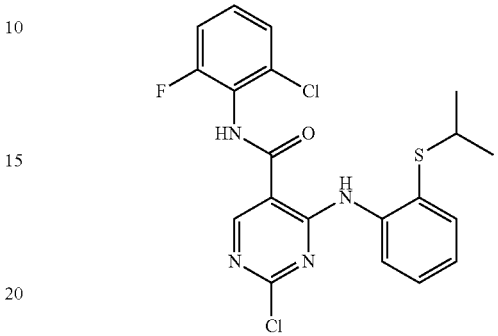

2-Chloro-N-(2-chloro-6-fluorophenyl)-4-(2-(isopropylthio)phenylamino)pyrimidine-5-carboxamide (YL7-040)

A solution of YL7-011 (7c), (1.000 g, 3.125 mmol), 2-isopropylthio aniline hydrochloride (0.770 g, 3.750 mmol) and DIPEA (1.30 mL, 7.500 mmol) in THF (5 mL) was heated in a microwave reactor at 120° C. for 1 h. The reaction mixture was evaporated to dryness, added water (20 mL) and the mixture was sonicated for 10 min. The resulting precipitate was filtered and washed with water (20 mL). The yellow solid obtained at this point was sonicated in DCM (10 mL), filtered, washed with DCM (2 mL), and dried under vacuum to afford the title compound 10b as a pure white solid (1.187 g, 84%), mp: 202-205° C. $^1$H NMR (400 MHz, DMSO-d$_6$): δ 11.28 (s, 1H), 10.66 (s, 1H), 8.98 (s, 1H), 8.22 (d, J=8.4 Hz, 1H), 7.54 (d, J=7.6 Hz, 1H), 7.50-7.38 (m, 4H), 7.17 (t, J=7.6 Hz, 1H), 3.23-3.14 (m, 1H), 1.11 (d, J=6.4 Hz, 6H),); LC-MS (ESI+) m/z 451.06 (M+H)$^+$; HRMS (ESI+) m/z calculated for C$_{20}$H$_{18}$Cl$_2$FN$_4$OS (M+H)$^+$ 451.0557. found 451.0552.

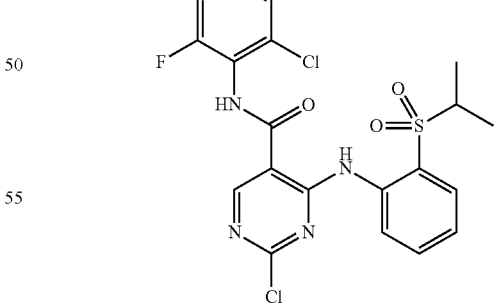

2-Chloro-N-(2-chloro-6-fluorophenyl)-4-(2-(isopropylsulfonyl)phenylamino)pyrimidine-5-carboxamide (YL7-041)

This compound was synthesized using the procedure described for YL7-034 except using YL7-040 (0.676 g, 1.500 mmol) and m-CPBA (77% max, 1.014 g, 4.500 mmol) to obtain the title compound as a pure white solid (0.657 g, 91%), mp: 225-227° C. $^1$H NMR (400 MHz, DMSO-d$_6$): δ 11.14 (s, 1H), 10.62 (s, 1H), 9.01 (s, 1H), 8.07 (d, J=8.0 Hz, 1H), 7.85 (dd, J=7.6, 1.6 Hz, 1H), 7.78 (appt, 1H), 7.50-7.37 (m, 4H), 1.09 (d, J=6.8 Hz, 6H); LC-MS (ESI+) m/z 483.04 (M+H)$^+$; HRMS (ESI+) m/z calculated for C$_{20}$H$_{18}$Cl$_2$FN$_4$O$_3$S (M+H)$^+$ 483.0455. found 483.0458.

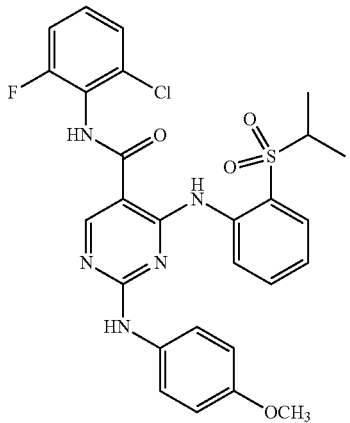 [SMILES: COc1ccc(Nc2ncc(C(=O)Nc3c(F)cccc3Cl)c(Nc3ccccc3S(=O)(=O)C(C)C)n2)cc1]

N-(2-chloro-6-fluorophenyl)-4-(2-(isopropylsulfonyl)phenylamino)-2-(4-methoxyphenylamino)pyrimidine-5-carboxamide (YL7-045-1)

This compound was synthesized using the procedure described for YL7-037 except using YL7-041 (0.054 g, 0.111 mmol) and 4-methoxyaniline (0.016 g, 0.133 mmol) to obtain the title compound as a pure white solid (0.058 g, 91%), mp: 246° C. (dec). HPLC 99.5% (t$_R$=5.49 min, 65% CH$_3$OH in 0.1% TFA water, 20 min); $^1$H NMR (400 MHz, DMSO-d$_6$): δ 11.13 (s, 1H disappear on D$_2$O shake), 10.15 (s, 1H disappear on D$_2$O shake), 9.91 (brs, 1H disappear on D$_2$O shake), 9.15 (brs, 1H disappear on D$_2$O shake), 8.92 (s, 1H), 8.06 (brs, 1H), 7.83 (dd, J=7.6, 1.2 Hz, 1H), 7.70 (appt, 1H), 7.47-7.34 (m, 6H), 6.74 (brs, 2H), 3.69 (s, 3H), 3.30-3.25 (m, 1H), 1.06 (d, J=6.8 Hz); $^{19}$F NMR (376 MHz, DMSO-d$_6$): δ −116.13--116.16 (m); LC-MS (ESI+) m/z 570.14 (M+H)$^+$; HRMS (ESI+) m/z calculated for C$_{27}$H$_{26}$ClFN$_5$O$_4$S (M+H)$^+$ 570.1373. found 570.1372.

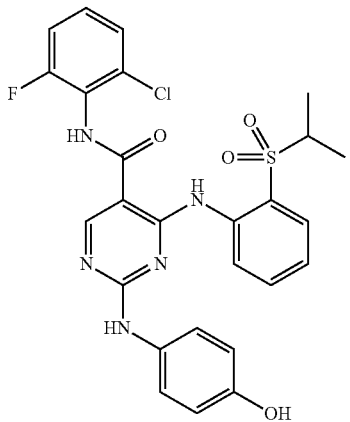 [SMILES: CC(C)S(=O)(=O)c1ccccc1Nc1nc(Nc2ccc(O)cc2)ncc1C(=O)Nc1c(F)cccc1Cl]

N-(2-chloro-6-fluorophenyl)-2-(4-hydroxyphenylamino)-4-(2-(isopropylsulfonyl)phenylamino)pyrimidine-5-carboxamide (YL7-045-2)

This compound was synthesized using the procedure described for YL7-037 except using 4-aminophenol (0.015 g, 0.133 mmol) and YL7-041 (0.054 g, 0.111 mmol), to obtain the title compound as a pure brown solid (0.045 g, 73%), mp: 168° C. (dec). HPLC 95.7% (t$_R$=3.10 min, 65% CH$_3$OH in 0.1% TFA water, 20 min); $^1$H NMR (400 MHz, DMSO-d$_6$): δ 11.06 (s, 1H), 10.06 (s, 1H), 9.72 (brs, 1H), 9.11 (brs, 1H), 8.90 (s, 1H), 8.05 (brs, 1H), 7.83 (d, J=8.0 Hz, 1H), 7.70 (t, J=7.6 Hz, 1H), 7.46-7.30 (m, 6H), 6.54 (brs, 2H), 1.06 (d, J=6.8 Hz); $^{19}$F NMR (376 MHz, DMSO-d$_6$): δ −116.12--116.16 (m); LC-MS (ESI+) m/z 556.12 (M+H)$^+$; HRMS (ESI+) m/z calculated for C$_{26}$H$_{24}$ClFN$_5$O$_4$S (M+H)$^+$ 556.1216. found 556.1216.

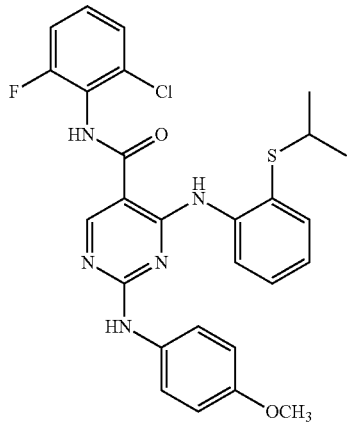 [SMILES: COc1ccc(Nc2ncc(C(=O)Nc3c(F)cccc3Cl)c(Nc3ccccc3SC(C)C)n2)cc1]

N-(2-chloro-6-fluorophenyl)-4-(2-(isopropylthio)phenylamino)-2-(4-methoxyphenylamino)pyrimidine-5-carboxamide (YL7-045-3)

This compound was synthesized using the procedure described for YL7-037 except using YL7-040 (0.050 g, 0.111 mmol) and 4-methoxyaniline (0.016 g, 0.113 mmol) to obtain the title compound as a pure white solid (0.031 g, 52%), mp: 237-240° C. HPLC 99.7% (t$_R$=7.03 min, 75% CH$_3$OH in 0.1% TFA water, 20 min); $^1$H NMR (400 MHz, DMSO-d$_6$): δ 11.41 (s, 1H), 10.29 (s, 1H), 10.03 (brs, 1H), 8.88 (s, 1H), 8.16 (brs, 1H), 7.49-7.34 (m, 6H), 7.28 (brs, 1H), 7.11 (t, J=7.2 Hz, 1H), 6.86 (d, J=8.0 Hz, 2H), 3.72 (s, 3H), 3.20-3.13 (m, 1H), 1.09 (d, J=6.8 Hz, 6H); $^{19}$F NMR (376 MHz, DMSO-d$_6$): δ −116.19--116.22 (m); LC-MS (ESI+) m/z 538.15 (M+H)$^+$; HRMS (ESI+) m/z calculated for C$_{27}$H$_{26}$ClFN$_5$O$_2$S (M+H)$^+$ 538.1474. found 538.1472.

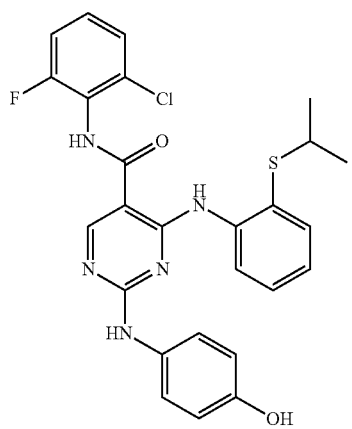 [SMILES: CC(C)Sc1ccccc1Nc1nc(Nc2ccc(O)cc2)ncc1C(=O)Nc1c(F)cccc1Cl]

N-(2-chloro-6-fluorophenyl)-2-(4-hydroxyphenylamino)-4-(2-(isopropylthio)phenylamino)pyrimidine-5-carboxamide (YL7-045-4)

This compound was synthesized using the procedure described for YL7-037 except using YL7-040 (0.050 g, 0.111 mmol) and 4-aminophenol (0.015 g, 0.113 mmol) to obtain the title compound as a pure beige color solid (0.057 g, 99%), mp: 232° C. (dec). HPLC 99.3% ($t_R$=12.68 min, 65% CH$_3$OH in 0.1% TFA water, 20 min); $^1$H NMR (400 MHz, DMSO-d$_6$): δ 11.29 (s, 1H), 10.10 (s, 1H), 9.68 (brs, 1H), 9.21 (brs, 1H), 8.85 (s, 1H), 8.19 (brs, 1H), 7.47-7.33 (m, 6H), 7.23 (brs, 1H), 7.07 (t, J=7.6 Hz, 1H), 6.66 (d, J=8.0 Hz, 2H), 3.19-3.12 (m, 1H), 1.08 (d, J=6.4 Hz, 6H); $^{19}$F NMR (376 MHz, DMSO-d$_6$): δ −116.19−−116.23 (m); LC-MS (ESI+) m/z 524.14 (M+H)$^+$; HRMS (ESI+) m/z calculated for C$_{26}$H$_{24}$ClFN$_5$O$_2$S (M+H)$^+$ 524.1318. found 524.1310.

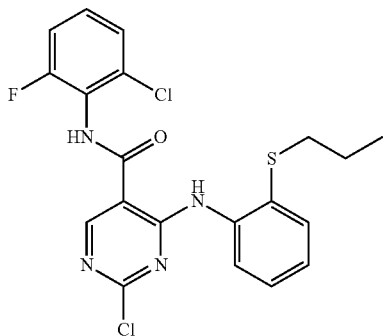 [SMILES: CCCSc1ccccc1Nc1nc(Cl)ncc1C(=O)Nc1c(F)cccc1Cl]

2-Chloro-N-(2-chloro-6-fluorophenyl)-4-(2-(propylthio)phenylamino)pyrimidine-5-carboxamide (YL7-051)

A solution of YL7-011 (7c) (1.00 g, 3.12 mmol), 2-(propylthio)aniline hydrochloride (0.70 g, 3.43 mmol) and DIPEA (1.19 mL, 6.87 mmol) in THF (5 mL) was heated in a microwave reactor at 120° C. for 1 h. The reaction mixture was evaporated to dryness, added water (20 mL) and the mixture was sonicated for 10 min. The resulting precipitate was filtered and washed with water (20 mL). The yellow solid obtained was sonicated in DCM:Hexane (6 mL, 1:2), filtered and dried under vacuum to afford the title compound as a pure white solid (1.08 g, 77%), mp: 197-200° C. $^1$H NMR (400 MHz, DMSO-d$_6$): δ 11.04 (s, 1H), 10.66 (s, 1H), 8.99 (s, 1H), 8.04 (d, J=8.0 Hz, 1H), 7.52-7.38 (m, 4H), 7.34 (appt, 1H), 7.18 (td, J=7.6, 1.2 Hz, 1H), 2.79 (t, J=7.2 Hz, 2H), 1.49-1.40 (m, 2H), 0.86 (t, J=7.2 Hz, 3H); LC-MS (ESI+) m/z 451.05 (M+H)$^+$; HRMS (ESI+) m/z calculated for C$_{20}$H$_{18}$Cl$_2$FN$_4$OS (M+H)$^+$ 451.0557. found 451.0551.

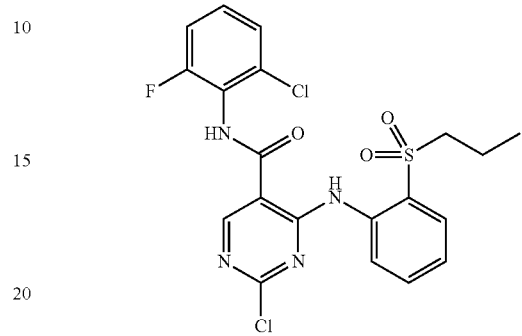

2-Chloro-N-(2-chloro-6-fluorophenyl)-4-(2-(propylsulfonyl)phenylamino)pyrimidine-5-carboxamide (YL7-052)

To a suspension of YL7-051 (0.676 g, 1.500 mmol) in EtOAc (40 mL), added m-CPBA (77% max, 1.014 g, 4.500 mmol) at 0° C. The mixture was warmed to r.t. and stirred for 2 h. The resulting precipitate was filtered and washed with EtOAc (5 mL×2) to afford the pure YL7-052 (0.510 g) as a white solid. The filtrate was concentrated to dryness and slurried with EtOAc (5 mL), filtered and washed with EtOAc (3 mL) to afford the second crop of pure product, which was combined with the first crop of solid to afford the title compound 11c (0.629 g, 87%), mp: 226-229° C. $^1$H NMR (400 MHz, DMSO-d$_6$): δ 11.10 (s, 1H), 10.63 (s, 1H), 9.03 (s, 1H), 8.03 (d, J=8.0 Hz, 1H), 7.88 (dd, J=7.6, 1.6 Hz, 1H), 7.78 (appt, 1H), 7.50-7.40 (m, 4H), 3.20 (t, J=7.6 Hz, 2H), 1.55-1.46 (m, 2H), 0.81 (t, J=7.6 Hz, 3H); LC-MS (ESI+) m/z 483.04 (M+H)$^+$; HRMS (ESI+) m/z calculated for C$_{20}$H$_{18}$Cl$_2$FN$_4$O$_3$S (M+H)$^+$ 483.0455. found 483.0449.

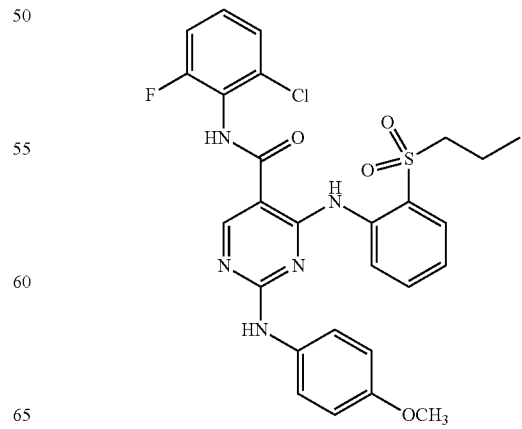

N-(2-chloro-6-fluorophenyl)-2-(4-methoxyphenylamino)-4-(2-(propylsulfonyl)phenylamino)pyrimidine-5-carboxamide (YL7-055-1)

This compound was synthesized using the procedure described for YL7-037 except using YL7-052 (0.054 g, 0.111 mmol) and 4-methoxyaniline (0.016 g, 0.133 mmol) to obtain the title compound as a beige color solid (0.043 g, 68%), mp: 234-235° C. HPLC 99.2% ($t_R$=5.79 min, 65% $CH_3OH$ in 0.1% TFA water, 20 min); $^1$H NMR (400 MHz, DMSO-$d_6$): δ 11.01 (s, 1H), 10.09 (s, 1H), 9.80 (brs, 1H), 9.15 (brs, 1H), 8.94 (s, 1H), 8.05 (brs, 1H), 7.86 (dd, J=8.0, 1.6 Hz, 1H), 7.75 (t, J=7.6 Hz, 1H), 7.47-7.34 (m, 6H), 6.71 (brs, 2H), 3.68 (s, 3H), 3.12 (appt, 2H), 1.47-1.42 (m, 2H), 0.69 (brs, 3H); $^{19}$F NMR (376 MHz, DMSO-$d_6$): δ -116.07--116.10 (m); LC-MS (ESI+) m/z 570.13 (M+H)$^+$; HRMS (ESI+) m/z calculated for $C_{27}H_{26}ClFN_5O_4S$ (M+H)$^+$ 570.1373. found 570.1364.

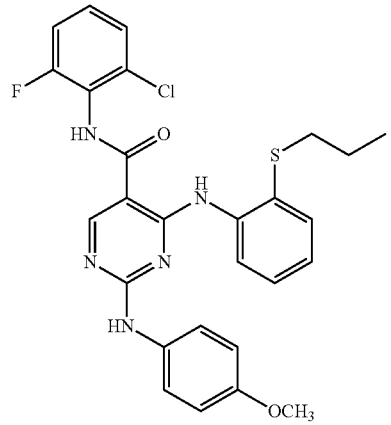

N-(2-chloro-6-fluorophenyl)-2-(4-hydroxyphenylamino)-4-(2-(propylsulfonyl)phenylamino)pyrimidine-5-carboxamide (YL7-055-2)

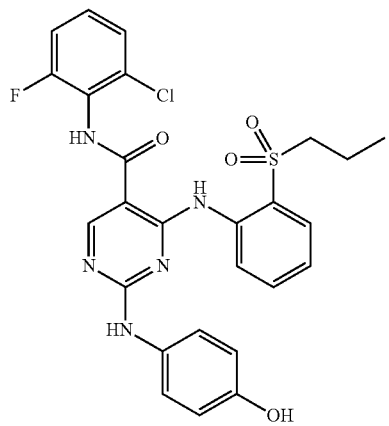 [SMILES: CCCS(=O)(=O)c1ccccc1Nc1nc(Nc2ccc(O)cc2)ncc1C(=O)Nc1c(F)cccc1Cl]

This compound was synthesized using the procedure described for YL7-037 except using YL7-052 (0.054 g, 0.111 mmol) and 4-aminophenol (0.015 g, 0.133 mmol) to obtain the title compound as a grey color solid (0.056 g, 90%), mp: 165° C. (dec). HPLC 95.9% ($t_R$=3.20 min, 65% $CH_3OH$ in 0.1% TFA water, 20 min); $^1$H NMR (400 MHz, DMSO-$d_6$): δ 11.05 (s, 1H), 10.15 (s, 1H), 9.81 (brs, 1H), 8.93 (s, 1H), 8.01 (brs, 1H), 7.86 (dd, J=8.0 Hz, 1H), 7.72 (t, J=7.6 Hz, 1H), 7.47-7.27 (m, 6H), 6.53 (brs, 2H), 3.13 (appt, 2H), 1.47-1.41 (m, 2H), 0.69 (brs, 3H); $^{19}$F NMR (376 MHz, DMSO-$d_6$): δ -116.03--116.07 (m); LC-MS (ESI+) m/z 556.11 (M+H)$^+$; HRMS (ESI+) m/z calculated for $C_{26}H_{24}ClFN_5O_4S$ (M+H)$^+$ 556.1216. found 556.1209.

N-(2-chloro-6-fluorophenyl)-2-(4-methoxyphenylamino)-4-(2-(propylthio)phenylamino)pyrimidine-5-carboxamide (YL7-055-3)

This compound was synthesized using the procedure described for YL7-037 except using YL7-051 (0.050 g, 0.111 mmol) and 4-methoxyaniline (0.016 g, 0.133 mmol) to obtain the title compound as a beige color solid (0.040 g, 67%), mp: 248-249° C. HPLC 98.8% ($t_R$=6.99 min, 75% $CH_3OH$ in 0.1% TFA water, 20 min); $^1$H NMR (400 MHz, DMSO-$d_6$): δ 11.01 (s, 1H), 10.07 (s, 1H), 9.69 (brs, 1H), 8.90 (s, 1H), 8.10 (brs, 1H), 7.50-7.34 (m, 6H), 7.25 (appt, 1H), 7.11 (t, J=7.6 Hz, 1H), 6.80 (d, J=6.4 Hz, 1H), 3.71 (s, 3H), 2.76 (t, J=7.2 Hz, 2H), 1.48-1.39 (m, 2H), 0.85 (t, J=7.2 Hz, 3H); $^{19}$F NMR (376 MHz, DMSO-$d_6$): δ -116.15--116.18 (m); LC-MS (ESI+) m/z 538.14 (M+H)$^+$; HRMS (ESI+) m/z calculated for $C_{27}H_{26}ClFN_5O_2S$ (M+H)$^+$ 538.1474. found 538.1464.

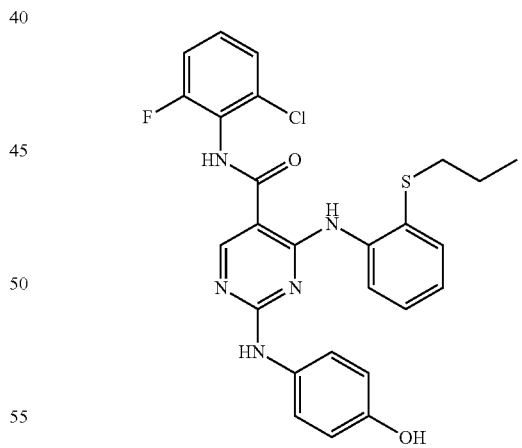

N-(2-chloro-6-fluorophenyl)-2-(4-hydroxyphenylamino)-4-(2-(propylthio)phenylamino)pyrimidine-5-carboxamide (YL7-055-4)

This compound was synthesized using the procedure described for YL7-037 except using YL7-051 (0.050 g, 0.111 mmol) and 4-aminophenol (0.015 g, 0.133 mmol) to obtain the title compound as a beige color solid (0.047 g, 81%), mp: 208° C. (dec). HPLC 99.1% ($t_R$=12.16 min, 65%

CH₃OH in 0.1% TFA water, 20 min); ¹H NMR (400 MHz, DMSO-d₆): δ 11.08 (s, 1H), 10.15 (s, 1H), 9.73 (brs, 1H), 9.20 (brs, 1H), 8.87 (s, 1H), 8.04 (brs, 1H), 7.47-7.35 (m, 6H), 7.20 (brs, 1H), 7.12 (t, J=7.6 Hz, 1H), 6.64 (d, J=6.4 Hz, 1H), 2.76 (t, J=7.2 Hz, 2H), 1.48-1.39 (m, 2H), 0.85 (t, J=7.2 Hz, 3H); ¹⁹F NMR (376 MHz, DMSO-d₆): δ −116.13−−116.17 (m); LC-MS (ESI+) m/z 524.13 (M+H)⁺; HRMS (ESI+) m/z calculated for C₂₆H₂₄ClFN₅O₂S (M+H)⁺ 524.1318. found 524.1307.

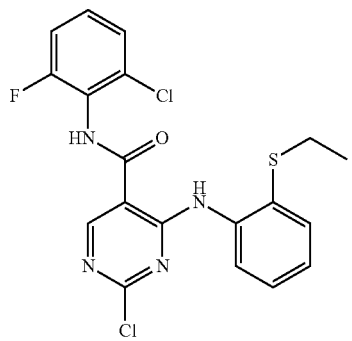 [SMILES: CCSc1ccccc1Nc1nc(Cl)ncc1C(=O)Nc1c(F)cccc1Cl]

2-Chloro-N-(2-chloro-6-fluorophenyl)-4-(2-(ethylthio)phenylamino)pyrimidine-5-carboxamide (YL7-053)

A solution of YL7-011 (7c) (1.000 g, 3.125 mmol), 2-(ethylthio)aniline (0.526 g, 3.438 mmol) and DIPEA (0.652 mL, 3.75 mmol) in THF (5 mL) was heated in microwave reactor at 120° C. for 1 h. The reaction mixture was evaporated to dryness added water (20 mL) and sonicated for 10 min. The resulting precipitate was isolated by filtration and washed with water (10 mL). The resulting light yellow solid was sonicated in DCM:Hexane (10 mL, 1:1), filtered and quickly washed with DCM (2 mL), and dried under high vacuum to afford the title compound as a white solid (1.35 g, 99%), mp: 205-208° C. ¹H NMR (400 MHz, DMSO-d₆): δ 11.04 (s, 1H), 10.67 (s, 1H), 8.99 (s, 1H), 8.04 (d, J=8.4 Hz, 1H), 7.51-7.38 (m, 4H), 7.34 (t, J=7.6 Hz, 1H), 7.19 (t, J=7.6 Hz, 1H), 2.83 (q, J=7.2 Hz, 2H), 1.10 (t, J=7.2 Hz, 3H); LC-MS (ESI+) m/z 437.04 (M+H)⁺; HRMS (ESI+) m/z calculated for C₁₉H₁₆Cl₂FN₄OS (M+H)⁺ 437.0400. found 437.0390.

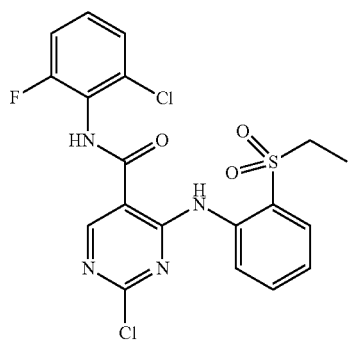 [SMILES: CCS(=O)(=O)c1ccccc1Nc1nc(Cl)ncc1C(=O)Nc1c(F)cccc1Cl]

2-Chloro-N-(2-chloro-6-fluorophenyl)-4-(2-(ethylsulfonyl)phenylamino)pyrimidine-5-carboxamide (YL7-054)

To a suspension of YL7-053 (0.740 g, 1.695 mmol) in EtOAc (40 mL), added m-CPBA (77% max, 1.146 g, 5.086 mmol) at 0° C. The mixture was warmed up to r.t. and stirred for 2 h. The resulting precipitate was filtered and washed with EtOAc (10 mL×2) to afford the pure YL7-054 (0.183 g). The filtrate was washed with sat. Na₂S₂O₃/NaHCO₃ (30 mL, 1:1), then washed with sat. NaHCO₃ (25 mL), brine (25 mL). The organic phase was dried over Na₂SO₄, filtered and concentrated to dryness to afford a light brown solid. The solid was sonicated with DCM (5 mL), filtered and washed with DCM (3 mL) to afford the second crop of pure product, which was combined with the first crop of solid to afford the title compound as a white solid (0.555 g, 70%), mp: 230-233° C. ¹H NMR (400 MHz, DMSO-d₆): δ 11.11 (s, 1H), 10.63 (s, 1H), 9.02 (s, 1H), 8.04 (d, J=8.0 Hz, 1H), 7.87 (dd, J=8.0, 1.2 Hz, 1H), 7.78 (appt, 1H), 7.50-7.40 (m, 4H), 3.23 (q, J=7.2 Hz, 2H), 1.03 (t, J=7.2 Hz, 3H); LC-MS (ESI+) m/z 469.03 (M+H)⁺; HRMS (ESI+) m/z calculated for C₁₉H₁₆Cl₂FN₄O₃S (M+H)⁺ 469.0299. found 469.0295.

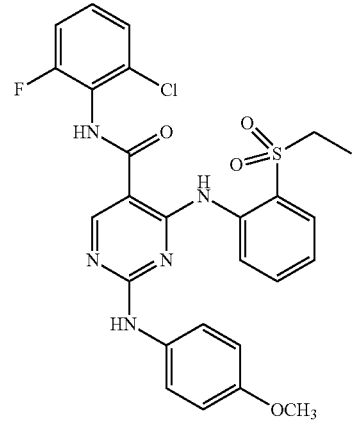 [SMILES: CCS(=O)(=O)c1ccccc1Nc1nc(Nc2ccc(OC)cc2)ncc1C(=O)Nc1c(F)cccc1Cl]

N-(2-chloro-6-fluorophenyl)-4-(2-(ethylsulfonyl)phenylamino)-2-(4-methoxyphenylamino)pyrimidine-5-carboxamide (YL7-058-1)

This compound was synthesized using the procedure described for YL7-037 except using YL7-054 (0.055 g, 0.117 mmol) and 4-methoxyaniline (0.017 g, 0.141 mmol) to obtain the title compound as a light brown color solid (0.045 g, 69%), mp: 263-265° C. HPLC 95.7% ($t_R$=4.95 min, 65% CH₃OH in 0.1% TFA water, 20 min); ¹H NMR (400 MHz, DMSO-d₆): δ 11.03 (s, 1H), 10.08 (s, 1H), 9.78 (brs, 1H), 9.15 (brs, 1H), 8.93 (s, 1H), 8.08 (brs, 1H), 7.85 (dd, J=8.0, 1.2 Hz, 1H), 7.74 (appt, 1H), 7.47-7.34 (m, 6H), 6.74 (brs, 2H), 3.69 (s, 3H), 3.16 (q, J=7.2 Hz, 2H), 0.98 (t, J=7.2 Hz, 3H); ¹⁹F NMR (376 MHz, DMSO-d₆): δ −116.00−−116.03 (m); LC-MS (ESI+) m/z 556.13 (M+H)⁺; HRMS (ESI+) m/z calculated for C₂₆H₂₄ClFN₅O₄S (M+H)⁺ 556.1216. found 556.1199.

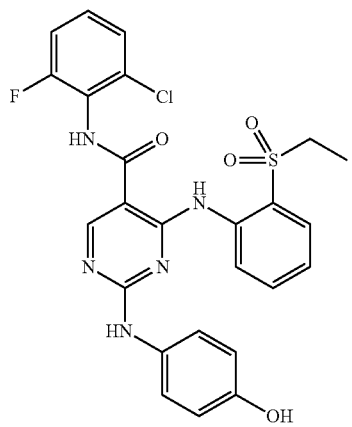 [SMILES: CCS(=O)(=O)c1ccccc1Nc1nc(Nc2ccc(O)cc2)ncc1C(=O)Nc1c(F)cccc1Cl]

N-(2-chloro-6-fluorophenyl)-4-(2-(ethylsulfonyl)
phenylamino)-2-(4-hydroxyphenylamino)pyrimidine-5-carboxamide (YL7-058-2)

This compound was synthesized using the procedure described for YL7-037 except using YL7-054 (0.051 g, 0.117 mmol) and 4-aminophenol (0.015 g, 0.141 mmol) to obtain the title compound as a beige color solid (0.043 g, 68%), mp: 201° C. (dec). HPLC 96.1% ($t_R$=5.53 min, 55% CH$_3$OH in 0.1% TFA water, 20 min); $^1$H NMR (400 MHz, DMSO-d$_6$): δ 11.16 (s, 1H), 10.25 (s, 1H), 9.96 (brs, 1H), 8.93 (s, 1H), 8.02 (brs, 1H), 7.86 (d, J=7.6 Hz, 1H), 7.72 (t, J=7.6 Hz, 1H), 7.45-7.26 (m, 6H), 6.56 (brs, 2H), 3.13 (appq, 2H), 0.98 (brs, 3H); $^{19}$F NMR (376 MHz, DMSO-d$_6$): δ-115.98 (brs); LC-MS (ESI+) m/z 542.11 (M+H)$^+$; HRMS (ESI+) m/z calculated for C$_{25}$H$_{22}$ClFN$_5$O$_4$S (M+H)$^+$ 542.1060. found 542.1052.

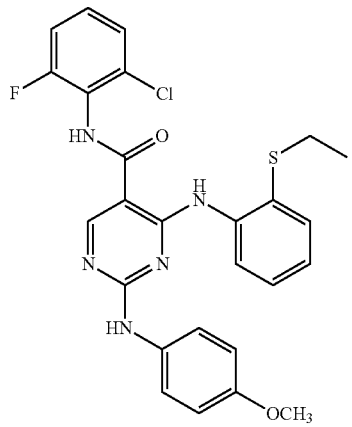 [SMILES: CCSc1ccccc1Nc1nc(Nc2ccc(OC)cc2)ncc1C(=O)Nc1c(F)cccc1Cl]

N-(2-chloro-6-fluorophenyl)-4-(2-(ethylthio)phenylamino)-2-(4-methoxyphenylamino)pyrimidine-5-carboxamide (YL7-058-3)

This compound was synthesized using the procedure described for YL7-037 except using YL7-053 (0.051 g, 0.117 mmol) and 4-methoxyaniline (0.017 g, 0.141 mmol) to obtain the title compound as a beige color solid (0.043 g, 70%), mp: 250° C. (dec). HPLC 98.5% ($t_R$=5.66 min, 75% CH$_3$OH in 0.1% TFA water, 20 min); $^1$H NMR (400 MHz, DMSO-d$_6$): δ 11.15 (s, 1H), 10.26 (s, 1H), 9.96 (brs, 1H), 8.90 (s, 1H), 8.02 (brs, 1H), 7.48-7.35 (m, 6H), 7.25 (appt, 1H), 7.15 (t, J=7.6 Hz, 1H), 6.56 (appd, J=5.6 Hz, 2H), 3.72 (s, 3H), 2.81 (q, J=7.2 Hz, 2H), 1.09 (t, J=7.2 Hz, 3H); $^{19}$F NMR (376 MHz, DMSO-d$_6$): δ -116.11-116.14 (m); LC-MS (ESI+) m/z 524.13 (M+H)$^+$; HRMS (ESI+) m/z calculated for C$_{26}$H$_{24}$ClFN$_5$O$_2$S (M+H)$^+$ 524.1318. found 524.1317.

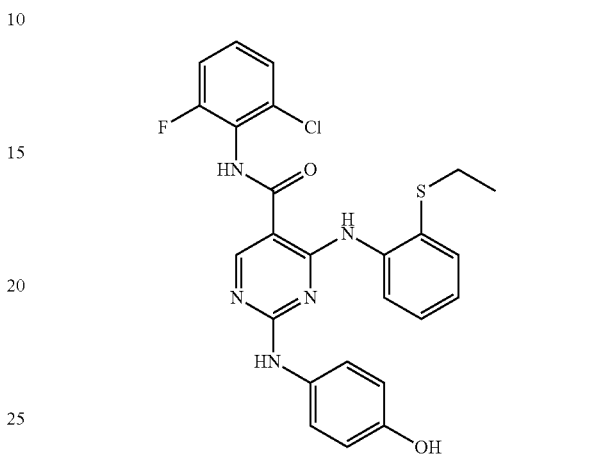

N-(2-chloro-6-fluorophenyl)-4-(2-(ethylthio)phenylamino)-2-(4-hydroxyphenylamino)pyrimidine-5-carboxamide (YL7-058-4)

This compound was synthesized using the procedure described for YL7-037 except using YL7-053 (0.051 g, 0.117 mmol) and 4-aminophenol (0.015 g, 0.141 mmol) to obtain the title compound as a light brown color solid (0.058 g, 97%), mp: 233° C. (dec). HPLC 98.6% ($t_R$=7.86 min, 65% CH$_3$OH in 0.1% TFA water, 20 min); $^1$H NMR (400 MHz, DMSO-d$_6$): δ 10.99 (s, 1H), 10.05 (s, 1H), 9.60 (brs, 1H), 9.14 (s, 1H), 8.88 (s, 1H), 8.08 (brs, 1H), 7.46-7.34 (m, 6H), 7.21 (brs, 1H), 7.10 (t, J=7.6 Hz, 1H), 6.62 (appd, J=6.8 Hz, 2H), 2.80 (q, J=7.2 Hz, 2H), 1.09 (t, J=7.2 Hz, 3H); $^{19}$F NMR (376 MHz, DMSO-d$_6$): δ -116.12--116.16; MS (ESI+) m/z 510.13 (M+H)$^+$; HRMS (ESI+) m/z calculated for C$_{25}$H$_{22}$ClFN$_5$O$_2$S (M+H)$^+$ 510.1161. found 510.1154.

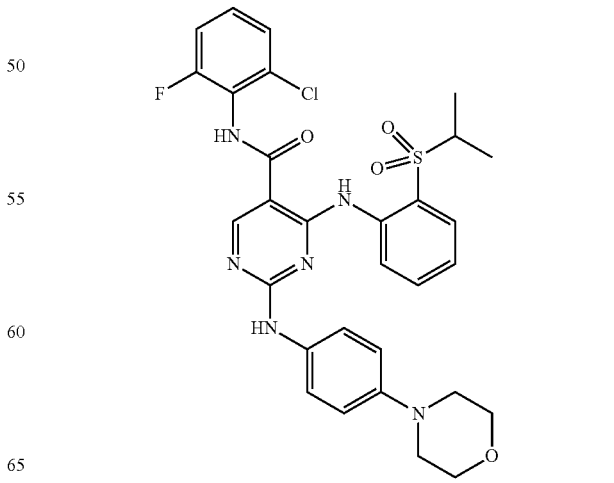

N-(2-chloro-6-fluorophenyl)-4-(2-(isopropylsulfonyl)phenylamino)-2-(4-morpholinophenylamino)pyrimidine-5-carboxamide (YL7-097-1)

A mixture of YL7-041 (0.054 g, 0.112 mmol), 4-morpholinoaniline (0.024 g, 0.134 mmol), 4 M HCl in dioxane (0.035 mL, 0.132 mmol) in dioxane (0.5 mL) was heated in microwave reactor at 180° C. for 30 min. The solvent was removed and the mixture was re-dissolved in DMC (15 mL) and washed with sat. NaHCO$_3$ (10 mL). The organic layer was dried over Na$_2$SO$_4$, filtered and concentrated to dryness. The crude material was crystallized with EtOAC/Hex (5 mL, 1:1) to afford the title compound as a grey color solid (0.051 g, 73%), mp: 220° C. (dec). HPLC 99.3% ($t_R$=12.33 min, 55% CH$_3$OH in 0.1% TFA water, 20 min); $^1$H NMR (400 MHz, DMSO-d$_6$): δ 11.08 (s, 1H), 10.06 (s, 1H), 9.77 (brs, 1H), 8.91 (s, 1H), 8.09 (brs, 1H), 7.83 (dd, J=8.0, 1.2 Hz, 1H), 7.74 (appt, 1H), 7.47-7.34 (m, 6H), 6.74 (brs, 2H), 3.71 (t, J=4.4 Hz, 4H), 3.00 (appt, 4H), 1.07 (d, J=6.4 Hz, 6H); $^{19}$F NMR (376 MHz, DMSO-d$_6$): δ −116.13−−116.17 (m); LC-MS (ESI+) m/z 625.17 (M+H)$^+$; HRMS (ESI+) m/z calculated for C$_{30}$H$_{31}$ClFN$_6$O$_4$S (M+H)$^+$ 625.1795. found 625.1784.

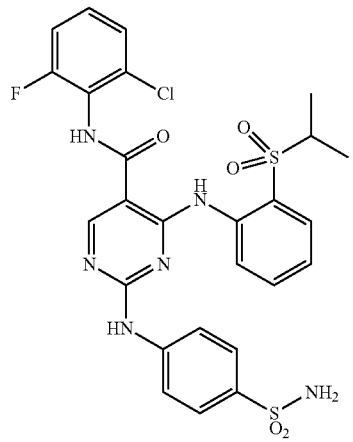 [SMILES: CC(C)S(=O)(=O)c1ccccc1Nc1nc(Nc2ccc(S(N)(=O)=O)cc2)ncc1C(=O)Nc1c(F)cccc1Cl]

N-(2-chloro-6-fluorophenyl)-4-(2-(isopropylsulfonyl)phenylamino)-2-(4-sulfamoyl)phenylamino)pyrimidine-5-carboxamide (YL7-100-1)

A mixture of YL7-041 (0.054 g, 0.112 mmol), 4-aminobenzenesulfonamide (0.023 g, 0.134 mmol), 4 M HCl in dioxane (0.035 mL, 0.132 mmol) in dioxane (0.5 mL) was heated in microwave reactor at 180° C. for 30 min. The solvent was removed and the mixture was re-dissolved with EtOAC (20 mL) and washed with aq. HCl (1M, 15 mL), then sat. NaHCO$_3$ (15 mL). The organic layer was dried over Na$_2$SO$_4$, filtered and concentrated to dryness to afford the title compound as a creamy color solid (0.058 g, 84%), mp: 192° C. (dec). HPLC 92.1% ($t_R$=9.38 min, 55% CH$_3$OH in 0.1% TFA water, 20 min); $^1$H NMR (400 MHz, DMSO-d$_6$): δ 11.08 (s, 1H disappear on D$_2$O shake), 10.29 (brs, 1H disappear on D$_2$O shake), 10.23 (s, 1H disappear on D$_2$O shake), 9.02 (s, 1H), 8.07 (brd, J=7.6 Hz, 1H), 7.89 (d, J=8.0 Hz, 1H), 7.79 (t, J=7.6 Hz, 1H), 7.72 (d, J=6.8 Hz, 2H), 7.56-7.35 (m, 6H), 7.19 (brs, 2H disappear on D$_2$O shake), 3.31-3.24 (m, 1H), 1.06 (d, J=6.8 Hz, 6H); $^{19}$F NMR (376 MHz, DMSO-d$_6$): δ −116.09−−116.13 (m); LC-MS (ESI+) m/z 619.07 (M+H)$^+$; HRMS (ESI+) m/z calculated for C$_{26}$H$_{25}$ClFN$_6$O$_5$S$_2$ (M+H)$^+$ 619.0995. found 619.0988.

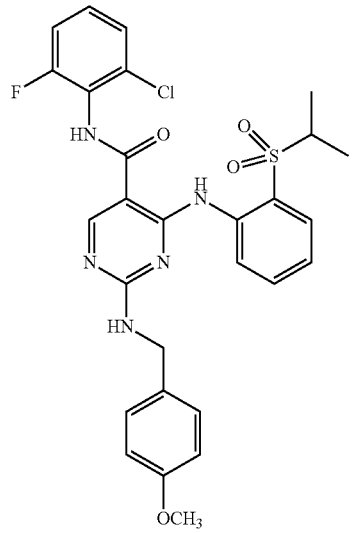 [SMILES: COc1ccc(CNc2ncc(C(=O)Nc3c(F)cccc3Cl)c(Nc3ccccc3S(=O)(=O)C(C)C)n2)cc1]

N-(2-chloro-6-fluorophenyl)-4-(2-(isopropylsulfonyl)phenylamino)-2-(4-methoxybenzylamino)pyrimidine-5-carboxamide (YL7-106-1)

The mixture of YL7-041 (0.054 g, 0.112 mmol), (4-methoxyphenyl)methanamine (0.018 g, 0.134 mmol) and 4M HCl in dioxane (0.034 mL) in dioxane was heated in a microwave reactor at 180° C. for 30 minutes. The dioxane was removed under reduced pressure. The resulting precipitate was slurried in ethyl acetate (3 mL) and sonicated. The precipitate was filtered. The solid was then slurried and sonicated in saturated NaHCO$_3$ (3 mL×2), filtered, washed with water (3 mL×3), and dried under high vacuum to afford the title compound as a white solid (0.058 g, 89%). Mp: 227° C. (dec); HPLC 99.1% ($t_R$=5.66 min, 65% CH$_3$OH in 0.1% TFA water, 20 min); The $^1$H NMR showed 2:1 ratio of atropisomers. $^1$H NMR (400 MHz, DMSO-d$_6$): δ 11.04 (s, 1H, [11.02 minor isomer]), 9.93 (s, 1H, [9.95 minor isomer]), 8.80 (s, 1H, [8.82 minor isomer]), 8.31-8.27 (m, 1H), 7.93 (d, J=8.4 Hz, 1H), 7.79 (dd, J=7.6, 1.2 Hz, 1H), 7.58 (appt, J=7.6 Hz, 1H, [7.68 minor isomer]), 7.45-7.30 (m, 4H), 6.99 (d, J=8.4 Hz, 2H, [7.23 minor isomer]), 6.74 (d, J=8.8 Hz, 2H, [6.85 minor isomer]), 4.24 (d, J=6.4 Hz, 2H, [4.44 minor isomer]), 3.66 (s, 3H, [3.70 minor isomer]), 3.22-3.15 (m, 1H), 1.00 (d, J=6.8 Hz, [1.09 minor isomer]); $^{19}$F NMR (376 MHz, DMSO-d$_6$): δ −114.49 (s, [−114.10 minor isomer]); LC-MS (ESI+) m/z 584.12 (M+H)$^+$; HRMS (ESI+) m/z calculated for C$_{28}$H$_{28}$ClFN$_5$O$_4$S (M+H)$^+$ 584.1529. found 584.1515.

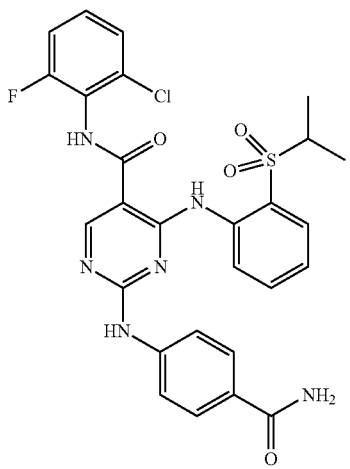 [SMILES: CC(C)S(=O)(=O)c1ccccc1Nc1nc(Nc2ccc(C(N)=O)cc2)ncc1C(=O)Nc1c(F)cccc1Cl]

2-(4-Carbamoylphenylamino)-N-(2-chloro-6-fluorophenyl)-4-(2-(isopropylsulfonyl)phenylamino)pyrimidine-5-carboxamide (YL7-106-3)

This compound was synthesized according to the procedure for YL7-106-1 except using YL7-041 (0.054 g, 0.112 mmol) and 4-aminobenzamide (0.018 g, 0.134 mmol) to afford the title compound as a beige colored solid (0.051 g, 78%). Mp: 230° C. (dec); HPLC 93.9% ($t_R$=10.61 min, 55% $CH_3OH$ in 0.1% TFA water, 20 min); $^1H$ NMR (400 MHz, DMSO-$d_6$): δ 11.09 (s, 1H), 10.21 (s, 1H), 10.18 (s, 1H), 9.01 (s, 1H), 8.08 (br d, J=7.6 Hz, 1H), 7.88 (d, J=8.0 Hz, 1H), 7.83-7.79 (m, 2H), 7.64 (br s, 4H), 7.52-7.35 (m, 4H), 7.20 (br s, 1H), 3.31-3.24 (m, 1H), 1.07 (d, J=6.8 Hz, 6H); $^{19}F$ NMR (376 MHz, DMSO-$d_6$): δ −116.09−−116.12 (m); LC-MS (ESI+) m/z 583.12 (M+H)$^+$; HRMS (ESI+) m/z calculated for $C_{27}H_{24}ClFN_6O_4SNa$ (M+Na)$^+$ 605.1145. found 605.1138.

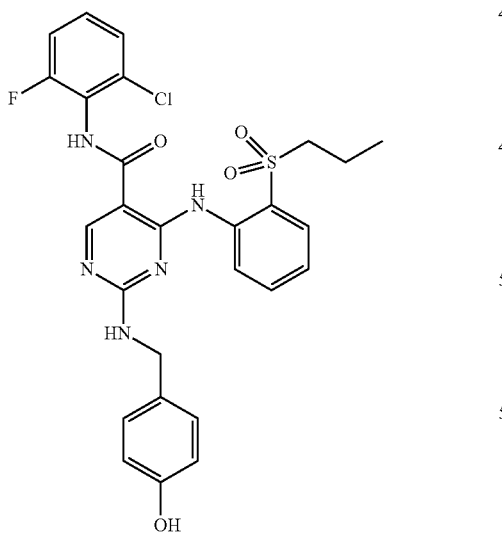

N-(2-chloro-6-fluorophenyl)-4-(2-(isopropylsulfonyl)phenylamino)-2-(4-sulfamoylphenylamino)pyrimidine-5-carboxamide (YL7-109)

To a solution of 4-(aminomethyl)phenol (0.015 g, 0.124 mmol) in DMF (0.7 mL) at 0° C. was added EtN(iPr)$_2$ (0.016 g, 0.124 mmol) and stirred for an hour, followed by the addition of 11c YL7-052 (0.050 g, 0.104 mmol). The mixture was heated at 100° C. for 20 h (reaction was monitored by HPLC-MS). 1M HCl (20 mL) was added upon cooling. The resulting solution was extracted with EtOAc (50 mL). The organic phase was washed with sat. $NaHCO_3$ (20 mL), then dried over $Na_2SO_4$, filtered, and concentrated to dryness. The resulting solid was recrystalized with EtOAc/Hexane (3 mL/5 mL), sonicated, and filtered, and dried under high vacuum to afford the title compound as a white solid (0.053 g, 90%). Mp: 187° C. (dec). HPLC 93.9% ($t_R$=7.87 min, 55% $CH_3OH$ in 0.1% TFA water, 20 min); The $^1H$ NMR showed 2:1 ratio of atropisomers. $^1H$ NMR (400 MHz, DMSO-$d_6$): δ 10.98 (s, 1H, [10.96 minor isomer]), 9.94 (s, 1H, [9.97 minor isomer]), 9.20 (s, 1H, [9.24 minor isomer]), 8.82 (s, 1H, [8.84 minor isomer]), 8.24 (t, J=6.4 Hz, 1H), 7.92 (d, J=8.4 Hz, 1H), 7.82 (d, J=8.0 Hz, 1H), 7.57 (t, J=7.6 Hz, 1H, [7.66 minor isomer]), 7.44-7.30 (m, 4H), 6.85 (d, J=8.4 Hz, 2H, [7.09 minor isomer]), 6.57 (d, J=8.4 Hz, 2H, [6.66 minor isomer]), 4.18 (d, J=6.0 Hz, 2H, [4.40 minor isomer]), 3.04 (t, J=7.6 Hz, 2H, [3.15 minor isomer]), 1.40-1.34 (m, 2H, [1.52-1.46 minor isomer]), 0.66 (t, J=7.6 Hz, [0.78 minor isomer]); $^{19}F$ NMR (376 MHz, DMSO-$d_6$): δ −116.12−−116.18 (m); LC-MS (ESI+) m/z 570.13 (M+H)$^+$; HRMS (ESI+) m/z calculated for $C_{27}H_{26}ClFN_5O_4S$ (M+H)$^+$ 570.1373. found 570.1387.

The following syntheses make reference to Schemes 3 and 4.

Scheme 3: Design and synthesis of bisanilinopyrimidine library with (±)-tetrahydrofurfurylamine A-ring.

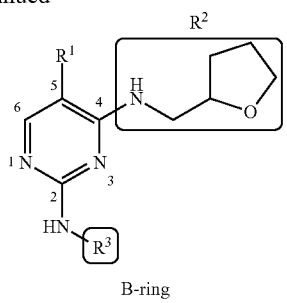

B-ring 7a, 8a: R¹ = Cl
7b, 8b: R¹ = Br
7c, 8c: R¹ = 2-Chloro-6-fluorocarboxamide
7d, 8d: R¹ = F
7e, 8e: R¹ = Me

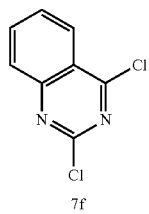

7f

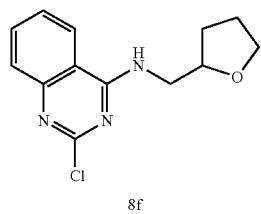

8f

R³ Aniline groups

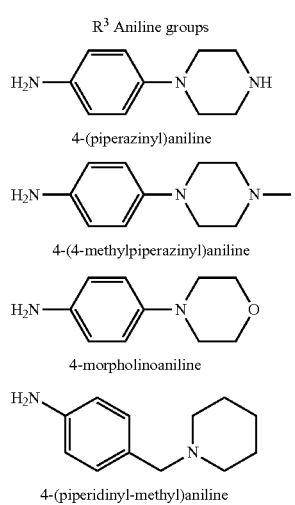

4-(piperazinyl)aniline 4-(4-methylpiperazinyl)aniline 4-morpholinoaniline 4-(piperidinyl-methyl)aniline

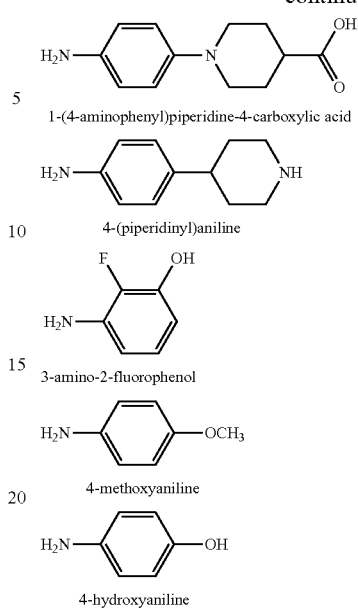

1-(4-aminophenyl)piperidine-4-carboxylic acid 4-(piperidinyl)aniline 3-amino-2-fluorophenol 4-methoxyaniline 4-hydroxyaniline Method a: (±)-Tetrahydrofurfurylamine, Et₃N, MeOH, 0° C.-r.t., 2 h. Method b: Cat. 4M HCl in dioxane, 2-methoxyethanol, sealed tube, 110° C., and aq. NaHCO₃ work-up.

Scheme 4: Synthesis of (R)-9b and (S)-9b as ACK1 inhibitors. The other represented chiral compounds were synthesized using the protocal in Scheme 4.

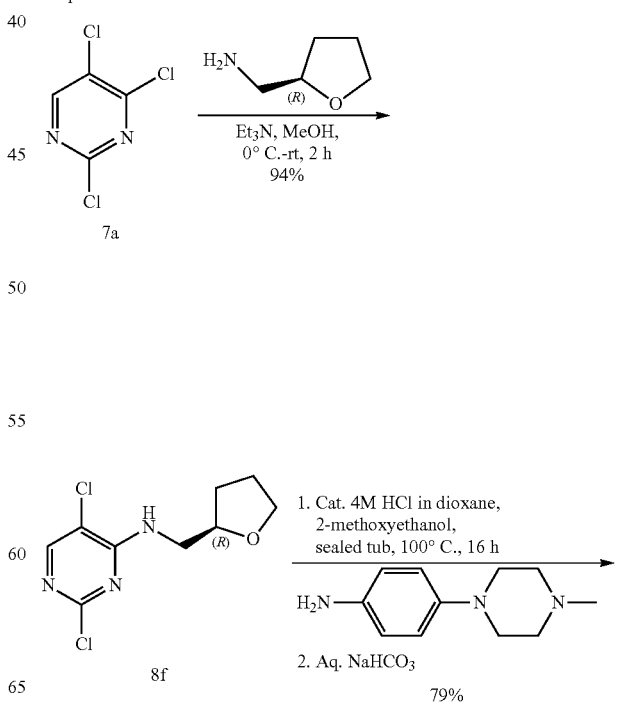

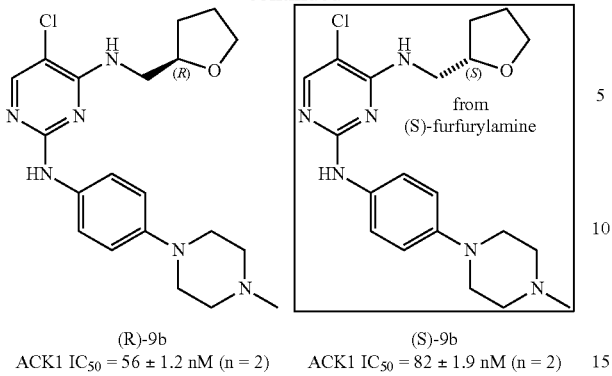

(R)-9b
ACK1 IC$_{50}$ = 56 ± 1.2 nM (n = 2)

(S)-9b
from (S)-furfurylamine
ACK1 IC$_{50}$ = 82 ± 1.9 nM (n = 2)

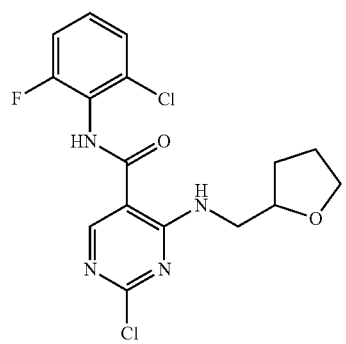 [SMILES: O=C(Nc1c(F)cccc1Cl)c1cnc(Cl)nc1NCC1CCCO1]

2-Chloro-N-(2-chloro-6-fluorophenyl)-4-((tetrahydrofuran-2-yl)methylamino)pyrimidine-5-carboxamide (YL7-102, 8c)

To a solution of (tetrahydrofuran-2-yl)methanamine (0.121 g, 1.2 mmol) in MeOH (2 mL) was added Et$_3$N (0.167 mL, 1.2 mmol) at 0° C. under inert atmosphere. After stirring at 0° C. for 10 min, YL7-011 (7c) (0.320 g, 1.0 mmol) in DMF (0.5 mL) was added dropwise. The mixture was warmed to r.t and stirred for 30 min. The solvent was removed and the crude mixture was purified by SiO$_2$ chromatography (silica gel, 10 g, 0-30% gradient EtOAC/Hexane) to afford the title compound as a pure white solid (0.283 g, 74%), mp: 142° C. (dec). $^1$H NMR (400 MHz, CDCl$_3$): δ 8.88 (appt, 1H), 8.55 (s, 1H), 7.58 (brs, 1H), 7.30-7.23 (m, 2H), 7.15-7.12 (m, 1H), 4.12-4.06 (m, 1H), 3.91-3.85 (m, 1H), 3.80-3.72 (m, 2H), 3.54-3.48 (m, 1H), 2.07-1.99 (m, 1H), 1.94-1.86 (m, 2H), 1.64-1.56 (m, 1H); LC-MS (ESI+) m/z 385.07 (M+H)$^+$; HRMS (ESI+) m/z calculated for C$_{16}$H$_{16}$Cl$_2$FN$_4$O$_2$ (M+H)$^+$ 385.0629. found 385.0623.

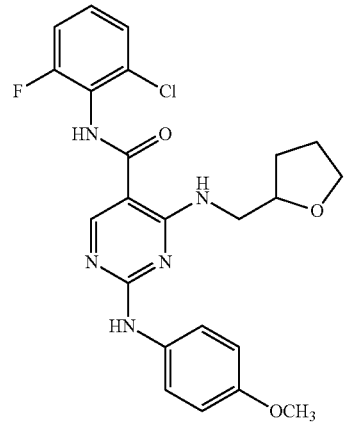 [SMILES: COc1ccc(Nc2ncc(C(=O)Nc3c(F)cccc3Cl)c(NCC3CCCO3)n2)cc1]

N-(2-chloro-6-fluorophenyl)-2-(4-methoxyphenylamino)-4-((tetrahydrofuran-2-yl)methylamino)pyrimidine-5-carboxamide (YL7-104-1)

This compound was synthesized using the procedure described for YL7-037 except using YL7-102 (8c, Scheme 3) (0.050 g, 0.130 mmol) and 4-methoxyaniline (0.019 g, 0.156 mmol) to obtain the title compound as a white solid (0.051 g, 84%), mp: 201° C. (dec). HPLC 99.5% (t$_R$=4.37 min, 65% CH$_3$OH in 0.1% TFA water, 20 min); $^1$H NMR (400 MHz, DMSO-d$_6$): δ 10.22 (s, 1H), 10.06 (brs, 1H), 9.27 (brs, 1H), 8.72 (s, 1H), 7.54 (d, J=7.6 Hz, 2H), 7.45-7.32 (m, 3H), 6.93 (d, J=8.8 Hz, 2H), 4.04-3.98 (m, 1H), 3.75-3.70 (m, 4H), 3.61-3.55 (m, 3H), 1.95-1.87 (m, 1H), 1.82-1.76 (m, 2H), 1.56-1.48 (m, 1H); $^{19}$F NMR (376 MHz, DMSO-d$_6$): δ −116.16-116.19 (m); LC-MS (ESI+) m/z 472.14 (M+H)$^+$; HRMS (ESI+) m/z calculated for C$_{23}$H$_{24}$ClFN$_5$O$_3$ (M+H)$^+$ 472.1546. found 472.1548.

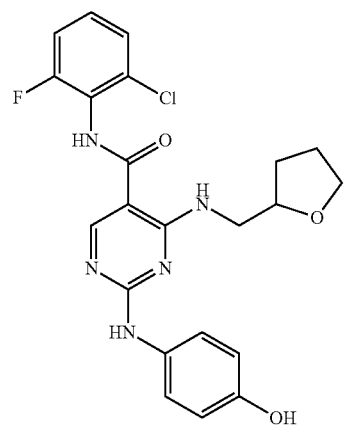 [SMILES: O=C(Nc1c(F)cccc1Cl)c1cnc(Nc2ccc(O)cc2)nc1NCC1CCCO1]

N-(2-chloro-6-fluorophenyl)-2-(4-hydroxyphenylamino)-4-((tetrahydrofuran-2-yl)methylamino)pyrimidine-5-carboxamide (YL7-104-2)

This compound was synthesized using the procedure described for YL7-037 except using YL7-102 (8c, Scheme 3) (0.050 g, 0.130 mmol) and 4-aminophenol (0.017 g, 0.156 mmol) to obtain the title compound as a beige color solid (0.046 g, 78%). Mp: 263° C. (dec). HPLC 99.4% (t$_R$=6.77 min, 55% CH$_3$OH in 0.1% TFA water, 20 min); $^1$H NMR (400 MHz, DMSO-d$_6$): δ 9.82 (s, 1H), 9.41 (brs, 1H), 9.09 (s, 1H), 8.83 (s, 1H), 8.72 (s, 1H), 7.49 (d, J=8.4 Hz, 2H), 7.43-7.30 (m, 3H), 6.67 (d, J=8.8 Hz, 2H), 4.02-3.98 (m, 1H), 3.76-3.71 (m, 1H), 3.62-3.57 (m, 2H), 3.42-3.37 (m, 1H), 1.93-1.87 (m, 1H), 1.84-1.75 (m, 2H), 1.56-1.47 (m, 1H); $^{19}$F NMR (376 MHz, DMSO-d$_6$): δ −116.15--116.19 (m); LC-MS (ESI+) m/z 458.13 (M+H)$^+$; HRMS (ESI+) m/z calculated for C$_{22}$H$_{22}$ClFN$_5$O$_3$ (M+H)$^+$ 458.1390. found 458.1390.

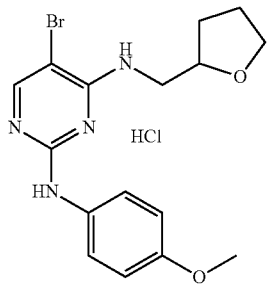

SK1-022

5-Bromo-N2-(4-methoxyphenyl)-N4-((tetrahydrofuran-2-yl)methyl)pyrimidine-2,4-diamine (SK1-022)

A suspension of SK1-008 (8b, Scheme 3) (100 mg, 0.34 mmol) and 4-amino-2-chlorophenol (40 mg, 0.32 mmol) in EtOH (2 mL) was heated in a microwave reactor at 150° C. for 20 minutes. The mixture was concentrated, added. EtOAc (3 mL) and the resulting mixture was sonicated for 5 minutes and filtered. The precipitate was washed again with EtOAc (2 mL) and dried under high vacuum to afford the title compound as a grey color solid (129 mg, 99%). HPLC-MS (ESI+) m/z 379.1 and 381.1 for Br-isotopes (M+H)$^+$; LC-MS (ESI+) m/z 381.0754; HRMS (ESI+) m/z calculated for C$_{16}$H$_{19}$BrN$_4$O$_2$ (M+H)$^+$ 379.0764 found 379.0766.

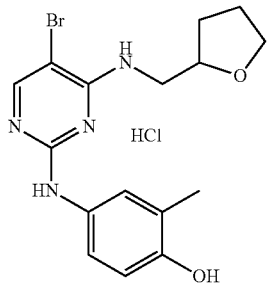

SK1-040

4-(5-bromo-4-((tetrahydrofuran-2-yl)methylamino) pyrimidin-2-ylamino)-2-methylphenol (SK1-040)

A suspension of SK1-008 (8b, Scheme 3) (400 mg, 1.4 mmol) and 4-amino-2-chlorophenol (168 mg, 1.4 mmol) in EtOH (3-4 mL) was heated in a microwave reactor at 150° C. for 20 minutes. The mixture was concentrated, added. EtOAc (3 mL) and the resulting mixture was sonicated for 5 minutes and filtered. The precipitate was washed again with EtOAc (2-5 mL) and dried under high vacuum to afford the title compound as a grey color solid (600 mg, 99%). HPLC-MS (ESI+) m/z 379.1 and 381.1 for Br-isotopes (M+H)$^+$; LC-MS (ESI+) m/z 381.0754; HRMS (ESI+) m/z calculated for C$_{16}$H$_{19}$BrN$_4$O$_2$ (M+H)$^+$ 379.0764 found 379.0760.

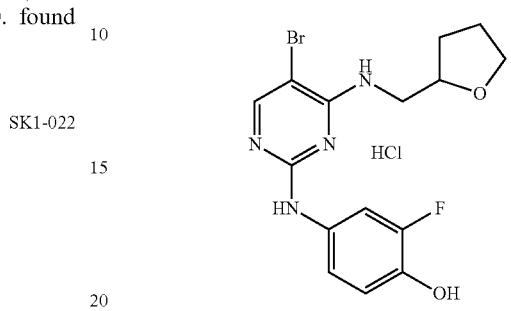

SK1-044

4-(5-bromo-4-((tetrahydrofuran-2-yl)methylamino) pyrimidin-2-ylamino)-2-fluorophenol (SK1-044)

A suspension of SK1-008 (8b, Scheme 3) (400 mg, 1.4 mmol) and 4-amino-2-chlorophenol (168 mg, 1.4 mmol) in EtOH (3 mL) was heated in a microwave reactor at 150° C. for 20 minutes. The mixture was concentrated, added. EtOAc (3 mL) and the resulting mixture was sonicated for 5 minutes and filtered. The precipitate was washed again with EtOAc (2-5 mL) and dried under high vacuum to afford the title compound as a grey color solid (600 mg, 98%). HPLC-MS (ESI+) m/z 383.1 and 385.2 for Br-isotopes (M+H)$^+$; HRMS (ESI+) m/z calculated for C$_{15}$H$_{16}$BrFN$_4$O$_2$ (M+H)$^+$ 383.0531 found 383.0525.

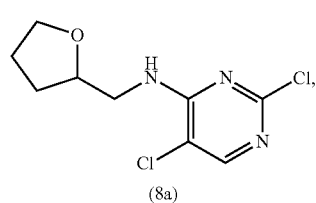

MH1-004

(8a)

2,5-dichloro-N-((tetrahydrofuran-2-yl)methyl)pyrimidin-4-amine (MH1-004) (8a)

Tetrahydrofurfurylamine (1.103 g, 10.90 mmol) in MeOH (10 ml) was added drop-wise to a solution of 2,4,5-trichloropyrimidine (2.000 g, 10.90 mmol) and triethylamine (1.103 g, 10.90 mmol) in MeOH (10 ml) at 0° C., and allowed to react for an hour under argon. After this time, the reaction mixed was allowed to warm to room temperature. The solvent was removed under reduced pressure, and the solid re-suspended in water, then filtered out (washing with water), and dried under vacuum to afford the title as a white solid (2.387 g, 9.62 mmol, 88%). HPLC-MS (m/z 248.1) 98.6% [R$_f$=11.14 min, Grad. MeOH-water 5-95 (with 0.1% formic acid) 20 min]; $^1$H NMR (400 MHz, CDCl$_3$) δ 8.01 (s, 1H), 5.91 (s, 1H), 4.09 (qd, J=7.3, 3.3 Hz, 1H), 3.94-3.86 (m, 1H), 3.86-3.75 (m, 2H), 3.41 (ddd, J=13.7, 7.7, 4.8 Hz, 1H), 2.11-2.00 (m, 1H), 1.98-1.89 (m, 2H), 1.64-1.54 (m, 1H).

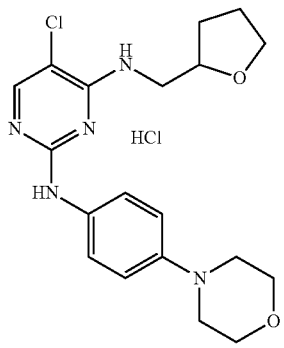

5-chloro-N2-(4-morpholinophenyl)-N4-((tetrahydro-furan-2-yl)methyl)pyrimidine-2,4-diamine hydrochloride (MH1-006-3)

The MH1-004 (0.100 g, 0.403 mmol) and 4-morpholinoaniline (0.072 g, 0.403 mmol) were mixed in EtOH (1 ml) in a 5 ml microwave vial, and heated to 150° C. for 20 minutes in a microwave. The solid product was filtered out of the resulting mixture, washing with ethyl acetate, and subsequently dried under reduced pressure to afford the product as a off white solid (0.072 g, 0.185 mmol, 46%). HPLC-MS (m/z 390.2 (M-Cl)$^+$) 99.0% [$R_t$=9.90 min, Grad. MeOH-water 5-95 (with 0.1% formic acid) 20 min]; $^1$H NMR (400 MHz, CDCl$_3$) δ 10.32 (s, 1H), 7.67 (s, 1H), 7.45 (d, J=9.0 Hz, 2H), 6.91 (d, J=8.4 Hz, 2H), 6.62 (t, J=5.2 Hz, 1H), 4.09 (qd, J=7.1, 3.2 Hz, 1H), 3.95-3.75 (m, 7H), 3.44 (ddd, J=13.1, 7.6, 5.0 Hz, 1H), 3.22-3.10 (m, 4H), 2.11-1.99 (m, 1H), 1.99-1.88 (m, 2H), 1.64-1.51 (m, 1H). LC-MS (ESI+) m/z 390.17 (M-Cl)$^+$; HRMS (ESI+) m/z calculated for C$_{19}$H$_{25}$ClN$_5$O$_2$$^+$ (M-Cl)$^+$ 390.1691. found, 390.1694.

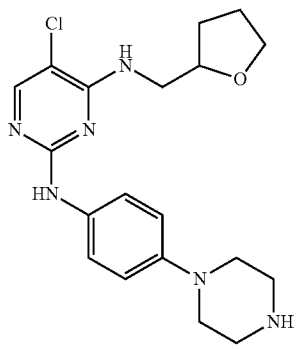

5-chloro-N2-(4-(piperazin-1-yl)phenyl)-N4-((tetrahydrofuran-2-yl)methyl)pyrimidine-2,4-diamine (MH1-007-3)

The MH1-004 (0.100 g, 0.403 mmol) and 1-boc-4-(4'-aminophenyl)piperazine (0.112 g, 0.403 mmol) were mixed in EtOH (1 ml) in a 5 ml microwave vial, and heated to 150° C. for 20 minutes in a microwave, after which a drop of concentrated HCl was added, before returning it to the microwave for a further 20 minutes at 150° C. The solid precipitate produced was filtered out of the mixture and washed with a saturated solution of NaHCO$_3$, and the solid product again collected by filtration. The resulting white solid was dried under reduced pressure (0.074 g, 0.190 mmol, 47%). HPLC-MS {m/z 195.2 [(M+2H)/2]$^{2+}$} 97.8% [$R_t$=6.99 min, Grad. MeOH-water 5-95 (with 0.1% formic acid) 20 min]; $^1$H NMR (400 MHz, DMSO-d$_6$) δ 8.93 (s, 1H), 7.86 (s, 1H), 7.50 (d, J=9.0 Hz, 2H), 7.00 (t, J=5.7 Hz, 1H), 6.79 (d, J=9.1 Hz, 2H), 4.10-4.03 (m, 1H), 3.75 (dd, J=13.6, 7.5 Hz, 1H), 3.60 (dd, J=14.5, 7.4 Hz, 1H), 3.41 (t, J=6.0 Hz, 3H), 2.96-2.88 (m, 4H), 2.84-2.76 (m, 4H), 1.94-1.72 (m, 3H), 1.64-1.53 (m, 1H). LC-MS (ESI+) m/z 389.19 (M+H)$^+$; HRMS (ESI+) m/z calculated for C$_{19}$H$_{26}$ClN$_6$O$^+$ (M+H)$^+$ 389.1851. found, 389.1860.

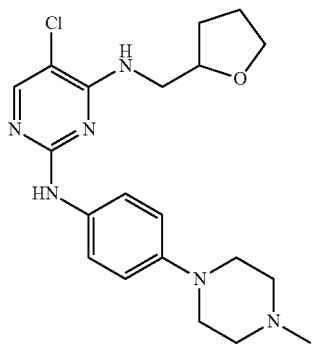

5-chloro-N2-(4-(4-methylpiperazin-1-yl)phenyl)-N4-((tetrahydrofuran-2-yl)methyl)pyrimidine-2,4-diamine (MH1-022-5)

The MH1-004 (0.100 g, 0.403 mmol) and 4-(4-methylpiperazin-1-yl)aniline (0.077 g, 0.403 mmol) were mixed in t-BuOH (2 ml) in a 5 ml microwave vial under argon with Xphos (0.019 g, 0.040 mmol), Pd(dba)$_2$ (0.023 g, 0.040 mmol) and K$_2$CO$_3$ (0.122 g, 0.887 mmol). The reaction mixture was heated on a heating block at 105° C. for 80 hours. The reaction mixture was filtered to remove the catalyst, washed with MeOH, and the crude product was then purified using automated flash chromatography (hexane/EtOAc/MeOH), and the solvent removed, to give a yellow solid (0.014 g, 0.035 mmol, 9%). HPLC-MS {m/z 202.3 [(M+2H)/2]$^{2+}$} 95.3% [$R_t$=7.10 min, Grad. MeOH-water 5-95 (with 0.1% formic acid) 20 min]; $^1$H NMR (400 MHz, CD$_3$OD) δ 7.77 (s, 1H), 7.46 (d, J=6.1 Hz, 2H), 6.93 (d, J=6.0 Hz, 2H), 4.20-4.09 (m, 1H), 3.86 (m, 1H), 3.78-3.70 (m, 1H), 3.54 (ddd, J=20.5, 13.6, 5.9 Hz, 2H), 3.19-3.11 (m, 4H), 2.71-2.62 (m, 4H), 2.38 (s, 3H), 2.04-1.80 (m, 3H), 1.70-1.59 (m, 1H). LC-MS (ESI+) m/z 403.20 (M+H)$^+$; HRMS (ESI+) m/z calculated for C$_{20}$H$_{28}$ClN$_6$O$^+$ (M+H)$^+$ 403.2008. found, 403.2040.

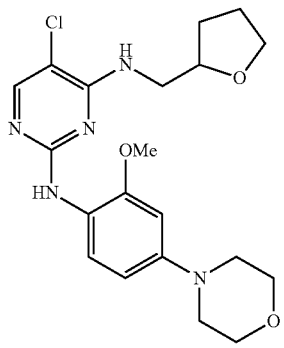

MH1-030-4

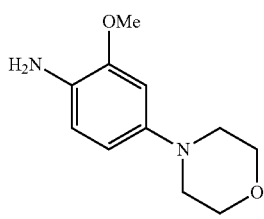

MH1-028

5-chloro-N2-(2-methoxy-4-morpholinophenyl)-N4-((tetrahydrofuran-2-yl)methyl)pyrimidine-2,4-diamine (MH1-030-4)

The MH1-004 (0.100 g, 0.403 mmol) and MH1-028 (0.084 g, 0.403 mmol) were mixed in EtOH (1 ml) in a sealed 5 ml microwave vial, and run for a 20 min cycle in the microwave at 150° C. Saturated NaHCO$_3$ (10 ml) and EtOAc (20 ml) was added, and the organic layer separated, dried (MgSO$_4$), filtered and the solvent removed under reduced pressure. The crude product was purified using flash chromatography (EtOAc/hexanes/MeOH). The obtained solid was suspended in MeOH, filtered, and washed with MeOH, followed by diethyl ether, to afford the product as a pale yellow solid (0.061 g, 0.145 mmol, 36%). HPLC-MS (m/z 420.3 (M+H)) 95.2% [R$_t$=9.76 min, Grad. MeOH-water 5-95 (with 0.1% formic acid) 20 min]; $^1$H NMR (400 MHz, CD$_3$OD) δ 8.02 (d, J=8.8 Hz, 1H), 7.78 (s, 1H), 6.65 (d, J=2.5 Hz, 1H), 6.54 (dd, J=8.8, 2.5 Hz, 1H), 4.21-4.13 (m, 1H), 3.93 (s, 1H), 3.88 (s, 3H), 3.86-3.81 (m, 4H), 3.75 (dd, J=14.4, 7.4 Hz, 1H), 3.56 (ddd, J=20.5, 13.6, 5.9 Hz, 2H), 3.41-3.37 (m, 1H), 3.14-3.07 (m, 4H), 2.06-1.84 (m, 3H), 1.73-1.61 (m, 1H). LC-MS (ESI+) m/z 420.18 (M+H)$^+$; HRMS (ESI+) m/z calculated for C$_{20}$H$_{27}$ClN$_5$O$_3^+$ (M+H)$^+$ 420.1797. found, 420.1825.

MH1-035-3

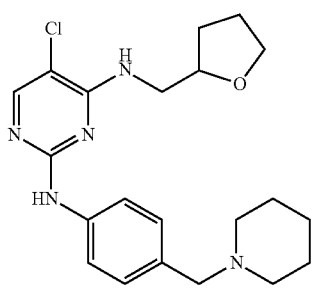

5-chloro-N2-(4-(piperidin-1-ylmethyl)phenyl)-N4-((tetrahydrofuran-2-yl)methyl)pyrimidine-2,4-diamine (MH1-035-3)

The MH1-004 (0.100 g, 0.403 mmol) and 4-piperidin-1-ylmethylphenylamine (0.107 g, 0.564 mmol) were mixed in 2-methoxyethanol (1.5 ml), and 0.05 ml of 12 M aqueous HCl solution added. The reaction mixture was heated in an oil bath at 120° C. with stirring for 5.5 hrs, and then allowed to cool to room temperature. The solvent was evaporated under reduced pressure and saturated NaHCO$_3$ solution (10 ml) added, followed by EtOAc (20 ml). The organic layer was extracted and dried with anhydrous MgSO$_4$, and the solvent evaporated. The resulting solid was slurried in diethyl ether and filtered to afford the product as a white powder (0.051 g, 0.127 mmol, 31%). HPLC-MS {m/z 201.7 [(M+2H)/2]$^{2+}$} 98.0% [R$_t$=8.09 min, Grad. MeOH-water 5-95 (with 0.1% formic acid) 20 min]; $^1$H NMR (400 MHz, CD$_3$OD) δ 7.82 (s, 1H), 7.58 (d, J=8.6 Hz, 2H), 7.23 (d, J=8.6 Hz, 2H), 4.22-4.13 (m, 1H), 3.89 (dd, J=13.3, 6.6 Hz, 1H), 3.75 (dd, J=14.3, 7.4 Hz, 1H), 3.58 (ddd, J=20.6, 13.7, 5.9 Hz, 2H), 3.45 (s, 2H), 2.43 (s, 4H), 2.08-1.83 (m, 3H), 1.73-1.64 (m, 1H), 1.64-1.55 (m, 4H), 1.46 (s, 2H). LC-MS (ESI+) m/z 317.12 (M-Piperidine)$^+$; HRMS (ESI+) m/z calculated for C$_{21}$H$_{29}$ClN$_5$O$^+$ (M+H)$^+$ 402.2055. found, 402.2063.

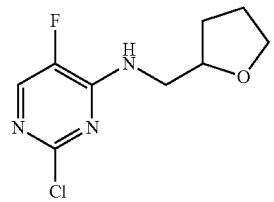 [SMILES: Fc1cnc(Cl)nc1NCC1CCCO1]

2-Chloro-5-fluoro-N-((tetrahydrofuran-2-yl)methyl)pyrimidin-4-amine (YL7-160, 8d, Scheme 3)

To a solution of (tetrahydrofuran-2-yl)methanamine (0.607 g, 6 mmol) in MeOH (10 mL) was added triethylamine under argon at 0° C. The mixture was stirred at 0° C. for 10 minutes, then 2,4-dichloro-5-fluoropyrimidine 7d (0.835 g, 5 mmol) in MeOH (4 mL) was added dropwise at 0° C. The reaction mixture was warmed up to room temperature and stirred for 2 hours. The solvent was removed And the resulting precipitate was dissolved in EtOAc (30 mL), washed with water (2×20 mL). The organic phase was dried over Na$_2$SO4, filtered, and concentrated to dryness. The crude material obtained was purified by SiO$_2$ chromatography (silica gel, 20 g, EtOAc/Hexane, 0%-25%) to afford the title compound as a white solid (0.936 g, 81%). Mp: 77-78° C.; $^1$H NMR (400 MHz, CDCl$_3$): δ 7.86 (d, J=2.8 Hz, 1H), 5.63 (br s, 1H), 4.08 (ddd, J=14.8, 7.2, 3.2 Hz, 1H), 3.92-3.76 (m, 3H), 3.37 (ddd, J=13.6, 8.0, 4.4 Hz, 1H), 2.10-2.02 (m, 1H), 1.97-1.90 (m, 2H), 1.64-1.56 (m, 2H); HPLC-MS (ESI+) m/z 232.1 (M+H)$^+$.

123

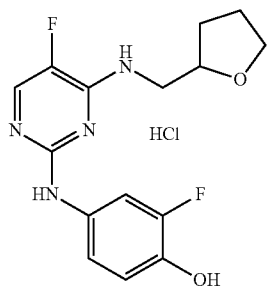 [SMILES: Oc1ccc(Nc2ncc(F)c(NCC3CCCO3)n2)cc1F ; Cl]

2-Fluoro-4-(5-fluoro-4-((tetrahydrofuran-2-yl)methylamino)pyrimidin-2-ylamino)phenol hydrochloride (YL7-164)

A mixture of YL7-160 (8d) (0.116 g, 0.5 mmol) and 4-amino-2-fluorophenol (0.064 g, 0.5 mmol) in EtOH (2 mL) was heated with a microwave reactor at 150° C. for 20 minutes. The solvent was removed and the resulting residue was slurried and sonicated with EtOAc (3 mL); the resulting mixture was filtered, and the precipitate was washed with EtOAc (2 mL), then dried under high vacuum to afford the title compound as a dark brown color solid (0.152 g, 84%). Mp: 201° C. (dec.). HPLC 98.5% ($t_R$=7.72 min, 35% CH$_3$OH in 0.1% TFA water, 20 min); $^1$H NMR (400 MHz, DMSO-d$_6$): δ 10.23 (s, 1H), 9.87 (br s, 1H), 10.18 (s, 1H), 9.19 (br s, 1H), 8.08 (d, J=5.2 Hz, 1H), 7.43 (dd, J=13.2, 2.0 Hz, 1H), 7.01 (dd, J=8.8, 1.6 Hz, 1H), 6.94 (t, J=9.6 Hz, 1H), 4.07-4.01 (m, 1H), 3.75-3.69 (m, 1H), 3.63-3.58 (m, 1H), 1.93-1.85 (m, 1H), 1.83-1.75 (m, 2H), 1.59-1.51 (m, 1H); $^{19}$F NMR (376 MHz, DMSO-d$_6$): δ −134.70 (s), −163.23 (s); LC-MS (ESI+) m/z 323.14 (M+H)$^+$; HRMS (ESI+) m/z calculated for C$_{15}$H$_{17}$F$_2$N$_4$O$_2$ (M+H)$^+$ 323.1314. found 323.1314.

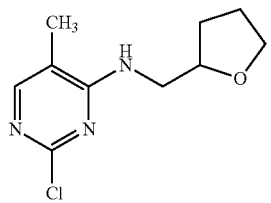

2-Chloro-5-methyl-N-((tetrahydrofuran-2-yl)methyl)pyrimidin-4-amine (YL7-167 8e, Scheme 3)

This compound was synthesized according to the procedure described for YL7-160 (8d, Scheme 3) except using 2,4-dichloro-5-methylpyrimidine (2.680 g, 16.440 mmol) in MeOH (20 mL) and (tetrahydrofuran-2-yl)methanamine (1.997 g, 19.730 mmol) in MeOH (5 mL) and triethylamine (2.750 mL) to afford the title compound as a white solid (1.997 g, 53%). Mp: 86-89° C.; $^1$H NMR (400 MHz, CDCl$_3$): δ 7.78 (d, J=0.8 Hz, 1H), 5.24 (br t, 1H), 4.10-4.04 (m, 1H), 3.90-3.81 (m, 2H), 3.80-3.74 (m, 1H), 3.33 (ddd, J=13.6, 8.0, 4.4 Hz, 1H), 2.08-2.01 (m, 2H), 1.99 (d, J=0.8 Hz, 3H), 1.95-1.88 (m, 2H), 1.63-1.54 (m, 1H); HPLC-MS (ESI+) m/z 228.1 (M+H)$^+$.

124

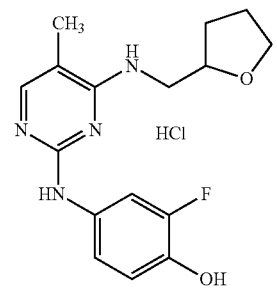 [SMILES: Cc1cnc(Nc2ccc(O)c(F)c2)nc1NCC1CCCO1 ; Cl]

2-Fluoro-4-(5-methyl-4-((tetrahydrofuran-2-yl)methylamino)pyrimidin-2-ylamino)phenol hydrochloride (YL7-170-1)

To a suspension of YL7-167 (8e, Scheme 3) (0.114 g, 0.5 mmol) and 4-amino-2-fluorophenol (0.064 g, 0.5 mmol) in EtOH (1 mL) was heated in a microwave reactor at 150° C. for 20 minutes. The mixture was concentrated to dryness and the resulting residue was then recrystalized with MeOH/EtOAc, filtered, and washed with EtOAc (2 mL) to afford the title compound as a dark brown color solid. The filtrate was concentrated and recrystalized again with MeOH/EtOAc to afford 2$^{nd}$ crop of solid. The solid was combined to afford the title compound as a dark brown color solid (0.163 g, 92%). Mp: 199° C. (dec.). HPLC 98.8% ($t_R$=12.26 min, 35% CH$_3$OH in 0.1% TFA water, 20 min); $^1$H NMR (400 MHz, CD$_3$OD): δ 7.45 (s, 1H), 7.29 (dd, J=12.0, 1.6 Hz, 1H), 7.03-6.93 (m, 2H), 4.20-4.13 (m, 1H), 3.88-3.83 (m, 1H), 3.78-3.72 (m, 1H), 3.64-3.51 (m, 2H), 2.04 (s, 3H), 1.96-1.87 (m, 2H), 1.66-1.57 (m, 1H); $^{19}$F NMR (376 MHz, CD$_3$OD): δ −136.94 (s); LC-MS (ESI+) m/z 319.16 (M+H)$^+$; HRMS (ESI+) m/z calculated for C$_{16}$H$_{20}$FN$_4$O$_2$ (M+H)$^+$ 319.1565. found 319.1566.

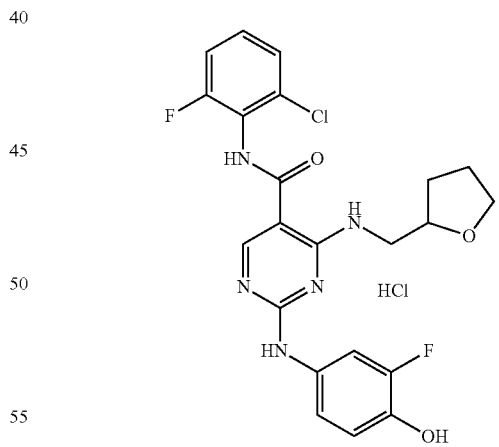

N-(2-chloro-6-fluorophenyl)-2-(3-fluoro-4-hydroxyphenylamino)-4-((tetrahydrofuran-2-yl)methylamino)pyrimidine-5-carboxamide hydrochloride (YL7-170-2)

This compound was synthesized according to the procedure described for YL7-170-1 except using YL7-102 (8c, Scheme 3) (0.050 g, 0.130 mmol), 4-amino-2-fluorophenol (0.017 g, 0.130 mmol) and EtOH (1 mL). The EtOAc/

Hexane was used for recrystallization to afford the title compound as a brown color solid (0.051 g, 76%). Mp: 183° C. (dec.). HPLC 99.4% ($t_R$=6.53 min, 55% $CH_3OH$ in 0.1% TFA water, 20 min); $^1H$ NMR (400 MHz, $CD_3OD$): δ 8.54 (s, 1H), 7.43-7.38 (m, 3H), 7.24-7.19 (m, 1H), 7.10 (d, J=8.4 Hz, 1H), 6.96 (t, J=8.4 Hz, 1H), 4.15-4.09 (m, 1H), 3.90-3.85 (m, 1H), 3.77-3.59 (m, 3H), 2.05-1.99 (m, 1H), 1.96-1.88 (m, 1H), 1.67-1.58 (m, 1H); $^{19}F$ NMR (376 MHz, $CD_3OD$): δ −118.25 (d); LC-MS (ESI+) m/z 476.12 (M+H)$^+$; HRMS (ESI+) m/z calculated for $C_{22}H_{21}F_2N_5O_3$ (M+H)$^+$ 476.1296. found 476.1290.

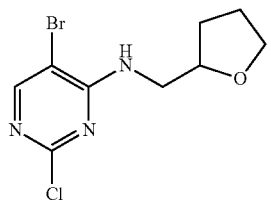

5-Bromo-2-chloro-N-((tetrahydrofuran-2-yl)methyl) pyrimidin-4-amine (SK1-008-B2 8b, Scheme 3)

This compound was synthesized using the same procedure described for YL7-160 (8d, Scheme 3), except using 5-bromo-2,4-dichloropyrimidine 7b (Scheme 3) (0.500 g, 2.195 mmol) in MeOH (2 mL) and (tetrahydrofuran-2-yl) methanamine (0.222 g, 2.195 mmol) in MeOH (2 mL) and triethylamine (0.305 mL, 2.195 mmol) to afford the title compound as a white solid (0.620 g, 97%). Mp: 85-86° C.; $^1H$ NMR (400 MHz, DMSO-$d_6$): δ 8.23 (s, 1H), 7.62 (t, J=6.0 Hz, 1H), 4.03-3.98 (m, 1H), 3.77-3.71 (m, 1H), 3.62-3.57 (m, 1H), 3.45-3.38 (m, 1H), 3.36-3.30 (m, 1H), 1.90-1.75 (m, 3H), 1.60-1.52 (m, 1H). HPLC-MS (ESI+) m/z 292 and 294.1 for Br-isotopes (M+H)$^+$.

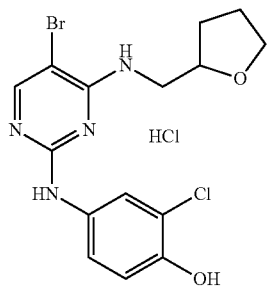 [SMILES: Oc1ccc(Nc2ncc(Br)c(NCC3CCCO3)n2)cc1Cl ; Cl]

4-(5-Bromo-4-((tetrahydrofuran-2-yl)methylamino) pyrimidin-2-ylamino)-2-chlorophenol hydrochloride (YL7-172-1)

A suspension of SK1-008 (8b, Scheme 3) (0.073 g, 0.250 mmol) and 4-amino-2-chlorophenol (0.036 g, 0.250 mmol) in EtOH (1 mL) was heated in a microwave reactor at 150° C. for 20 minutes. The mixture was concentrated, added. EtOAc (3 mL) and the resulting mixture was sonicated for 5 minutes and filtered. The precipitate was washed again with EtOAc (2 mL) and dried under high vacuum to afford the title compound as a grey color solid (0.071 g, 65%). Mp: 193° C. (dec.); HPLC 94.0% ($t_R$=6.50 min, 45% $CH_3OH$ in 0.1% TFA water, 20 min); $^1H$ NMR (400 MHz, $CD_3OD$): δ 7.96 (s, 1H), 7.51 (s, 1H), 7.15 (dd, J=8.8, 2.4 Hz, 1H), 6.96 (d, J=8.4 Hz, 1H), 4.18-4.11 (m, 1H), 3.86-3.80 (m, 1H), 3.76-3.71 (m, 1H), 3.56 (appt. d, J=6.0 Hz, 2H), 2.05-1.97 (m, 1H), 1.93-1.86 (m, 2H), 1.65-1.56 (m, 1H); LC-MS (ESI+) m/z 399.02 and 401.02 for Br-isotopes (M+H)$^+$; HRMS (ESI+) m/z calculated for $C_{15}H_{17}BrClN_4O_2$ (M+H)$^+$ 399.0218. found 399.0213.

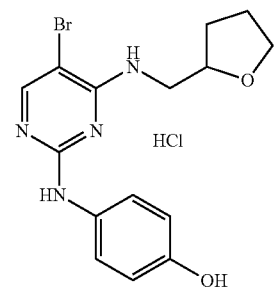 [SMILES: Oc1ccc(Nc2ncc(Br)c(NCC3CCCO3)n2)cc1 ; Cl]

4-(5-Bromo-4-((tetrahydrofuran-2-yl)methylamino) pyrimidin-2-ylamino)phenol hydrochloride (SK1-028)

This compound was synthesized according to the procedure described for YL7-172-1 except using SK1-008 (8b, Scheme 3) (0.073 g, 0.250 mmol) and 4-aminophenol (0.027 g, 0.250 mmol) in EtOH (1 mL). The product was slurried with DCM/Hexane (3 mL) to afford the title compound as a white solid (0.078 g, 78%). Mp: 206-207° C. HPLC 99.4% ($t_R$=6.50 min, 35% $CH_3OH$ in 0.1% TFA water, 20 min); $^1H$ NMR (400 MHz, $CD_3OD$): δ 7.89 (s, 1H), 7.21 (d, J=8.4 Hz, 2H), 6.85 (d, J=8.8 Hz, 2H), 4.18-4.13 (m, 1H), 3.86-3.81 (m, 1H), 3.77-3.71 (m, 1H), 3.57 (appt. d, J=4.8 Hz, 2H), 2.01-1.88 (m, 3H), 1.65-1.59 (m, 1H); LC-MS (ESI+) m/z 365.07 and 367.07 for Br-isotopes (M+H)$^+$; HRMS (ESI+) m/z calculated for $C_{15}H_{18}BrN_4O_2$ (M+H)$^+$ 365.0608. found 365.0606.

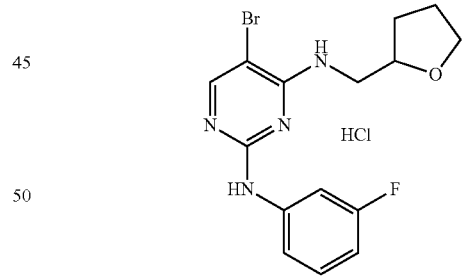

5-Bromo-N2-(3-fluorophenyl)-N4-((tetrahydrofuran-2-yl)methyl)pyrimidine-2,4-diamine hydrochloride (YL7-172-3)

This compound was synthesized using the procedure described for YL7-172-2 except using SK1-008 (8b, Scheme 3) (0.073 g, 0.250 mmol), 3-fluoroaniline (0.028 g, 0.250 mmol) in EtOH (1 mL). The product was recrystalized with DCM/Hexane (2/5) to afford the title compound as a white solid (0.080 g, 79%). %). Mp: 194-197° C.; HPLC 98.4% ($t_R$=15.31 min, 45% $CH_3OH$ in 0.1% TFA water, 20 min); $^1H$ NMR (400 MHz, $CD_3OD$): δ 8.06 (s, 1H), 7.49-7.40 (m, 2H), 7.25 (ddd, J=8.0, 2.0, 0.8 Hz, 1H), 7.00 (tdd, J=8.4, 2.4, 0.8 Hz, 1H), 4.20-4.14 (m, 1H), 3.87-3.82 (m, 1H), 3.77-3.71 (m, 1H), 3.62 (d, J=6.0 Hz, 2H), 2.07-1.99 (m, 1H), 1.96-1.87 (m, 2H), 1.67-1.59 (m, 1H); $^{19}$F NMR (376 MHz, CD$_3$OD): δ −113.53; LC-MS (ESI+) m/z 367.05 and 369.05 for Br-isotopes (M+H)$^+$; HRMS (ESI+) m/z calculated for C$_{15}$H$_{17}$BrFN$_4$O (M+H)$^+$ 367.0564. found 367.0562.

CD$_3$OD): δ 8.08 (s, 1H), 7.93 (d, J=8.8 Hz, 2H), 7.65 (d, J=8.4 Hz, 2H), 4.21-4.14 (m, 1H), 3.87-3.82 (m, 1H), 3.77-3.72 (m, 1H), 3.64-3.62 (m, 2H), 2.27 (s, 3H), 2.07-1.99 (m, 1H), 1.96-1.90 (m, 2H), 1.70-1.62 (m, 1H); LC-MS (ESI+) m/z 392.07 and 394.07 for Br-isotopes (M+H)$^+$; HRMS (ESI+) m/z calculated for C$_{16}$H$_{19}$BrN$_5$O$_2$ (M+H)$^+$ 392.0717. found 392.0711.

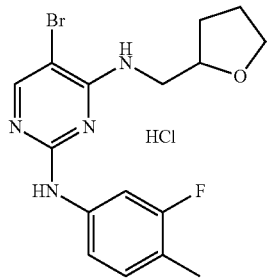 [SMILES: Cc1ccc(Nc2ncc(Br)c(NCC3CCCO3)n2)cc1F ; Cl]

5-Bromo-N2-(3-fluoro-4-methylphenyl)-N4-((tetrahydrofuran-2-yl)methyl)pyrimidine-2,4-diamine hydrochloride (YL7-172-4)

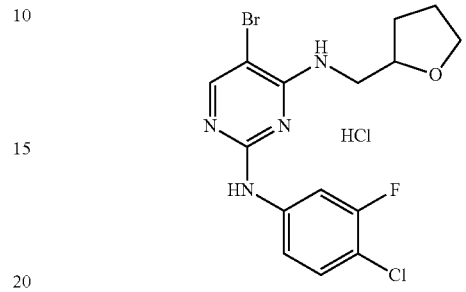

5-Bromo-N2-(4-chloro-3-fluorophenyl)-N4-((tetrahydrofuran-2-yl)methyl)pyrimidine-2,4-diamine hydrochloride (YL7-172-7)

This compound was synthesized using the procedure described for YL7-172-2, except using 3-fluoro-4-methylaniline (0.031 g, 0.250 g) to afford the title compound as a white solid (0.090 g, 87%). Mp: 189° C. (dec.); HPLC 98.2% (t$_R$=8.67 min, 45% CH$_3$OH in 0.1% TFA water, 20 min); $^1$H NMR (400 MHz, CD$_3$OD): δ 8.03 (s, 1H), 7.36 (d, J=11.2 Hz, 1H), 7.29 (t, J=8.4 Hz, 1H), 7.13 (dd, J=8.4, 2.0 Hz, 1H), 4.20-4.13 (m, 1H), 3.87-3.82 (m, 1H), 3.77-3.71 (m, 1H), 3.60 (d, J=6.4 Hz, 2H), 2.27 (s, 3H), 2.06-1.98 (m, 1H), 1.96-1.87 (m, 2H), 1.67-1.58 (m, 1H); $^{19}$F NMR (376 MHz, CD$_3$OD): δ −117.36; LC-MS (ESI+) m/z 381.08 and 383.08 for Br-isotopes (M+H)$^+$; HRMS (ESI+) m/z calculated for C$_{16}$H$_{19}$BrFN$_4$O (M+H)$^+$ 381.0721. found 381.0720.

This compound was synthesized using the procedure described for YL7-172-2 except using 4-chloro-3-fluoroaniline (0.035 g, 0.250 mmol) to afford the title compound as a white solid (0.076 g, 70%). Mp: 172° C. (dec.); HPLC 98.5% (t$_R$=14.23 min, 55% CH$_3$OH in 0.1% TFA water, 20 min); $^1$H NMR (400 MHz, CD$_3$OD): δ 8.07 (s, 1H), 7.68 (dd, J=11.2, 2.4 Hz, 1H), 7.49 (t, J=8.4 Hz, 1H), 7.26 (ddd, J=8.8, 2.4, 1.2 Hz, 1H), 4.19-4.13 (m, 1H), 3.86-3.83 (m, 1H), 3.77-3.72 (m, 1H), 3.61 (d, J=6.0 Hz, 2H), 2.07-1.99 (m, 1H), 1.97-1.89 (m, 2H), 1.68-1.60 (m, 1H); $^{19}$F NMR (376 MHz, CD$_3$OD): δ −115.76; LC-MS (ESI+) m/z 401.03 and 403.01 for Br-isotopes (M+H)$^+$; HRMS (ESI+) m/z calculated for C$_{15}$H$_{16}$BrClFN$_4$O (M+H)$^+$ 401.0175. found 401.0175.

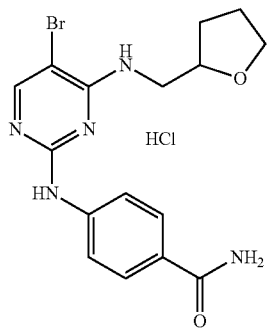 [SMILES: NC(=O)c1ccc(Nc2ncc(Br)c(NCC3CCCO3)n2)cc1 ; Cl]

4-(5-Bromo-4-((tetrahydrofuran-2-yl)methylamino)pyrimidin-2-ylamino)benzamide hydrochloride (YL7-172-5)

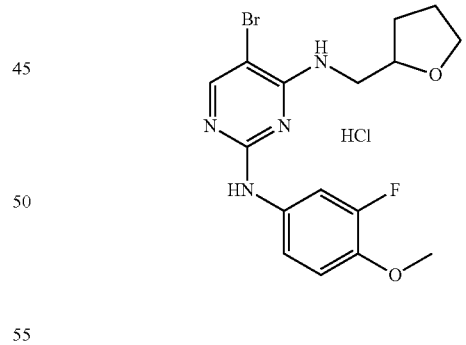

5-Bromo-N2-(3-fluoro-4-methoxyphenyl)-N4-((tetrahydrofuran-2-yl)methyl)pyrimidine-2,4-diamine hydrochloride (YL7-172-8)

This compound was synthesized using the procedure described for YL7-172-2, except using 4-aminobenzamide (0.034 g, 0.250 mmol) and recrystallized with MeOH/DCM (1/2) to afford the title compound as a white solid (0.079 g, 75%). Mp: 251° C. (dec.). HPLC 98.8% (t$_R$=7.44 min, 35% CH$_3$OH in 0.1% TFA water, 20 min); $^1$H NMR (400 MHz, This compound was synthesized using the procedure described for YL7-172-2 except using 3-fluoro-4-methoxyaniline (0.035 g, 0.250 mmol) to afford the title compound as a purple color solid (0.070 g, 65%). Mp: 169° C. (dec.). HPLC 97.4% (t$_R$=4.21 min, 55% CH$_3$OH in 0.1% TFA water, 20 min); $^1$H NMR (400 MHz, CD$_3$OD): δ 7.98 (s, 1H), 7.38 (d, J=12.8 Hz, 1H), 7.18-7.13 (m, 2H), 4.18-4.12 (m, 1H), 3.87-3.81 (m, 1H), 3.77-3.71 (m, 1H), 3.58 (d, J=6.0 Hz, 2H), 2.05-1.96 (m, 1H), 1.95-1.89 (m, 2H), 1.66-1.57 (m, 1H); $^{19}$F NMR (376 MHz, CD$_3$OD): δ −134.79; LC-MS (ESI+) m/z 397.07 and 399.07 for Br-isotopes (M+H)$^+$; HRMS (ESI+) m/z calculated for C$_{16}$H$_{19}$BrFN$_4$O$_2$ (M+H)$^+$ 397.0670. found 397.0667.

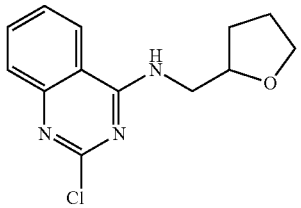 [SMILES: Clc1nc(NCC2CCCO2)c2ccccc2n1]

2-Chloro-N-((tetrahydrofuran-2-yl)methyl)quinazolin-4-amine (YL7-176, 8f, Scheme 3)

To a solution of (tetrahydrofuran-2-yl)methanamine (0.620 mL, 6.000 mmol) in MeOH (10 mL) was added triethylamine (0.836 mL) at 0° C. under argon. The mixture was stirred at 0° C. for 10 minutes and 2,4-dichloroquinazoline (7f) (1.000 g, 5.000 mmol) in DCM (5 mL) was added drop wise at 0° C. After the addition, the reaction mixture was warmed up to r.t. and stirred for 30 minutes. The solvent was removed and water (30 mL) was added to the resulting residue. The suspension was sonicated, filtered and washed with water (10 mL×2), then dried under high vacuum to afford the title compound as a white solid (1.309 g, 99%). Mp: 132-135° C.; $^1$H NMR (400 MHz, CDCl$_3$): δ 7.78-7.71 (m, 3H), 7.45 (td, J=8.0, 1.6 Hz, 1H), 6.46 (s, 1H), 4.18 (ddd, J=16.0, 7.6, 3.6 Hz, 1H), 4.05 (ddd, J=13.6, 6.4, 3.2 Hz, 1H), 3.97-3.91 (m, 1H), 3.86-3.80 (m, 1H), 2.15-2.07 (m, 1H), 2.00-1.93 (m, 2H), 1.71-1.62 (m, 1H); HPLC-MS (ESI+) m/z 264.2 (M+H)$^+$.

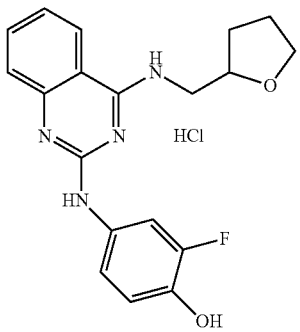 [SMILES: Oc1ccc(Nc2nc(NCC3CCCO3)c3ccccc3n2)cc1F ; Cl]

2-Fluoro-4-(4-((tetrahydrofuran-2-yl)methylamino) quinazolin-2-ylamino)phenol hydrochloride (YL8-001)

This compound was synthesized using the procedure described for YL7-172-2 except using YL7-176 (8f, Scheme 3) (0.066 g, 0.250 mmol) and 4-amino-2-fluorophenol (0.032 g, 0.250 mmol) and recrystalized with MeOH/DCM/Hexane (5 mL, 1:4:5) to afford the title compound as a grey color solid (0.077 g, 79%). Mp.: 144° C. (dec.); HPLC 98.6% (t$_R$=9.31 min, 45% CH$_3$OH in 0.1% TFA water, 20 min); $^1$H NMR (400 MHz, CD$_3$OD): δ 8.14 (d, J=8.4 Hz, 1H), 7.81 (t, J=7.6 Hz, 1H), 7.52 (d, J=8.4 Hz, 1H), 7.47 (td, J=7.6, 0.8 Hz, 1H), 7.32 (d, J=12.4 Hz, 1H), 7.07 (ddd, J=8.4, 2.4, 0.1.2 Hz, 1H), 7.00 (t, J=8.4 Hz, 1H), 4.27-4.21 (m, 1H), 3.79-3.74 (m, 2H), 3.67-3.63 (m, 1H), 2.08-2.00 (m, 1H), 1.97-1.87 (m, 2H), 1.69-1.61 (m, 1H); LC-MS (ESI+) m/z 355.15 (M+H)$^+$; HRMS (ESI+) m/z calculated for C$_{19}$H$_{20}$FN$_4$O$_2$ (M+H)$^+$ 355.1565. found 355.1564.

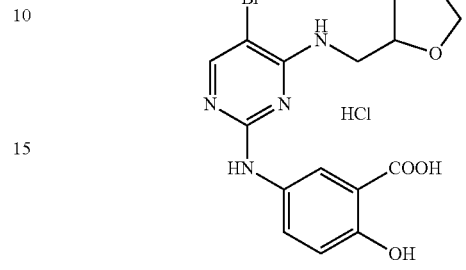

5-(5-Bromo-4-((tetrahydrofuran-2-yl)methylamino) pyrimidin-2-ylamino)-2-hydroxybenzoic acid hydrochloride (YL8-003-1)

This compound was synthesized using the same procedure described for YL7-172-2 except using SK1-008 (8b, Scheme 3) (0.073 g, 0.250 mmol) and 5-amino-2-hydroxybenzoic acid (0.038 g, 0.250 mmol). The compound was then slurried with MeOH/DCM (4 mL, 1:1) and sonicated. The mixture was filtered, and the resulting solid was dried to afford the title compound as a grey solid (0.068 g, 61%). %). Mp.: 211° C. (dec.); HPLC 98.4% (t$_R$=6.77 min, 45% CH$_3$OH in 0.1% TFA water, 20 min); $^1$H NMR (400 MHz, DMSO-d$_6$): δ 11.09 (br s, 1H disappeared on D$_2$O shake), 9.98 (s, 1H disappeared on D$_2$O shake), 8.15 (s, 1H disappeared on D$_2$O shake), 8.07 (s, 1H overlapping with br s), 8.03 (br s, 1H overlapping with singlet, disappeared on D$_2$O shake), 7.58 (d, J=8.8 Hz, 1H), 6.95 (d, J=8.8 Hz, 1H), 4.06-4.00 (m, 1H), 3.70-3.65 (m, 2H overlapping with water peak), 1.83-1.73 (m, 3H), 1.54-1.48 (m, 1H); LC-MS (ESI+) m/z 409.05 and 411.05 for Br-isotopes (M+H)$^+$; HRMS (ESI+) m/z calculated for C$_{16}$H$_{18}$BrN$_4$O$_4$ (M+H)$^+$ 409.0506. found 409.0509.

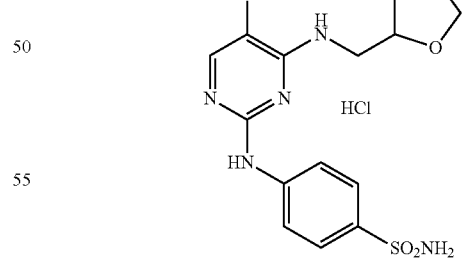

4-(5-Bromo-4-((tetrahydrofuran-2-yl)methylamino) pyrimidin-2-ylamino)benzenesulfonamide hydrochloride (YL8-003-3)

This compound was synthesized using the same procedure described for YL7-172-2 except using SK1-008 (8b, Scheme 3) (0.073 g, 0.250 mmol) and 4-aminobenzenesulfonamide (0.043 g, 0.250 mmol). The resulting precipitate was filtered upon cooling and washed with MeOH (1 mL×2) to afford the title compound as a white solid (0.066 g, 57%). Mp.: 214° C. (dec.); HPLC 96.3% ($t_R$=6.21 min, 35% $CH_3OH$ in 0.1% TFA water, 20 min); $^1H$ NMR (400 MHz, DMSO-$d_6$): δ 10.20 (s, 1H disappeared on $D_2O$ shake), 8.19 (s, 1H), 7.81 (d, J=8.8 Hz, 3H overlapping with singlet), 7.24 (br s, 2H disappeared on $D_2O$ shake), 4.13-4.07 (m, 1H), 3.79-3.73 (m, 2H overlapping with water peak), 1.94-1.77 (m, 3H), 1.66-1.59 (m, 1H); LC-MS (ESI+) m/z 428.03 and 430.03 for Br-isotopes $(M+H)^+$; HRMS (ESI+) m/z calculated for $C_{15}H_{19}BrN_5O_3S$ $(M+H)^+$ 428.0387. found 428.0384.

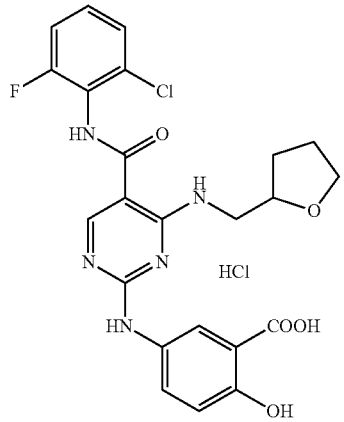 [SMILES: O=C(O)c1cc(Nc2ncc(C(=O)Nc3c(F)cccc3Cl)c(NCC3CCCO3)n2)ccc1O ; Cl]

2-(3-Chloro-4-hydroxyphenylamino)-N-(2-chloro-6-fluorophenyl)-4-((tetrahydrofuran-2-yl)methylamino)pyrimidine-5-carboxamide hydrochloride (YL8-009-1)

This compound was synthesized using the same procedure described for YL7-172-2 except using YL7-102 (8c, Scheme 3) (0.050 g, 0.130 mmol) and 4-amino-2-chlorophenol (0.019 g, 0.130 mmol). The resulting mixture was concentrated and the resulting residue was recrystallized with DCM/Hexane (1:2) to yield the title compound as a gray solid (0.053 g, 77%). Mp.: 158° C. (dec.); HPLC 97.5% ($t_R$=9.27 min, 55% $CH_3OH$ in 0.1% TFA water, 20 min); $^1H$ NMR (400 MHz, $CD_3OD$): δ 8.53 (s, 1H), 8.19 (s, 1H), 7.60 (br s, 1H), 7.41-7.38 (m, 2H), 7.25-7.20 (m, 2H), 6.97 (d, J=8.4 Hz, 1H), 4.16-4.10 (m, 1H), 3.89-3.84 (m, 1H), 3.77-3.59 (m, 3H), 2.08-2.00 (m, 1H), 1.95-1.89 (m, 2H), 1.66-1.60 (m, 1H); $^{19}F$ NMR (376 MHz, $CD_3OD$): δ -118.23--118.26 (m); LC-MS (ESI+) m/z 492.09 $(M+H)^+$; HRMS (ESI+) m/z calculated for $C_{22}H_{21}Cl_2FN_5O_3$ $(M+H)^+$ 492.1000. found 492.0992.

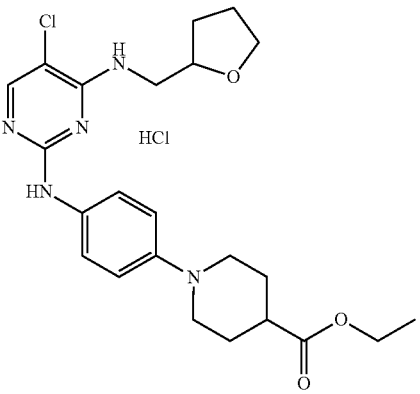 [SMILES: CCOC(=O)C1CCN(c2ccc(Nc3ncc(Cl)c(NCC4CCCO4)n3)cc2)CC1 ; Cl]

5-(5-(2-Chloro-6-fluorophenylcarbamoyl)-4-((tetrahydrofuran-2-yl)methylamino)pyrimidin-2-ylamino)-2-hydroxybenzoic acid hydrochloride (YL8-009-2)

This compound was synthesized using the same procedure described for YL7-172-2 except using YL7-102 (8c, Scheme 3) (0.050 g, 0.130 mmol) and 5-amino-2-hydroxybenzoic acid (0.020 g, 0.130 mmol). The resulting precipitate was filtered upon cooling, and washed with MeOH (2 mL). The solid was dried under high vacuum to afford the title compound as a white solid (0.050 g, 71%). Mp.: 298° C. (dec.); HPLC 99.7% ($t_R$=11.31 min, 55% $CH_3OH$ in 0.1% TFA water, 20 min); $^1H$ NMR (400 MHz, DMSO-$d_6$): δ 10.99 (br s, 1H disappeared on $D_2O$ shake), 9.91 (s, 1H disappeared on $D_2O$ shake), 9.74 (br s, 1H disappeared on $D_2O$ shake), 8.93 (s, 1H disappeared on $D_2O$ shake), 8.76 (s, 1H), 8.57 (br s, 1H), 7.64 (d, J=8.8 Hz, 1H), 7.42-7.33 (m, 3H), 6.90 (d, J=8.8 Hz, 1H), 4.01-3.95 (m, 1H), 3.74-3.66 (m, 2H), 3.63-3.57 (m, 1H), 3.44-3.38 (m, 2H), 1.96-1.87 (m, 1H), 1.83-1.75 (m, 2H), 1.57-1.48 (m, 1H); $^{19}F$ NMR (376 MHz, DMSO-$d_6$): δ -116.22--116.26 (m); LC-MS (ESI+) m/z 502.12 $(M+H)^+$; HRMS (ESI+) m/z calculated for $C_{23}H_{22}ClFN_5O_5$ $(M+H)^+$ 502.1288. found 502.1294.

Ethyl 1-(4-(5-chloro-4-((tetrahydrofuran-2-yl)methylamino)pyrimidin-2-ylamino)phenyl)piperidine-4-carboxylate hydrochloride (YL8-047B2)

was synthesized according to the same procedure as YL7-172-2 except using NJL 25 (0.100 g, 0.403 mmol) and ethyl 1-(4-aminophenyl)piperidine-4-carboxylate (0.200 g, 0.806 mmol) in EtOH (4 mL). The resulting mixture was concentrated via rotavaporator, and the residue was recrystalized with EtOAc/Hexane (5 mL, 1:2). The resulting mixture was filtered and the residue dried under high vacuum to afford the title compound as a grey solid (0.273 g, 68%). HPLC 99.0% ($t_R$=5.65 min, 45% $CH_3OH$ in 0.1% TFA water, 20 min); $^1H$ NMR (400 MHz, $CD_3OD$): δ 7.88 (s, 1H), 7.49 (br s, 2H), 7.26 (br s, 2H), 4.19-4.14 (m, 3H), 3.88-3.82 (m, 1H), 3.77-3.68 (m, 3H), 3.58 (d, J=5.6 Hz, 2H), 3.13-3.03 (m, 2H), 2.61 (appt. t, 1H), 2.10 (appt. d, 2H), 2.03-1.85 (m, 5H), 1.69-1.60 (m, 1H), 1.27 (t, J=6.8 Hz, 3H); LC-MS (ESI+) m/z 460.2 (M+H)$^+$; HRMS (ESI+) m/z calculated for $C_{23}H_{31}ClN_5O_3$ (M+H)$^+$ 460.2110. found 460.2112.

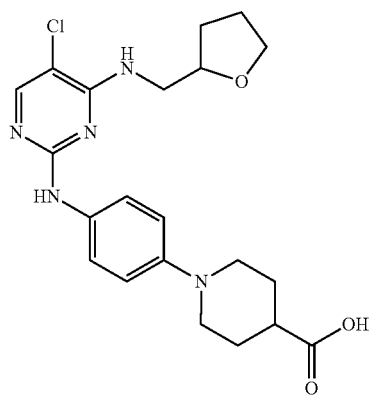

1-(4-(5-Chloro-4-((tetrahydrofuran-2-yl)methylamino)pyrimidin-2-ylamino)phenyl)piperidine-4-carboxylic acid: (YL8-050B2)

To the suspension of YL8-047B2 (0.272 g, 0.548 mmol) in THF (2.192 mL) was added NaOH (2M, 1.096 mL). The reaction mixture was stirred at room temperature for 18 h. The THF was removed by rotavaporator. Water (2 mL) was added and extracted with DCM (2 mL). The aqueous solution was acidified with HCl (1 M) to a pH of 4-5. The resulting precipitate was filtered and washed with water (5 mL×4), then quickly washed with MeOH (2 mL) and dried under high vacuum to afford first crop of the title compound (0.112 g). The solid precipitated in the filtrate was filtered and washed with water (5 mL×2) and dried under high vacuum to afford the second crop of the title compound (0.096 g). The solids were combined to afford the title compound as a dark grey solid (0.208 g, 81%). Mp.: 93° C. (dec.); HPLC 99.0% ($t_R$=8.59 min, 30% $CH_3OH$ in 0.1% TFA water, 20 min); $^1H$ NMR (400 MHz, $CD_3OD$): δ 7.81 (s, 1H), 7.46 (d, J=8.4 Hz, 2H), 7.09 (d, J=8.8 Hz, 2H), 4.20-4.13 (m, 1H), 3.89-3.84 (m, 1H), 3.77-3.72 (m, 1H), 3.62-3.48 (m, 4H), 2.79 (t, J=11.2, 2.4 Hz, 2H), 2.45 (tt, J=11.2, 4.0 Hz, 1H), 2.06-1.80 (m, 7H), 1.70-1.62 (m, 1H); LC-MS (ESI+) m/z 432.17; (M+H)$^+$; HRMS (ESI+) m/z calculated for $C_{21}H_{27}ClN_5O_3$ (M+H)$^+$ 431.1719. found 431.1717.

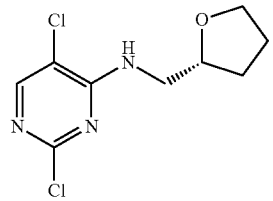

(R)-2,5-dichloro-N-((tetrahydrofuran-2-yl)methyl)pyrimidin-4-amine (DZ1-061, Scheme 4)

(R)-(−)-Tetrahydrofurfurylamine (0.992 g, 9.81 mmol) was added to a solution of 2,4,5-trichloropyrimidine (1.00 g, 5.45 mmol) in MeOH (10 mL) and triethylamine at 0° C., stirred for ten minutes, and allowed to react for an hour under argon. The solution was then warmed to room temperature and stirred for two hours. The solvent was removed under reduced pressure. The solid obtained was suspended in chloroform and washed with $NaHCO_3$ (aq). The organic layer was collected, dried with $Na_2SO_4$, filtered, dried under vacuum to afford (R)-2,5-dichloro-N-((tetrahydrofuran-2-yl)methyl)pyrimidin-4-amine DZ1-061 as a white solid (1.354 g, 87%). HPLC 97.3% [$R_t$=3.36 min, 70% $CH_3OH$ in 0.1% TFA water 20 min]; $^1H$ NMR (400 MHz, $CDCl_3$) δ 8.01 (s, 1H), 5.91 (s, 1H), 4.12-4.06 (m, 1H), 3.94-3.88 (m, 1H), 3.85-3.77 (m, 2H), 3.44-3.37 (m, 1H), 2.09-2.01 (m, 1H), 1.97-1.90 (m, 2H), 1.60-1.57 (m, 1H); LC-MS (ESI+) m/z 247.02792 (M+H)$^+$; HRMS (ESI+) m/z calculated for $C_9H_{11}Cl_2N_3O^+$ (M+H)$^+$ 248.0356. found, 248.03683.

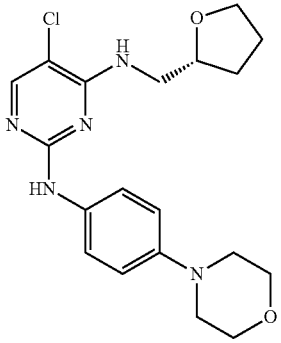

(R)-5-chloro-N2-(4-morpholinophenyl)-N4-(tetrahydrofuran-2-1)methyl)pyrimidine-2,4-diamine (DZ1-064, Scheme 4)

DZ1-061 (0.100 g, 0.403 mmol) and 4-morpholinoalanine (0.093 g, 0.484 mmol) were mixed in EtOH (1 mL) in a 5 mL microwave vial and heated to 150° C. for 20 minutes in a microwave reactor. The resulting precipitate formed upon cooling was filtered, washed with ethyl acetate, and subsequently dried under vacuum to afford 5-chloro-N2-(4-morpholinophenyl)-N4-(tetrahydrofuran-2-yl)methyl)pyrimidine-2,4-diamine DZ1-064 as a white solid (0.176 g, 51.3%). Mp: 140° C. (decomposed). HPLC 99.6% [$R_t$=5.06 min, 45% $CH_3OH$ in 0.1% TFA water 20 min]; $^1H$ NMR (400 MHz, $CD_3OD$) δ 7.84 (s, 1H), 7.32 (d, J=8.4 Hz, 2H), 7.05 (d, J=9.2 Hz, 2H), 4.19-4.12 (m, 1H), 3.85-3.79 (m, 4H), 3.76-3.70 (m, 1H), 3.58 (d, J=5.2, 2H), 3.17 (t, J=4.8, 4H), 2.02-1.88 (m, 4H), 1.67-1.7 (m, 1H). $^{13}$C NMR (100 MHz, CD$_3$OD) δ 159.13 [159.20 minor isomer], 151.82, 149.53, 139.21, 124.69, 116.19, 105.03, 76.72, 67.63, 66.37, 49.32, 45.14, 28.53, 25.03. LC-MS (ESI+) m/z 389.1616 (M+H)$^+$; HRMS (ESI+) m/z calculated for C$_{19}$H$_{24}$ClN$_5$O$_2$$^+$ (M+H)$^+$ 389.1613. found, 390.1610.

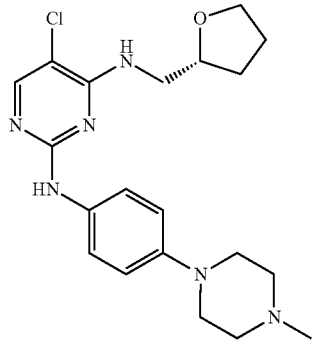

DZI-067

(R)-5-chloro-N2-(4-(4-methylpiperazin-1-yl)phenyl)-N4-((tetrahydrofuran-2-yl)methyl)pyrimidine-2,4-diamine (DZ1-067)

Substrates DZ1-061 (0.200 g, 0.806 mmol) and 4-4-methylpiperazinoaniline (0.170 g, 0.889 mmol) were mixed in a sealed tube with 4.0M HCl in dioxane (200 μL) 2-Methoxyethanol (6.50 mL) was added to the mixture and warmed to 110° C. for 48 hours. The resulting solution was concentrated under reduced pressure, and the product was partitioned between CHCl$_3$ and saturated aqueous NaHCO$_3$. The organic phase was then dried over Na$_2$SO$_4$, filtered, and concentrated under reduced pressure. The resulting product was purified using a silica gel column with 5:95 methanol-dichloromethane to afford the pure compound DZ1-067 as a white solid (0.220 g, 68%). Mp: 148-150° C. HPLC 96.1% [R$_t$=6.11 min, 30% CH$_3$OH in 0.1% TFA water 20 min]; $^1$H NMR (400 MHz, CD$_3$OD) δ 7.77 (s, 1H), 7.46 (d, J=9.2 Hz, 2H), 6.94 (d, J=8.8 Hz, 2H), 4.18-4.12 (m, 1H), 3.89-3.82 (t, J=7.6, 10H), 3.78-3.72 (m, 1H), 3.59-3.47 (d, J=4.8 Hz, 2H), 3.14 (t, J=4.8, 6H), 2.63 (t, J=4.8 Hz, 2H), 2.02-1.88 (m, 4H), 1.67-1.7 (m, 1H); $^{13}$C NMR (100 MHz, CD$_3$OD) δ 158.08 [158.36 minor isomer], 152.18, 146.37, 139.41, 133.53, 120.95, 116.79, 103.54, 77.46 [76.94 minor isomer], 67.61, 54.48, 49.32, 44.46 [44.18 minor isomer], 28.44, 25.15. LC-MS (ESI+) m/z 403.20076 (M+H)$^+$; HRMS (ESI+) m/z calculated for C$_{20}$H$_{27}$ClN$_6$O$^+$ (M+H)$^+$ 403.2008. found, 403.2008.

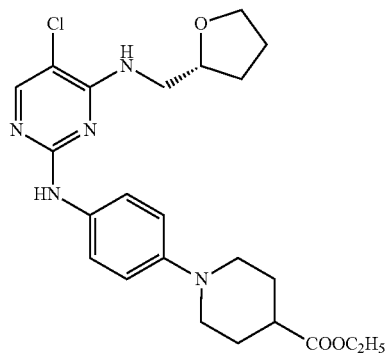

DZI-070

(R)-ethyl1-(4-(5-chloro-4-((tetrahydrofuran-2-yl)methylamino)pyrimidin-2-ylamino)phenyl)piperidine-4-carboxylate (DZ1-070, Scheme 4)

The DZ1-061 (0.100 g, 0.403 mmol) and ethyl 1-(4-aminophenyl)piperidine-4-carboxylate (0.119 g, 0.443 mmol) were mixed in EtOH (2 mL) in a sealed tube and heated to 150° C. for 60 minutes in a microwave reactor. The resulting solution was concentrated under reduced pressure, and the resulting residue was re-crystallized with EtOAc and Hexane. The solid obtained was filtered and dried under high vacuum to afford the pure product DZ1-070 as a gray solid (0.127 g, 69%). Mp: 184-186° C. HPLC 97.7% [R$_t$=5.473 min, 45% CH$_3$OH in 0.1% TFA water 20 min]; $^1$H NMR (400 MHz, CD$_3$OD) δ 7.85 (s, 1H), 7.45 (s, 1H), 7.19 (s, 1H), 4.20-4.14 (m, 2H), 3.87-3.82 (dd, J=4.0, 1H), 3.75-3.67 (m, 3H), 3.58 (d, J=8.0, 1H), 3.07 (s, 1H), 2.61 (s, 1H), 2.12-2.08 (broad d, 2H), 2.05-1.85 (m, 4H), 1.69-1.60 (m, 1H), 1.27 (t, J=8.0 Hz, 3H). LC-MS (ESI+) m/z 460.21099 (M+H)$^+$; HRMS (ESI+) m/z calculated for C$_{23}$H$_{30}$ClN$_5$O$_3$$^+$ (M+H)$^+$ 460.2101. found 460.2112.

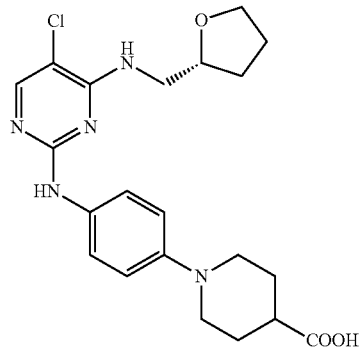

DZI-072

(R)-1-(4-(5-chloro-4-((tetrahydrofuran-2-yl)methylamino)pyrimidin-2-ylamino)phenyl)piperidine-4-carboxylic acid (DZ1-072, Scheme 4)

DZ1-070 (0.257 g, 0.518 mmol), THF (2.09 mL), and 2M NaOH (1.045 mL) were stirred at room temperature for 18 hours. The resulting solution was concentrated, and the solid obtained was dissolved in water (2 mL). The aqueous solution was acidified with 1M HCl (pH 4-5). The solid obtained was then filtered to afford (R)-1-(4-(5-chloro-4-

((tetrahydrofuran-2-yl)methylamino)pyrimidin-2-ylamino) phenyl)piperidine-4-carboxylic acid (DZ1-072) as a white solid (0.095 g, 42%). Mp: 140° C. (decomposed). HPLC 95.0% [$R_t$=8.57 min, 30% CH$_3$OH in 0.1% TFA water 20 min]; $^1$H NMR (400 MHz, CD$_3$OD) δ 7.79 (s, 1H), 7.46 (d, J=8.8 Hz, 2H), 7.03 (d, J=8.8 Hz, 2H), 4.19-4.13 (m, 1H), 3.90-3.84 (m, 1H), 3.78-3.72 (m, 1H), 3.61-3.49 (m, 4H), 2.83 (t, J=4.8, 11.6 Hz, 2H), 2.49-2.44 (m, 1H), 2.07-1.81 (m, 7H), 1.70-1.63 (m, 1H). $^{13}$C NMR (100 MHz, CD$_3$OD) δ 177.21, 158.32, 156.83, 149.226, 146.39, 133.08, 121.64, 117.80, 104.01, 77.28, 67.63, 50.63, 44.42, 40.19, 28.47, 27.74, 25.12. LC-MS (ESI+) m/z 432.179 (M+H)$^+$; HRMS (ESI+) m/z calculated for C$_{21}$H$_{26}$ClN$_5$O$_3$$^+$ (M+H)$^+$ 431.1797. found 432.1794.

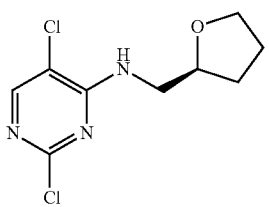

DZI-057

(S)-2,5-dichloro-N-((tetrahydrofuran-2-yl)methyl) pyrimidin-4-amine (DZ1-057, Scheme 4)

(S)-(−)-Tetrahydrofurfurylamine (0.992 g, 9.81 mmol) was added to a solution of 2,4,5-trichloropyrimidine (1.00 g, 5.45 mmol) in MeOH (10 mL). Triethylamine was added at 0° C., stirred for ten minutes, and allowed to react for an hour under argon. The solution was then warmed to room temperature and stirred for two hours. The solvent was removed under reduced pressure. The solid was dissolved in chloroform, and washed with sat. NaHCO$_3$. The organic layer was collected, dried with Na$_2$SO$_4$, filtered, and dried under vacuum to afford (S)-2,5-dichloro-N-((tetrahydrofuran-2-yl)methyl)pyrimidin-4-amine DZ1-057) as a white solid (1.054 g, 68%). HPLC 95.4% [$R_t$=3.36 min, 70% CH$_3$OH in 0.1% TFA water 20 min]; $^1$H NMR (400 MHz, CDCl$_3$) δ 8.01 (s, 1H), 5.91 (s, 1H), 4.12-4.06 (m, 1H), 3.94-3.88 (m, 1H), 3.85-3.77 (m, 1H), 3.44-3.37 (m, 1H), 2.09-2.01 (m, 1H), 1.97-1.90 (m, 3H); LC-MS (ESI+) m/z 247.02792 (M+H)$^+$; HRMS (ESI+) m/z calculated for C$_9$H$_{11}$C$_{12}$N$_3$O$^+$ (M+H)$^+$ 248.0356. found, 248.0353.

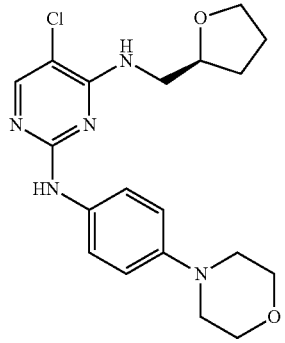

DZI-074

(S)-5-chloro-N2-(4-morpholinophenyl)-N4-(tetrahydrofuran-2-1)methyl)pyrimidine-2,4-diamine (DZ1-074, Scheme 4)

DZ1-057 (0.100 g, 0.403 mmol) and 4-morpholinoalanine (0.093 g, 0.484 mmol) were mixed in EtOH (1 mL) in a 5 mL microwave vial and heated to 150° C. for 20 minutes in a microwave reactor. The resulting precipitate formed upon cooling was filtered, washed with ethyl acetate, and subsequently dried under vacuum to afford (S)-5-chloro-N2-(4-morpholinophenyl)-N4-(tetrahydrofuran-2-yl)methyl)pyrimidine-2,4-diamine DZ1-074 as a white solid (0.254 g, 74.1%). Mp: 129° C. (decomposed). HPLC 99.9% [$R_t$=5.140 min, 45% CH$_3$OH in 0.1% TFA water 20 min]; $^1$H NMR (400 MHz, CD$_3$OD) δ 7.84 (s, 1H), 7.32 (d, J=8.4 Hz, 2H), 7.05 (d, J=9.2 Hz, 2H), 4.15-4.18 (m, 1H), 3.85-3.72 (t, J=4.4, 4H), 3.78-3.72 (m, 1H), 3.59-3.57 (d, J=5.2, 2H), 3.17 (t, J=4.8, 6H), 2.02-1.88 (m, 4H), 1.67-1.7 (m, 1H); $^{13}$C NMR (100 MHz, CD$_3$OD) δ 159.14, 151.85, 149.62, 139.16, 124.77, 116.19, 105.05, 76.72, 67.63, 66.37, 49.31, 45.13, 28.53, 25.02. LC-MS (ESI+) m/z 389.1616 (M+H)$^+$; HRMS (ESI+) m/z calculated for C$_{19}$H$_{24}$ClN$_5$O$_2$$^+$ (M+H)$^+$ 389.1691. found, 390.1694.

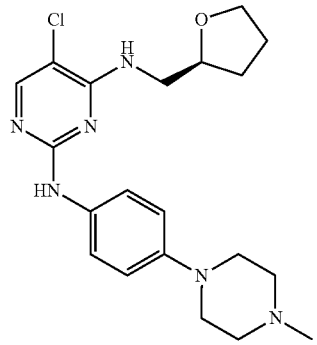

DZI-077

(S)-5-chloro-N2-(4-(4-methylpiperazin-1-yl)phenyl)-N4-((tetrahydrofuran-2-yl)methyl)pyrimidine-2,4-diamine (DZ1-077 Scheme 4)

Substrates DZ1-057 (0.200 g, 0.806 mmol) and 4-4-methylpiperazinoaniline (0.170 g, 0.889 mmol) were mixed in a microwave vial with 4.0M HCl in dioxane (200 μL). 2-Methoxyethanol (6.50 mL) was added to the mixture, sealed the vial and heated to 110° C. for 48 hours. The resulting solution was concentrated, and the product was partitioned between CHCl$_3$ and saturated aqueous NaHCO$_3$. The organic phase was separated, then dried over Na$_2$SO$_4$, filtered, and concentrated. The product obtained was purified using a silica gel column with 5:95 methanol-dichloromethane to afford the pure compound DZ1-077 as a white solid. [$R_t$=6.09 min, 30% CH$_3$OH in 0.1% TFA water 20 min]; $^1$H NMR (400 MHz, CD$_3$OD) δ 7.77 (s, 1H), 7.45 (d, J=9.2 Hz, 2H), 6.94 (d, J=8.8 Hz, 2H), 4.17-4.14 (m, 1H), 3.89-3.84 (m, 1H), 3.78-3.72 (m, 1H), 3.61-3.47 (m, 3H), 3.14 (t, J=4.8 Hz, 2H), 2.63 (t, J=4.8 Hz, 2H), 2.02-1.88 (m, 4H), 1.67-1.7 (m, 1H). $^{13}$C NMR (100 MHz, CD$_3$OD) δ 158.09 [158.38 minor isomer], 152.19, 146.50, 139.42, 133.46, 120.98, 116.75, 103.51, 77.47 [76.95 minor isomer], 67.61, 54.58, 49.49, 44.66 [44.17 minor isomer], 28.43, 25.15. LC-MS (ESI+) m/z 403.20076 (M+H)+; HRMS (ESI+) m/z calculated for $C_{20}H_{27}ClN_6O^+$ (M+H)+ 402.19349. found, 403.20079.

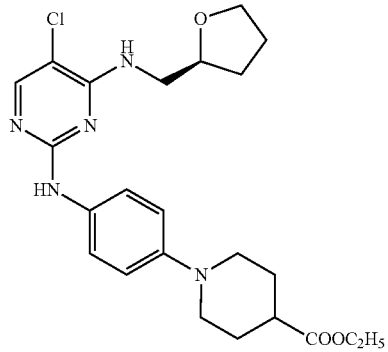

DZI-079

(S)-ethyl1-(4-(5-chloro-4-((tetrahydrofuran-2-yl)methylamino)pyrimidin-2-ylamino)phenyl)piperidine-4-carboxylate (DZ1-079, Scheme 4)

The DZ1-057 (0.100 g, 0.403 mmol) and ethyl 1-(4-aminophenyl)piperidine-4-carboxylate (0.119 g, 0.443 mmol) were mixed in EtOH (2 mL) in a 5 mL microwave vial and heated to 150° C. for 60 minutes in a microwave reactor. The resulting solution was concentrated, and the solid obtained was re-crystallized using EtOAc and Hexane. The resulting solid was filtered and dried under high vacuum to afford the pure product DZ1-079 as a gray solid (0.127 g, 69%). Mp: 179-181.8° C. HPLC 97.7% [$R_t$=5.59 min, 45% $CH_3OH$ in 0.1% TFA water 20 min] $^1H$ NMR (400 MHz, $CD_3OD$) δ 7.85 (s, 1H), 7.45 (broad d, 1H), 7.19 (broad d, 1H), 4.20-4.14 (m, 2H), 3.87-3.82 (dd, J=4.0 Hz, 1H), 3.75-3.67 (m, 3H), 3.58 (d, J=8.0, 1H), 3.07 (broad s, 1H), 2.61 (broad s, 1H), 2.12-2.08 (broad d, 2H), 2.05-1.85 (m, 4H), 1.69-1.60 (m, 1H), 1.26 (t, J=7.2 Hz, 3H). LC-MS (ESI+) m/z 460.210 (M+H)+; HRMS (ESI+) m/z calculated for $C_{23}H_{30}ClN_5O_3^+$ (M+H)+ 460.2109 found 460.2106.

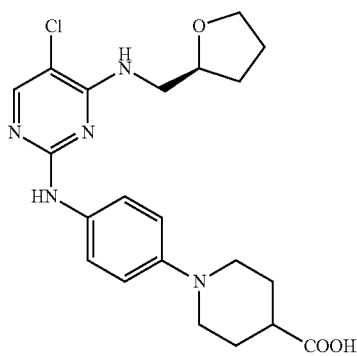

DZI-082

(S)-1-(4-(5-chloro-4-((tetrahydrofuran-2-yl)methylamino)pyrimidin-2-ylamino)phenyl)piperidine-4-carboxylic acid (DZ1-082, Scheme 4)

The DZ1-079 (0.100 g, 0.201 mmol), THF (1.02 mL), and 2M NaOH (0.508 mL) were stirred at room temperature for 18 hours, the resulting solution was concentrated and the product obtained was dissolved in water (2 mL). The aqueous solution was acidified with 1M HCl to a pH of 4-5. The solution was then filtered to afford (R)-1-(4-(5-chloro-4-((tetrahydrofuran-2-yl)methylamino)pyrimidin-2-ylamino)phenyl) piperidine-4-carboxylic acid (DZ1-082) as a white solid (0.058 g, 67%). HPLC 99.7% [$R_t$=8.67 min, 30% $CH_3OH$ in 0.1% TFA water 20 min]; $^1H$ NMR (400 MHz, $CD_3OD$) δ 7.84 (s, 1H), 7.44 (broad d, 2H), 7.018 (broad d, 2H), 4.19-4.13 (m, 2H), 3.987-3.82 (m, 1H), 3.78-3.66 (m, 2H), 3.58 (d, J=6.0 Hz, 1H), 2.83 (t, J=11.6, 2H), 2.49-2.44 (m, 1H), 2.07-1.81 (m, 7H), 1.70-1.63 (m, 1H). $^{13}C$ NMR (100 MHz, $CD_3OD$) δ 177.28, 158.29, 157.01, 149.61, 146.47, 133.14, 121.53, 117.77, 103.94, 77.30, 67.63, 50.59, 44.39, 40.25, 28.46, 27.78, 25.12. LC-MS (ESI+) m/z 432.17969 (M+H)+; HRMS (ESI+) m/z calculated for $C_{21}H_{26}ClN_5O_3^+$ (M+H)+ 431.17242. found 432.17969.

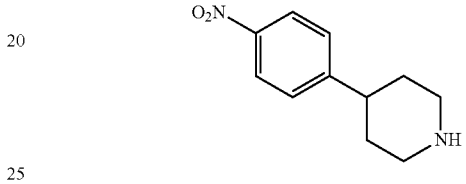

4-(4-Nitrophenyl)piperidine (NT1-001)

A solution of concentrated $H_2SO_4$ (2.65 mL) in acetic acid (40 mL) and a solution of concentrated $HNO_3$ (2.1 mL) in acetic acid (20 mL) were added sequentially and dropwise to a solution of 4-phenylpiperidine (8.15 g, 53.9 mmol) in acetic acid (40 mL), maintaining the temperature below 20° C. Then concentrated $H_2SO_4$ was added (no cooling applied, internal temperature reached 45° C.). The reaction mixture was allowed to cool to room temperature and then refrigerated overnight. The mixture was then poured onto ice/water (100 g), neutralized by addition of solid $NaHCO_3$ (150 g), and extracted with DCM. The organic phase was washed with brine, dried ($Na_2SO_4$), filtered, and concentrated. The residue was purified by trituration with diethyl ether to afford 4-(4-nitrophenyl)piperidine (NT1-001) as a white powder (5.5 g, 50%). HPLC 95.4% [$R_t$=6.74 min, 30% $CH_3OH$ in 0.1% TFA water 20 min]. $^1H$ NMR (400 MHz, Chloroform-d) δ 8.21 (d, J=8.9 Hz, 2H), 7.43 (d, J=8.9 Hz, 2H), 3.72-3.62 (m, 2H), 3.08-2.98 (m, 1H), 2.95-2.86 (m, 2H), 2.33-2.21 (m, 2H), 2.12-2.03 (m, 2H). LC-MS (ESI+) m/z 207.11218 (M+H)+; HRMS (ESI+) m/z calculated for $C_{11}H_{14}N_2O_2$ (M+H)+ 207.1128. found, 207.1132 (*J. Med. Chem.* 2011; 54:7066-7083).

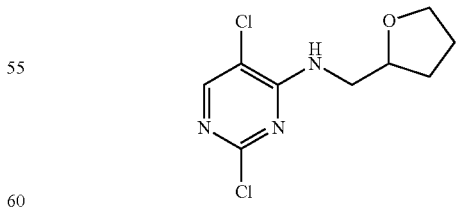

2,5-Dichloro-N-((tetrahydrofuran-2-yl)methyl)pyrimidin-4-amine (NT1-003)

Tetrahydrofurfurylamine (1.251 g, 12.36 mmol) in MeOH (11 mL) was added dropwise to a solution of 2,4,5-trichloropyrimidine (2.27 g, 12.36 mmol), and triethylamine (1.251 g, 12.36 mmol) in MeOH (11 mL) at 0° C. and allowed to react for 1.5 hours under argon. After this time, the reaction mixture was allowed to warm to room temperature. The solvent was removed under reduced pressure, the residue dissolved in DCM, washed with water, dried, and evaporated to afford 2,5-dichloro-N-((tetrahydrofuran-2-yl)methyl)pyrimidin-4-amine (NT1-003) as a yellow solid (2.86 g, 93%). HPLC 92.0% [$R_t$=11.167 min, 30% $CH_3OH$ in 0.1% TFA water 20 min]. $^1H$ NMR (400 MHz, Methanol-d4) δ 8.01 (s, 1H), 4.16-4.09 (m, 1H), 3.91-3.85 (m, 1H), 3.78-3.72 (m, 1H), 3.60-3.48 (m, 2H), 2.06-1.83 (m, 3H), 1.70-1.58 (m, 1H). LC-MS (ESI+) m/z 248.03536 (M+H)$^+$; HRMS (ESI+) m/z calculated for $C_9H_{11}Cl_2N_3O^+$ (M+H)$^+$ 248.0352. found, 248.0359.

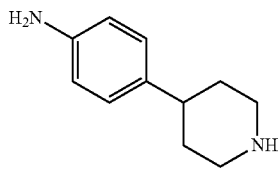 [SMILES: O=[N+]([O-])c1ccc(C2CCNCC2)cc1]

4-(Piperidin-4-yl)aniline (NT1-004)

NT1-001 (400 mg, 1.942 mmol) in MeOH (30 mL) was combined with a palladium catalyst (144 mg) under argon. The argon was removed and $H_2$ gas was introduced into the system. After 3.5 hours at room temperature, the palladium catalyst was filtered, the solvent removed under reduced pressure. The residue was purified by trituration with DCM to afford 4-(piperidin-4-yl)aniline (NT1-004) as a white solid (340 mg, 99%). HPLC 95.0% [$R_t$=6.74 min, 30% $CH_3OH$ in 0.1% TFA water 20 min]. $^1H$ NMR (400 MHz, Methanol-d4) δ 6.99 (d, J=8.4 Hz, 2H), 6.69 (d, J=8.4 Hz, 2H), 3.46-3.22 (m, 2H), 2.95 (td, J=12.8, 3.0 Hz, 2H), 2.70-2.62 (m, 1H), 1.96-1.84 (m, 2H), 1.82-1.70 (m, 2H). LC-MS (ESI+) m/z 177.13808 (M+H)$^+$; HRMS (ESI+) m/z calculated for $C_{11}H_{16}N_2$ (M+H)$^+$ 177.1386. found, 177.1382.

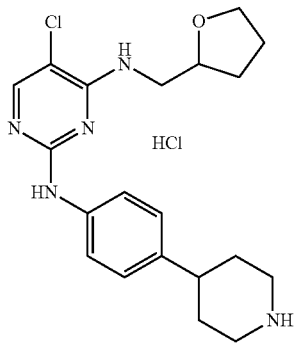 [SMILES: Clc1cnc(Nc2ccc(C3CCNCC3)cc2)nc1NCC1CCCO1 ; Cl]

5-Chloro-$N^2$-(4-(piperidin-4-yl)phenyl)-$N^4$-((tetrahydrofuran-2-yl)methyl)pyrimidine-2,4-diamine (NT1-005)

Substrates NT1-003 (80 mg, 0.32 mmol) and NT1-004 (28.4 mg, 0.32 mmol) were mixed in a microwave tube with EtOH (1 mL). Then 0.1N HCl (1 mL) was added to the tube. The vessel was sealed and heated to 150° C. for 40 minutes. The solvent was removed under reduced pressure, the residue washed with DCM, and filtered to afford 5-chloro-$N^2$-(4-(piperidin-4-yl)phenyl)-$N^4$-((tetrahydrofuran-2-yl)methyl)pyrimidine-2,4-diamine (NT1-005) as a peach solid (90 mg, 72.0%), mp 160° C. (dec.). HPLC 85.6% [$R_t$=7.51 min, 30% $CH_3OH$ in 0.1% TFA water 20 min]. $^1H$ NMR (400 MHz, Methanol-d4) δ 7.94 (s, 1H), 7.49 (d, J=8.2 Hz, 2H), 7.35 (d, J=8.4 Hz, 2H), 4.16 (p, J=6.2 Hz, 1H), 3.86-3.68 (m, 2H), 3.65-3.46 (m, 4H), 3.22-3.09 (m, 2H), 3.00-2.90 (m, 1H), 2.14-1.82 (m, 8H), 1.69-1.58 (m, 1H). $^{13}C$ NMR (101 MHz, Methanol-d4) δ 159.20, 151.43, 141.84, 139.72, 135.04, 127.16, 122.99, 105.19, 76.74, 67.63, 45.23, 44.15, 39.15, 29.68, 28.54, 25.01. LC-MS (ESI+) m/z 388.18965 (M+H)$^+$; HRMS (ESI+) m/z calculated for $C_{20}H_{26}ClN_5O^+$ (M+H)$^+$ 388.1899. found, 388.1900.

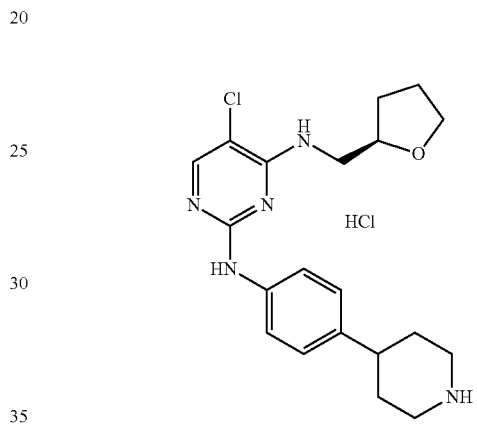

(R)-5-Chloro-$N^2$-(4-(piperidin-4-yl)phenyl)-$N^4$-((tetrahydrofuran-2-yl)methyl)pyrimidine-2,4-diamine (NT1-010)

Substrates NT1-008 (100 mg, 0.403 mmol) and NT1-004 (71 mg, 0.403 mmol) were mixed in a microwave tube with EtOH (1.5 mL). Then 0.1N HCl (1 mL) was added to the tube. The vessel was sealed and heated to 150° C. for 40 minutes. The solvent was removed under reduced pressure, the residue washed with DCM, and filtered to afford (R)-5-chloro-$N^2$-(4-(piperidin-4-yl)phenyl)-$N^4$-((tetrahydrofuran-2-yl)methyl)pyrimidine-2,4-diamine (NT1-010) as a white solid (87 mg, 56%), mp 160° C. (dec.). HPLC 95.3% [$R_t$=7.55 min, 30% $CH_3OH$ in 0.1% TFA water 20 min]. $^1H$ NMR (400 MHz, Methanol-d4) δ 7.94 (s, 1H), 7.48 (d, J=8.2 Hz, 2H), 7.36 (d, J=8.4 Hz, 2H), 4.16 (p, J=6.2 Hz, 1H), 3.86-3.67 (m, 2H), 3.64-3.44 (m, 4H), 3.22-3.09 (m, 2H), 3.02-2.90 (m, 1H), 2.14-1.84 (m, 8H), 1.69-1.58 (m, 1H). $^{13}C$ NMR (101 MHz, Methanol-d4) δ 159.18, 151.36, 141.70, 139.82, 135.13, 128.13, 127.11, 122.75, 105.10, 76.76, 67.64, 45.27, 44.16, 39.16, 29.68, 28.57, 25.03. LC-MS (ESI+) m/z 388.19139 (M+H)$^+$; HRMS (ESI+) m/z calculated for $C_{20}H_{26}ClN_5O^+$ (M+H)$^+$ 388.1899. found, 388.1913.

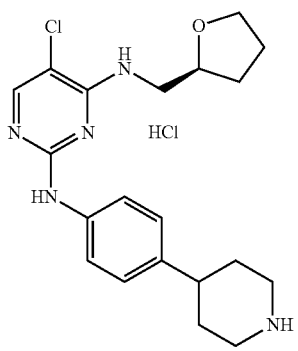 [SMILES: Clc1cnc(Nc2ccc(C3CCNCC3)cc2)nc1NC[C@@H]1CCCO1 ; Cl]

(S)-5-Chloro-N²-(4-(piperidin-4-yl)phenyl)-N⁴-((tetrahydrofuran-2-yl)methyl)pyrimidine-2,4-diamine (NT1-011)

Substrates NT1-009 (100 mg, 0.403 mmol) and NT1-004 (71 mg, 0.403 mmol) were mixed in a microwave tube with EtOH (1.5 mL). Then 0.1N HCl (1 mL) was added to the tube. The vessel was sealed and heated to 150° C. for 40 minutes. The solvent was removed under reduced pressure, the residue washed with DCM, and filtered to afford (S)-5-chloro-N²-(4-(piperidin-4-yl)phenyl)-N⁴-((tetrahydrofuran-2-yl)methyl)pyrimidine-2,4-diamine (NT1-011) as a white solid (12 9 mg, 86%), mp 160° C. (dec.). HPLC 92.3% [$R_f$=7.58 min, 30% CH$_3$OH in 0.1% TFA water 20 min]. $^1$H NMR (400 MHz, Methanol-d4) δ 7.94 (s, 1H), 7.48 (d, J=8.2 Hz, 2H), 7.36 (d, J=8.4 Hz, 2H), 4.16 (p, J=6.2 Hz, 1H), 3.85-3.66 (m, 2H), 3.62-3.44 (m, 4H), 3.20-3.10 (m, 2H), 3.02-2.92 (m, 1H), 2.14-1.85 (m, 8H), 1.69-1.56 (m, 1H). $^{13}$C NMR (101 MHz, Methanol-d4) δ 159.27, 151.02, 142.26, 138.84, 134.66, 127.29, 123.33, 105.34, 76.70, 67.63, 45.30, 44.15, 39.16, 29.65, 28.55, 25.01. LC-MS (ESI+) m/z 388.19163 (M+H)$^+$; HRMS (ESI+) m/z calculated for $C_{20}H_{26}ClN_5O^+$ (M+H)$^+$ 388.1899. found, 388.1913.

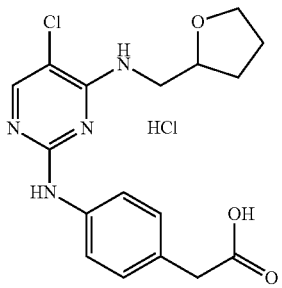 [SMILES: O=C(O)Cc1ccc(Nc2ncc(Cl)c(NCC3CCCO3)n2)cc1 ; Cl]

2-(4-(5-Chloro-4-((tetrahydrofuran-2-yl)methylamino)pyrimidin-2-ylamino)phenyl)acetic acid (NT1-006)

Substrates NT1-003 (60 mg, 0.242 mmol) and 4-aminophenylacetic acid (24.32 mg, 0.161 mmol) were mixed in a microwave tube with acetonitrile (2 mL). Then 3 drops of 2M HCl were added to the tube. The vessel was sealed and heated to 150° C. for 120 minutes. Upon cooling, a precipitate formed. The reaction mixture was filtered, and the solid purified by trituration with DCM to afford 2-(4-(5-chloro-4-((tetrahydrofuran-2-yl)methylamino)pyrimidin-2-ylamino)phenyl)acetic acid (NT1-006) as a yellow solid (40 mg, 69%), mp 160° C. (dec.). HPLC 91.9% [$R_f$=9.40 min, 30% CH$_3$OH in 0.1% TFA water 20 min]. $^1$H NMR (400 MHz, Methanol-d4) δ 7.92 (s, 1H), 7.44 (d, J=8.4 Hz, 2H), 7.37 (d, J=8.5 Hz, 2H), 4.16 (p, J=6.5 Hz, 1H), 3.85-3.68 (m, 2H), 3.64 (s, 2H), 3.62-3.56 (m, 2H), 2.05-1.82 (m, 3H), 1.67-1.56 (m, 1H). $^{13}$C NMR (101 MHz, Methanol-d4) δ 173.82, 159.25, 151.11, 138.86, 130.02, 123.14, 105.33, 76.75, 67.64, 45.33, 39.86, 28.53, 25.00. LC-MS (ESI+) m/z 363.12267 (M+H)$^+$; HRMS (ESI+) m/z calculated for $C_{17}H_{19}ClN_4O_3^+$ (M+H)$^+$ 363.1218. found, 363.1226.

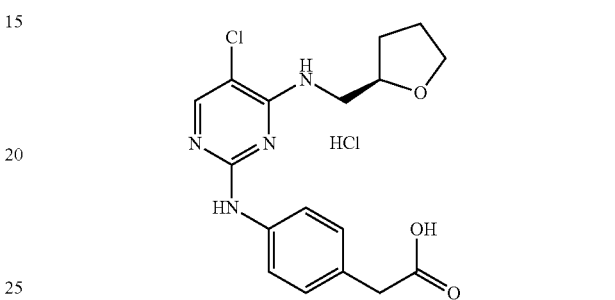

(R)-2-(4-(5-Chloro-4-((tetrahydrofuran-2-yl)methylamino)pyrimidin-2-ylamino)phenyl)acetic acid (NT1-012)

Substrates NT1-008 (100 mg, 0.403 mmol) and 4-aminophenylacetic acid (40.63 mg, 0.269 mmol) were mixed in a microwave tube with acetonitrile (3 mL). Then 5 drops of 0.1M HCl were added to the tube. The vessel was sealed and heated to 150° C. for 120 minutes. Upon cooling, a precipitate formed. The reaction mixture was filtered, and the solid purified by trituration with DCM to afford (R)-2-(4-(5-chloro-4-((tetrahydrofuran-2-yl)methylamino)pyrimidin-2-ylamino)phenyl)acetic acid (NT1-012) as a yellow solid (85 mg, 87%), mp 160° C. (dec.). HPLC 96.3% [$R_f$=9.45 min, 30% CH$_3$OH in 0.1% TFA water 20 min]. $^1$H NMR (400 MHz, Methanol-d4) δ 7.89 (s, 1H), 7.46 (d, J=8.4 Hz, 2H), 7.32 (d, J=8.5 Hz, 2H), 4.16 (p, J=6.5 Hz, 1H), 3.87-3.68 (m, 2H), 3.62 (s, 2H), 3.60-3.56 (m, 2H), 2.05-1.85 (m, 3H), 1.68-1.59 (m, 1H). $^{13}$C NMR (101 MHz, Methanol-d4) δ 173.89, 159.16, 139.82, 135.15, 132.43, 129.86, 122.66, 105.13, 76.80, 67.63, 45.27, 39.87, 28.53, 25.00. LC-MS (ESI+) m/z 363.12289 (M+H)$^+$; HRMS (ESI+) m/z calculated for $C_{17}H_{19}ClN_4O_3^+$ (M+H)$^+$ 363.1218. found, 363.1228.

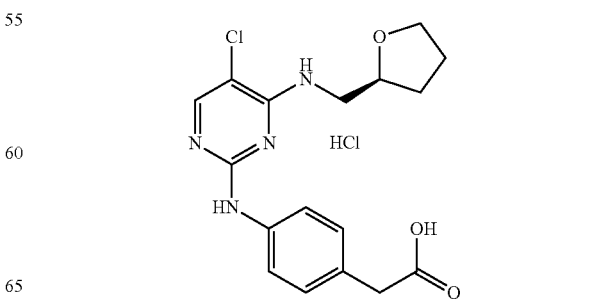

(S)-2-(4-(5-Chloro-4-((tetrahydrofuran-2-yl)methyl-amino)pyrimidin-2-ylamino)phenyl)acetic acid (NT1-013)

Substrates NT1-009 (100 mg, 0.403 mmol) and 4-aminophenylacetic acid (40.63 mg, 0.269 mmol) were mixed in a microwave tube with acetonitrile (3 mL). Then 5 drops of 0.1M HCl were added to the tube. The vessel was sealed and heated to 150° C. for 120 minutes. Upon cooling, a precipitate formed. The reaction mixture was filtered, and the solid purified by trituration with DCM to afford (S)-2-(4-(5-chloro-4-((tetrahydrofuran-2-yl)methylamino)pyrimidin-2-ylamino)phenyl)acetic acid (NT1-013) as a yellow solid (79 mg, 81%), mp 160° C. (dec.). HPLC 96.4% [$R_t$=9.43 min, 30% $CH_3OH$ in 0.1% TFA water 20 min]. $^1H$ NMR (400 MHz, Methanol-d4) δ 7.90 (s, 1H), 7.46 (d, J=8.4 Hz, 2H), 7.33 (d, J=8.5 Hz, 2H), 4.16 (p, J=6.5 Hz, 1H), 3.86-3.68 (m, 2H), 3.62 (s, 2H), 3.60-3.57 (m, 2H), 2.05-1.84 (m, 3H), 1.67-1.58 (m, 1H). $^{13}C$ NMR (101 MHz, Methanol-d4) δ 173.88, 159.17, 151.50, 139.78, 135.14, 132.46, 129.87, 122.68, 105.16, 76.80, 67.63, 45.28, 39.87, 28.53, 25.00. LC-MS (ESI+) m/z 363.12285 (M+H)$^+$; HRMS (ESI+) m/z calculated for $C_{17}H_{19}ClN_4O_3^+$ (M+H)$^+$ 363.1218. found, 363.1231.

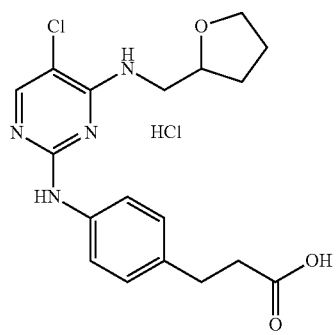 [SMILES: O=C(O)CCc1ccc(Nc2ncc(Cl)c(NCC3CCCO3)n2)cc1 ; Cl]

3-(4-(5-Chloro-4-((tetrahydrofuran-2-yl)methyl-amino)pyrimidin-2-ylamino)phenyl)propanoic acid (NT1-007)

Substrates NT1-003 (240 mg, 0.966 mmol) and 3-(4-aminophenyl)propionic acid (106.5 mg, 0.644 mmol) were mixed in a microwave tube with acetonitrile (8 mL). Then 12 drops of 2M HCl were added to the tube. The vessel was sealed and heated to 150° C. for 120 minutes. Upon cooling, a precipitate formed. The reaction mixture was filtered, and the solid purified by trituration with DCM to afford 3-(4-(5-chloro-4-((tetrahydrofuran-2-yl)methylamino)pyrimidin-2-ylamino)phenyl)propanoic acid (NT1-007) as a light yellow solid (230 mg, 95%), mp ° C. (dec.). HPLC 95.9% [$R_t$=9.79 min, 30% $CH_3OH$ in 0.1% TFA water 20 min]. $^1H$ NMR (400 MHz, Methanol-d4) δ 7.91 (s, 1H), 7.39 (d, J=8.2 Hz, 2H), 7.32 (d, J=8.2 Hz, 2H), 4.16 (p, J=6.5 Hz, 1H), 3.89-3.65 (m, 2H), 3.65-3.54 (m, 2H), 2.94 (t, J=7.5 Hz, 2H), 2.62 (t, J=7.5 Hz, 2H), 2.05-1.85 (m, 3H), 1.68-1.57 (m, 1H). $^{13}C$ NMR (101 MHz, Methanol-d4) δ 173.47, 159.25, 138.73, 128.96, 123.31, 105.31, 76.72, 67.63, 45.29, 34.99, 29.90, 28.54, 25.01. LC-MS (ESI+) m/z 377.13904 (M+H)$^+$; HRMS (ESI+) m/z calculated for $C_{18}H_{21}ClN_4O_3^+$ (M+H)$^+$ 377.1375. found, 377.1383.

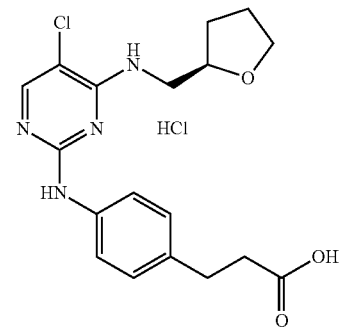 [SMILES: O=C(O)CCc1ccc(Nc2ncc(Cl)c(NC[C@H]3CCCO3)n2)cc1 ; Cl]

(R)-3-(4-(5-Chloro-4-((tetrahydrofuran-2-yl)methyl-amino)pyrimidin-2-ylamino)phenyl)propanoic acid (NT1-014)

Substrates NT1-008 (80 mg, 0.323 mmol) and 3-(4-aminophenyl)propionic acid (35.4 mg, 0.215 mmol) were mixed in a microwave tube with acetonitrile (3 mL). Then 5 drops of 2M HCl were added to the tube. The vessel was sealed and heated to 150° C. for 120 minutes. Upon cooling, a precipitate formed. The reaction mixture was filtered, and the solid purified by trituration with DCM to afford (R)-3-(4-(5-chloro-4-((tetrahydrofuran-2-yl)methylamino)pyrimidin-2-ylamino)phenyl)propanoic acid (NT1-014) as a light yellow solid (80 mg, 99%), mp 180° C. (dec.). HPLC 96.7% [$R_t$=9.83 min, 30% $CH_3OH$ in 0.1% TFA water 20 min]. $^1H$ NMR (400 MHz, DMSO-d6) δ 10.56 (s, 1H), 8.74 (s, 1H), 8.20 (s, 1H), 7.51-7.39 (m, 2H), 7.31 (s, 1H), 7.24-7.15 (m, 2H), 4.07 (p, J=6.3 Hz, 1H), 3.74-3.66 (m, 1H), 3.62-3.54 (m, 1H), 3.49-3.39 (m, 2H), 2.78 (t, J=7.6 Hz, 2H), 2.54-2.44 (m, 2H), 1.91-1.72 (m, 3H), 1.62-1.52 (m, 1H). $^{13}C$ NMR (101 MHz, DMSO-d6) δ 174.16, 158.73, 137.33, 135.73, 129.08, 121.38, 104.26, 76.62, 67.58, 45.76, 35.71, 30.18, 29.03, 25.38. LC-MS (ESI+) m/z 377.13859 (M+H)$^+$; HRMS (ESI+) m/z calculated for $C_{18}H_{21}ClN_4O_3^+$ (M+H)$^+$ 377.1375. found, 377.1386.

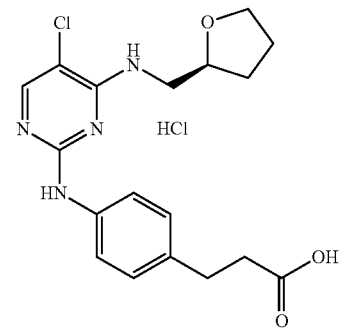 [SMILES: O=C(O)CCc1ccc(Nc2ncc(Cl)c(NC[C@@H]3CCCO3)n2)cc1 ; Cl]

(S)-3-(4-(5-Chloro-4-((tetrahydrofuran-2-yl)methyl-amino)pyrimidin-2-ylamino)phenyl)propanoic acid (NT1-015)

Substrates NT1-009 (80 mg, 0.323 mmol) and 3-(4-aminophenyl)propionic acid (35.4 mg, 0.215 mmol) were mixed in a microwave tube with acetonitrile (3 mL). Then 5 drops of 2M HCl were added to the tube. The vessel was sealed and heated to 150° C. for 120 minutes. Upon cooling, a precipitate formed. The reaction mixture was filtered, and the solid purified by trituration with DCM to afford (S)-3-(4-(5-chloro-4-((tetrahydrofuran-2-yl)methylamino)pyrimidin-2-ylamino)phenyl)propanoic acid (NT1-015) as a light yellow solid (77 mg, 95%), mp 180° C. (dec.). HPLC 96.4% [$R_t$=9.82 min, 30% $CH_3OH$ in 0.1% TFA water 20 min]. $^1H$ NMR (400 MHz, DMSO-d6) δ 10.56 (s, 1H), 8.75 (s, 1H), 8.21 (s, 1H), 7.48-7.39 (m, 2H), 7.29 (s, 1H), 7.24-7.13 (m, 2H), 4.07 (p, J=6.4 Hz, 1H), 3.75-3.66 (m, 1H), 3.63-3.54 (m, 1H), 3.47-3.39 (m, 2H), 2.78 (t, J=7.7 Hz, 2H), 2.54-2.44 (m, 2H), 1.94-1.69 (m, 3H), 1.65-1.47 (m, 1H). $^{13}C$ NMR (101 MHz, DMSO-d6) δ 174.16, 158.74, 151.89, 142.40, 137.39, 135.69, 129.09, 121.47, 104.29, 76.61, 67.59, 45.76, 35.70, 30.18, 29.03, 25.38. LC-MS (ESI+) m/z 377.13848 (M+H)$^+$; HRMS (ESI+) m/z calculated for $C_{18}H_{21}ClN_4O_3^+$ (M+H)$^+$ 377.1375. found, 377.1389.

4-(4-(5-Chloro-4-((tetrahydrofuran-2-yl)methylamino)pyrimidin-2-ylamino)phenyl)butanoic acid (NT1-025)

Substrates NT1-003 (200 mg, 0.806 mmol) and 4-(4-aminophenyl)-butyric acid (96.3 mg, 0.537 mmol) were mixed in a microwave tube with acetonitrile (6 mL). Then 10 drops of 2M HCl were added to the tube. The vessel was sealed and heated to 150° C. for 120 minutes. Upon cooling, a precipitate formed. The reaction mixture was filtered, and the solid purified by trituration with DCM to afford 4-(4-(5-chloro-4-((tetrahydrofuran-2-yl)methylamino)pyrimidin-2-ylamino)phenyl)butanoic acid (NT1-025) as a white solid (164 mg, 78%), mp 180° C. (dec.). HPLC 94.1% [$R_t$=10.34 min, 30% $CH_3OH$ in 0.1% TFA water 20 min]. $^1H$ NMR (400 MHz, Methanol-d4) δ 7.90 (s, 1H), 7.38 (d, J=8.1 Hz, 2H), 7.30 (d, J=8.1 Hz, 2H), 4.21-4.11 (m, 1H), 3.86-3.69 (m, 2H), 3.60-3.53 (m, 2H), 2.69 (t, J=8.0 Hz, 2H), 2.31 (t, J=8.0 Hz, 2H), 2.04-1.83 (m, 4H), 1.67-1.57 (m, 2H). $^{13}C$ NMR (101 MHz, Methanol-d4) δ 175.77, 159.25, 138.71, 129.09, 123.45, 105.28, 76.72, 67.61, 45.27, 34.10, 32.68, 28.53, 26.45, 24.99. LC-MS (ESI+) m/z 391.15401 (M+H)$^+$; HRMS (ESI+) m/z calculated for $C_{19}H_{23}ClN_4O_3^+$ (M+H)$^+$ 391.1531. found, 391.1541.

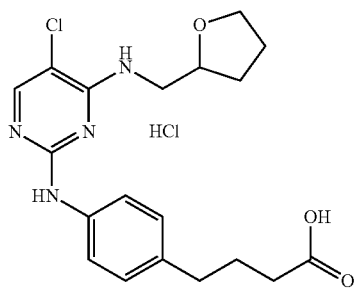 [SMILES: O=C(O)CCCc1ccc(Nc2ncc(Cl)c(NCC3CCCO3)n2)cc1 ; Cl]

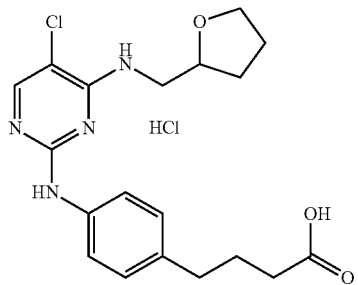 [SMILES: O=C(O)CCCc1ccc(Nc2ncc(Cl)c(NCC3CCCO3)n2)cc1 ; Cl]

(R)-4-(4-(5-Chloro-4-((tetrahydrofuran-2-yl)methylamino)pyrimidin-2-ylamino)phenyl)butanoic acid (NT1-026)

Substrates NT1-008 (80 mg, 0.323 mmol) and 4-(4-aminophenyl)-butyric acid (38.5 mg, 0.215 mmol) were mixed in a microwave tube with acetonitrile (3 mL). Then 5 drops of 2M HCl were added to the tube. The vessel was sealed and heated to 150° C. for 120 minutes. Upon cooling, a precipitate formed. The reaction mixture was filtered, and the solid purified by trituration with DCM to afford (R)-4-(4-(5-chloro-4-((tetrahydrofuran-2yl)methylamino)pyrimidin-2-ylamino)phenyl)butanoic acid (NT1-026) as a white solid (67 mg, 80%), mp 180° C. (dec.). HPLC 95.4% [$R_t$=10.35 min, 30% $CH_3OH$ in 0.1% TFA water 20 min]. $^1H$ NMR (400 MHz, Methanol-d4) δ 7.90 (s, 1H), 7.38 (d, J=8.1 Hz, 2H), 7.30 (d, J=8.1 Hz, 2H), 4.21-4.11 (m, 1H), 3.86-3.69 (m, 2H), 3.60-3.53 (m, 2H), 2.69 (t, J=8.0 Hz, 2H), 2.31 (t, J=8.0 Hz, 2H), 2.04-1.83 (m, 4H), 1.67-1.57 (m, 2H). $^{13}C$ NMR (101 MHz, Methanol-d4) δ 175.77, 174.19, 159.25, 138.72, 129.08, 123.41, 105.28, 76.72, 67.61, 45.27, 34.08, 32.59, 28.53, 26.36, 24.99. LC-MS (ESI+) m/z 391.15439 (M+H)$^+$; HRMS (ESI+) m/z calculated for $C_{19}H_{23}ClN_4O_3^+$ (M+H)$^+$ 391.1531. found, 391.1550.

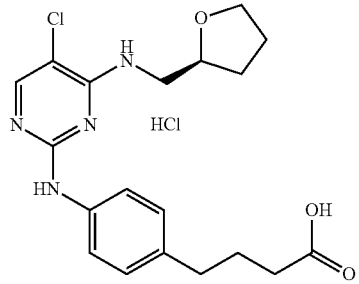 [SMILES: O=C(O)CCCc1ccc(Nc2ncc(Cl)c(NC[C@@H]3CCCO3)n2)cc1 ; Cl]

(S)-4-(4-(5-Chloro-4-((tetrahydrofuran-2-yl)methylamino)pyrimidin-2-ylamino)phenyl)butanoic acid (NT1-027)

Substrates NT1-009 (8 0 mg, 0.323 mmol) and 4-(4-aminophenyl)-butyric acid (38.5 mg, 0.215 mmol) were mixed in a microwave tube with acetonitrile (3 mL). Then 5 drops of 2M HCl were added to the tube. The vessel was sealed and heated to 150° C. for 120 minutes. Upon cooling, a precipitate formed. The reaction mixture was filtered, and the solid purified by trituration with DCM to afford (S)-4-(4-(5-chloro-4-((tetrahydrofuran-2-yl)methylamino)pyrimidin-2-ylamino)phenyl)butanoic acid (NT1-027) as a white solid (83 mg, 99%), mp 180° C. (dec.). HPLC 94.7% [$R_t$=10.36 min, 30% $CH_3OH$ in 0.1% TFA water 20 min]. $^1H$ NMR (400 MHz, Methanol-d4) δ 7.90 (s, 1H), 7.38 (d, J=8.0 Hz, 2H), 7.29 (d, J=8.0 Hz, 2H), 4.16 (p, J=6.5z, 1H), 3.85-3.69 (m, 2H), 3.61-3.55 (m, 2H), 2.69 (t, J=7.6H, 2H), 2.31 (t, J=7.3 Hz, 2H), 2.04-1.83 (m, 4H), 1.66-1.57 (m, 2H). $^{13}C$ NMR (101 MHz, Methanol-d4) δ 174.19, 159.25, 138.71, 129.08, 123.42, 105.29, 76.71, 67.61, 45.26, 34.06, 32.58, 28.53, 26.35, 24.99. LC-MS (ESI+) m/z 391.15333 (M+H)$^+$; HRMS (ESI+) m/z calculated for $C_{19}H_{23}ClN_4O_3^+$ (M+H)$^+$ 391.1531. found, 391.1545.

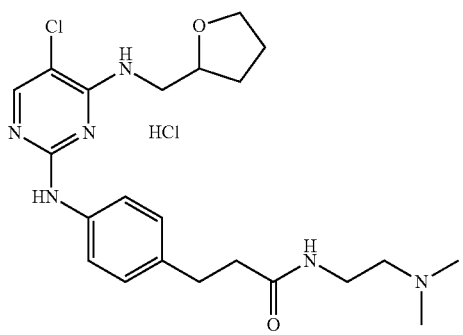 [SMILES: CN(C)CCNC(=O)CCc1ccc(Nc2ncc(Cl)c(NCC3CCCO3)n2)cc1 ; Cl]

3-(4-(5-Chloro-4-((tetrahydrofuran-2-yl)methyl-amino)pyrimidin-2-ylamino)phenyl)-N-(2-(dimethylamino)ethyl)propanamide (NT1-028)

EDC-HCl (66.26 mg, 0.346 mmol) was added to a solution of NT1-007 (100 mg, 0.266 mmol), N,N-dimethylethylenediamine (30.5 mg, 0.346 mmol), HOBt (46.68 mg, 0.346 mmol), and triethylamine (61.92 mg, 0.612 mmol) in DMF (1 mL) and stirred under argon at room temperature for 18 hours. The solvents were removed under reduced pressure, the reaction residue dissolved in ethyl acetate, and the solution washed with saturated $Na_2CO_3$ solution. The organic phase was dried, filtered, and evaporated to afford 3-(4-(5-chloro-4-((tetrahydrofuran-2-yl)methylamino)pyrimidin-2-ylamino)phenyl)-N-(2-(dimethylamino)ethyl) propanamide (NT1-028) as a light yellow powder (60 mg, 51%), mp 120° C. (dec.). HPLC 92.0% [$R_t$=7.79 min, 30% $CH_3OH$ in 0.1% TFA water 20 min]. $^1H$ NMR (400 MHz, Methanol-d4) δ 7.80 (s, 1H), 7.51 (d, J=8.7 Hz, 2H), 7.11 (d, J=8.0 Hz, 2H), 4.16 (p, 1H), 3.92-3.85 (m, 1H), 3.79-3.70 (m, 1H) 3.64-3.48 (m, 2H), 3.27 (t, J=7.7 Hz, 2H), 2.86 (t, J=7.7 Hz, 2H), 2.45 (t, J=7.7 Hz, 2H), 2.39 (t, J=7.7 Hz, 2H), 2.25 (s, 6H), 2.08-1.84 (m, 3H), 1.73-1.63 (m, 1H). $^{13}C$ NMR (101 MHz, Methanol-d4) δ 173.96, 158.17, 158.09, 152.26, 138.49, 134.17, 128.08, 119.36, 103.87, 77.46, 67.63, 57.67, 44.26, 43.93, 37.77, 36.39, 30.84, 28.46, 25.17. LC-MS (ESI+) m/z 447.22732 (M+H)$^+$; HRMS (ESI+) m/z calculated for $C_{22}H_{32}ClN_6O_2^+$ (M+H)$^+$ 447.2270. found, 447.2270.

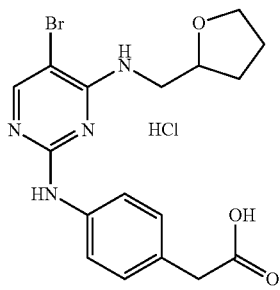 [SMILES: O=C(O)Cc1ccc(Nc2ncc(Br)c(NCC3CCCO3)n2)cc1 ; Cl]

2-(4-(5-Bromo-4-((tetrahydrofuran-2-yl)methyl-amino)pyrimidin-2-ylamino)phenyl)acetic acid (NT1-022)

Substrates DZ1-090 (100 mg, 0.242 mmol) and 4-aminophenylacetic acid (34.4 mg, 0.228 mmol) were mixed in a microwave tube with acetonitrile (3 mL). Then 5 drops of 2M HCl were added to the tube. The vessel was sealed and heated to 150° C. for 120 minutes Upon cooling, a precipitate formed. The reaction mixture was filtered, and the solid purified by trituration with DCM to afford 2-(4-(5-bromo-4-((tetrahydrofuran-2-yl)methylamino)pyrimidin-2-ylamino)phenyl)acetic acid (NT1-022) as a light gray solid (70 mg, 76%), mp 120° C. (dec.). HPLC 81.3% [$R_t$=9.48 min, 30% $CH_3OH$ in 0.1% TFA water 20 min]. $^1H$ NMR (400 MHz, DMSO-d6) δ 10.47 (s, 1H), 8.23 (s, 1H), 7.55-7.41 (m, 2H), 7.35 (s, 1H), 7.27-7.13 (m, 2H), 4.06 (p, J=6.8, 6.3 Hz, 1H), 3.75-3.65 (m, 1H), 3.62-3.54 (m, 1H), 3.51 (s, 2H), 3.47-3.35 (m, 2H), 1.94-1.68 (m, 3H), 1.63-1.46 (m, 1H). LC-MS (ESI+) m/z 409.06954 (M+H)$^+$; HRMS (ESI+) m/z calculated for $C_{17}H_{19}BrN_4O_3^+$ (M+H)$^+$ 407.0713. found, 407.0718.

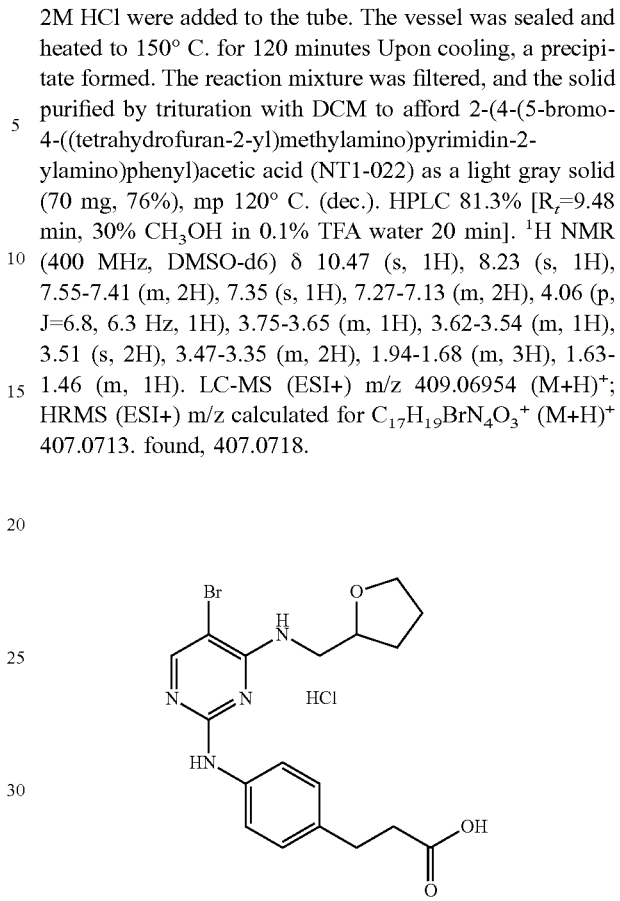

3-(4-(5-Bromo-4-((tetrahydrofuran-2-yl)methyl-amino)pyrimidin-2-ylamino)phenyl)propanoic acid (NT1-023)

Substrates DZ1-090 (100 mg, 0.34 mmol) and 3-(4-aminophenyl)propionic acid (37.6 mg, 0.228 mmol) were mixed in a microwave tube with acetonitrile (3 mL). Then 5 drops of 2M HCl were added to the tube. The vessel was sealed and heated to 150° C. for 120 minutes. Upon cooling, a precipitate formed. The reaction mixture was filtered, and the solid purified by trituration with DCM to afford 3-(4-(5-bromo-4-((tetrahydrofuran-2-yl)methylamino)pyrimidin-2-ylamino)phenyl)propanoic acid (NT1-023) as a light gray solid (69 mg, 72.6%), mp 180° C. (dec.). HPLC 81.0% [$R_t$=9.85 min, 30% $CH_3OH$ in 0.1% TFA water 20 min]. $^1H$ NMR (400 MHz, DMSO-d6) δ 10.53 (s, 1H), 8.46 (s, 1H), 8.25 (s, 1H), 7.44 (d, J=8.2 Hz, 2H), 7.20 (d, J=8.2 Hz, 2H), 4.05 (q, J=6.6 Hz, 1H), 3.74-3.64 (s, 1H), 3.62-3.53 (m, 1H), 3.50-3.33 (m, 2H), 2.77 (t, J=7.7 Hz, 1H), 2.56-2.30 (m, 2H), 1.90-1.68 (m, 3H), 1.61-1.46 (m, 1H). LC-MS (ESI+) m/z 421.08660 (M+H)$^+$; HRMS (ESI+) m/z calculated for $C_{17}H_{19}BrN_4O_3^+$ (M+H)$^+$ 421.0870. found, 421.0878.

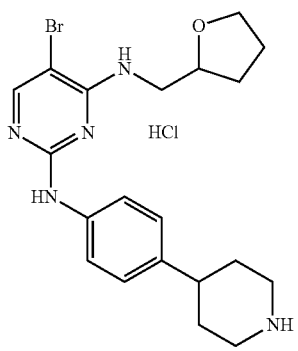 [SMILES: Brc1cnc(Nc2ccc(C3CCNCC3)cc2)nc1NCC1CCCO1 ; Cl]

5-bromo-N2-(4-(piperidin-4-yl)phenyl)-N4-((tetrahydrofuran-2-yl)methyl)pyrimidine-2,4-diamine (DZ1-088)

A mixture of SK1-008 (8b, Scheme 3) (0.047 g, 0.161 mmol) and NT1-004 (0.028 g, 0.161 mmol) in EtOH (1 mL) and 0.1 M aq. HCl (1 mL) was heated with microwave reactor at 150° C. for 40 min. The solvent was removed and the resulting residue was slurried with DCM, filtered and dried under high vacuum to afford the entitle compound as a white solid (0.014 mg, 19%).); HPLC 98.8% ($R_t$=2.50 min, 45% CH$_3$OH in 0.1% TFA water, 20 min); $^1$H NMR (400 MHz, DMSO-d$_6$): δ 8.01 (s, 1H), 7.47 (d, J=9.2 Hz, 2H), 7.37 (d, J=9.2 Hz, 2H), 4.17-4.14 (m, 1H), 3.83-3.70 (m, 2H), 3.60-3.50 (m, 4H), 3.15 (t, J=11.2 Hz, 2H), 2.96 (t, J=12.0 Hz, 1H), 2.10-1.87 (m, 6H), 1.66-1.58 (m, 1H). LC-MS (ESI+) m/z 432.13; (M+H)$^+$; HRMS (ESI+) m/z calculated for C$_{20}$H$_{27}$N$_5$O (M+H)$^+$ 432.1394. found 432.1392.

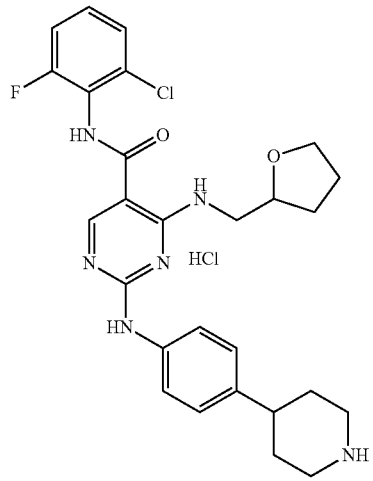 [SMILES: O=C(Nc1c(F)cccc1Cl)c1cnc(Nc2ccc(C3CCNCC3)cc2)nc1NCC1CCCO1 ; Cl]

N-(2-chloro-6-fluorophenyl)-2-(4-(piperidin-4-yl)phenylamino)-4-((tetrahydrofuran-2-yl)methylamino)pyrimidine-5-carboxamide (DZ1-089)

A mixture of YL7-102 (0.062 g, 0.161 mmol) and NT1-004 (0.028 g, 0.161 mmol) in EtOH (1 mL) and 0.1 M aq. HCl (1 mL) was heated with microwave reactor at 150° C. for 40 min. The solvent was removed and the resulting residue was slurried with DCM, filtered and dried under high vacuum to afford the entitle compound as a solid (0.032 mg, 36%)); HPLC 89.4% ($R_t$=10.37 min, 45% CH$_3$OH in 0.1% TFA water, 20 min); $^1$H NMR (400 MHz, DMSO-d$_6$): δ 8.60 (d, J=4.0 Hz, 1H), 7.55 (d, J=7.6 Hz, 2H), 7.40 (s, 1H), 7.39 (d, J=2.8 Hz, 2H), 7.25-7.19 (m, 1H), 4.19-4.10 (m, 1H), 3.93-3.80 (m, 1H), 3.75-3.60 (m, 3H), 3.53-3.50 (d, J=12.0 Hz, 2H), 3.16 (t, J=10.4 Hz, 2H), 3.00-2.93 (t, J=12.0 Hz, 1H), 2.11-1.89 (m, 6H), 1.67-1.60 (m, 1H). LC-MS (ESI+) m/z 525.2; (M+H)$^+$; HRMS (ESI+) m/z calculated for C$_{27}$H$_{31}$ClFN$_6$O$_2$ (M+H)$^+$ 525.2176. found 525.2175.

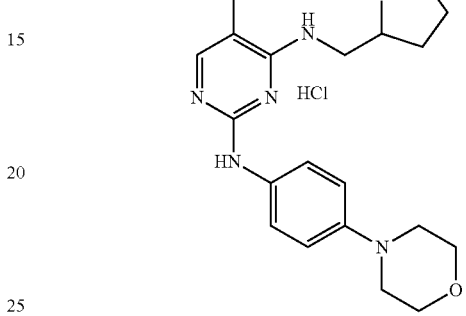

5-bromo-N2-(4-morpholinophenyl)-N4-((tetrahydrofuran-2-yl)methyl)pyrimidine-2,4-diamine (DZ1-091)

A mixture of SK1-008 (8b, Scheme 3) (0.100 g, 0.342 mmol) and 4-morpholinoaniline (0.067 g, 0.376 mmol) in EtOH (1 mL) was heated with microwave reactor at 150° C. for 20 min. The resulting precipitate was filtered and washed with ethyl acetate and dried under high vacuum to afford the title compound as a white solid (0.115 mg, 65%). HPLC 82.6% ($R_t$=6.00 min, 45% CH$_3$OH in 0.1% TFA water, 20 min); $^1$H NMR (400 MHz, DMSO-d$_6$): δ 7.94 (s, 1H), 7.36 (d, J=8.4 Hz, 2H), 7.13 (d, J=9.2 Hz, 2H), 4.19-4.10 (m, 1H), 3.95-3.80 (m, 6H), 3.76-3.70 (m, 1H), 3.63-3.57 (m, 3H), 3.25-3.22 (t, J=4.8 Hz, 4H), 2.01-1.88 (m, 3H), 1.67-1.59 (m, 1H). LC-MS (ESI+) m/z 434.13; (M+H)$^+$; HRMS (ESI+) m/z calculated for C$_{19}$H$_{25}$BrN$_5$O$_2$ (M+H)$^+$ 434.1186. found 434.1182.

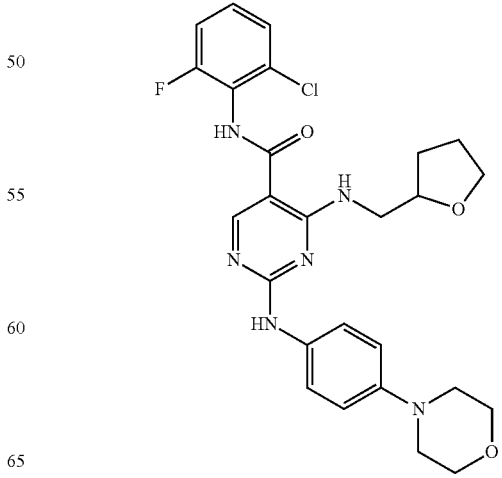

N-(2-chloro-6-fluorophenyl)-2-(4-morpholinophenylamino)-4-((tetrahydrofuran-2-yl)methylamino)pyrimidine-5-carboxamide (DZ1-092)

Substrates YL7-102 (100 mg, 0.26 mmol) and 4-morpholinoaniline (0.069 g, 0.38 mmol) were mixed in a microwave tube with 4.0M HCl in dioxane (110 µL) and 2-methoxyethanol (4.00 mL) was added to the mixture and heated at 110° C. for 16 hours. The resulting solution was concentrated, and the product was partitioned between $CHCl_3$ and saturated aqueous $NaHCO_3$. The organic phase was then dried over $Na_2SO_4$, filtered, and concentrated. The resulting solid was slurried twice with dichloromethane and hexane, filtered, and dried under reduced pressure to yield DZ1-092 as a light green solid (0.080 g). $^1$H NMR (400 MHz, DMSO-$d_6$): 8.50 (s, 1H), 7.38 (m, 3H), 7.24-7.19 (m, 1H), 7.08 (d, J=8.8 Hz, 2H), 4.16-4.10 (m, 1H), 3.85 (t, J=4.8 Hz, 4H), 3.76-3.59 (m, 3H), 3.20 (t, J=4.8 Hz, 4H), 2.01-1.91 (m, 3H), 1.66-1.58 (m, 1H). HPLC-MS (ESI+) m/z 527.2 (100%), HRMS (ESI+) m/z calculated for $C_{27}H_{31}ClFN_6O_3$ (M+H) 527.1968. found, 527.1962.

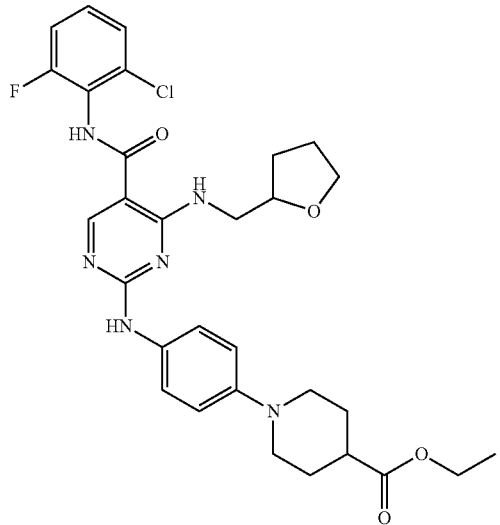

Ethyl 1-(4-(5-(2-chloro-6-fluorophenylcarbamoyl)-4-((tetrahydrofuran-2-yl)methylamino)pyrimidin-2-ylamino)phenyl)piperidine-4-carboxylate (DZ1-094)

The mixture of YL8-102 (0.200 g, 0.519 mmol) and ethyl 1-(4-aminophenyl)piperidine-4-carboxylate (0.141 g, 0.571 mmol) in EtOH (2 mL) was heated in a microwave reactor at 150° C. for 20 min. The resulting precipitate was filtered and washed with ethyl acetate and dried under high vacuum to afford the title compound as a gray solid (0.215 mg, 71%). HPLC 94.1% [$R_t$=12.01 min, Grad. 5-95% $CH_3OH$ in water (0.1% formic acid) 20 min]; $^1$H NMR (400 MHz, DMSO) δ 8.99 (s, 1H), 7.94 (s, 1H), 7.53 (d, J=8.8 Hz, 2H), 6.84 (d, J=8.8 Hz, 2H), 6.76 (t, J=4.8 Hz, 1H), 4.10-4.03 (m, 1H), 3.78-3.73 (m, 1H), 3.42 (t, J=5.6 Hz, 2H), 3.13-3.04 (m, 4H), 2.44-2.35 (m, 4H), 1.92-1.75 (m, 4H), 1.62-1.56 (m, 2H). LC-MS (ESI+) m/z 596.2 (M+H)$^+$; HRMS (ESI+) m/z calculated for $C_{30}H_{37}ClFN_6O_4$ (M+H)$^+$ 597.23778. found 597.23778.

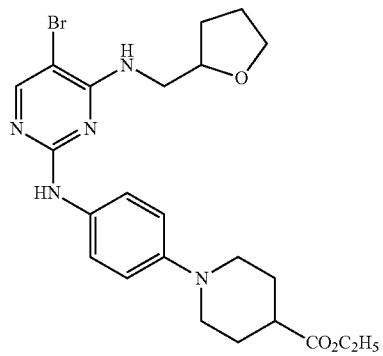 [SMILES: CCOC(=O)C1CCN(c2ccc(Nc3ncc(Br)c(NCC4CCCO4)n3)cc2)CC1]

Ethyl 1-(4-(5-bromo-4-((tetrahydrofuran-2-yl)methylamino)pyrimidin-2-ylamino)phenyl)piperidine-4-carboxylate (DZ1-093)

A mixture of SK1-008 (8b, Scheme 3) (0.200 g, 0.683 mmol) and ethyl 1-(4-aminophenyl)piperidine-4-carboxylate (0.186 g, 0.752 mmol) in EtOH (2 mL) was heated with microwave reactor at 150° C. for 20 min. The resulting precipitate was filtered and washed with ethyl acetate and dried under high vacuum to afford the title compound as a brown solid (0.070 mg, 22%). HPLC 99.7% [$R_t$=6.55 min, 45% $CH_3OH$ in water (0.1% TFA) 20 min]; $^1$H NMR (400 MHz, DMSO) δ 7.86 (s, 1H), 7.45 (d, J=9.2 Hz, 2H), 6.96 (d, J=9.2 Hz, 2H), 4.16-4.12 (m, 3H), 3.90-3.86 (m, 1H), 3.78-3.72 (m, 1H), 3.62-3.45 (m, 4H), 2.76-2.72 (t, J=12 Hz, 2H), 2.50-2.42 (m, 1H), 2.03-1.78 (m, 7H), 1.69-1.60 (m, 1H). LC-MS (ESI+) m/z 503.2 (M+H)$^+$; HRMS (ESI+) m/z calculated for $C_{23}H_{30}BrN_5O_3$ (M+H)$^+$ 504.16048. found 504.15966.

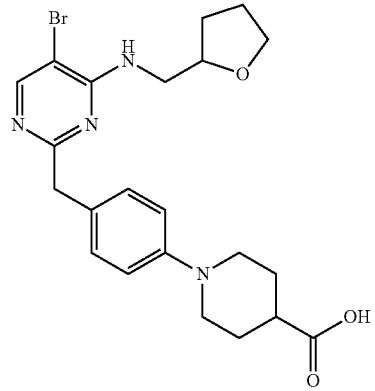

1-(4-((5-bromo-4-((tetrahydrofuran-2-yl)methylamino)pyrimidin-2-yl)methyl)phenyl)piperidine-4-carboxylic acid (DZ1-095)

The DZ1-093 (0.025 g, 0.050 mmol), THF (0.248 mL), and 2M NaOH (0.200 mL) were stirred at room temperature for 18 hours, the resulting solution was concentrated, and the product obtained was dissolved in water (2 mL). The aqueous solution was acidified with 1M HCl to a pH of 4-5. The solution was then filtered to afford DZ1-095 as a light brown solid (0.019 g, 81%). $^1$H NMR (400 MHz, DMSO) δ 12.27 (s, 1H), 8.95 (s, 1H), 7.93 (s, 1H), 7.51-7.48 (d, J=9.2 Hz, 2H), 6.83-6.81 (d, J=4.8 Hz, 2H), 6.75-6.73 (t, J=4.4 Hz, 1H), 4.09-4.03 (m, 1H), 3.78-3.73 (m, 1H), 3.63-3.57 (m, 2H), 3.46-3.39 (m, 3H), 2.66-2.60 (t, J=9.2 Hz, 2H), 2.35-2.30 (m, 1H), 1.89-1.73 (m, 5H), 1.67-1.53 (m, 2H). LC-MS (ESI+) m/z 475.12190 (M+H)$^+$; HRMS (ESI+) m/z calculated for $C_{21}H_{26}BrN_5O_3$(M+H) 476.12918. found, 476.12854.

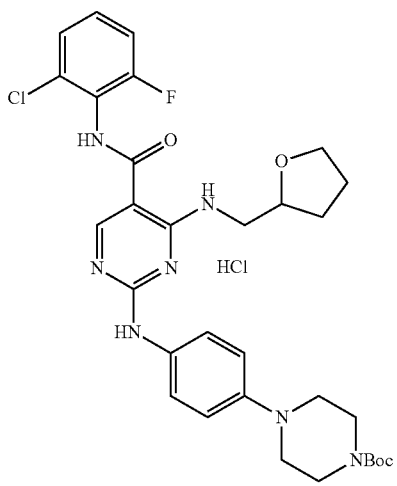 [SMILES: CC(C)(C)OC(=O)N1CCN(c2ccc(Nc3ncc(C(=O)Nc4c(F)cccc4Cl)c(NCC4CCCO4)n3)cc2)CC1 ; Cl]

tert-Butyl4-(4-(5-(2-chloro-6-fluorophenylcarbamoyl)-4-((tetrahydrofuran-2-yl)methylamino)pyrimidin-2-ylamino)phenyl)piperazine-1-carboxylate hydrochloride (YL9-161)

A mixture of YL7-102 (8c, Scheme 3) (0.308 g, 0.8 mmol) and tert-butyl 4-(4-aminophenyl)piperazine-1-carboxylate (0.222 g, 0.8 mmol) in 2-propanol (4 mL) was heated at 80° C. in a sealed tube for 5 h. The resulting precipitate was filtered upon cooling, and washed with 2-propanol (2 mL×3), then dried under high vacuum to afford the title compound as a light green solid (0.440 g, 83%). Mp.: 184-186° C.; HPLC 99.8% ($t_R$=5.23 min, 70% CH$_3$OH in 0.1% TFA water, 20 min); $^1$H NMR (400 MHz, DMSO-d$_6$): δ 10.26 (brs, 1H disappear on D$_2$O shake), 10.12 (brs, 1H disappear on D$_2$O shake), 9.31 (brs, 1H disappear on D$_2$O shake), 8.71 (s, 1H), 7.51-7.33 (m, 4H), 7.02 (appd, J=6.0 Hz, 2H), 4.05-3.98 (m, 1H), 3.75-3.70 (m, 1H overlapping with water peak), 3.63-3.57 (m, 1H overlapping with water peak), 3.47-3.42 (m, 6H), 3.10 (brs, 4H), 1.96-1.88 (m, 1H), 1.83-1.76 (m, 2H), 1.56-1.48 (m, 1H), 1.40 (s, 9H); $^{19}$F NMR (376 MHz, DMSO-d$_6$): δ −116.16−−116.20 (m); LC-MS (ESI+) m/z 626.25; (M+H)$^+$; HRMS (ESI+) m/z calculated for $C_{31}H_{38}ClFN_7O_4$ (M+H)$^+$ 626.2652. found 626.2651.

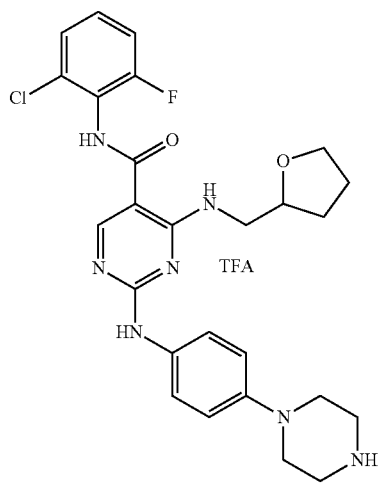 [SMILES: O=C(Nc1c(F)cccc1Cl)c1cnc(Nc2ccc(N3CCNCC3)cc2)nc1NCC1CCCO1 ; "TFA"]

N-(2-chloro-6-fluorophenyl)-2-(4-(piperazin-1-yl)phenylamino)-4-((tetrahydrofuran-2-yl)methylamino)pyrimidine-5-carboxamide TFA salt (YL9-162)

To a solution of YL9-161 (0.408 g, 0.616 mmol) in DCM (4 mL) at 0° C. was added TFA (4 mL). The reaction mixture was warmed up to r.t. and stirred for 1 h. The solvent was removed under reduced pressure. The resulting residue was slurried in EtOAC/Hexane (1:2) and sonicated. The precipitate was filtered and washed with EtOAC/Hexane (1:1) (3 mL×2) and dried under high vacuum to afford the title compound as a grey solid (0.400 g, 102%). Mp.: 205° C. (dec.); HPLC 99.5% ($t_R$=4.44 min, 50% CH$_3$OH in 0.1% TFA water, 20 min); $^1$H NMR (400 MHz, DMSO-d$_6$): δ 9.99 (s, 1H disappear on D$_2$O shake), 9.80 (brs, 1H disappear on D$_2$O shake), 9.04 (brs, 1H disappear on D$_2$O shake) 8.73 (s, 1H), 7.60 (d, J=8.8 Hz, 2H), 7.44-7.31 (m, 3H), 6.96 (d, J=8.8 Hz, 2H), 4.04-3.98 (m, 1H), 3.77-3.71 (m, 1H), 3.63-3.58 (m, 2H), 3.46-3.39 (m, 1H), 3.27-3.23 (m, 8H), 1.94-1.88 (m, 1H), 1.83-1.77 (m, 2H), 1.57-1.49 (m, 1H); $^{19}$F NMR (376 MHz, DMSO-d$_6$): δ −74.24 (s, 3H), −116.17−−116.21 (m, 1H); LC-MS (ESI+) m/z 526.22; (M+H)$^+$; HRMS (ESI+) m/z calculated for $C_{26}H_{30}ClFN_7O_2$ (M+H)$^+$ 526.2128. found 526.2123.

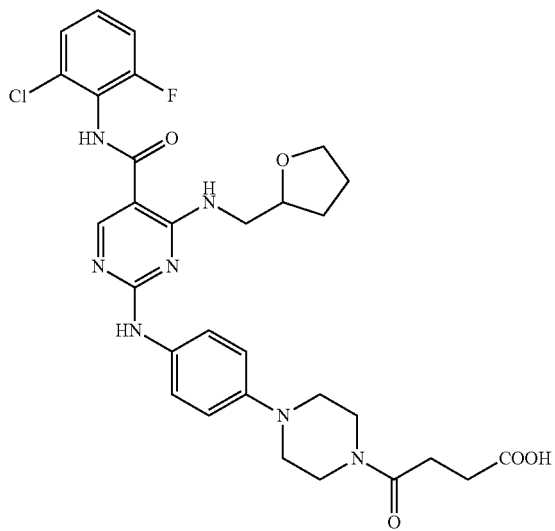 [SMILES: O=C(O)CCC(=O)N1CCN(c2ccc(Nc3ncc(C(=O)Nc4c(F)cccc4Cl)c(NCC4CCCO4)n3)cc2)CC1]

4-(4-(4-(5-(2-Chloro-6-fluorophenylcarbamoyl)-4-((tetrahydrofuran-2-yl)methylamino)pyrimidin-2-ylamino)phenyl)piperazin-1-yl)-4-oxobutanoic acid (YL9-163)

To a suspension of YL9-162 (0.096 g, 0.15 mmol) in chloroform under inert atmosphere was added DIPEA (0.194 g, 1.5 mmol). The mixture became a clear solution and cooled to 0° C. Succinic anhydride (0.015 g, 0.15 mmol) was added slowly and the reaction mixture was warmed up to r.t. and stirred for 1 h. The solvent was removed under reduced pressure and the resulting residue was sonicated in water (5 mL), filtered and washed with water (3 mL), then dried under vacuum to afford the title compound as a light green solid (0.084 g, 89%). Mp.: 189° C. (dec.); HPLC 99.0% ($t_R$=3.71 min, 60% CH$_3$OH in 0.1% TFA water, 20 min); $^1$H NMR (400 MHz, DMSO-d$_6$): δ 12.03 (s, 1H disappear on D$_2$O shake), 9.84 (s, 1H disappear on D$_2$O shake), 9.51 (s, 1H disappear on D$_2$O shake), 8.85 (s, 1H disappear on D$_2$O shake), 8.73 (s, 1H), 7.61 (d, J=8.8 Hz, 2H), 7.43-7.30 (m, 3H), 6.90 (d, J=8.8 Hz, 2H), 4.03-3.97 (m, 1H), 3.77-3.72 (m, 1H), 3.63-3.57 (m, 6H), 3.44-3.39 (m, 1H), 3.07 (appt, 2H), 3.00 (appt, 2H), 2.56 (t, J=6.4 Hz, 2H), 2.42 (t, J=5.6 Hz, 2H), 1.96-1.89 (m, 1H), 1.85-1.78 (m, 2H), 1.57-1.49 (m, 1H); $^{19}$F NMR (376 MHz, DMSO-d$_6$): δ -116.16--116.19 (m); LC-MS (ESI+) m/z 626.22; (M+H)$^+$; HRMS (ESI+) m/z calculated for C$_{30}$H$_{34}$ClFN$_7$O$_5$ (M+H)$^+$ 626.2289. found 626.2289.

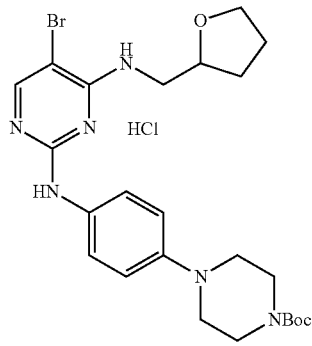 [SMILES: CC(C)(C)OC(=O)N1CCN(c2ccc(Nc3ncc(Br)c(NCC4CCCO4)n3)cc2)CC1 ; Cl]

tert-Butyl4-(4-(5-bromo-4-((tetrahydrofuran-2-yl)methylamino)pyrimidin-2-ylamino)phenyl)piperazine-1-carboxylate hydrochloride (YL9-157)

A mixture of SK1-008 (8b, Scheme 3) (0.176 g, 0.6 mmol) and tert-butyl 4-(4-aminophenyl)piperazine-1-carboxylate (0.167 g, 0.6 mmol) in 2-propanol (3 mL) was heated at 80° C. in sealed tube for 40 h (monitored with HPLC-MS). The resulting precipitate was filtered upon cooling, and washed with 2-propanol (2 mL×2), then dried under high vacuum to afford the title compound as a light green solid (0.300 g, 88%). Mp.: 124° C. (dec.); HPLC 98.5% ($t_R$=7.51 min, 60% CH$_3$OH in 0.1% TFA water, 20 min); $^1$H NMR (400 MHz, DMSO-d$_6$): δ 9.00 (s, 1H disappear on D$_2$O shake), 7.94 (s, 1H), 7.53 (d, J=8.8 Hz, 2H), 6.84 (d, J=8.8 Hz, 2H), 6.77 (brt, J=5.6 Hz, 1H disappear on D$_2$O shake), 4.10-4.03 (m, 1H), 3.78-3.73 (m, 1H), 3.63-3.58 (m, 1H), 3.43-3.40 (m, 6H), 2.96 (t, J=4.8 Hz, 4H), 1.90-1.77 (m, 3H), 1.62-1.56 (m, 1H), 1.40 (s, 9H); LC-MS (ESI+) m/z 533.19, 535.19 (Br isotope); (M+H)$^+$; HRMS (ESI+) m/z calculated for C$_{24}$H$_{34}$BrN$_6$O$_3$ (M+H)$^+$ 533.1870. found 533.1862.

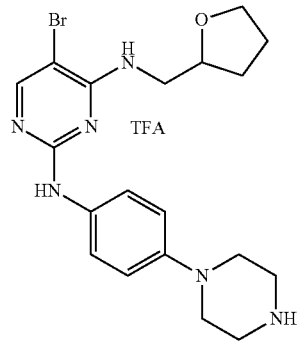 [SMILES: Brc1cnc(Nc2ccc(N3CCNCC3)cc2)nc1NCC1CCCO1 ; "TFA"]

5-Bromo-N2-(4-(piperazin-1-yl)phenyl)-N4-((tetrahydrofuran-2-yl)methyl)pyrimidine-2,4-diamine TFA salt (YL9-167)

To a solution of YL9-157 (0.291 g, 0.511 mmol) in DCM (2 mL) at 0° C. was added TFA (2 mL). The reaction mixture was warmed up to r.t. and stirred for 1 h. The solvent was removed under reduced pressure. The resulting residue was slurried in DCM/EtOAC/Hexane (1:1:2) and sonicated. The precipitate was filtered and washed with EtOAC/Hexane (1:1) (3 mL×2) and dried under high vacuum to afford the title compound as a grey solid (0.340 g, 98%). Mp.: 200° C. (dec.); HPLC 100% ($t_R$=4.28 min, 35% CH$_3$OH in 0.1% TFA water, 20 min); $^1$H NMR (400 MHz, DMSO-d$_6$): δ 9.50 (brs, 1H disappear on D$_2$O shake), 8.76 (s, 1H disappear on D$_2$O shake), 8.04 (s, 1H), 7.49 (d, J=8.8 Hz, 2H), 6.92 (d, J=8.85 Hz, 2H), 4.08-4.03 (m, 1H), 3.74-3.71 (m, 1H), 3.63-3.57 (m, 1H), 3.41 (t, J=6.4 Hz, 2H), 3.24-3.22 (m, 8H), 1.91-1.74 (m, 3H), 1.61-1.54 (m, 1H); $^{19}$F NMR (376 MHz, DMSO-d$_6$): δ-74.19 (s); LC-MS (ESI+) m/z 433.12, 435.12 (Br isotope); (M+H)$^+$; HRMS (ESI+) m/z calculated for C$_{19}$H$_{26}$BrN$_6$O (M+H)$^+$ 433.1346. found 433.1335.

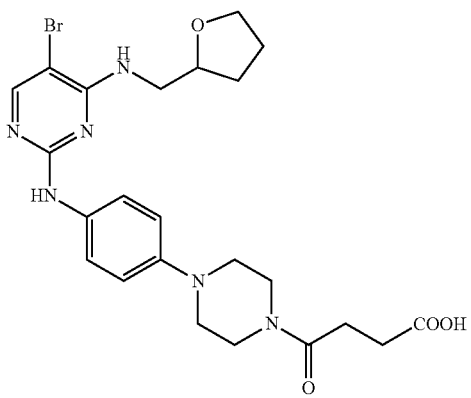 [SMILES: O=C(O)CCC(=O)N1CCN(c2ccc(Nc3ncc(Br)c(NCC4CCCO4)n3)cc2)CC1]

4-(4-(4-(5-Bromo-4-((tetrahydrofuran-2-yl)methyl-amino)pyrimidin-2-ylamino)phenyl)piperazin-1-yl)-4-oxobutanoic acid (YL9-168)

To a suspension of YL9-167 (0.129 g, 0.20 mmol) in chloroform under inert atmosphere was added DIPEA (0.259 g, 2.0 mmol). The mixture became a clear solution and cooled to 0° C. Succinic anhydride (0.020 g, 0.20 mmol) was added slowly. Then the reaction mixture was warmed up to r.t. and stirred for 1 h. The solvent was removed under reduced pressure. The residue was slurried with DCM/Hexane (1:1) and filtered to afford the title compound as a grey solid (0.095 g, 89%). Mp.: 177° C. (dec.); HPLC 98.5% ($t_R$=3.20 min, 50% $CH_3OH$ in 0.1% TFA water, 20 min); $^1H$ NMR (400 MHz, DMSO-$d_6$): δ 12.03 (s, 1H disappear on $D_2O$ shake), 9.00 (s, 1H disappear on $D_2O$ shake), 7.94 (s, 1H), 7.54 (d, J=8.8 Hz, 2H), 6.85 (d, J=9.2 Hz, 2H), 6.77 (appt., J=5.2 Hz, 1H disappear on $D_2O$ shake), 4.10-4.04 (m, 1H), 3.78-3.73 (m, 1H), 3.63-3.56 (m, 5H), 3.42 (apt, 2H), 3.03 (apt, 2H), 2.96 (apt, 2H), 2.56 (t, J=6.0 Hz, 2H), 2.42 (t, J=6.0 Hz, 2H), 1.92-1.77 (m, 3H), 1.62-1.54 (m, 1H); LC-MS (ESI+) m/z 533.16, 535.16 (Br isotope); (M+H)$^+$; HRMS (ESI+) m/z calculated for $C_{23}H_{30}BrN_6O_4$ (M+H)$^+$ 533.1506

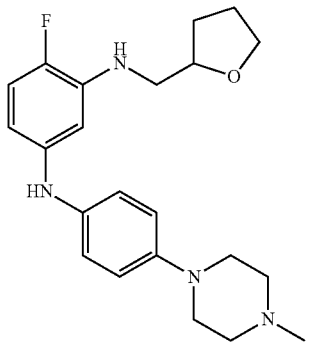

DZ1-098

5-fluoro-N2-(4-(4-methylpiperazin-1-yl)phenyl)-N4-((tetrahydrofuran-2-yl)methyl)pyrimidine-2,4-di-amine (DZ1-098)

Substrates YL7-160 (0.150 g, 0.650 mmol) and 4-4-methylpiperazinoaniline (0.138 g, 0.720 mmol) were mixed in a microwave tube with 4.0M HCl in dioxane (180 μL) and 2-methoxyethanol (4.00 mL) was added to the mixture and heated at 110° C. for 16 hours. The resulting solution was concentrated under reduced pressure, and the product was partitioned between $CHCl_3$ and saturated aqueous $NaHCO_3$. The organic phase was then dried over $Na_2SO_4$, filtered, and concentrated. The resulting solid was slurried with dichloromethane and hexane, filtered, and dried under reduced pressure to yield DZ1-098 as a dark gray solid (0.184 g, 73%). Mp: 86° C. (decomposed). HPLC 97.7% [$R_t$=6.15 min, Gradient 5-95% $CH_3OH$ in water (0.1% formic acid) 20 min]; $^1H$ NMR (400 MHz, DMSO) δ 8.75 (s, 1H), 7.79 (d, J=3.7 Hz, 1H), 7.51 (d, J=9.0 Hz, 2H), 7.37 (t, J=5.5 Hz, 1H), 6.79 (d, J=9.2 Hz, 2H), 4.09-3.98 (m, 1H), 3.75 (m, 1H), 3.60 (m, 1H), 3.05-2.93 (m, 4H), 2.45-2.36 (m, 4H), 2.19 (s, 3H), 1.98-1.71 (m, 3H), 1.65-1.51 (m, 1H). LC-MS (ESI+) m/z 386.22304 (M+H)$^+$; HRMS (ESI+) m/z calculated for $C_{20}H_{27}FN_6O$ (M+H) 387.23031. found, 387.22950.

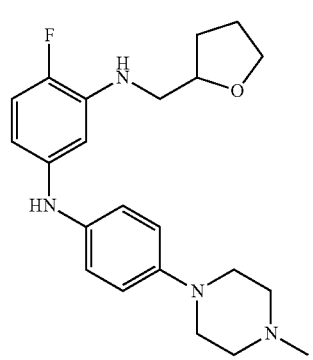

DZ1-098

5-fluoro-N2-(4-(4-methylpiperazin-1-yl)phenyl)-N4-((tetrahydrofuran-2-yl)methyl)pyrimidine-2,4-di-amine (DZ1-098)

Substrates YL7-160 (0.150 g, 0.650 mmol) and 4-4-methylpiperazinoaniline (0.138 g, 0.720 mmol) were mixed in a microwave tube with 4.0M HCl in dioxane (180 μL). 2-Methoxyethanol (4.00 mL) was added to the mixture and warmed to 110° C. for 16 hours. The resulting solution was concentrated under reduced pressure, and the product was partitioned between $CHCl_3$ and saturated aqueous $NaHCO_3$. The organic phase was then dried over $Na_2SO_4$, filtered, and concentrated. The resulting solid was slurried with dichloromethane and hexane, filtered, and dried to yield DZ1-098 as a dark gray solid (0.184 g, 73%). Mp: 86° C. (decomposed). HPLC 97.7% [$R_t$=6.15 min, Gradient 5-95% $CH_3OH$ in water (0.1% formic acid) 20 min]; $^1H$ NMR (400 MHz, DMSO) δ 8.75 (s, 1H), 7.79 (d, J=3.7 Hz, 1H), 7.51 (d, J=9.0 Hz, 2H), 7.37 (t, J=5.5 Hz, 1H), 6.79 (d, J=9.2 Hz, 2H), 4.09-3.98 (m, 1H), 3.75 (m, 1H), 3.60 (m, 1H), 3.05-2.93 (m, 4H), 2.45-2.36 (m, 4H), 2.19 (s, 3H), 1.98-1.71 (m, 3H), 1.65-1.51 (m, 1H). LC-MS (ESI+) m/z 386.22304 (M+H)$^+$; HRMS (ESI+) m/z calculated for $C_{20}H_{27}FN_{60}$ (M+H) 387.23031. found, 387.22950.

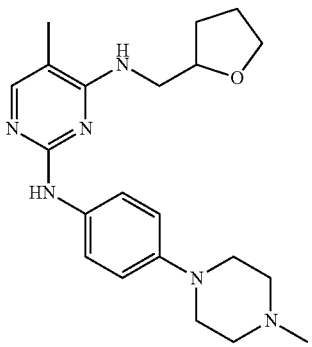

5-methyl-N2-(4-(4-methylpiperazin-1-yl)phenyl)-
N4-((tetrahydrofuran-2-yl)methyl)pyrimidine-2,4-
diamine (DZ1-100)

Substrates YL7-167 (0.150 g, 0.660 mmol) and 4-4-methylpiperazinoaniline (0.140 g, 0.730 mmol) were mixed in a microwave tube with 4.0M HCl in dioxane (180 μL) and 2-methoxyethanol (4.00 mL) was added to the mixture and warmed to 110° C. for 16 hours. The resulting solution was concentrated under reduced pressure, and the product was partitioned between CHCl$_3$ and saturated aqueous NaHCO$_3$. The organic phase was then dried over Na$_2$SO$_4$, filtered, and concentrated under reduced pressure. The resulting solid was slurried twice with dichloromethane and hexane, filtered, and dried under reduced pressure to yield DZ1-100 as a dark gray solid (0.162 g, 63%). Mp: 151.7° C. (decomposed). HPLC 97.7% [R$_t$=6.70 min, Gradient 5-95% CH$_3$OH in water (0.1% formic acid) 20 min]; $^1$H NMR (400 MHz, DMSO) δ 8.52 (s, 1H), 7.56 (t, J=7.2, 2H), 6.78 (d, J=9.2 Hz, 2H), 6.54 (t, J=5.6 Hz, 1H), 4.12-3.99 (m, 1H), 3.76 (m, 1H), 3.60 (m, 1H), 3.47-3.33 (m, 2H), 3.05-2.87 (t, J=4.4 Hz, 4H), 2.43-2.36 (t, J=5.2 Hz, 4H), 2.19 (s, 3H), 1.90-1.63 (m, 5H), 1.59 (m, 1H). LC-MS (ESI+) m/z 382.24811 (M+H)$^+$; HRMS (ESI+) m/z calculated for C$_{21}$H$_{30}$N$_6$O (M+H) 383.25539. found, 383.25539.

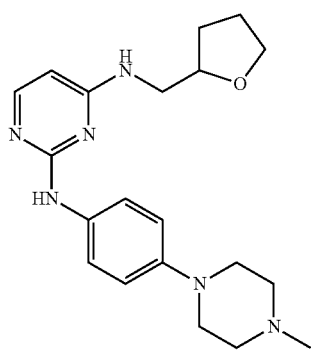

2-(4-(4-methylpiperazin-1-yl)benzyl)-N-((tetrahydrofuran-2-yl)methyl)pyrimidin-4-amine (DZ1-104)

Substrates SK1-008 (8b, Scheme 3) (0.150 g, 0.510 mmol) and 4-4-methylpiperazinoaniline (0.107 g, 0.560 mmol) were mixed in a microwave tube with 4.0M HCl in dioxane (140 μL) and 2-methoxyethanol (4.00 mL) was added to the mixture and warmed to 110° C. for 16 hours. The resulting solution was concentrated, and the product was partitioned between CHCl$_3$ and saturated aqueous NaHCO$_3$. The organic phase was then dried over Na$_2$SO$_4$, filtered, and concentrated under reduced pressure. The resulting solid was slurried twice with dichloromethane and hexane, filtered, and dried under reduced pressure to yield DZ1-104 as a dark brown solid (0.108 g, 58%). $^1$H NMR (400 MHz, DMSO) δ 8.64 (s, 1H), 7.71 (s, 1H), 7.57-7.55 (d, J=9.2 Hz, 2H), 7.16 (s, 1H), 6.81-6.79 (d, J=9.2, 2H), 5.90-5.88 (d, J=5.6 Hz, 1H), 3.99-3.93 (m, 1H), 3.77-3.74 (m, 1H), 3.64-3.62 (m, 2H), 3.01-2.99 (t, J=5.2 Hz, 4H), 2.43-2.41 (t, J=4.8 Hz, 4H), 2.19 (s, 1H), 1.92-1.77 (m, 3H), 1.57-1.50 (m, 1H). LC-MS (ESI+) m/z 369.23246 (M+H)$^+$; HRMS (ESI+) m/z calculated for C$_{20}$H$_{28}$N$_6$O (M+H) 369.23974. found, 369.24075.

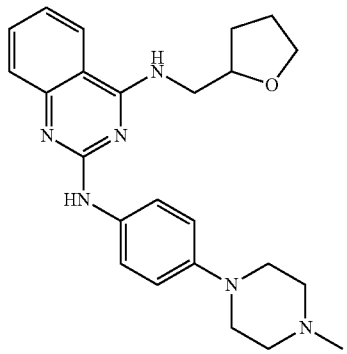

N2-(4-(4-methylpiperazin-1-yl)phenyl)-N4-((tetrahydrofuran-2-yl)methyl)quinazoline-2,4-diamine (DZ1-106)

Substrates YL7-176 (0.150 g, 0.570 mmol) and 4-4-methylpiperazinoaniline (0.120 g, 0.330 mmol) were mixed in a microwave tube with 4.0M HCl in dioxane (160 μL) and 2-methoxyethanol (4.00 mL) was added to the mixture and warmed to 110° C. for 16 hours. The resulting solution was concentrated under reduced pressure, and the product was partitioned between CHCl$_3$ and saturated aqueous NaHCO$_3$. The organic phase was then dried over Na$_2$SO$_4$, filtered, and concentrated under reduced pressure. The organic phase was then dried over Na$_2$SO$_4$, filtered, and concentrated. The resulting solid was slurried twice with dichloromethane and hexane, filtered, and dried under reduced pressure to yield DZ1-106 as a dark brown solid (0.158 g, 66%). Mp: 60.1° C. (decomposed). HPLC 96.8% [R$_t$=8.00 min, Gradient 5-95% CH$_3$OH in water (0.1% formic acid) 20 min]; $^1$H NMR (400 MHz, DMSO) δ 8.75 (s, 1H), 8.08-8.03 (t, J=8.4 Hz, 2H), 7.72-7.69 (d, J=8.8 Hz, 2H), 7.54-7.50 (t, J=7.2 Hz, 1H), 7.32-7.30 (d, J=8.4 Hz, 1H), 7.10-7.07 (t, J=8.0 Hz, 1H), 6.85-6.83 (d, J=9.2 Hz, 2H), 4.19-4.13 (m, 1H), 3.82-3.77 (m, 1H), 3.66-3.62 (m, 1H), 3.59-3.56 (t, J=5.6 Hz, 2H), 3.04-3.01 (t, J=4.4 Hz, 4H), 2.44-2.42 (t, J=4.8 Hz, 4H), 2.20 (s, 3H), 1.98-1.78 (m, 3H), 1.67-1.59 (m, 1H).

LC-MS (ESI+) m/z 418.24811 (M+H)+; HRMS (ESI+) m/z calculated for $C_{24}H_{30}N_6O$ (M+H) 419.25539. found, 419.25639.

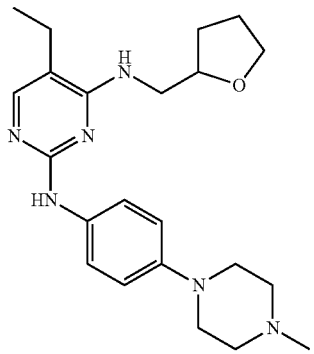

DZ1-108

5-ethyl-N2-(4-(4-methylpiperazin-1-yl)phenyl)-N4-((tetrahydrofuran-2-yl)methyl)pyrimidine-2,4-diamine (DZ1-108)

Substrates DZ1-102 (0.150 g, 0.620 mmol) and 4-4-methylpiperazinoaniline (0.130 g, 0.680 mmol) were mixed in a microwave tube with 4.0M HCl in dioxane (170 μL), added 2-methoxyethanol (4.00 mL) to the mixture and warmed to 110° C. for 16 hours. The resulting solution was concentrated, and the product was partitioned between CHCl₃ and saturated aqueous NaHCO₃. The organic phase was then dried over Na₂SO₄, filtered, and concentrated under reduced pressure. The resulting solid was slurried twice with dichloromethane and hexane, filtered, and dried under reduced pressure to yield DZ1-108 as a light gray solid (0.141 g, 62%). Mp: 209.5° C. (decomposed). HPLC 97.1% [$R_f$=7.22 min, Gradient 5-95% CH₃OH in water (0.1% formic acid) 20 min]; ¹H NMR (400 MHz, DMSO) δ 8.54 (s, 1H), 7.59-7.55 (t, J=7.2 Hz, 3H), 6.80-6.77 (d, J=9.2 Hz, 2H), 6.61-6.59 (t, J=5.6 Hz, 1H), 4.10-4.04 (m, 1H), 3.79-3.74 (m, 1H), 3.63-3.60 (m, 1H), 3.43-3.39 (m, 2H), 3.00-2.98 (t, J=4.4 Hz, 4H), 2.43-2.41 (t, J=4.4 Hz, 4H), 2.32-2.27 (m, 2H), 2.19 (s, 3H), 1.94-1.75 (m, 3H), 1.64-1.56 (m, 1H), 1.07-1.03 (t, J=7.2 Hz, 3H). LC-MS (ESI+) m/z 396.26376 (M+H)+; HRMS (ESI+) m/z calculated for $C_{22}H_{32}N_6O$ (M+H) 397.27104. found, 397.27199.

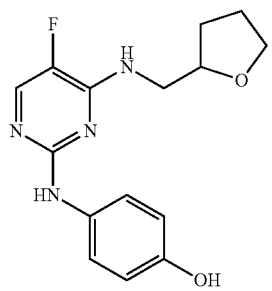

DZ1-112

4-(5-fluoro-4-((tetrahydrofuran-2-yl)methylamino)pyrimidin-2-ylamino)phenol (DZ1-112): The YL7-160 (0.050 g, 0.22 mmol) and 4-aminophenol (0.027 g, 0.24 mmol) were mixed in EtOH (0.500 mL) in a 2 mL microwave vial and heated to 150° C. for 20 minutes in a microwave reactor. The resulting precipitate formed upon cooling the mixture was filtered, washed with ethyl acetate, and dried under vacuum. The solid obtained was slurried with dichloromethane and hexane and filtered to afford DZ1-112 as a white solid (0.040 g, 59%). Mp: 214.5° C. (decomposed). HPLC 97.8% [$R_f$=8.13 min, Gradient 5-95% CH₃OH in water (0.1% formic acid) 20 min]; ¹H NMR (400 MHz, DMSO) δ 9.88 (s, 1H), 9.46 (s, 1H), 9.07 (s, 1H), 8.00-7.98 (d, J=4.8 Hz, 1H), 7.25-7.22 (d, J=8.8 Hz, 2H), 6.76-6.74 (d, J=8.8 Hz, 2H), 4.06-4.00 (m, 1H), 3.74-3.69 (m, 1H), 3.63-6.57 (m, 1H), 1.94-1.77 (m, 3H), 1.58-1.50 (m, 1H). LC-MS (ESI+) m/z 305.14083 (M+H)+; HRMS (ESI+) m/z calculated for $C_{15}H_{17}N_4O_2$ (M+H) 305.14093. found, 305.14074.

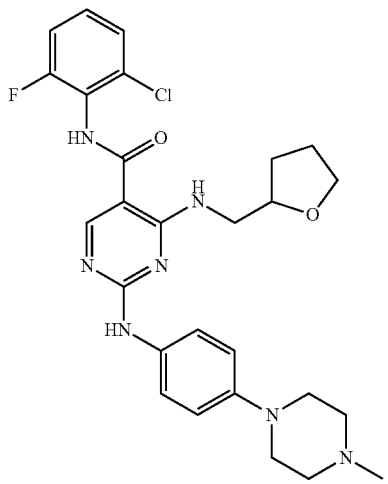

DZ1-114

N-(2-chloro-6-fluorophenyl)-2-(4-(4-methylpiperazin-1-yl)phenylamino)-4-((tetrahydrofuran-2-yl)methylamino)pyrimidine-5-carboxamide (DZ1-114)

Substrates YL7-102 (0.150 g, 0.390 mmol) and 4-4-methylpiperazinoaniline (0.082 g, 0.430 mmol) were mixed in a microwave tube with 4.0M HCl in dioxane (110 μL), 2-methoxyethanol (4.00 mL) was added to the mixture and warmed to 110° C. for 16 hours. The resulting solution was concentrated, and the product was partitioned between CHCl₃ and saturated aqueous NaHCO₃. The organic phase was then dried over Na₂SO₄, filtered, and concentrated. The solid obtained was slurried twice with dichloromethane and hexane, filtered, and dried under vacuum to yield DZ1-114 as a dark gray solid (0.097 g, 47%). Mp: 210.4° C. (decomposed). HPLC 90.8% [$R_t$=10.2 min, Gradient 5-95% $CH_3OH$ in water (0.1% formic acid) 20 min]; $^1H$ NMR (400 MHz, DMSO) δ 9.83 (s, 1H), 9.46 (s, 1H), 8.85 (s, 1H), 8.73 (s, 1H), 7.59-7.57 (d, J=8.8 Hz, 2H), 7.43-7.30 (m, 3H), 6.88-6.85 (d, J=8.8 Hz, 2H), 4.01-3.99 (m, 1H), 3.77-3.72 (m, 1H), 3.61-3.59 (m, 2H), 3.44-3.39 (m, 2H), 3.06-3.04 (t, J=4.0 Hz, 4H), 2.44-2.42 (t, J=4.4 Hz, 4H), 2.20 (s, 3H), 1.96-1.78 (m, 3H), 1.57-1.49 (m, 1H). LC-MS (ESI+) m/z 539.22118 (M+H)$^+$; HRMS (ESI+) m/z calculated for $C_{27}H_{31}ClN_7O_2$ (M+H) 540.22846. found, 540.22830.

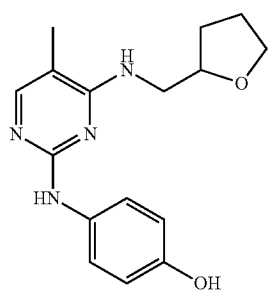

DZ1-116

4-(5-methyl-4-((tetrahydrofuran-2-yl)methylamino)pyrimidin-2-ylamino)phenol (DZ1-116)

The YL7-167 (0.050 g, 0.22 mmol) and 4-aminophenol (0.027 g, 0.24 mmol) were mixed in EtOH (0.500 mL) in a 2 mL microwave vial and heated to 150° C. for 20 minutes in a microwave reactor. The resulting precipitate formed upon cooling the mixture was filtered, washed with ethyl acetate, and subsequently dried under vacuum to obtain a solid. The solid was slurried with dichloromethane and hexane and filtered to afford DZ1-116 as a white solid (0.045 g, 61%). Mp: 145.4° C. (decomposed). HPLC 99.6% [$R_t$=8.82 min, Gradient 5-95% $CH_3OH$ in water (0.1% formic acid) 20 min]; $^1H$ NMR (400 MHz, DMSO) δ 11.55 (s, 1H), 9.90 (s, 1H), 9.50 (s, 1H), 8.39 (s, 1H), 7.58 (s, 1H), 7.24-7.22 (d, J=8.4 Hz, 2H), 6.78-6.75 (d, J=8.8 Hz, 2H), 4.05-3.98 (m, 1H), 3.75-3.69 (m, 1H), 3.63-3.57 (m, 1H), 3.42-3.39 (t, J=6.0 Hz, 2H), 1.97 (s, 3H), 1.97-1.77 (m, 3H), 1.57-1.51 (m, 1H), 1.17-1.14 (t, J=7.2 Hz, 1H). LC-MS (ESI+) m/z 300.15863 (M+H)$^+$; HRMS (ESI+) m/z calculated for $C_{16}H_{20}N_4O_2$(M+H) 301.16590. found, 301.16688.

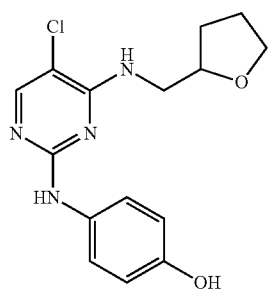

DZ1-120

4-(5-chloro-4-((tetrahydrofuran-2-yl)methylamino)pyrimidin-2-ylamino)phenol (DZ1-120)

The 8a (0.050 g, 0.20 mmol) and 4-aminophenol (0.024 g, 0.22 mmol) were mixed in EtOH (0.500 mL) in a 2 mL microwave vial and heated to 150° C. for 20 minutes in a microwave reactor. The resulting precipitate formed upon cooling the mixture was filtered, washed with ethyl acetate, and subsequently dried under reduced pressure. The solid was slurried with dichloromethane and hexane and filtered to afford DZ1-120 as a brown solid (0.027 g, 42%). Mp:214.0° C. (decomposed). HPLC 100% [$R_t$=8.90 min, Gradient 5-95% $CH_3OH$ in water (0.1% formic acid) 20 min]; $^1H$ NMR (400 MHz, DMSO) δ 9.85 (s, 1H), 9.43 (s, 1H), 8.45 (s, 1H), 8.03 (s, 1H) 7.28-7.26 (d, J=8.8 Hz, 2H), 6.75-6.73 (d, J=8.8 Hz, 2H), 4.08-4.01 (m, 1H), 3.73-3.68 (m, 1H), 3.62-3.57 (m, 2H), 1.90-1.74 (m, 3H), 1.58-1.50 (m, 1H). LC-MS (ESI+) m/z 320.10400 (M+H)$^+$; HRMS (ESI+) m/z calculated for $C_{15}H_{17}ClN_4O_2$(M+H) 321.11128. found, 321.11161.

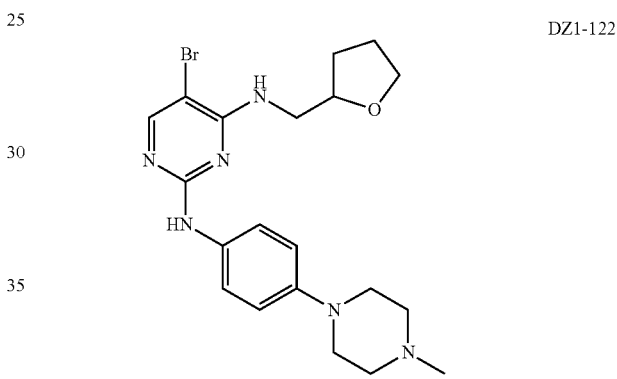

DZ1-122

5-bromo-N2-(4-(4-methylpiperazin-1-yl)phenyl)-N4-((tetrahydrofuran-2-yl)methyl)pyrimidine-2,4-diamine (DZ1-122)

The YL7-167 (0.055 g, 0.10 mmol), iodomethane (0.014 g, 0.10 mmol), and potassium carbonate (0.55 g, 0.40 mmol) were mixed in MeOH (2 mL) and stirred at room temperature for 8 hours. The mixture was then concentrated, and the solid was purified by $SiO_2$ chromatography (0-5% MeOH) to afford DZ1-122 as a yellow solid (0.012 g, 27%). $^1H$ NMR (400 MHz, DMSO) δ 8.99 (s, 1H), 7.94 (s, 1H), 7.54-7.51 (d, J=8.8 Hz, 2H), 6.85-6.83 (d, J=8.8 Hz, 2H), 6.77-6.75 (t, J=5.6 Hz, 1H), 4.08-4.03 (m, 1H), 3.78-3.73 (m, 1H), 3.63-3.58 (m, 1H), 3.43-3.40 (m, 2H), 3.09-3.06 (t, J=5.6 Hz, 4H), 2.44-2.40 (t, J=4.8 Hz, 4H), 1.91-1.56 (m, 3H), 1.63-1.56 (m, 1H). LC-MS (ESI+) m/z 446.14297 (M+H)$^+$; HRMS (ESI+) m/z calculated for $C_{15}H_{17}ClN_4O_2$ (M+H) 447.15025. found, 447.14936.

The synthesis of library 9 with R$^1$, R$^2$ and R$^3$ groups was achieved from a set of 2,4-dichloropyrimidine building blocks 7 (Scheme 5) by sequential reactions with two amine fragments. The starting materials 7 reacted with (±)-tetrahydrofurfurylamine using method a (Scheme 5) to obtain the intermediate library 8, which was subsequently reacted with requisite anilines ($R^3$—$NH_2$, Scheme 5) using method b to obtain the final library 9 with A- and B-rings (Scheme 5). The synthesis of building block 7c was achieved from readily available dihydroxypyrimidine-5-carboxylic acid via dichloropyrimidine-5-carbonyl chloride as shown in Scheme 1 in good yield.

Scheme 5:

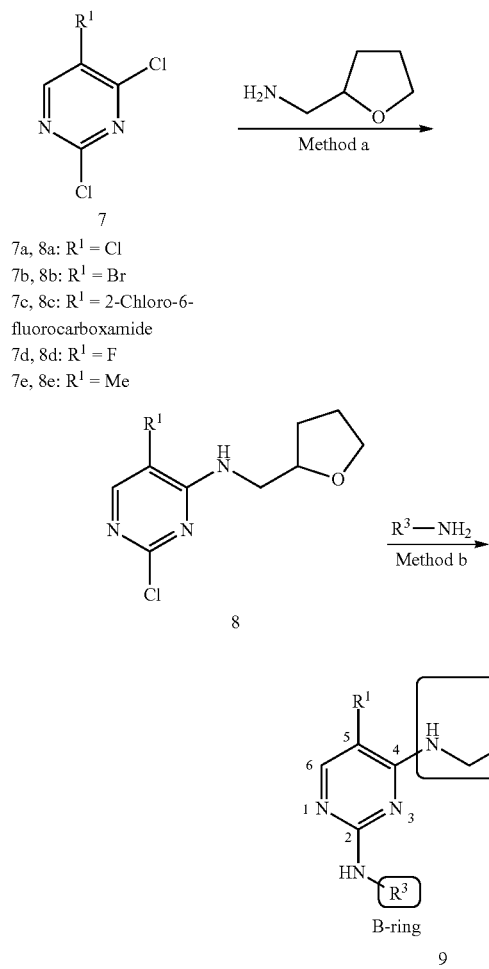

7a, 8a: $R^1$ = Cl
7b, 8b: $R^1$ = Br
7c, 8c: $R^1$ = 2-Chloro-6-fluorocarboxamide
7d, 8d: $R^1$ = F
7e, 8e: $R^1$ = Me -continued
Library 9
9a: $R^1$ = Cl, $R^3$ = piperazine
9b: $R^1$ = Cl, $R^3$ = 4-methylpiperazine
9c: $R^1$ = Cl, $R^3$ = morpholine
9d: $R^1$ = Cl, $R^3$ = piperadinyl-methyl
9e: $R^1$ = Cl, $R^3$ = piperidine-4-carboxylic acid
9f: $R^1$ = Cl, $R^3$ = 4-piperadine
9g: $R^1$ = Br, $R^3$ = piperadinyl-methyl
9h: $R^1$ = Br, $R^3$ = morpholine
9i: $R^1$ = Br, $R^3$ = piperazine
9j: $R^1$ = Br, $R^3$ = piperidine-4-carboxylic acid
9k: $R^1$ = Br, $R^3$ = 4-piperadine
9l: $R^1$ = 2-Chloro-6-fluorocarboxamide, $R^3$ = piperidine-4-carboxylic acid
9m: $R^1$ = 2-Chloro-6-fluorocarboxamide, $R^3$ = piperazine
9n: $R^1$ = 2-Chloro-6-fluorocarboxamide, $R^3$ = 4-morpholine
9o: $R^1$ = 2-Chloro-6-fluorocarboxamide, $R^3$ = 4-piperadine
9p: $R^1$ = 2-Chloro-6-fluorocarboxamide, $R^3$ = 2-fluoro-4-hydroxyphenyl
9q: $R^1$ = 2-Chloro-6-fluorocarboxamide, $R^3$ = 4-methoxyphenyl
9r: $R^1$ = 2-Chloro-6-fluorocarboxamide, $R^3$ = 4-hydroxyphenyl
9s: $R^1$ = 2-chloro-6-fluorocarboxamide, $R^3$ = piperadine-4-carboxylic acid
9t: $R^1$ = F, $R^3$ = 2-fluoro-4-hydroxyphenyl
9u: $R^1$ = Me, $R^3$ = 2-fluoro-4-hydroxyphenyl

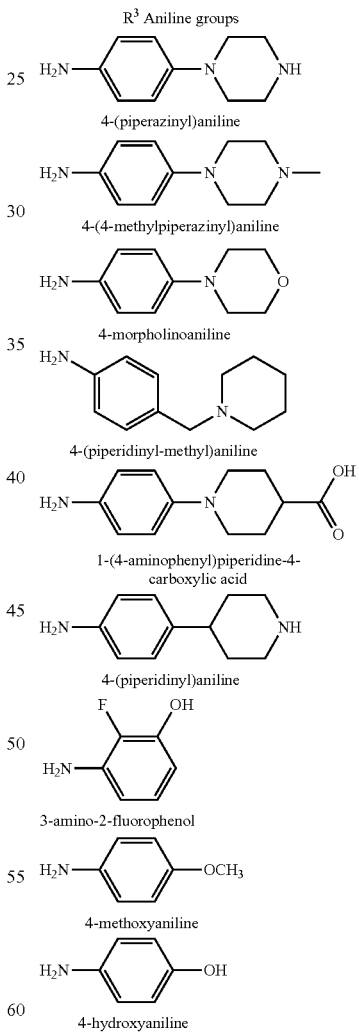

$R^3$ Aniline groups 4-(piperazinyl)aniline 4-(4-methylpiperazinyl)aniline 4-morpholinoaniline 4-(piperidinyl-methyl)aniline 1-(4-aminophenyl)piperidine-4-carboxylic acid 4-(piperidinyl)aniline 3-amino-2-fluorophenol 4-methoxyaniline 4-hydroxyaniline Design and synthesis of bisanilinopyrimidine library 9 with (±)-tetrahydrofurfurylamine A-ring. Method a: (±)-Tetrahydrofurfurylamine, Et$_3$N, MeOH, 0° C.-r.t., 2 h. Method b: Cat. 4M HCl in dioxane, 2-methoxyethanol, sealed tube, 110° C., and aq. NaHCO$_3$ work-up.

SAR Studies

The ability of the compound libraries to inhibit ACK1 kinase activity was first examined using an ELISA (Enzyme-Linked Immunosorbent Assay). This assay measured the ability of ACK1 to specifically phosphorylate a tyrosine residue in a peptide derived from AKT (of sequence ATGRYYAMKIL (SEQ ID NO.:1) followed by detection of phosphorylation by antibody based approach (Mahajan et al, *PLOS ONE*, 2010). Subsequently, $IC_{50}$ was determined for those compounds that inhibited ACK1 activity by >80% at concentration of 10 µM in the ELISA in a 32P Hotspot assay (Reaction Biology). Structure Activity Relationship (SAR) studies using the ELISA and dose response data obtained from the $^{32}P$ Hotspot assay. The AIM-100 (FIG. 1(*b*)) (±)-tetrahydrofurfurylamine fragment was incorporated to design and synthesize the library 9 (i.e., $R^2$ group, Scheme 5), and the final compound library 9 was obtained as a racemic mixture with >95% purity as determined by HPLC. The $R^1$ substituents at the 5-position of the pyrimidine and $R^3$ aniline fragments (Scheme 5 and FIG. 1(*d*)) in library 9 were chosen from Amgen #2 (FIG. 1(*a*)) and TAE684 (FIG. 1(*c*)). The $R^3$ aniline building blocks shown in Scheme 5 were chosen to aid inhibitor binding interactions as well as to modulate the drug-like properties such as solubility, hydrophobicity (c Log P<5), cell permeability, polar surface area <140 Å. Anilines possessing polar hydrophilic groups (or water solubilizing groups such as morpholine, piperazine, piperadine) were incorporated as $R^3$. Initial SAR from library 9 (Scheme 5) indicated that compounds bearing Cl, Br or 2-chloro-6-fluorocarboxamide groups in the 5-position of the pyrimidine ring (i.e., $R^1$) are important for ACK1 inhibitory activities, while methyl and F groups in the 5-position of the pyrimidine core weakened the ACK1 inhibition. This observation is consistent with library 9. For example, compounds 13 (76% at 10 µM entry 3, Table 2) and 14 (66% at 10 µM, entry 4, Table 2) with Br and 2-chloro-6-fluorocarboxamide respectively as $R^1$ and meta-F-para-hydroxyaniline as $R^3$ showed improved ACK1 inhibition compared to corresponding F and Me analogs 9t (41% at 10 µM) and 9u (49% at 10 µM) (entries 1, 2, Table 2). Similarly, compounds 16 (83% at 10 µM) and 9r (85% at 10 µM) that contain Br and 2-chloro-6-fluorocarboxamide fragments in the 5-position as $R^1$ (entries 6 and 7, Table 2) respectively and para-hydroxyaniline as $R^3$ showed 2-10-fold improvement in ACK1 inhibition comparing to analogs with F (41% at 10 µM) and methyl (8% at 10 µM) as $R^1$. The related compounds 18 and 9q (entries 9 and 10, Table 2) with hydrophobic methoxyaniline as $R^3$ showed moderate ACK1 inhibition, 67% and 68% respectively indicating hydrophilic anilines as $R^3$ are beneficial to maintain the in vitro ACK1 inhibitory activities.

The synthesis of library 12 (Scheme 2) was also undertaken in parallel based on the initial SAR information that was available from the library 9 (Scheme 5). The building block 7c was used as the starting point; in which the 5-position of the pyrimidine ring occupied 2-chloro-6-fluorocarboxamide group (similar to $R^1$ group in the library 9) and introduced sulfonyl substituted anilines as $R^2$ (A-ring, Scheme 2) similar to the isopropylsulfonamide containing A-ring of TAE684 (FIG. 1(*c*)). The hydrophilic groups such para-hydroxyaniline was introduced as the B-ring (Scheme 2). All analogs from the library 12 showed weak ACK1 inhibitory activities (i.e. <60% at 10 µM) in the ELISA. These observations were critical to guide further SAR and synthetic/medicinal chemistry efforts. The subsequent synthetic chemistry was predominantly focused on building blocks that contain Cl, Br or 2-chloro-6-fluorocarboxamide as the $R^1$ group (8a, 8b and 8c, Scheme 5) while keeping (±) tetrahydrofurfurylamine group as $R^2$.

Next, the $R^3$ group in library 9 was further modified using the anilines shown in Scheme 5 while keeping Cl, Br and 2-chloro-6-fluorocarboxamide groups as $R^1$. The compounds 9c, 9h and 9n that contain para-morpholino-aniline fragments (entries 11, 12 and 13, Table 2) as $R^3$ and Cl, Br and 2-chloro-6-fluorocarboxamide groups as $R^1$ showed improved ACK1 inhibitory activities with $IC_{50}$ 67.5 nM, 106 nM, and 48 nM respectively compared to earlier analogs and this observation further suggests aniline fragments with hydrophilic/water solubilizing moieties are well tolerated in the $R^3$ binding region. The 9a, 9i and 9m with para-piperazine aniline as $R^3$ also showed high ACK1 inhibitory activities (entries 14-16, Table 2) with $IC_{50}$s 81 nM, 94 nM and 33 nM respectively, similar to morpholine analogs further suggesting anilines with hydrophilic groups as $R^3$ have a positive effect on ACK1 inhibitory activity. As expected, compounds 9b, 19 and 20 with methylpiperazine aniline as $R^3$ (entries 17, 18 and 19, Table 2) followed a similar trend in ACK1 inhibitory activities with $IC_{50}$ of 54 nM, 48 nM and 48 nM respectively. The compound 9s (entry 25, Table 2) with piperadine carboxylic acid showed significantly improved ACK1 inhibitory activity with an $IC_{50}$ 34 nM, compared to related Cl and Br analogs 9e and 9j respectively (entries 23, 24, Table 2). The lack of activity of the bromo-analog 9j is probably due to poor solubility in the assay media. Interestingly, substitution of the methyl in compound 22 (entry 27, Table 2) with a carboxylic acid tether as shown in compound 21 (entry 26, Table 2) led to >1.5-fold improvement in ACK1 inhibitory with an $IC_{50}$:28 nM. Compounds 9e, 9s, and 22 (entries 24, 26 and 27, Table 2) with a carboxylic acid tether as H-bond donor/acceptor overall improved ACK1 inhibitory activities and this indicates this can be used as a handle to further explore SAR in the ACK1 binding region.

2-chloro-6-fluorocarboxamide as $R^1$ group significantly contributed to the ACK1 inhibitory activities in compounds 9n, 9m, 20, 9o and 22 (entries 13, 16, 19, 23 and 27, Table 2). The 90 (entry 23, Table 2) with 2-chloro-6-fluorocarboxamide as $R^1$ and para-4-piperadineaniline as $R^3$ showed markedly improved ACK1 inhibition with an $IC_{50}$ of 53.3 nM, which is 3-4 fold more potent comparing to the related 9f with an $IC_{50}$ of 231 nM and 9k with an $IC_{50}$ of 169 nM (entries 21, 22, Table 2) that have Cl, and Br respectively. Similarly, compound 9s (entry 26, Table 2) with piperadinecarboxylic acid as $R^3$ and 2-chloro-6-fluorocarboxamide as $R^1$ showed significantly improved ACK1 inhibition with an $IC_{50}$ of 32 nM in the enzymatic assay compared to its related Cl and methyl analogs 9e $IC_{50}$ of 85 nM and 9j 17% inhibition at 10 µM respectively (entries 24 and 25, Table 2). The improved inhibitory activities of 9n, 9m, 20, 9o and 9s (entries 13, 16, 20, 23 26, Table 2) can be attributed to the 2-chloro-6-fluorocarboxamide group in the 5-position of the pyrimidine undergoing a key H-bond contact in the gate keeper region. Altogether, the SAR demonstrates that Cl and Br groups are tolerated in the 5-position of the pyrimidine core, and substitution of the 5-position with hydrogen as in compound 21 (entry 20, Table 2) considerably lowered the ACK1 affinity (19% at 10 µM, ELISA).

Figure 8:
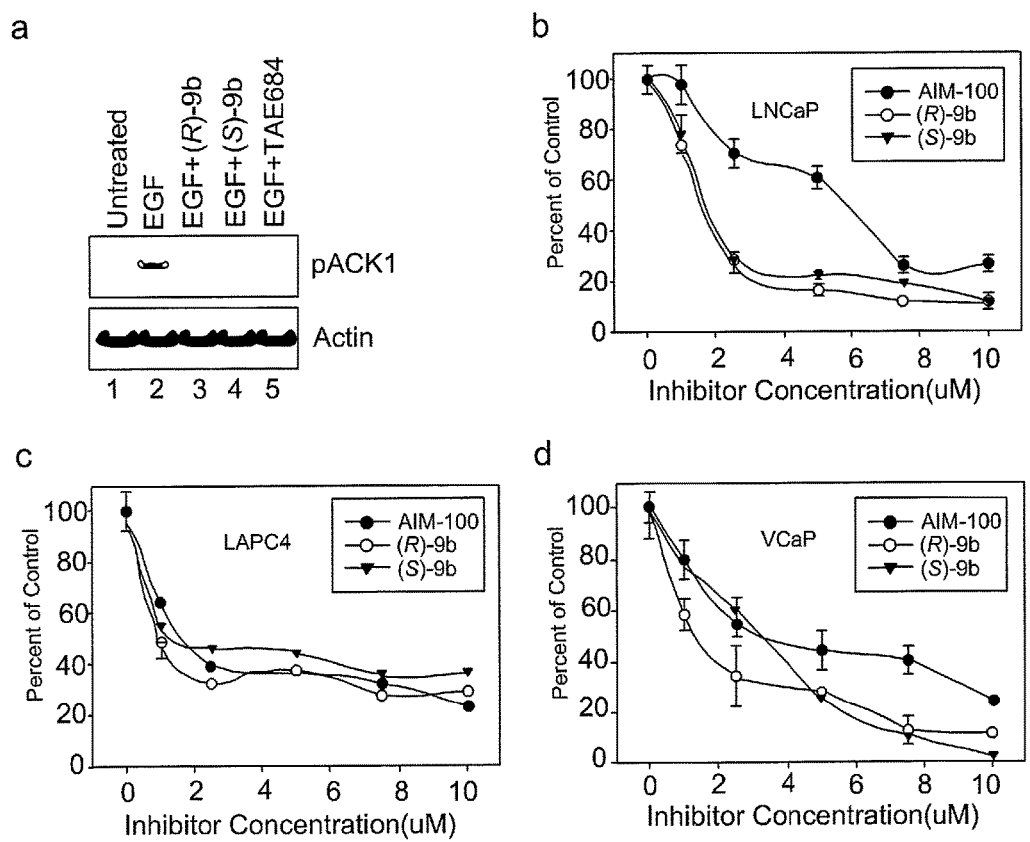
FIG. 8 shows the effect of ACK1 inhibitors (1 μM, overnight) on human prostate cancer cells. Inhibition of: LNCaP (FIG. 8(b)); LAPC4 (FIG. 8(c)), and VCaP (FIG. 8(d)) cell growth by AIM-100, (R)-9b, and (S)-9b. Inhibition of ACK1 autophosphorylation in LAPC4 cells treated 5 μM with (R)-9b and (S)-9b (FIG. 8(a)).

Although compounds 9n, 9m, 20, 9o and 22 with 2-chloro-6-fluorocarboxamide moiety showed higher potency for ACK1 in the enzymatic assay, these compounds did not display the expected cellular potency most probably due to lack of cell permeability. Selected compounds from the library 9 were chosen to evaluate the effects of ACK1 inhibition in LAPC4 human prostate cancer cells with inhibition of cell growth as a read out. The piperazine substituted chloro-pyrimidnes (±)-9b (entry 17, Table 2) showed promising ACK1 inhibitory activities in cellular assays. Based on the findings from cell culture data, enantiomers of 9b were synthesized to understand the ACK1 inhibitory activities of individual stereoisomers. The (R)-9b isomer (Scheme 4) demonstrated 1.5 fold better ACK1 inhibitory activity with an $IC_{50}$:56 nM, while (S)-9b showed an $IC_{50}$:82 nM in the $^{32}P$ hotspot assay. The synthesis of (R)-9b and (S)-9b are shown in the Scheme 4 and other examples of enantiomerically pure compounds (not reported here) were also synthesized using the protocols in the Scheme 4. Both (R)-9b and (S)-9b were able to inhibit ACK1 autophosphorylation in prostate cancer cells (FIG. 8(a)) and inhibit cell growth (FIG. 8(b-d)).

TABLE 2

SAR and in vitro inhibitory activities of library 9 and related compounds

| Entry | ID | $R^1$ | $R^3$ | % Inhibition @ 10 μM (ELISA) | $IC_{50}$ ($^{32}P$ Hotspot assay) |
|---|---|---|---|---|---|
| 1 | 9t | F | 3-F-4-OH-phenyl | 41 ± 6.3 | ND |
| 2 | 9u | $CH_3$ | 3-F-4-OH-phenyl | 49 ± 2.8 | ND |
| 3 | 13 | Br | 3-F-4-OH-phenyl | 76 ± 14 | 299 nM |
| 4 | 14 | 2-F-6-Cl-phenyl-NH-C(O)-C(CH3)- | 3-F-4-OH-phenyl | 66 ± 1.5 | ND |
| 5 | 15 | Cl | 4-OH-phenyl | 65 | ND |
| 6 | 16 | Br | 4-OH-phenyl | 83 ± 2.8 | 164 nM |

TABLE 2-continued

SAR and in vitro inhibitory activities of library 9 and related compounds

| Entry | ID | R¹ | R³ | % Inhibition @ 10 μM (ELISA) | IC$_{50}$ ($^{32}$P Hotspot assay) |
|---|---|---|---|---|---|
| 7 | 9r | F, HN-C(=O)-CH(Me)-, Cl (2-F-6-Cl-anilide of isobutyryl) | 4-hydroxyphenyl | 85 ± 0.2 | 54.4 nM |
| 8 | 17 | Br | 3-methyl-4-hydroxyphenyl | 75.5 ± 20 | 99 nM |
| 9 | 18 | Br | 4-methoxyphenyl | 67 ± 0.2 | ND |
| 10 | 9q | F, HN-C(=O)-CH(Me)-, Cl | 4-methoxyphenyl | 68 ± 10 | ND |
| 11 | 9c | Cl | 4-morpholinophenyl | 89 ± 1.4 | 67.5 nM |
| 12 | 9h | Br | 4-morpholinophenyl | 89 ± 1.4 | 106 nM |

TABLE 2-continued

SAR and in vitro inhibitory activities of library 9 and related compounds

| Entry | ID | R¹ | R³ | % Inhibition @ 10 μM (ELISA) | IC$_{50}$ ($^{32}$P Hotspot assay) |
|---|---|---|---|---|---|
| 13 | 9n | 2-F, 6-Cl phenyl amide (isobutyramide) | 4-morpholinophenyl | 82 ± 7.7 | 47.7 nM |
| 14 | 9a | Cl | 4-(piperazin-1-yl)phenyl | 82 ± 12.7 | 81.3 nM |
| 15 | 9i | Br | 4-(piperazin-1-yl)phenyl | 85.5 ± 0.70 | 94.7 nM |
| 16 | 9m | 2-F, 6-Cl phenyl amide (isobutyramide) | 4-(piperazin-1-yl)phenyl | 89.5 ± 2.1 | 33.2 nM |
| 17 | 9b | Cl | 4-(4-methylpiperazin-1-yl)phenyl | 90.5 ± 0.70 | 54.4 nM |
| 18 | 19 | Br | 4-(4-methylpiperazin-1-yl)phenyl | 93 ± 3 | 48.0 nM |

TABLE 2-continued
SAR and in vitro inhibitory activities of library 9 and related compounds
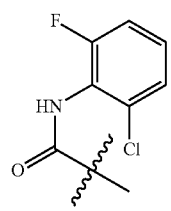 [SMILES: *C(=O)Nc1c(F)cccc1Cl]
| Entry | ID | R$^1$ | R$^3$ | % Inhibition @ 10 μM (ELISA) | IC$_{50}$ ($^{32}$P Hotspot assay) |
|---|---|---|---|---|---|
| 19 | 20 | 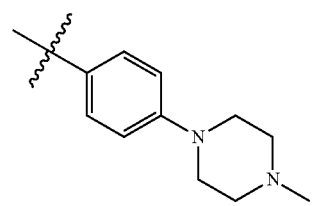 [SMILES: *c1ccc(N2CCN(C)CC2)cc1] | 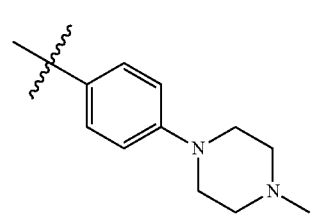 [SMILES: *c1ccc(N2CCN(C)CC2)cc1] | 97 ± 3 | 48.3 nM |
| 20 | 21 | H | 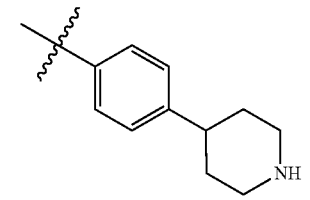 [SMILES: *c1ccc(C2CCNCC2)cc1] | 16 ± 4.2 | ND |
| 21 | 9f | Cl | 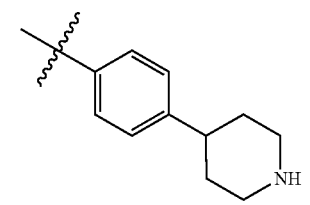 [SMILES: *c1ccc(C2CCNCC2)cc1] | 79.5 ± 0.70 | 231 nM |
| 22 | 9k | Br | 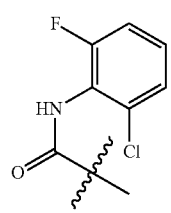 [SMILES: *C(=O)Nc1c(F)cccc1Cl] | 84.5 ± 0.70 | 169 nM |
| 23 | 9o | 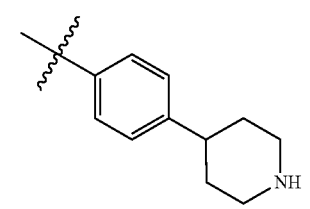 [SMILES: *c1ccc(C2CCNCC2)cc1] | | 97 | 53.3 nM |

TABLE 2-continued

SAR and in vitro inhibitory activities of library 9 and related compounds

| Entry | ID | R¹ | R³ | % Inhibition @ 10 μM (ELISA) | IC$_{50}$ ($^{32}$P Hotspot assay) |
|---|---|---|---|---|---|
| 24 | 9e | Cl | 4-(4-carboxypiperidin-1-yl)phenyl | 93 ± 5.1 | 85 nM |
| 25 | 9j | Br | 4-(4-carboxypiperidin-1-yl)phenyl | 17 ± 2.8 | ND |
| 26 | 9s | 2-chloro-6-fluorophenyl isobutyramide | 4-(4-carboxypiperidin-1-yl)phenyl | 98 | 34.2 nM |
| 27 | 22 | 2-chloro-6-fluorophenyl isobutyramide | 4-[4-(3-carboxypropanoyl)piperazin-1-yl]phenyl (pyridine linker) | 89 ± 5.6 | 28.4 nM |

ND: Not determined, IC$_{50}$ values were determined for compounds that showed >80% in the ELISA assay.

Cell Culture Data of Selected Compounds from Library 9

ACK1 is a tyrosine kinase that auto-phosphorylates at Tyr284, which is indicative of its kinase activation. To determine inhibitory potential of the compounds from library 9, prostate cancer derived cell line LAPC4 was treated with either EGF ligand alone or added to cells pretreated with the compounds, and equal amounts of cell lysates were subjected to immunoblotting. EGF (epidermal growth factor) ligand causes rapid activation of EGFR (epidermal growth factor receptor), which in turn lead to activation of the ACK1 kinase (FIG. 8(a), lane 2, top panel). In contrast, treatment of LAPC cells with (R)-9b and (S)-9b resulted in almost complete loss of ACK1 activation. TAE684 and AIM-100 also exhibited significant reduction in ACK1 activation. Actin was used as control, which indicates equal loading of cell lysates (FIG. 8(a), lower panel).

In addition to (R)-9b and (S)-9b many other compounds from library 9 were assessed for their potential to suppress ACK1 kinase activity using immunoblotting, as described herein. The percentage inhibition of ACK1 kinase activity is shown in the Table 2.

Effects of (R)-9b and (S)-9b in human cancel cells

Three distinct human prostate cancer derived cell lines, LNCaP, LAPC4 and VCaP were either DMSO treated or treated with 1, 2.5, 5, 7.5 and 10 µM of inhibitors, AIM-100, (R)-9b and (S)-9b for 36 hrs and the number of viable cells were counted by trypan blue exclusion assay. Both, (R)-9b and (S)-9b were significantly better ($IC_{50}$=1.8 µM) than AIM-100 ($IC_{50}$=7 µM) in their ability to inhibit cell growth in LNCaP cells (FIG. 8(b)). However, in LAPC4 cells, all the three inhibitors were comparable in their ability to suppress cell proliferation (FIG. 8(c)). In contrast, highly metastatic Castration Resistant Prostate Cancer (CRPC) forming VCaP cells were observed to be highly sensitive to (R)-9b ($IC_{50}$=2 µM), while AIM-100 and (S)-9b exhibited $IC_{50}$ of 4 uM (FIG. 8(d)). Taken together, it appears that (R)-9b is a superior ACK1 inhibitor in vivo and most significantly, exhibit ability to suppress proliferation of androgen-independent or CRPC VCaP cells.

Figure 9:
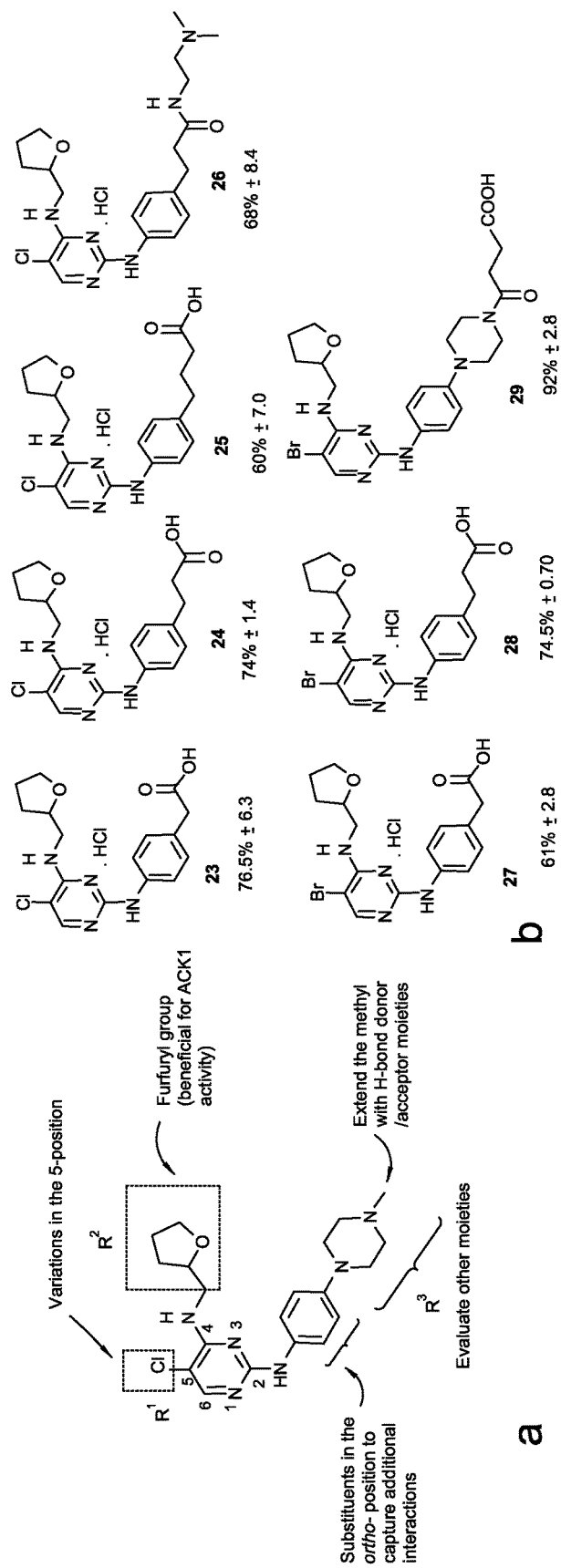
FIG. 9(a) shows a SAR overview.
FIG. 9(b) shows compounds with an extended carboxylic acid tether as ACK1 inhibitors (% inhibition at 10 μM in ELISA is shown).

For the compounds synthesized as ACK1 inhibitors, the $R^2$ group was kept constant, changing the 5-position of the pyrimidine ($R^1$) and aniline ($R^3$) groups. The SAR changes are highlighted in the FIG. 9(a). Since cell culture data indicated that (R)-9b and (S)-9b are potent in human cancer cells, the Cl moiety was included in subsequent analog synthesis. Therefore, based on the cell culture data, SAR obtained from the library 9 and by looking at the inhibitory activities of compounds that contain a carboxylic acid tether such as in 9e, 9j, 9s and 22 (entries 24-27, Table 2), the compounds shown in the FIG. 9(b) with Cl in the 5-position of the pyrimidine as $R^1$ were synthesized to explore the SAR. Compounds 23, 24, 26 and 28 (FIG. 9(b)) with 1 or 2 carbon tethered carboxylic acids showed moderate ACK1 inhibition. The bis-amine group in compound 26 (FIG. 9(b)) was introduced with the hope of facilitating cell permeability and solubility. The compound 29 (FIG. 9(b)) with piperazine-amide tethered carboxylic acid showed significant ACK1 inhibition similar to compounds 22 (entry 27, Table 2). The in vitro activities of compounds shown in the FIG. 9(b) demonstrate the importance of the piperazine moiety to retain potent ACK1 inhibitory activities.

Figure 10:
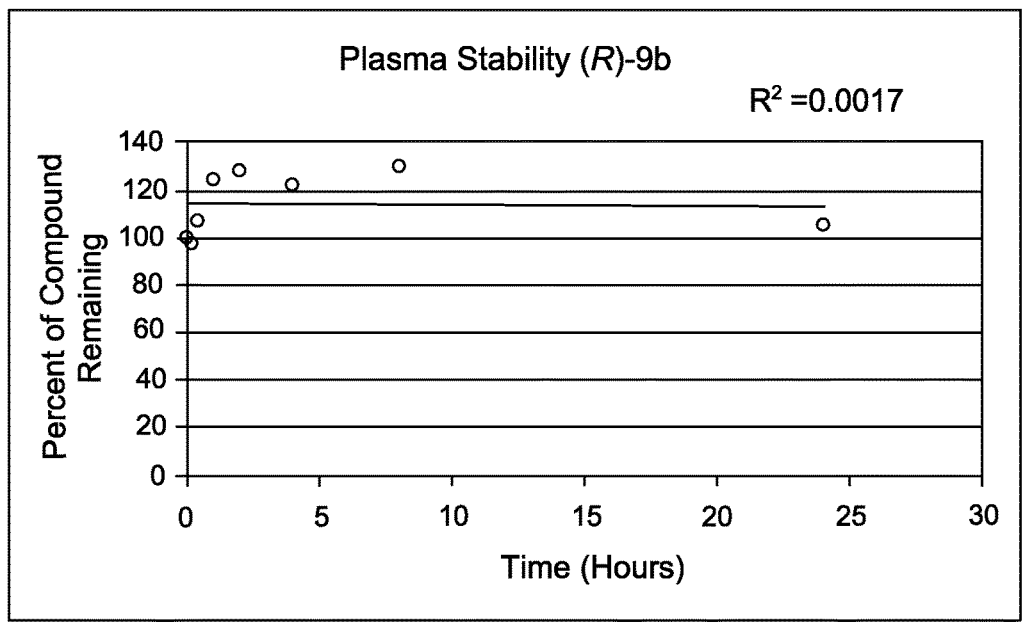
FIG. 10 shows the plasma stability of (R)-9b and (S)-9b using HPLC; area of the peak (Y-Axis) plotted against the time (X-Axis).
Figure 10:
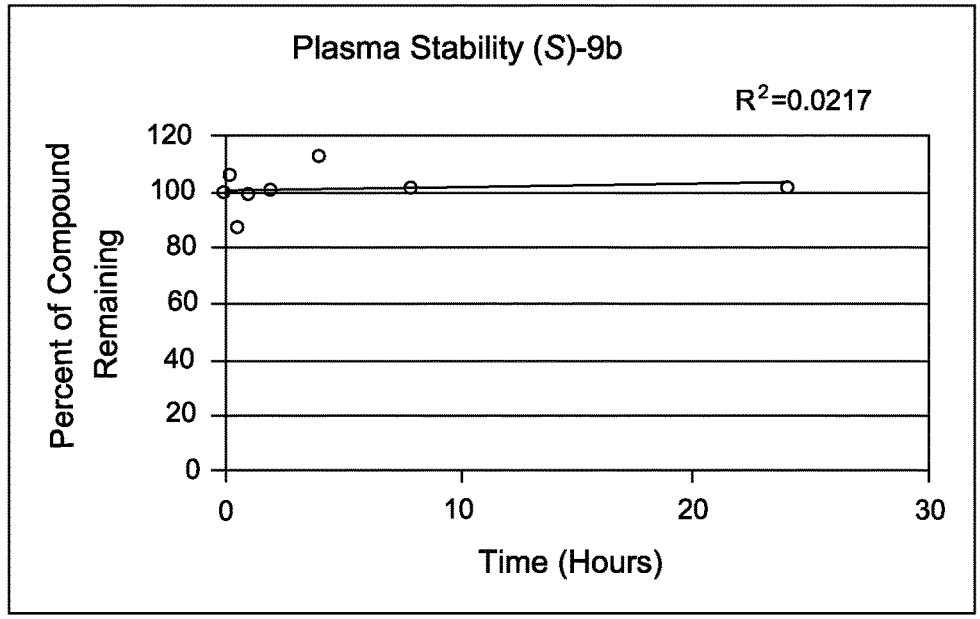

According to cell culture data both (R)-9b and (S)-9b can penetrate human cancer cell lines and inhibit cell growth in an ACK1 dependant manner. The in vitro human plasma stability of compounds (R)-9b and (S)-9b were evaluated using HPLC analysis, in a time-course experiment up to 24 hours (see experimental). Data showed both (R)-9b (S)-9b were stable in human plasma (FIG. 10) up to 24 hrs and displayed a long half-life ($t_{1/2}$>6 hrs). Procaine and procaineamide were used as standards (see experimental and SI) to generate the human plasma stability data of (R)-9b and (S)-9b also using HPLC analysis. The solubility of (R)-9b and (S)-9b were determined as 1 mg/mL and 0.9 mg/mL respectively in PBS with 10% DMSO (a clear solution) which suggests both R)-9b and (R)-9b are suitable for further in vivo animal experiments.

A combination of a fragment based approach of creating small molecule inhibitor libraries and a novel ELISA based assay of screening the compound libraries for their inhibitory potential lead to the identification of a novel class of ACK1 inhibitors. These inhibitors, (R)-9b and (S)-9b, not only were able to suppress the ACK1 kinase activity in vitro but were also shown to be potent ACK1 inhibitors in vivo, suppressing the growth of the prostate cancer derived cell lines. Further, (R)-9b and (S)-9b compounds displayed considerable selectivity towards ACK1, when compared with other related tyrosine kianses such as Src and ALK.

ACK1 Epigenetic Signaling in Castration Resistant Prostate Cancer: Role of ACK1 Small Molecule Inhibitors Androgen receptor (AR) plays a paramount role in the onset and progression of prostate cancer (PC) (Burnstein K L. Regulation of androgen receptor levels: implications for prostate cancer progression and therapy. *J. Cell. Biochem.* 2005; 95(4):657-69; Chen C D, et al. Molecular determinants of resistance to antiandrogen therapy. *Nature Med.* 2004; 10(1):33-9). This very facet underlies androgen deprivation therapy (ADT), a preferred treatment to negate AR transcriptional co-activator activity for advanced PC. While chemical treatment with AR antagonists or surgical treatment by orchiectomy provides immediate palliative benefits, these ADTs are ineffective long term, as the recalcitrant disease recurs within 2-3 years. Consequently, resistance to ADT has become one of the most vexing problems in prostate cancer therapy (Feldman B J, et al. The development of androgen-independent prostate cancer. *Nature Rev.* 2001; 1(1):34-45; Edwards J, et al. The androgen receptor and signal-transduction pathways in hormone-refractory prostate cancer. Part 1: Modifications to the androgen receptor. *BJU Intl.* 2005; 95(9):1320-6). Moreover, a majority of the PC patients' progress to a lethal stage of the disease, referred to as the Castration Resistant Prostate Cancer (CRPC). In a significant number of human CRPCs, AR mRNA is upregulated, suggesting that PC cells have reinvigorated AR transcription as a response to the loss of existing AR activity by ADT. Despite intensive efforts, targeting factors that regulate AR mRNA expression efficaciously with small molecule inhibitors has not been achieved.

ACK1 tyrosine kinase interacts with AR, modifies it by tyrosine phosphorylation (pY267-AR) and this ACK1/pY267-AR complex is targeted to the chromatin to regulate AR-dependent gene expression in P C cells (Mahajan N P, et al. Activated Cdc42-associated kinase Ack1 promotes prostate cancer progression via androgen receptor tyrosine phosphorylation. *Proc. Nat. Acad. Sci. U.S.A.* 2007; 104 (20):8438-43; Mahajan N P, et al. Activated tyrosine kinase Ack1 promotes prostate tumorigenesis: role of Ack1 in polyubiquitination of tumor suppressor Wwox. *Cancer Res.* 2005; 65(22):10514-2; Mahajan K, et al. Ack1 mediated AKT/PKB tyrosine 176 phosphorylation regulates its activation. *PloS one.* 2010; 5(3):e9646; Mahajan K, et al. Shepherding AKT and androgen receptor by Ack1 tyrosine kinase. *J. Cell. Physiol.* 2010; 224(2):327-33; Mahajan K, et al. Ack1 tyrosine kinase activation correlates with pancreatic cancer progression. *Am. J. Pathol.* 2012; 180(4):1386-9; Mahajan K, et al. Ack1-mediated androgen receptor phosphorylation modulates radiation resistance in castration-resistant prostate cancer. *J. Biol. Chem.* 2012; 287(26):22112-22; Mahajan K, et al. ACK1 tyrosine kinase: targeted inhibition to block cancer cell proliferation. *Cancer Lett.* 2013; 338(2):185-92). A critical role for ACK1 in PC pathogenesis is further underscored by several observations; namely, ACK1 mRNA is not only upregulated in prostate cancers, but activated ACK1 expression correlates positively with the progression to the malignant CRPC stage (Mahajan K, et al. Effect of Ack1 tyrosine kinase inhibitor on ligand-independent androgen receptor activity. *Prostate.* 2010; 70(12):1274-85). Indeed, 10 out 13 CRPC tumors exhibited 5- to >100-fold ACK1 overexpression (van der Horst E H, et al. Metastatic properties and genomic amplification of the tyrosine kinase gene ACK1. *Proc. Nat. Acad. Sci. U.S.A.* 2005; 102(44):15901-6). Consistently, LNCaP cells expressing activated ACK1, formed robust xenograft tumors in castrated nude male mice. Furthermore, transgenic mice expressing activated ACK1 in prostates develop prostatic intraepithelial neoplasia (mPINs) and rare carcinomas.

Notably, alterations in ACK1 expression is associated with median disease free state of only 1.3 months compared to 110 months for PC patients without ACK1 alteration (cBioPortal). These findings underscore a dominant role for ACK1 in hormone refractory PC.

ACK1 regulated AR transcription directly in multiple PC cell lines. ACK1 modified the chromatin via phosphorylation of histone H4 at a novel site, tyrosine 88 (pY88-H4). Importantly, the pY88-H4 epigenetic marks were deposited within the AR gene itself in an androgen-independent manner. Strikingly, reversal of this pY88-H4 histone modification, attained by ACK1 inhibition, significantly suppressed AR transcription. Moreover, our preliminary data reveal that WDR5/MLL2, members of the histone-Lysine N-Methyltransferase complex (Shahbazian M D, et al. Functions of site-specific histone acetylation and deacetylation. Ann. Rev. Biochem. 2007; 76:75-100; Shilatifard A. Molecular implementation and physiological roles for histone H3 lysine 4 (H3K4) methylation. Curr. Opin. Cell Biol. 2008; 20(3): 341-8), interact with the pY88-H4 epigenetic marks, revealing a novel mode of AR epigenetic regulation. Neoplastic PC cells adapt rapidly to ADT by recruiting the AR/ACK1 complex to the AR gene. In this androgen-deprived milieu, ACK1 catalyzes Y88-H4 phosphorylation that in turn recruits the chromatin remodeling protein WDR5, to stimulate AR transcription and facilitate CRPC development.

CRPC remains an incurable malignancy with limited treatment options and is a significant cause of deaths in men—both U S and worldwide (Greenlee R T, et al. Cancer Statistics, 2000. CA: a cancer journal for clinicians. 2000; 50(1):7-33). Androgen receptor signaling is found to be operational pre- and post-castration stage, albeit disparate mechanisms operate in PC cells to promote androgen dependent and independent AR transcriptional co-activator activity. These distinct AR regulatory activities are manifested as distinct transcriptional programs operational in PC cells that contribute favorably towards cell survival, proliferation and growth. Recently, Enzalutamide or MDV3100 (marketed as Xtandi), an AR antagonist, has been FDA approved for treatment of metastatic CRPC patients Tran C, et al. Development of a second-generation antiandrogen for treatment of advanced prostate cancer. Science. 2009; 324(5928):787-90). Although highly effective in suppressing AR transcriptional activity, and also nuclear translocation (seen by significant decrease in serum PSA levels), it is effective only in a subset of CRPC patients (12 out of 30 patients). Moreover, the overall survival advantage was found to be modest (4-6 months) and even the most responding patients relapsed within ~2 years (Bennett L L, et al. Enzalutamide (Xtandi) for patients with metastatic, resistant prostate cancer. Ann. Pharmacotherapy. 2014; 48(4):530-7). These relapsed patients exhibit renewed AR target gene expression by multiple mechanisms, suggesting that CRPC has bypassed Enzalutamide blockade (Balbas M D, et al. Overcoming mutation-based resistance to antiandrogens with rational drug design. eLife. 2013; 2:e00499; Arora V K, et al. Glucocorticoid receptor confers resistance to antiandrogens by bypassing androgen receptor blockade. Cell. 2013; 155 (6):1309-22; Joseph J D, et al. A clinically relevant androgen receptor mutation confers resistance to second-generation antiandrogens enzalutamide and ARN-509. Cancer Discovery. 2013; 3(9):1020-9; Korpal M, et al. An F876L mutation in androgen receptor confers genetic and phenotypic resistance to MDV3100 (enzalutamide). Cancer Discovery. 2013; 3(9):1030-43). These setbacks revealed two major caveats of tackling this complex disease; first, not all CRPCs are the same and second, other signaling events may be driving the disease, which explains the efficacy of Enzalutamide in a limited number of CRPC patients. Moreover, because CRPCs display de novo or intrinsic ability to increase AR levels, inhibition of AR protein activity is not enough (Knuuttila M, et al. Castration Induces Up-Regulation of Intratumoral Androgen Biosynthesis and Androgen Receptor Expression in an Orthotopic VCaP Human Prostate Cancer Xenograft Model. Am. J. Pathol. 2014). To achieve complete remission, ablation of AR transcription appears to be the key for all AR-dependent prostate cancers. However, targeted inhibition of AR transcription with small molecule inhibitors has not yet been accomplished.

Figure 2:
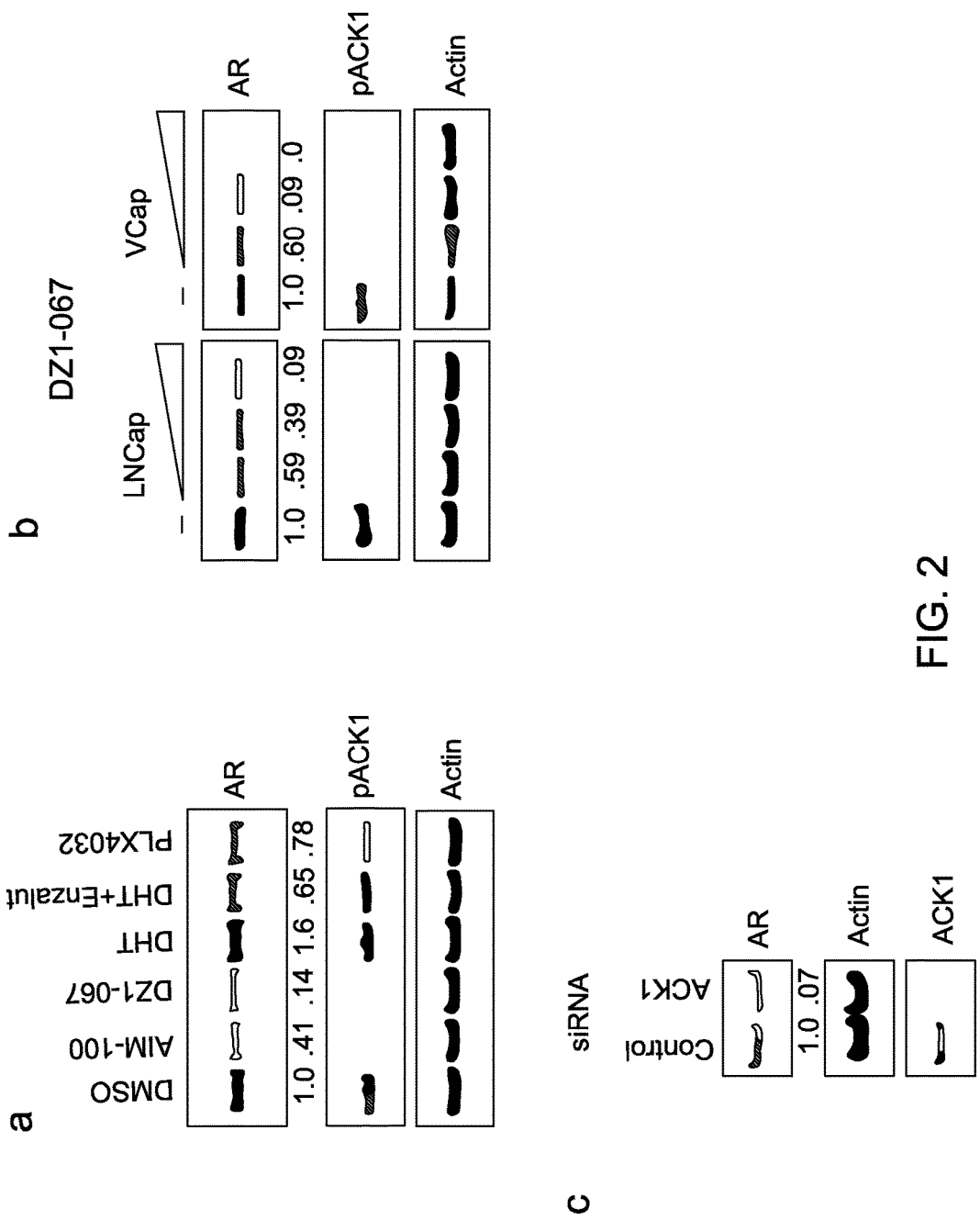
FIG. 2 shows that ACK1 kinase activity is required to maintain androgen-independent AR protein levels.

Transcriptional regulation of the AR gene itself is a paradigm that merits thorough investigation. Epigenetic modifications are intricately linked to transcription events, especially when activated by nuclear hormones (Xu K, et al. EZH2 oncogenic activity in castration-resistant prostate cancer cells is Polycomb-independent. Science. 2012; 338 (6113):1465-9; Cai C, et al. Androgen receptor gene expression in prostate cancer is directly suppressed by the androgen receptor through recruitment of lysine-specific demethylase 1. Cancer Cell. 2011; 20(4):457-71). Data obtained has indicated that ACK1 kinase is a unique tyrosine kinase that not only binds tightly to AR in androgen-deficient environment, but also 'piggybacks' AR to the nucleus to bind chromatin. Whether AR utilizes ACK1 to facilitate its transcriptional co-activator function is not known. Towards understanding the outcome of the androgen-independent AR/ACK1 cross talk, an unbiased approach was chosen wherein androgen-deprived prostate cancer cells LNCaP were treated with dihydrotestosterone (DHT) or Enzalutamide. Cells were also treated with ACK1-specific small molecule inhibitors, DZ1-067 or AIM-100. Interestingly, inhibition of ACK1 kinase by DZ1-067 resulted in a significant downregulation the AR protein, in contrast, both Enzalutamide and PLX4032, a B-Raf inhibitor that has modest ACK1 inhibitory activity (Bollag G, et al. Clinical efficacy of a RAF inhibitor needs broad target blockade in BRAF-mutant melanoma. Nature. 2010; 467 (7315):596-9), had little effect on AR expression (FIG. 2a). Expectedly, DHT treatment led to increased AR levels, primarily due to stabilization of AR.

To assess whether loss of AR levels is dependent on specific inhibition of ACK1 kinase activity, increasing concentrations of DZ1-067 were used. A concomitant decrease in AR protein levels was observed which correlated with increasing amounts of AIM-100 in two different PC lines, LNCaP and VCaP cells (FIG. 2b), suggesting that ACK1 kinase activity is critical for maintaining AR levels in androgen-deficient environment of prostate cancer cells. To examine that loss of AR levels is not due to 'off target effect' of ACK1 inhibitors, LAPC4 cells were transfected with ACK1 siRNA. Immunoblotting revealed significant decrease in AR levels upon loss of ACK1 (FIG. 2c).

8 compounds were tested against 2 kinases, ACK1, Src and ALK in various combinations. Compounds were tested in 10-dose $IC_{50}$ mode with 3-fold serial dilution starting at 10 μM. Control Compound, Staurosporine, was tested in 10-dose IC50 mode with 4-fold serial dilution starting at 20 uM. Reactions were carried out at 10 μM ATP. $IC_{50}$ Summary is shown in Table 3 and Table 4.

TABLE 3

$IC_{50}$ Summary

| | Compound $IC_{50}$* (M): | |
|---|---|---|
| Compound ID: | ACK1 | c-Src |
| DZ1-067 | 6.05E−08 | 4.38E−07 |
| DZ1-114 | 4.83E−08 | |

TABLE 3-continued

IC$_{50}$ Summary

| Compound ID: | Compound IC$_{50}$* (M): | |
|---|---|---|
| | ACK1 | c-Src |
| DZ1-122 | 4.80E−08 | |
| YL9-162 | 3.32E−08 | |
| YL9-167 | 9.47E−08 | |
| SK1-028 | 1.64E−07 | |
| YL9-163 | 2.84E−08 | |
| DZ1-120 | 1.63E−07 | |
| Staurosporine IC$_{50}$* (M) | 3.69E−08 | 2.76E−09 |

TABLE 4

| Kinases | Compound IC$_{50}$ (M) | | | | | |
|---|---|---|---|---|---|---|
| | DZ1-067 | DZ1-077 | Structure21 | DZ1-096 | MH1-022-5 | Staurosporine |
| ACK1 | 5.78E−08 | 8.33E−08 | 1.71E−07 | 3.22E−08 | 5.44E−08 | 4.75E−08 |
| ALK | 1.43E−07 | 2.96E−07 | 6.08E−10 | | | 1.47E−09 |

AR has been known to interact with an ubiquitin E3 ligase, RNF6, causing AR ubiquitination, which in turn promoted AR transcriptional activity (Xu K, et al. Regulation of androgen receptor transcriptional activity and specificity by RNF6-induced ubiquitination. *Cancer Cell.* 2009; 15(4):270-82). To determine whether post-translational modification has role to play in suppression of AR levels upon ACK1 kinase inhibition, LNCaP cells were treated with proteosomal inhibitor, MG-132 and AR levels were measured in presence or absence of DZ1-067. Proteosomal inhibitor did not prevent loss of AR caused by ACK1 kinase inhibition, suggesting that ACK1 regulates AR levels at transcriptional stage.

Figure 3:
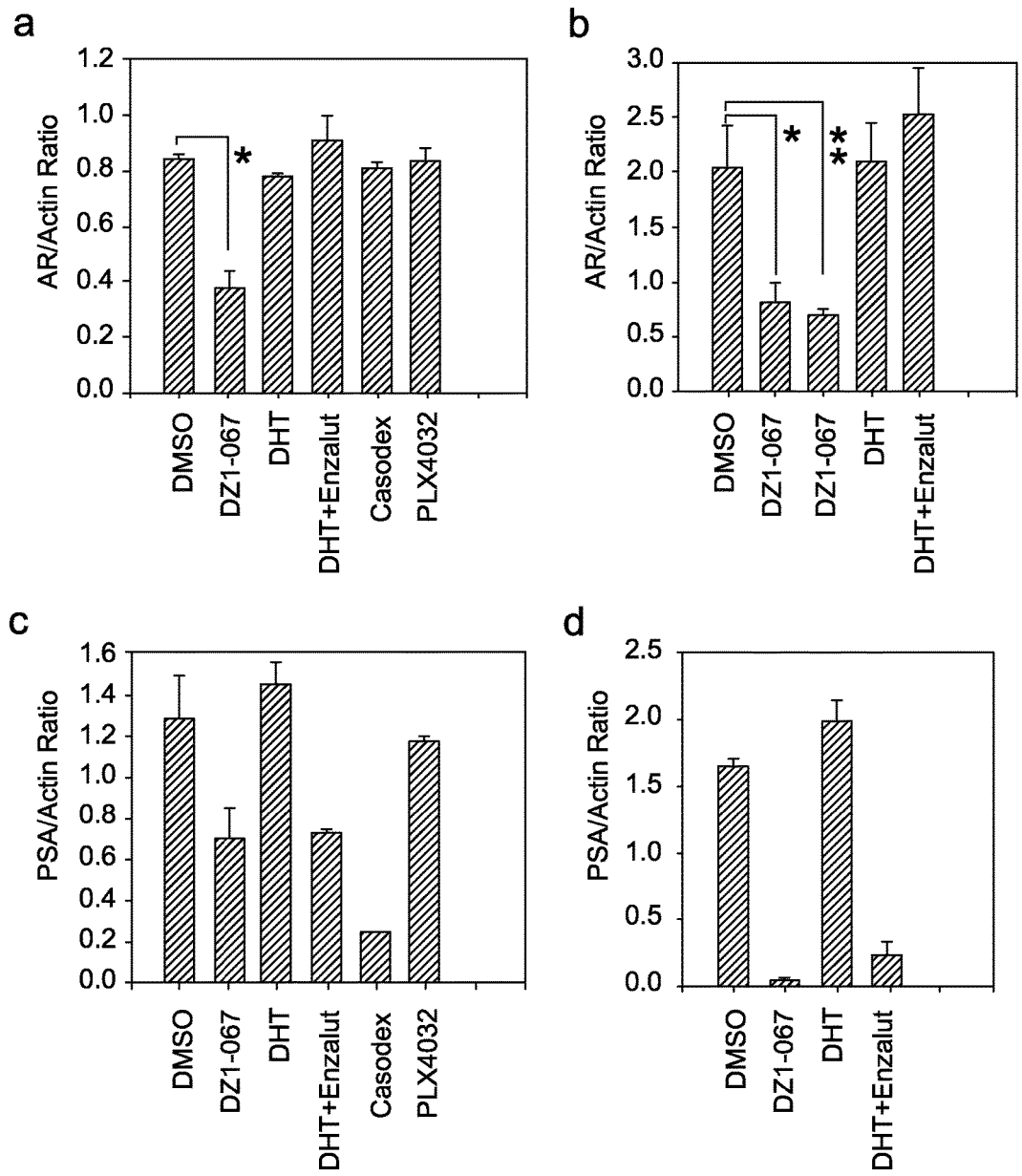
FIG. 3 shows that inhibition of ACK1 kinase activity suppresses AR transcription.

To validate this data further, androgen-deprived LAPC4 and LNCaP cells were treated with DZ1-067, DHT, Enzalutamide, Casodex or PLX4032. Total RNA was isolated followed by real time PCR, which revealed that AR mRNA levels were significantly suppressed upon DZ1-067 treatment, however, no significant change in AR mRNA levels were seen upon DHT, Enzalutamide, Casodex or PLX4032 treatments (FIG. 3a, b). Prostate specific antigen (PSA) is a major AR target gene whose expression reflects AR transcriptional co-activator ability, too exhibited significant loss upon ACK1 inhibitor treatment (FIG. 3c, d). Interestingly, first generation (Casodex) and second generation (Enzalutamide) of anti-androgens although did not overturn AR mRNA levels, significantly suppressed PSA mRNA levels, as reported in literature (FIG. 3c, d). Taken together, these data indicate that ACK1 kinase plays a crucial role in maintaining AR mRNA levels, in absence of androgen, by regulating its transcription.

Figure 4:
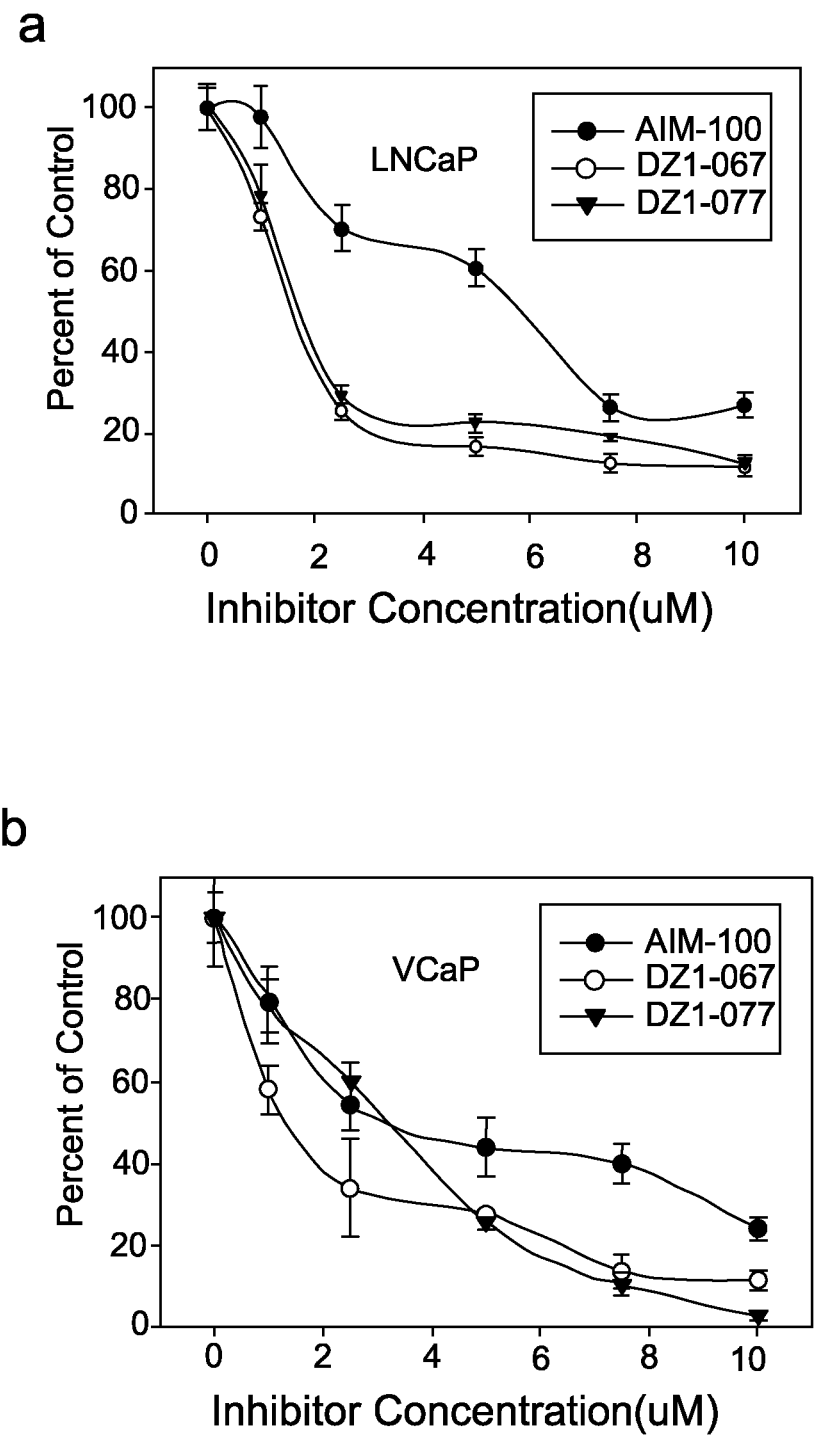
FIG. 4 shows a cell proliferation assay.

The ability of the ACK1 inhibitors to suppress proliferation of prostate cancer cell lines were also assessed. AIM-100, an ACK1 inhibitor, originally screened by Amgen was used as a control. Both, DZ1-067 and DZ1-077 were significantly better (IC$_{50}$=1.8 μM) than AIM-100 (IC$_{50}$=7 μM) in their ability to inhibit cell growth in LNCaP cells (FIG. 4a). Further, androgen-independent VCaP cells were observed to be highly sensitive to DZ1-067 (IC$_{50}$=2 μM), while AIM-100 and DZ1-077 exhibited IC$_{50}$ of 4 μM (FIG. 4b). Overall, it appears that ACK1 is needed for androgen-independent growth of prostate cancer cells. And that is why, DZ1-067, an excellent ACK1 inhibitor exhibit significant potential to suppress proliferation of androgen-independent or CRPC cells.

A larger cohort of data has recently become available at cBioPortal. Of the 216 patients with prostate adenocarcinoma, 33 patients with high ACK1 mRNA expression or mutation exhibited median disease free survival of 1.3 months (Table 5). In contrast, those patients that did not have alterations in ACK1 had significantly longer disease free survival (110 months). These data suggests that the fraction of prostate cancer patients that have aberrant ACK1 expression are likely to rapidly progress to CRPC, a major cause of death. Interestingly, ACK1 alteration and AR gene amplification or mutation had no co-relation (Odds Ratio: 1.36; 95% Confidence Interval: 0.54-3.43; Fisher's Exact Test p-value: 0.32), suggesting that ACK1 mediated AR transcriptional upregulation is an independent mechanism.

TABLE 5

| | # Total Cases | # Cases relapsed | Median months disease free |
|---|---|---|---|
| Cases with alteration in ACK1 | 33 | 10 | 1.38 |
| Cases without alteration in ACK1 | 163 | 50 | 110.33 |

Figure 5:
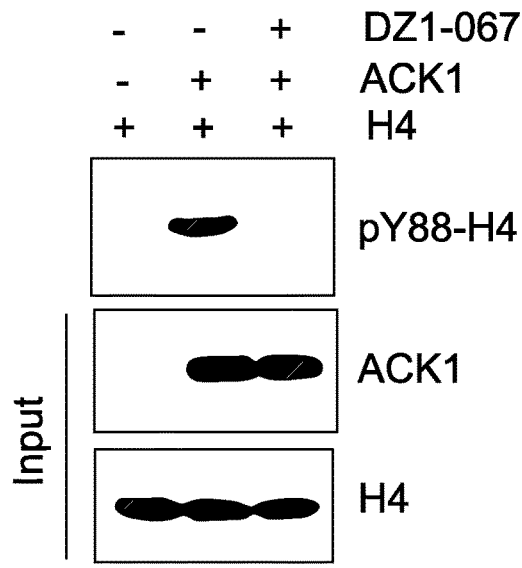
FIG. 5 shows that ACK1 phosphorylates histone H4 at Tyrosine 88.
Figure 5:
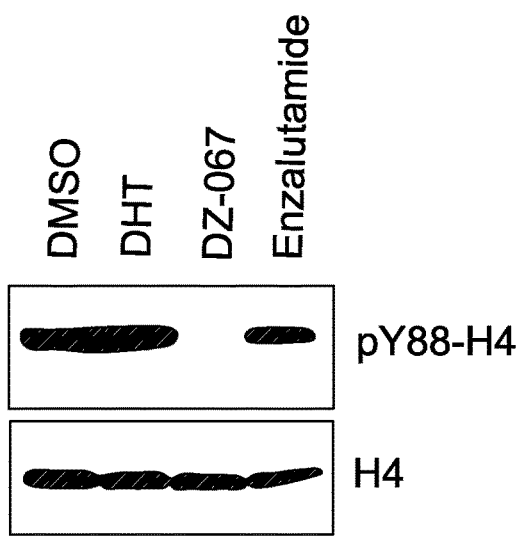

To assess direct binding of ACK1 to H4, in vitro kinase assay was performed using purified ACK1 and H4 (New England Biolabs). Human ACK1 was expressed in insect cells and purified to homogeneity. Immunoblotting with pY88-H4 and pTyr antibodies confirmed that indeed H4 is directly Tyr-phosphorylated by ACK1 (FIG. 5a). Further, H4 Tyr-phosphorylation is abrogated by treatment with ACK1 inhibitor, DZ1-067 (FIG. 5a), suggesting that ACK1 directly binds and phosphorylates histone H4.

LNCaP cells were treated with DZ1-067, DHT or Enzalutamide. LNCaP cells exhibited robust expression of endogenous pY88-phosphorylation of H4, which was eliminated upon treatment with DZ1-067 (FIG. 5b), but was unaffected by DHT or Enzalutamide. These data established that ACK1 tyrosine kinase is a novel epigenetic modifier and epigenetic marks deposited by ACK1 can be erased by ACK1 inhibitor, DZ1-067.

AR is essential for not only in normal prostate but also for malignant prostate tumor growth (Edwards J, et al. The androgen receptor and signal-transduction pathways in hormone-refractory prostate cancer. Part 2: Androgen-receptor cofactors and bypass pathways. *BJU Int.* 2005; 95(9):1327-35). The modus operandi of this hormone receptor is now conclusively established wherein androgen-bound AR initiates transcription of target genes e.g PSA, by binding to androgen-response elements (ARE) in promoter regions. However, this paradigm was shaken to core when CRPC tumors were found to be not only thriving under low castration levels of androgen but also maintained functional AR, suggesting that AR has 'learned' to deal with dwindling androgen levels.

It was observed that not only is AR/ACK1 complex bound to the chromatin in androgen-deficient environment, but our studies revealed that ACK1 inhibitors also caused significant loss of AR transcription. Taken together, the data uncovers a distinct epigenetic mechanism wherein AR regulates its own transcription in androgen deficient environment by availing the chromatin modifying activity of the ACK1 kinase.

Figure 6:
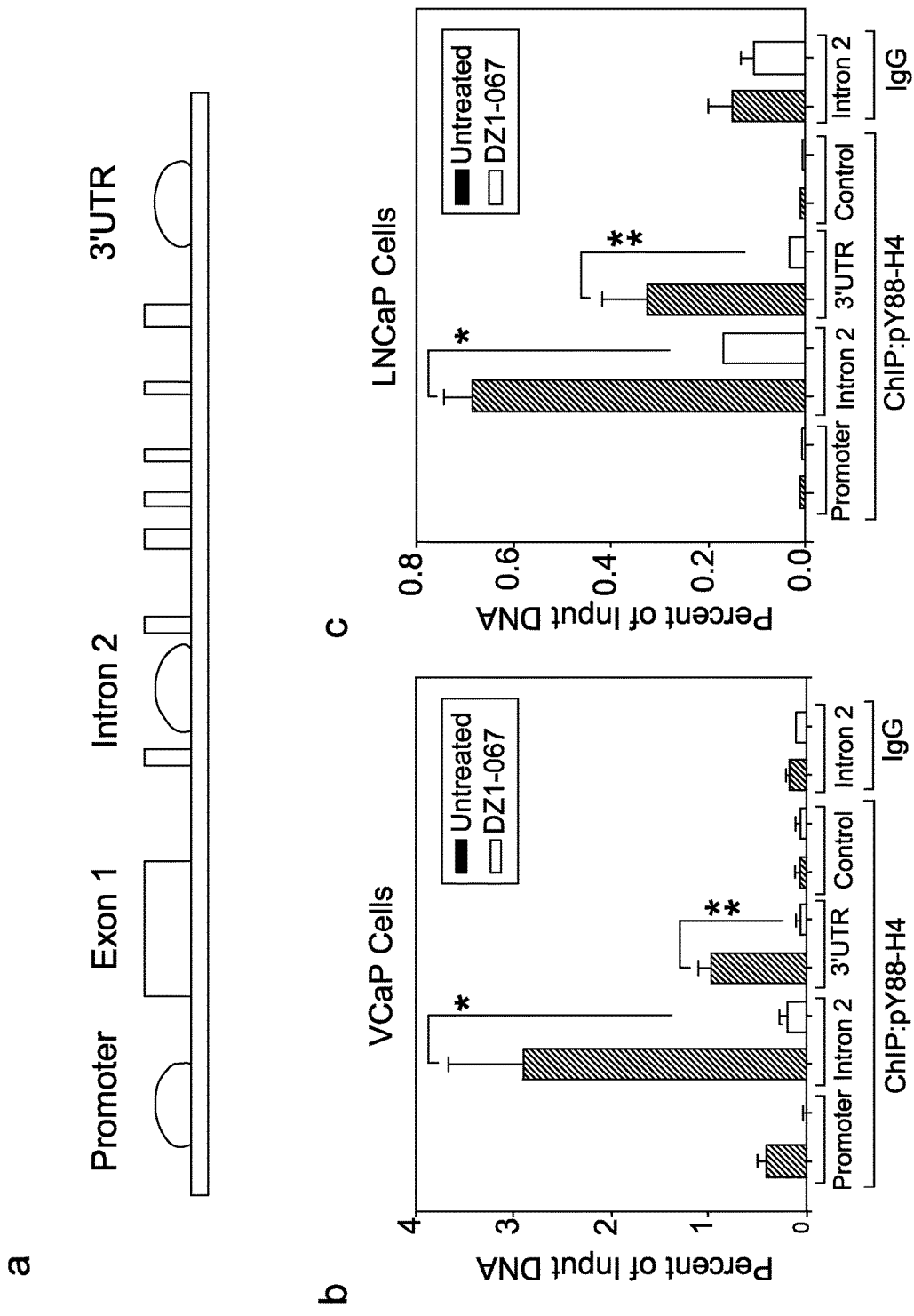
FIG. 6 shows H4 Y88-phosphorylation occurs within and downstream of AR gene.

To determine whether ACK1 modifies chromatin at AR gene locus, LNCaP and LAPC4 cells grown in the absence of androgen and were treated with DZ1-067. Chromatin immunoprecipitation (ChIP) was performed using pY88-H4 antibodies, followed by real time PCR with primers corresponding to the AR promoter, intron 2 and 3'UTR (FIG. 6a). ChIP data revealed the presence of pY88-H4 marks predominantly at the intron 2. These marks were also deposited at 3'UTR of the AR gene but not at the promoter region (FIG. 6b, c). Significantly, these epigenetic marks were erased in DZ1-067 treated samples, suggesting that deposition of pY88-H4 epigenetic marks in AR gene is a reversible event and can be accomplished using ACK1 inhibitors.

Collectively, the data reveal the role of a novel chromatin alteration event, histone H4 tyrosine phosphorylation mediated by the oncogenic kinase ACK1, as a critical factor driving AR mRNA expression in CRPC.

Figure 7:
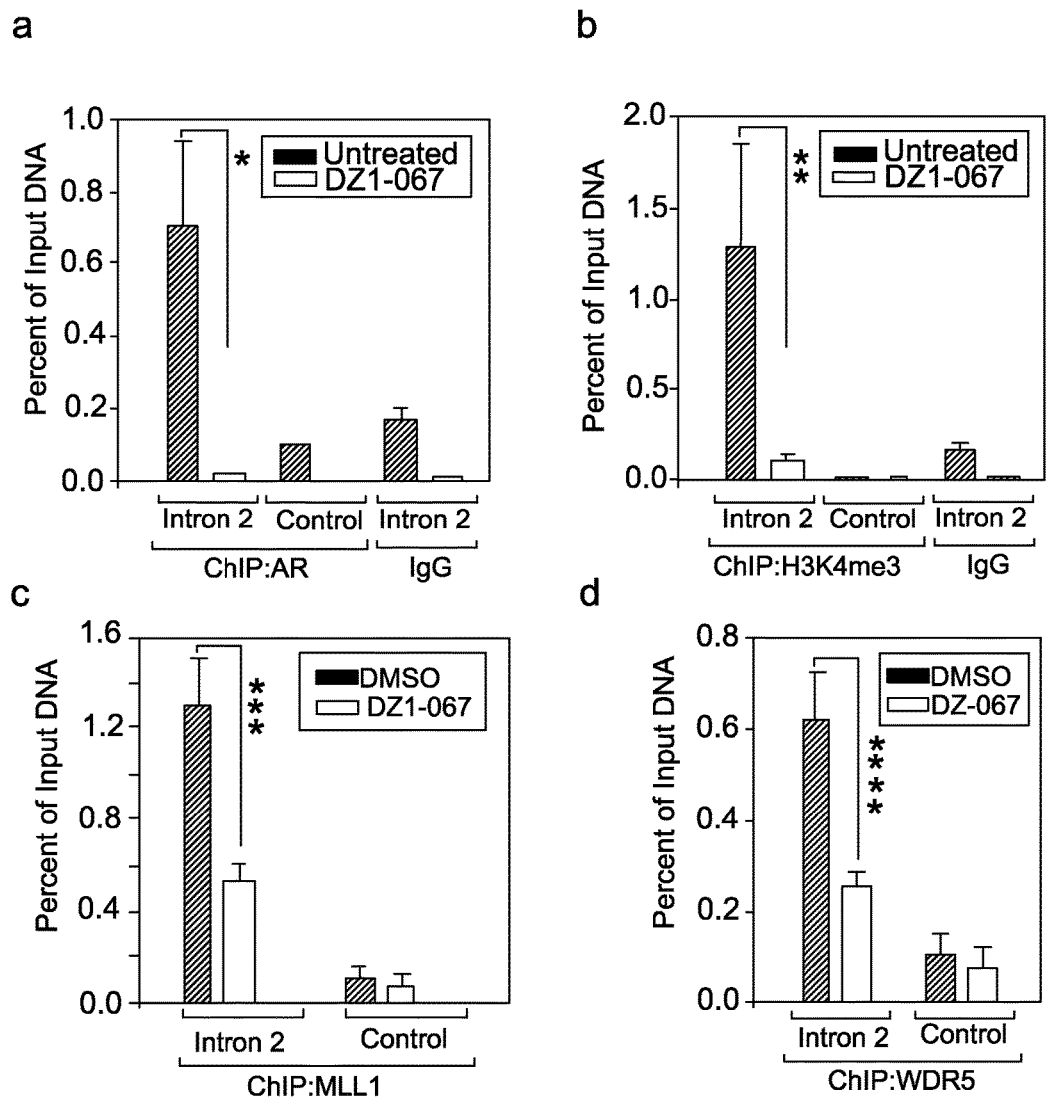
FIG. 7 shows recruitment of AR (FIG. 7(a)), MLL (FIG. 7(c)), WDR5 (FIG. 7(d)) and deposition of H3K4me3 (FIG. 7(b)) epigenetic marks within intron 2 of AR gene are dependent on ACK1 kinase activity and can be erased by DZ1-067. LNCaP cells treated with DZ1-067 and ChIP was performed using AR, H3K4me3, or IgG antibodies followed by qPCR using primers corresponding to intron 2, or control region. *p<0.05, p<0.05, *p<0.05, ****p<0.05.

To determine the functional and physiological relevance of pY88-H4/WDR5 interaction, and given the interaction of AR with MLL associated complex (Grasso C S, et al. The mutational landscape of lethal castration-resistant prostate cancer. *Nature.* 2012; 487(7406):239-43). ChIP experiments were performed to determine AR and H3K4me3 levels at the intron 2. Both, AR and H3K4me3 methyl marks were found to be specifically enriched at the intron 2 region, in absence of androgen, that were abolished by treatment with DZ1-067 (FIG. 7).

What is claimed is:

1. A compound having Formula IA:

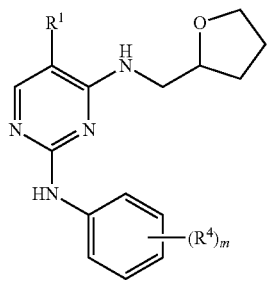

wherein
$R^1$ is Cl, Br, F, $CH_3$, or $C_2H_5$;
m is 1 or 2; and
at least one $R^4$ is a cycloalkyl or heterocycloalkyl that is unsubstituted or substituted with $R^6$, and, if present, the other $R^4$ is OH, Cl, Br, F, $C_1$-$C_6$ alkyl, CN, $NO_2$, or $OR^5$ where
$R^5$ is $C_1$-$C_6$ alkyl, heteroalkyl, cycloalkyl, heterocycloalkyl, or heteroaryl; and
$R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group, or PEG-sterol,
or a pharmaceutically acceptable salt thereof.

2. The compound of claim 1, wherein $R^1$ is Cl or Br.

3. The compound of claim 1, wherein m is 1 and $R^4$ is 4-morpholinyl, 4-piperazinyl, 1-piperidinyl, or 4-piperadinyl group that is unsubstituted or substituted with $R^6$.

4. The compound of claim 1, wherein m is 1 and $R^4$ is in the para position or m is 2 and each $R^4$ are in the para and meta positions.

5. The compound of claim 1 chosen from

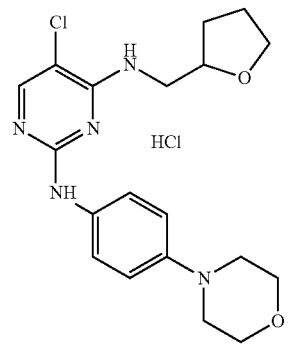

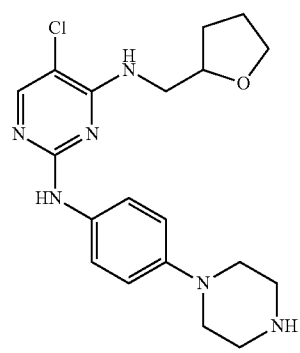

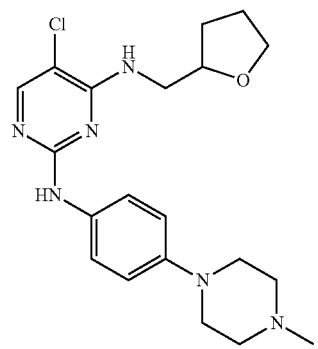

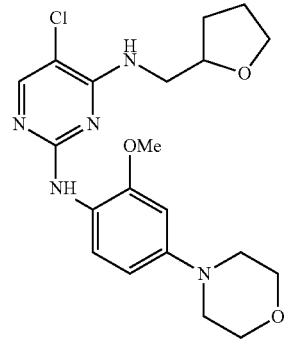

189
-continued
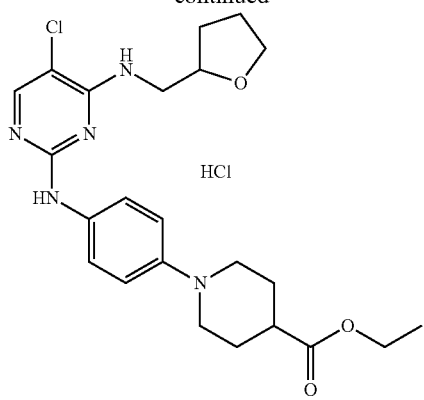
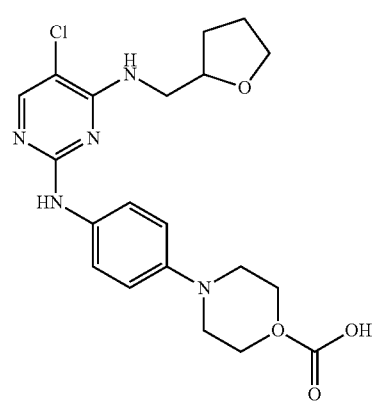
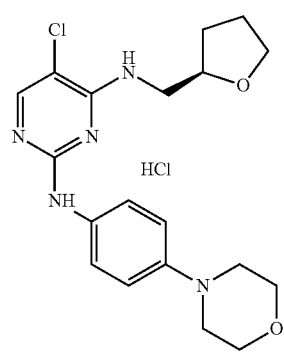
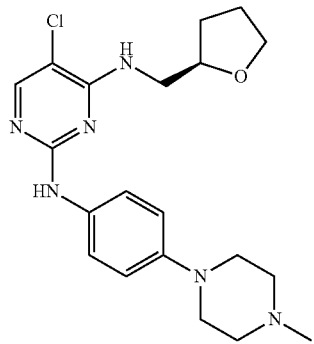
190
-continued
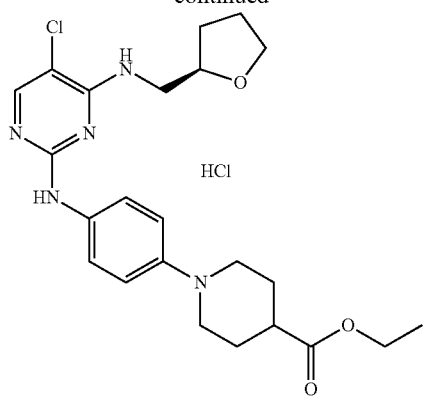
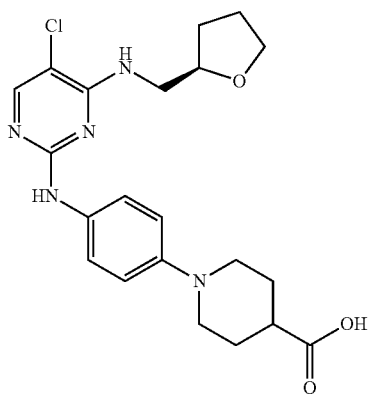
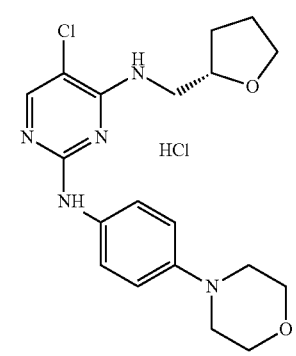
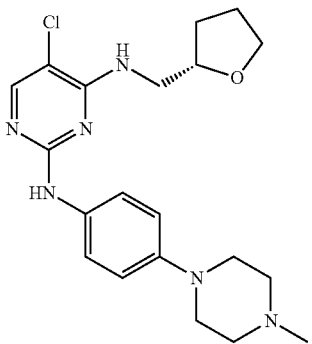 [SMILES: CN1CCN(c2ccc(Nc3ncc(Cl)c(NC[C@@H]4CCCO4)n3)cc2)CC1]

191
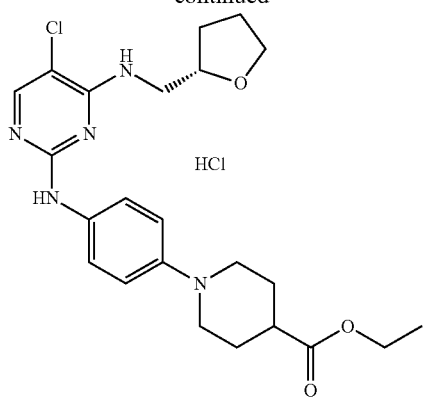
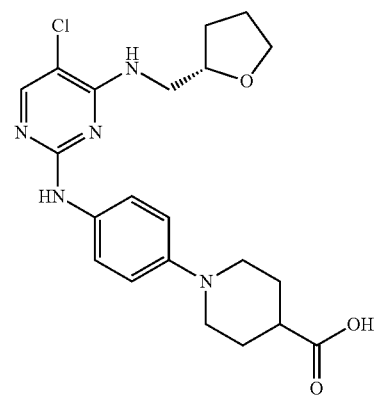
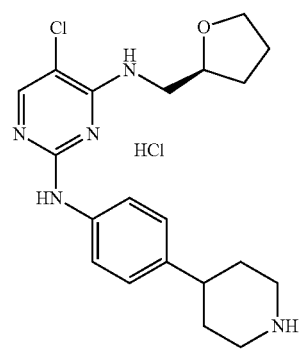
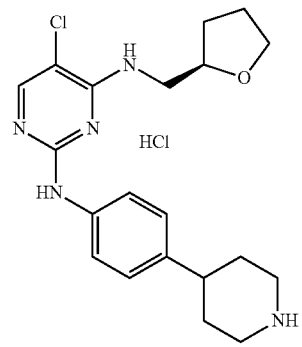
192
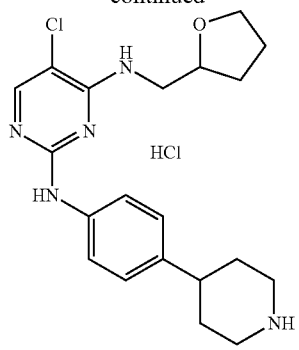
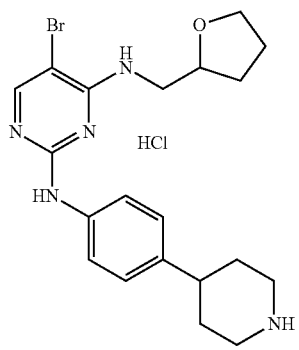
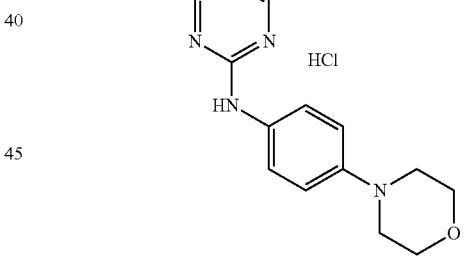
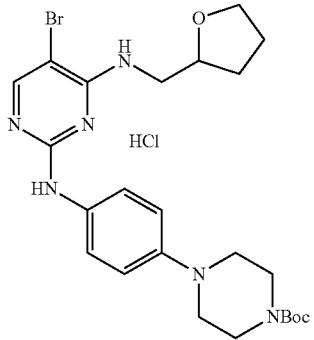

-continued
193
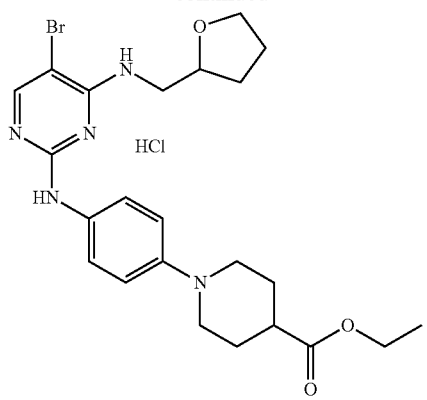
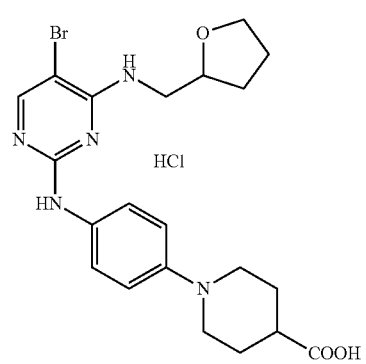
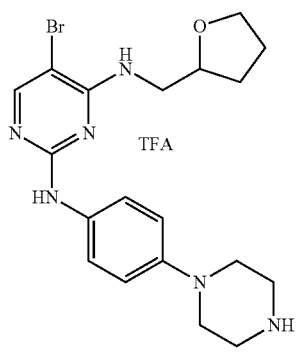
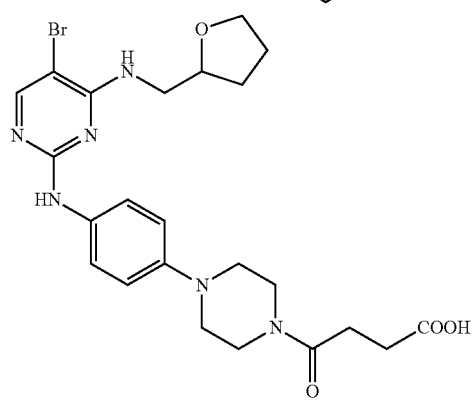
194
-continued
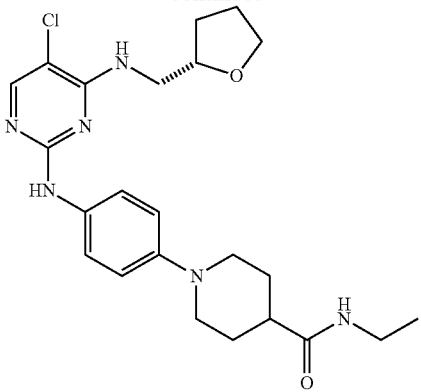
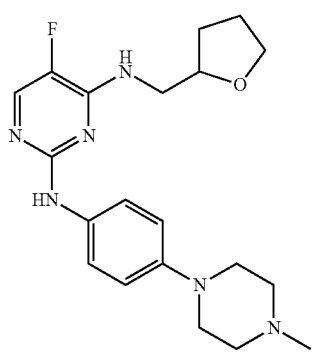
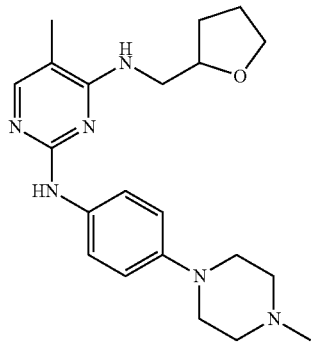

195
-continued
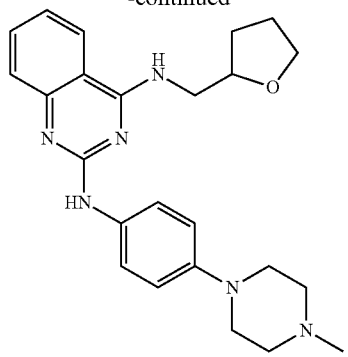
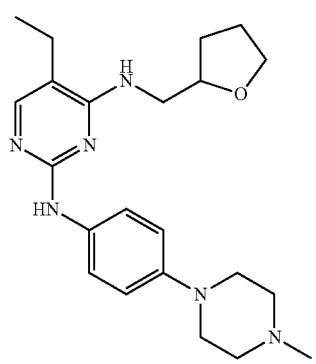
and
196
-continued
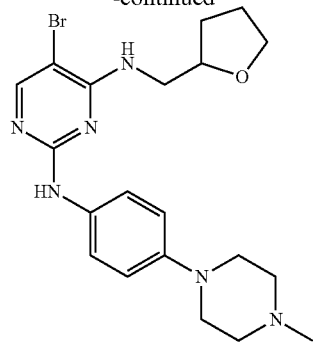
6. The compound of claim 1, wherein the compound is
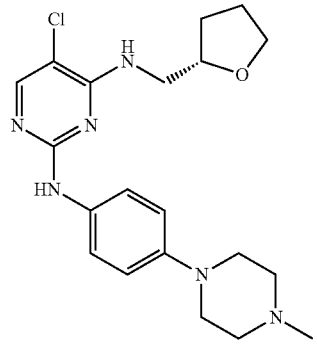
* * * * *